(12) United States Patent
Lioux et al.

(10) Patent No.: US 11,730,817 B2
(45) Date of Patent: Aug. 22, 2023

(54) PRO-CYCLIC DINUCLEOTIDES AND PRO-CYCLIC DINUCLEOTIDE CONJUGATES FOR CYTOKINE INDUCTION

(71) Applicant: INVIVOGEN, Toulouse (FR)

(72) Inventors: Thierry Lioux, Balma (FR); Fabienne Vernejoul, Toulouse (FR); Cédric Boularan, Toulouse (FR); Michèle Tiraby, Toulouse (FR)

(73) Assignee: INVIVOGEN, Toulouse (FR)

( * ) Notice: Subject to any disclaimer, the term of this patent is extended or adjusted under 35 U.S.C. 154(b) by 59 days.

(21) Appl. No.: 16/958,463

(22) PCT Filed: Dec. 28, 2018

(86) PCT No.: PCT/EP2018/097128
§ 371 (c)(1),
(2) Date: Jun. 26, 2020

(87) PCT Pub. No.: WO2019/129880
PCT Pub. Date: Jul. 4, 2019

(65) Prior Publication Data
US 2021/0353760 A1  Nov. 18, 2021
US 2022/0339287 A9  Oct. 27, 2022
US 2023/0116913 A2  Apr. 13, 2023

(30) Foreign Application Priority Data
Dec. 29, 2017 (EP) .................... 17306981

(51) Int. Cl.
*A61K 47/54* (2017.01)
*A61K 47/68* (2017.01)
(Continued)

(52) U.S. Cl.
CPC ........ *A61K 47/549* (2017.08); *A61K 31/7084* (2013.01); *A61K 45/06* (2013.01);
(Continued)

(58) Field of Classification Search
None
See application file for complete search history.

(56) References Cited

U.S. PATENT DOCUMENTS
2017/0340658 A1   11/2017   Invivogen

FOREIGN PATENT DOCUMENTS
WO   2017019896 A1   2/2017
WO   2017100305 A2   6/2017
(Continued)

OTHER PUBLICATIONS

The International Search Report and Written Opinion, dated Mar. 28, 2019, in PCT Appl No. PCT/EP2018/097128.
(Continued)

*Primary Examiner* — Karl J Puttlitz

(57) ABSTRACT

The present invention provides a Pro-cyclic dinucleotide (Pro-CDN) comprising a STING agonist cyclic dinucleotide which is coupled to a linker system. The Pro-CDNs of the present invention can be metabolized at a targeted site into CDNs and exert their full immunomodulatory effects at said targeted site. The present invention also provides conjugates wherein a Pro-CDN is conjugated to a Biologically Active Molecule (BAM) such as e.g. a cytotoxic molecule, a lipid, a protein, a peptide, a nucleic acid, a sugar or a PRR ligand. The invention provides also methods related to the use of such compounds to perform their activities at their targeted sites, to exert cytotoxic, cytostatic or immunomodulatory effects, to treat or to prevent diseases such as cancers, immunological disorders or infections.

25 Claims, 26 Drawing Sheets

(51) Int. Cl.
  *A61K 47/64* (2017.01)
  *A61K 47/65* (2017.01)
  *A61K 31/7084* (2006.01)
  *A61K 45/06* (2006.01)

(52) U.S. Cl.
  CPC ............ *A61K 47/643* (2017.08); *A61K 47/65* (2017.08); *A61K 47/6807* (2017.08); *A61K 47/6849* (2017.08); *A61K 47/6889* (2017.08)

(56) References Cited

FOREIGN PATENT DOCUMENTS

WO  2018100558 A2   6/2018
WO  2018200812   *  11/2018

OTHER PUBLICATIONS

The extended European search report, dated Jul. 5, 2018, in European Appl. No. 17306981.6.

* cited by examiner

A

B

C

PRO-CYCLIC DINUCLEOTIDES AND PRO-CYCLIC DINUCLEOTIDE CONJUGATES FOR CYTOKINE INDUCTION

CROSS-REFERENCE TO RELATED APPLICATIONS

This application is a National Stage Application of PCT/EP2018/097128 filed Dec. 28, 2018, which claims priority from European Patent Application No. 17306981.6, filed on Dec. 29, 2017. The priority of said PCT and European Patent Application are claimed. Each of the prior mentioned applications is hereby incorporated by reference herein in its entirety.

BRIEF SUMMARY OF THE INVENTION

The present invention provides a Pro-cyclic dinucleotide (Pro-CDN) comprising a STING agonist cyclic dinucleotide which is coupled to a linker system. The Pro-CDNs of the present invention can be metabolized at a targeted site into CDNs and exert their full immunomodulatory effects at said targeted site. The present invention also provides conjugates wherein a Pro-CDN is conjugated to a Biologically Active Molecule (BAM) such as e.g. a cytotoxic molecule, a lipid, a protein, a peptide, a nucleic acid, a sugar or a PRR ligand. The invention provides also methods related to the use of such compounds to perform their activities at their targeted sites, to exert cytotoxic, cytostatic or immunomodulatory effects, to treat or to prevent diseases such as cancers, immunological disorders or infections.

The Pro-CDN compound of the present invention is a compound of Formula (I), as represented in FIG. 12, wherein:

The CON unit is a compound of Formula ($II_a$): a cyclic dinucleotide monophosphorothioate or diphosphorothioate (CDN):

Formula ($II_a$)

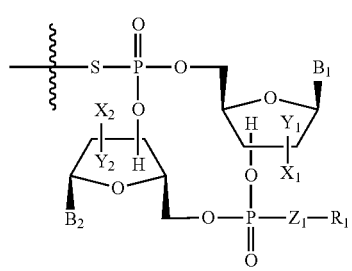

wherein:
$X_1$ and $Y_1$ are independently H or F;
$X_2$ and $Y_2$ are independently H or F;
$Z_1$ is O or S;
$R_1$ is H when $Z_1$ is O;
$R_1$ is H or a linker system when $Z_1$ is S;

$B_1$ and $B_2$ are purine bases chosen from:

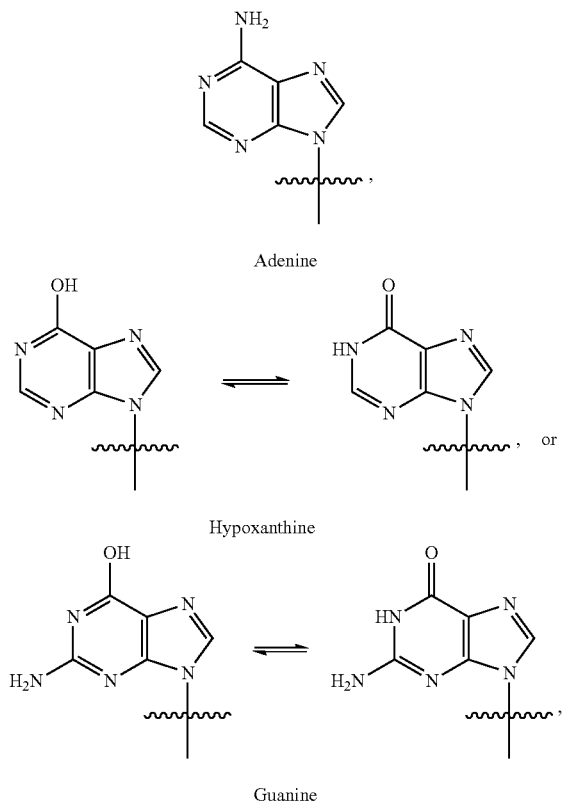

Adenine

Hypoxanthine

Guanine or pharmaceutically acceptable salts, stereoisomers, tautomers or solvates thereof;

The linker system comprises:
A connector which is a spontaneous self-eliminating group of Formulae ($III_a$) to ($III_g$) able to link with the CDN and the specifier:
Formula ($III_a$) is a Para-Amino-Benzyl (PAB) group:

Formula ($III_a$)

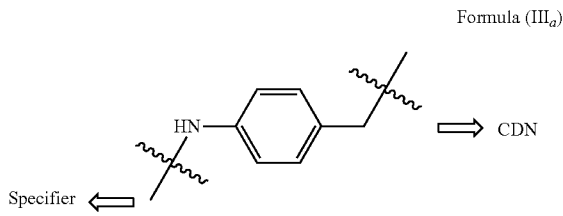 [SMILES: *Cc1ccc(N*)cc1 ; "CDN"]

Formula ($III_b$) is a Para-Hydroxy-Benzyl (PHB) group:

Formula ($III_b$)

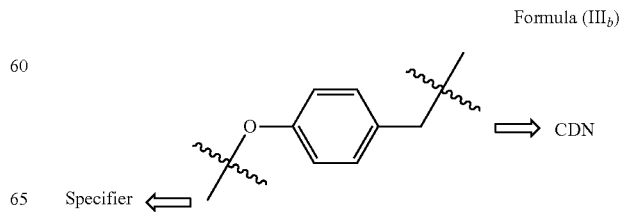

Formula (III$_c$) is a Para-Hydroxy-Meta-Trifluoromethyl-Benzyl (PHMTB) group:

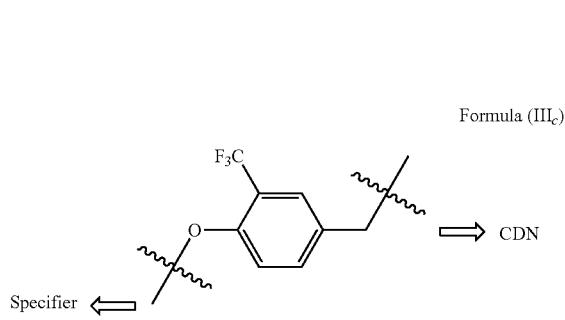 [SMILES: *Cc1ccc(O*)c(C(F)(F)F)c1 ; "CDN"]

Formula (III$_c$)

Formula (III$_d$) is a Para-Hydroxy-Meta-Nitro-Benzyl (PHMNB) group:

Formula (III$_d$)

Formula (III$_e$) is a Para-Hydroxy-Meta-Amino-Benzyl (PHMAB) group:

Formula (III$_e$)

A group of Formula (III$_f$):

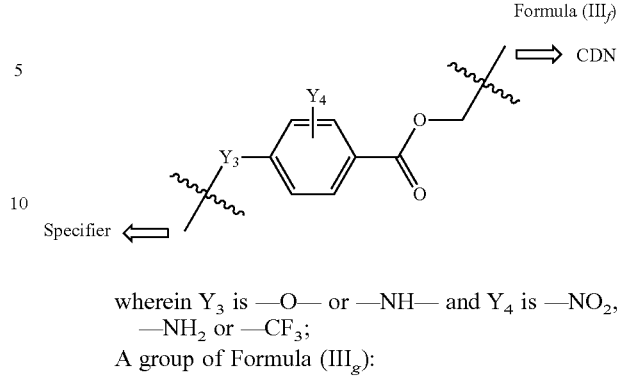

Formula (III$_f$)

wherein $Y_3$ is —O— or —NH— and $Y_4$ is —NO$_2$, —NH$_2$ or —CF$_3$;

A group of Formula (III$_g$):

Formula (III$_g$)

wherein $Y_3$ and $Y_4$ are as defined above;

A specifier which is an enzymatically cleavable unit.

The present invention concerns a Pro-CDN compound wherein a CDN compound which is a STING agonist compound is coupled to a linker system to enable the delivery of said CDN to a specific cell or tissue and thus exerts its activity to said targeted cell or tissue after being metabolized at the targeted site.

The Pro-CDN compound may further comprise a spacer either linked to the connector or to the specifier.

In one embodiment, and the spacer is a hydrophilic group selected from:
a polyethylene glycol (PEG);
a polyamine;
a compound of Formula (IV$_a$):

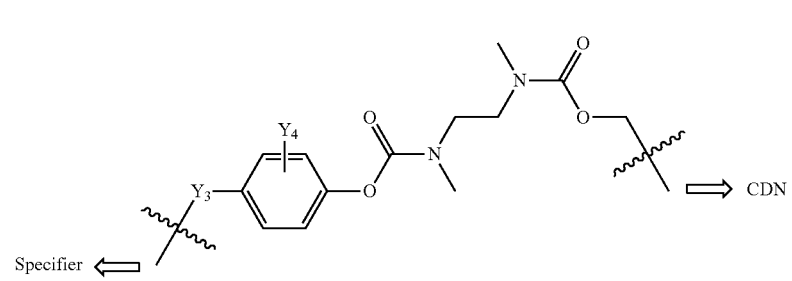

(IV$_a$)

wherein $X_3$ is —O— or —NH—, m, n and p are an integer ranging from 0 to 12;

a compound of Formula (IV$_b$):

(IV$_b$)

wherein q is an integer ranging from 1 to 6, more preferably 2 to 4;

r is an Integer ranging from 1 to 6, more preferably 1 to 2;

s Is an integer ranging from 1 to 6, more preferably 1 to 4;

a compound of Formula (IV$_c$):

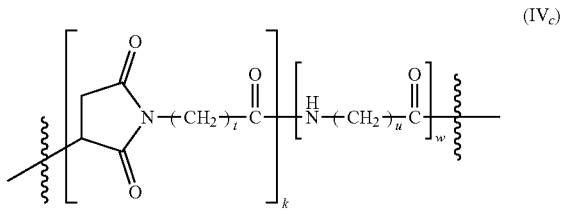

(IV$_c$)

wherein each t and u is independently an integer ranging from 1 to 10, preferably 3 to 7, more preferably 5;

k is 0 or 1, preferably 1;

w is an integer ranging from 0 to 6, preferably 0 or 1;

or a compound of Formula (IV$_d$):

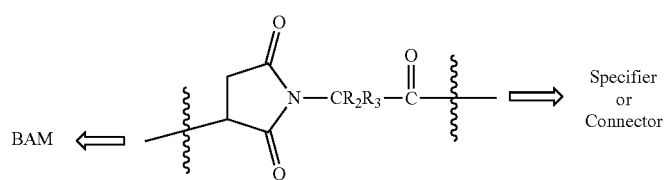

(IV$_d$)

wherein R$_2$ and R$_3$ and independently selected from H and an alkyl optionally substituted with an amino group, preferably from H and —CH$_2$—NH$_2$.

The present inventors have further demonstrated that it is possible to specifically combine the above-mentioned Pro-CDN with a biologically active molecule (BAM) so as to form a BAM-CDN conjugate. This "SAM-CDN" conjugate is particularly interesting because it allows the specific release of the BAM and of the CDN within a specific cell/tissue.

Thus, in a further embodiment, the present invention also provides a BAM-CDN conjugate wherein the BAM is connected to a CDN through a linker system which is able to release both CDN and BAM so that they can exert their own activities at a targeted site.

The linker system possesses a number of key attributes, including the requirement to be stable in plasma after drug administration for an extended period of time such that the BAM-CDN conjugate can specifically target e.g. immune or cancer cells. Upon processing, uptake or internalization, the BAM-CDN conjugate is able to release the CDN such that the CDN can bind to an intracellular target STING. In addition to these two basic functions, the linker system can have a profound effect on the physico-chemical properties of the BAM-CDN conjugate. In particular, most of the CDNs are polar molecule with poor penetration into cells. Thus, linking them to a BAM via a linker system containing a hydrophobic moiety can increase the uptake of CDNs.

The BAM-CDN conjugate comprising the Pro-CDN compound of Formula (I) and a biologically active molecule can be linked directly to the Pro-CDN compound of Formula (I) or through a spacer.

In specific embodiments, the BAM-CDN conjugate is a compound of the Formulae (V$_a$) to (V$_f$), as represented in FIGS. 13 to 18, wherein:

BAM is a Biologically Active Molecule;

The connector, connector 1 and connector 2 are spontaneous self-eliminating groups able to link the CDN and the specifier, independently chosen from groups of Formulae (III$_a$) to (III$_g$) as defined above;

The specifier, specifier 1 and specifier 2 are enzymatically cleavable units, identical or different;

The spacer is a hydrophilic group selected from a polyethylene glycol (PEG), a polyamine or a compound of Formula (IV$_a$), (IV$_b$), (IV$_c$) or (IV$_d$) as defined above;

v is 1 or 0;

The CON unit is a compound of Formula (II$_a$) as defined above.

The present invention provides a Pro-CDN conjugated to a Biologically Active Molecule (BAM) to enhance the CDN activity and/or exert a further biological activity at a targeted site defined by the enzymatic cleavage(s) of the specifier(s).

DETAILED DESCRIPTION

The present invention provides a Pro-CDN comprising a STING ligand CDN moiety which is coupled to a linker system which can be cleaved outside, in the vicinity or in the intracellular space of a target site defined by the enzymatic cleavage of the specifier.

The Pro-CDN of Formula (I) comprises at least one mono- or diphosphorothioate CDN of Formula (II$_a$) and an enzymatically cleavable specifier, wherein the CDN and the specifier are linked together through a spontaneous self-eliminating connector of Formulae (III$_a$) to (III$_g$). The specifier and the connector form a linker system. When the specifier is cleaved by a specific enzyme, the spontaneous self-eliminating connector releases the full CDN activity at the targeted site as summarized in Schemes 1.1 and 1.2, as represented in FIGS. 19 and 20.

The scheme 1.2 describes the release of a CDN when the connector is, for example, of Formula (III$_a$).

As used herein, the term "STING" is meant to include, without limitation, homologous and/or orthologous STING molecules, isoforms, precursors, mutants, variants, derivatives, splice variants, alleles, different species, and active fragments thereof.

The present invention provides also a BAM-CDN conjugate comprising a Biologically Active Molecule linked to a Pro-CDN, notably via a spacer. The spacer is connected either to a specifier or to a connector of the linker system of the Pro-CDN. The BAM-CDN conjugate is selectively activable outside, in the vicinity or in the intracellular space of a target site defined by the enzymatic cleavage(s) of the specifier(s).

The BAM-CDN conjugate of Formulae (V$_a$) to (V$_f$) of this invention comprises at least one mono- or diphosphorothioate CDN of Formula (II$_a$), a linker system comprising a specifier linked to a connector of Formulae (III$_a$) to (III$_g$)

and a BAM as defined above via notably a spacer. When the specifier is cleaved by a specific enzyme, the spontaneous self-eliminating connector releases the active form of CDN and the BAM linked to specifier or spacer-specifier at the targeted site as summarized, for example, for Formula ($V_a$) in Scheme 1.3, as represented in FIG. 21.

The BAM-CDN conjugates of Formulae ($V_e$ and $V_d$ to $V_f$) may contain another linker system between the BAM and the Pro-CDN to release the active form of CDN and the native form of BAM.

One aspect of the present invention provides a CON conjugate which Is selectively activable in the intracellular space.

Another aspect of the invention provides a cell specific CDN conjugate which is a highly selective substrate for drug-activating enzymatic cleavage of a target cell. The specific release of the CDN and the BAM at the vicinity or in the intracellular space of a target site is defined by the enzymatic cleavage of the specifier.

A description of the different parts of the compound of the Invention will be detailed below: Specifier, BAM, Connector, Spacer and CDN.

Specifier

The term specifier used herein Is defined as an enzymatically cleavable unit, i.e. a substrate which can be cleaved by an enzyme, and that can thus be specifically cleaved in a specific environment depending on the presence or not of said enzyme. The specifier thus allows for the specific release of the CDN and of the BAM within a specific cell/tissue depending on the specific conditions found in this specific cell/tissue. Once the specifier is cleaved, the biologically active drugs (the BAM on the one hand and the CON on the other hand) are released and thus can exert their respective biological functions.

There are two types of cleavable specifiers: a specific peptide sequence or a specific sugar:

- A specific peptide sequence offers improved control of molecule (BAM or CON) release by attaching the BAM to the CON via a peptide linkage. The peptide sequence is chosen among those which can be cleaved by a specific protease whose location, expression or activity varies according to the targeted site. Thus, CON and/or BAM are only active at a defined location thereby reducing side effects of the respective compounds. For example, the specifier can be cleaved in acidic environment within lysosomes by lysosomal proteases, such as cathepsin-B or plasmin.
- A specific sugar can be glucuronic acid or galactose and can be cleaved to release the CDN and BAM by a β-Glucuronidase or a β-Galactosidase whose location, expression or activity vary according to the targeted site.

One aspect of the present invention provides BAM-CDN conjugates which are stable in biological fluids until they reach their target.

Due to a specific release of the CDN and the BAM to the targeted site, the administration of the compounds according to the present invention is less toxic than the administration of the CDN or of the BAM alone; the activities of the present compounds being maximal after the specifier cleavage.

In the compounds of the invention, the specifier is typically a substrate that is specifically cleaved by an enzyme present in the vicinity of, or inside the targeted cells. More preferably, the specifier is a substrate that is specifically cleaved by an enzyme present at elevated levels in the vicinity of, or inside the target cells as compared to other parts of the body, and most preferably the enzyme is present only in the vicinity of or inside the target cells.

In one embodiment, the specifier is a targeting moiety able to target specific cells and deliver a compound to the targeted cells.

In one embodiment, the specifier is a substrate of a lysosomal enzyme. According to this embodiment, the specifier allows targeting the intracellular space of targeted cells/tissues . . . .

In one embodiment, the specifier is a di-, tri- or oligopeptide consisting of an amino acid sequence specifically recognized and cleaved by a protease. The specifier may be chosen to be preferably targeted by a non-mammalian protease or by an endogenous mammalian protease present in the vicinity of or inside the target cells and chosen from the list (but not restricted): beta-site APP-cleaving enzyme 1 (BACE1), Cathepsin D (CTSD), Calpain-1 (CAPN1), Caspase 1 (CASP1), Caspase 2 (CASP2), Caspase 3 (CASP3), Caspase 5 (CASP5), Caspase 6 (CASP6), Caspase 7 (CASP7), Caspase 8 (CASP8), Caspase 9 (CASP9), Cathepsin B (CTSB), Cathepsin K (CTSK), Cathepsin L (CTSL), Cathepsin S (CTSS), angiotensin I converting enzyme (ACE), angiotensin I converting enzyme 2 (ACE2), ADAM metallopeptidase domain 10 (ADAM10), dipeptidyl-peptidase 3 (DPP3), insulin-degrading enzyme (IDE), matrix metallopeptidase 1 (MMP1), matrix metallopeptidase 12 (MMP12), matrix metallopeptidase 13 (MMP13), matrix metallopeptidase 14 (membrane-inserted) (MMP14), matrix metallopeptidase 2 (MMP2), matrix metallopeptidase 3 (MMP3), matrix metallopeptidase 7 (MMP7), matrix metallopeptidase 8 (MMP8), matrix metallopeptidase 9 (MMP9), membrane metallo-endopeptidase (NEPRILYSIN) (MME), ADAM metallopeptidase domain 17 (TACE) (ADAM17), dipeptidyl-peptidase 4 (DPP4), dipeptidyl-peptidase 8 (DPP8), dipeptidyl-peptidase 9 (DPP9), blood-coagulation factor Xa (FACTOR Xa), blood-coagulation factor VIIa (FACTOR VII), fibroblast activation protein, alpha (FAP), furin (paired basic amino acid cleaving enzyme) (FURIN), granzyme A (granzyme 1, cytotoxic T-lymphocyte-associated (GZMA), serine esterase 3), granzyme B (granzyme 2, cytotoxic T-lymphocyte-associated (GZMB), serine esterase 1), granzyme K (granzyme 3; tryptase II) (GZMK), Kallikrein-1 (KLK1), Kallikrein-2 (KLK2), Plasma Kallikrein (PSA, KLK3), Kallikrein-11 (KLK11), Kallikrein-13 (KLK13), Kallikrein-13 (KLK15), Matriptase (ST14), Spinesin (TMPRSS5), Plasmin (PLG), Prolyl Oligopeptidase (PREP), Thrombin (F2), tPA, plasminogen activator, tissue type (PLAT), UPA, plasminogen activator, urokinase (PLAU), HtrA serine peptidase 2 (HTRA2), caseinolytic mitochondrial matrix peptidase proteolytic subunit (ClpP/X), Constitutive Proteasome Chymotrypsin like (PSMB5, beta 5), Constitutive Proteasome Trypsin-like (PSMB7, beta 7), Constitutive Proteasome Caspase like (PSMB6, beta 6), Immuno Proteasome Chymo-trypsin like (PSMB8, LMP7), Immuno Proteasome Trypsin-like (PSMB10, MECL1), Immuno Proteasome Caspase like (PSMB9, LMP2).

A specifier which is a substrate of Cathepsins allows specifically targeting the intracellular medium.

It should be noted that the specifier, either in the form of a di-, tri- or oligopeptide, or in any other form, may contain protective groups. Such compounds comprising protected specifier may not, when contacted with for instance specific enzymes, release the leaving groups. However, when deprotected and suitably activated such compounds will release leaving groups and thus such compounds comprising a protected specifier also fall under the scope of this invention.

In another embodiment the specifier peptide sequence may be chosen among those which can be cleaved upon acidic condition, by an extracellular enzyme or by an intracellular enzyme.

In a further embodiment, the specifier sequence is selected from D-alanylphenylalanyllysine, D-valylleucyllysine, D-alanylleucyllysine, D-valylphenylalanyllysine, D-valyl-tryptophanyllysine D-alanyltryptophanyllysine, valylalanine, valylcitrilline, Gly-Phe-Leu-Gly, Ala-Leu-Ala-Leu; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Phe-Lys; Lys-Phe; Val-Lys; Lys-Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; and Trp-Cit, or salts thereof.

In one embodiment, the specifier is a dipeptide selected from the group consisting of valine-citrulline and valine-alanine. Dipeptides can have lower hydrophobicity compared to longer peptides.

In another embodiment, the specifier is an amino-terminal capped peptide covalently linked via the C-terminus to the self-eliminating spacer or linker system. In particular, the specifier may be a peptide linked to the spacer or linker system via the carboxylic group of a terminal amino acid. The amino group of the other terminal amino acid may be capped with a protecting group. Examples of suitable amino protecting groups include Fmoc and BOC.

In one embodiment, the specifier can be cleaved by a specific enzyme of tumoral tissue or tumor micro-environment. The activating enzyme generates the release of the CDN and the BAM in the vicinity or inside the tumor cell. Several proteolytic enzymes have been shown to be associated with tumor invasion and metastasis. Several proteases, like cathepsins, proteases from the urokinase-type plasminogen activator (u-PA) system or the Serine protease plasmin are all involved in tumor metastasis. The proteolytically active form of plasmin is formed from its inactive Pro-enzyme form plasminogen by u-PA. The tumor-associated presence of plasmin can be exploited for targeting of plasmin-cleavable conjugates or prodrugs.

In a particular embodiment, the specifier is a substrate of cathepsins. Such specifiers would thus be selected from the group consisting of valine-citrulline and valine-alanine.

In another embodiment, the specifier can be a sugar such as galactose. In that case, as the S-galactosidase enzyme is mainly active intracellularly, it will promote the releases of CDN and BAM within the targeted cells.

In one further embodiment, the specifier can be a sugar such as Glucuronic acid. As β-glucuronidase is highly concentrated in the microenvironment of a wide range of solid tumors including lung, breast, and gastrointestinal tract carcinomas, molecules containing Glucuronide specifier can be prepared with the aim to deliver CDN and BAM units in the vicinity of the tumor. In particular the specifier may be a glucuronic acid corresponding to the following formula:

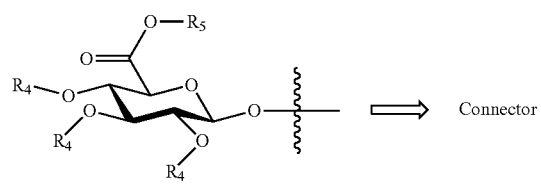

wherein each $R_4$ is independently H or a protecting group such as acetyl (—COCH$_3$), trifluoroacetyl (—COCF$_3$) trimethylacetyl (—CO-tBu), benzoyl (—COPh), a silyl ether (—Si(O-Alkyl)$_3$), benzyl (—CH$_2$Ph), para-methoxybenzyl (—CH$_2$-Ph-OMe), methoxymethyl (—CH$_2$—OMe), trityl (—CPh$_3$), tetrahydropyranyl or an alkyl; and $R_5$ is H or an alkyl such as methyl.

In another embodiment the specifier is a nitro group that can be reduced under hypoxic conditions or by nitroreductases.

In an aspect of the invention, the reactive moiety in specifier is reacted with a nucleophilic group on a targeting moiety, e.g., a thiol group, an amino group, or an aldehyde group, to form a new specifier that contains a targeting moiety.

In a preferred aspect of the invention, the reactive moiety of specifier is reacted with a nucleophilic group on a BAM, e.g., a thiol group, an amino group, or an aldehyde group, to form a new specifier that contains SAM as the targeting moiety.

The technology of this invention relates to novel linker systems that can be either coupled to the CON to form a Pro-CDN or that can be inserted between a CON and a BAM to release each moiety at their targeted site.

Biologically Active Molecules: BAM.

As mentioned above, one aspect of the present invention requires conjugating a BAM to a CON through a specifier and a self-eliminating group (connector) and optionally a spacer to target an appropriate site. Targeting is defined by the specifier and after the enzymatic cleavage reaction will remove the specifier moiety from the CON or/and BAM conjugate and selectively release the different agents in pharmacologically active form at the target site.

The BAM according to the present invention is e.g. selected from the group consisting of:
- a protein for example an antigen or an antibody molecule. Suitable antibodies include, for example, monoclonal antibodies, such as chimeric, humanized or human antibodies or an antigen-binding fragment thereof;
- a peptide for example extracellular matrix (ECM)-super-affinity peptide derived from placenta growth factor-2 (PIGF-2$_{123-144}$);
- a lipid to form for example a liposome;
- a fluorescent probe (FAM, HEX, TET, Cyanine dyes, JOE, ROX, TAMRA, Texas red . . . );
- a PRR ligand (TLR, NOD ligands . . . );
- a cytotoxic agent;
- a radio-sensitizing element;
- a small molecule inhibitor of protein for example a selective tyrosine kinase inhibitor or an Hsp90 inhibitor or IDO inhibitor or Carbonic Anhydrase IX/XII inhibitor;
- a small molecule antagonist targeting PD-1/PD-L1 or other immune checkpoint;
- an activatory small molecule;
- a heterocycle molecule like folic acid;
- a particle like a liposome, a polymer based vehicles, or hyaluronic acid based delivery vehicles In some embodiment, said Biologically Active Molecule is a protein. The "protein" may be an antibody, antibody fragments, immunoglobulin, peptides, enzymes, growth factors, cytokines, chemokines, transcription factors, toxins, antigen peptides, hormones, carrier proteins, channels, motor function proteins, receptors, signaling proteins, scaffolding proteins, storage proteins, membrane proteins, transmembrane proteins, internal proteins, external proteins, secretory proteins, viral proteins, glycoproteins, glycopeptides, cleaved proteins, protein complexes, chemically modified proteins.

In some embodiments, the Biologically Active Molecule unit is an antibody. Non-limiting examples of antibodies used for cancer application are Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); or immune checkpoint inhibitor antibody that targets an immune checkpoint receptor selected from the group consisting of CTLA-4, PD-1, PD-L1, PD-1-PD-L1, PD-1-PD-L2, interleukin 2 (IL 2), indoleamine 2,3-dioxygenase (IDO), IL 10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II— LAG3, 4 1BB-4 1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7 H3, 87 H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155.

In some aspects, BAM is an immune-stimulatory compound.

In some aspects, said Biologically Active Molecule compound is a damage-associated molecular pattern molecules (DAMPs) or a Pathogen-Associated Molecular Pattern molecules, (PAMPs) to provide multi-PRR ligands. Thus BAM-CDN conjugates can be recognized by receptors of the innate immune system, such as Toll-like receptors (TLRs), Nod-like receptors, C-type lectins, cytosolic dsDNA sensors, RIG-I-like receptors and proteins involved in those pathways. These receptors can be transmembrane or intra-endosomal proteins which can prime activation of the immune system in response to infectious agents such as pathogens. In some aspects, said immune-stimulatory compound is a toll-like receptor agonist, STING agonist, or RIG-I agonist. In some aspects, said Biologically Active Molecule compound is a TLR1 agonist, a TLR2 agonist, a TLR3 agonist, a TLR4 agonist, a TLR5 agonist, a TLR6 agonist, a TLR7 agonist, a TLR8 agonist, a TLR9 agonist or a TLR10 agonist.

In some aspects, said Biologically Active Molecule compound is a bioactive molecule including (but not restricted) inhibitor (for example growth factors inhibitor, IDO inhibitor, MAPK/ERK inhibitors, COX inhibitor, inflammatory inhibitor, TBK1 inhibitor, angiogenesis inhibitor, Carbonic Anhydrase IX/XII Inhibitor, enzymes inhibitor used in the treatment of auto-immune, fungal, bacterial, viral and parasite diseases or in cancer treatment), agonist or a partial agonist (for example Adora-2a receptor agonist).

In some aspects, said Biologically Active Molecule compound is a particle, for example (but not restricted) polymeric micelle nanoparticles, polymer coated iron oxide nanoparticles, carbon nanoparticles.

In some aspects, said Biologically Active Molecule compound is a lipid. For example, but not limited, lipids may be fatty acids, glycerolipids, glycerophospholipids, sphingolipids, saccharolipids, and polyketides sterol lipids and prenol lipids.

In some embodiments, the Biologically Active Molecule unit comprises a lipid to form liposomal structure with CDN or a nanoparticle to protect and to increase the uptake of CDN. A liposome being a lipid vesicle is capable of containing many substances irrespective of whether such substances are water-soluble or hydrophobic and thus is expected to be a prospective carrier especially for a drug delivery system.

In some aspects, said Biologically Active Molecule compound is a fluorescent probe belonging (but not restricted) to Xanthene derivatives (fluorescein, rhodamine, Oregon green, eosin, Texas red . . . ), Cyanine derivatives (cyanine, indocarbocyanine, oxacarbocyanine, thiacarbocyanine, merocyanine . . . ), Squaraine derivatives and ring-substituted squaraines, Naphthalene derivatives (dansyl, prodan derivatives), Coumarin derivatives (6,8-difluoro-7-hydroxycoumarin-3-carboxylic acid: pacific blue, . . . ), oxadiazole derivatives (pyridyloxazole, nitrobenzoxadiazole, benzoxadiazole . . . ), Anthracene derivatives (anthraquinones, including DRAQ5, DRAQ7, CyTRAK Orange), Pyrene derivatives (cascade blue, . . . ), Oxazine derivatives (Nile red, Nile blue, cresyl violet, oxazine 170, . . . ), Acridine derivatives (proflavin, acridine orange, acridine yellow, . . . ), Arylmethine derivatives (auramine, crystal violet, malachite green . . . ), Tetrapyrrole derivatives (porphin, phthalocyanine, bilirubin . . . ), Fluorescent protein derivatives (GFP, YFP, CFP, mCherry, . . . ), Quantum dot, DAPI, Hoescht derivatives or other fluorescent probes.

In some aspects, said Biologically Active Molecule compound is a cytotoxic agent for example but not restricted) Actinomycin, Doxifluridine, Methotrexate, All-trans retinoic acid, Doxorubicin, Mitoxantrone, Azacytidine, Epirubicin, Oxaliplatin, Azathioprine, Epothilone, Paclitaxel, Bleomycin, Etoposide, Pemetrexed, Bortezomib, Fluorouracil, Teniposide, Carboplatin, Gemcitabine, Tioguanine, Capecitabine, Hydroxyurea, Topotecan, Cisplatin, Idarubicin, Valrubicin, Chlorambucil, Imatinib, Vemurafenib, Cyclophosphamide, Irinotecan, Vinblastine, Cytarabine, Mechlorethamine, Vincristine, Daunorubicin, Mercaptopurine, Vindesine, Docetaxel, Vinorelbine.

In some embodiments, the Biologically Active Molecule compound is a radio-sensitizing molecule including (but not restricted to) nicotinamide, carbogen, metronidazole and metronidazole analogs, hypoxic cell cytotoxic agents (mitomycin-c), membrane active agents (chlorpromazine), radiosensitizing nucleosides (5-FU, Bromodeoxyuridine, Gemcitabine), texaphyrins.

In some aspects, said Biologically Active Molecule compound Is folic acid (FA). FA is one of the most widely used in anticancer nanomedicine. Folate receptor is generally overexpressed in most types of tumor cells (such as ovarian and breast cancer) and has limited expression in normal cells. Furthermore, FA has other advantages, such as non-immunogenicity, high stability and good tumor penetration. For these reasons, FA has been widely used as a tumor-targeting ligand in cancer imaging and therapy (ref 10.1016/j.xphs.2017.02.019) because of its commercial availability, small size and its easy conjugation.

In some embodiments, the BAM-CDN conjugates induce cell death.

In some aspects of the invention, and especially when BAM is a protein, 2 to m (m being an integer greater than 2) Pro-CDN units are conjugated to 1 BAM unit through connectors and/or spacer in order to increase the number of CDN bound per BAM. A number of recent publications have described the use of branched linkers in combination with antibody-containing prodrugs or bioconjugates with the aim of increasing the number of drugs bound per antibody.

In a particular embodiment, the BAM is selected from the group consisting of:
- a protein for example an antigen, a peptide or an antibody molecule;
- a lipid;
- a fluorescent probe; and
- an activatory or inhibitory small molecule.

Connector

The use of a spontaneous self-eliminating connector can allow for the elimination of the fully active, chemically unmodified compound.

The present invention relates the use of a connector, such as Para-Amino-Benzyl (PAB) or Para-amino-benzyl-carbonyl (PABC) which is a self-eliminating group through 1,6-elimination principle (Carl et al., J. Med. Chem., 1981, vol. 24, 479-480.) and is able to release spontaneously the BAM moiety or CDN as described in Scheme 1.4, as represented in FIG. 22.

The principle of 1,6-elimination, developed by Carl et al. in 1981, can be considered one of the most versatile self-elimination principles that can be used in prodrug design. According to this principle, PAB or PABC elimination proceeds via the mechanism depicted in Scheme 1.5, as represented in FIG. 23.

This particular elimination process has proven to be very successful (WO 98/13059) when applied in the prodrug concept. Self-eliminating system of PAB or PABC through an electronic cascade sequence is as indicated in Scheme 1.5.

The present invention relates to the use of a connector, such as Para-Amino-Benzyl (PAB), which is able to make a phosphorothioate triester link with a CDN or such as Para-amino-benzyl-carbonyl (PABC) which is able to make a carbamate link with the BAM.

In another embodiment, the connector is a compound of Formulae (III$_a$) to (III$_g$):

Formula (III$_a$) is a Para-Amino-Benzyl (PAB) group:

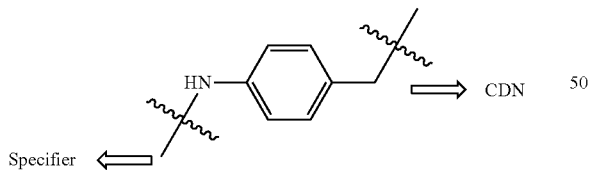

Formula (III$_a$)

Formula (III$_b$) is a Para-Hydroxy-Benzyl (PHB) group:

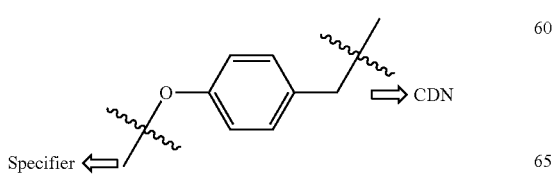

Formula (III$_b$)

Formula (III$_c$) is a Para-Hydroxy-Meta-Trifluoromethyl-Benzyl (PHMTB) group:

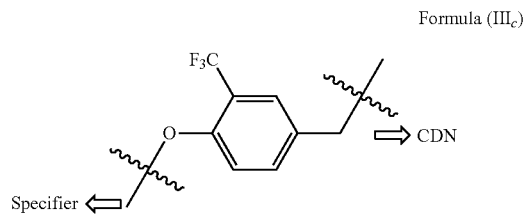

Formula (III$_c$)

Formula (III$_d$) is a Para-Hydroxy-Meta-Nitro-Benzyl (PHMNB) group:

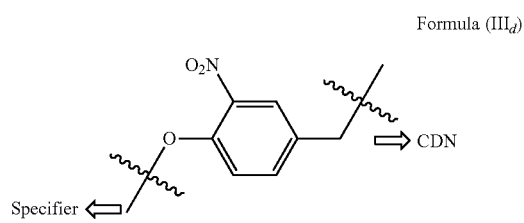

Formula (III$_d$)

Formula (III$_e$) is a Para-Hydroxy-Meta-Amino-Benzyl (PHMAB) group:

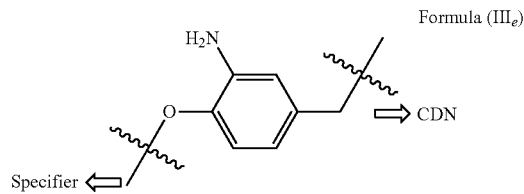

Formula (III$_e$)

A group of Formula (III$_f$):

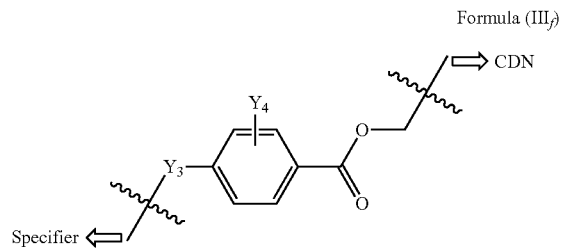

Formula (III$_f$)

wherein $Y_3$ is —O— or —NH—, and $Y_4$ is —NO$_2$, —NH$_2$ or —CF$_3$;

A group of Formula (III$_g$):

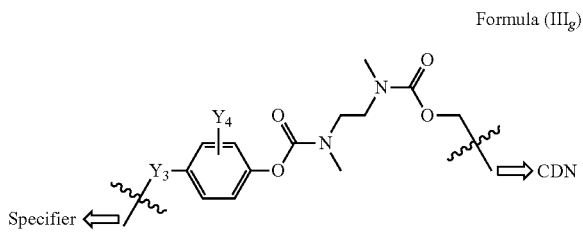

wherein Y$_3$ and Y$_4$ are as defined above;

In some aspects of the invention, the connectors of formulae (III$_e$) and (III$_f$) are a di or tri-functional chemical moiety that is capable of covalently linking to the BAM or to the CDN to promote the release the native form of the BAM or the CDN.

In some aspects, the leaving group PAB or PABC must react with functionality at the end of the specifier. Typically, the end of the specifier is a carboxylic group, but it can also be another functionality according the specifier chosen.

In particular, when the connector is linked to a CDN, the connector may be represented by one of formula (III$_a$)-(III$_g$), preferably the connector may be selected from PAB, PHMNB and PHMAB. When the connector is linked to a CDN and a specifier that is a dipeptide, the connector is preferably selected from PAB. When the connector is linked to a CDN and a specifier that is a sugar, the connector is preferably selected from PHMNB and PHMAB. In some aspects of the invention, a connector described above (either the same than the one linked to the CDN or different) can be coupled to the BAM in order to promote the release of the native form of the BAM.

In particular, when the connector is linked to a BAM, the connector may be represented by one of formula (III$_a$)-(III$_g$) or the connector may be para-aminobenzyl carbonyl represented by the following formula (III$_h$):

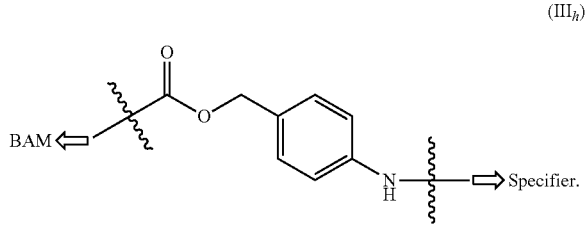 [SMILES: *Nc1ccc(COC(*)=O)cc1]

Spacer

A hydrophilic spacer can be incorporated in the Pro-CDN or between the Pro-CDN and the BAM in order to Improve hydrophilic property of the Pro-CDN or the BAM-CDN conjugate (and thus its water solubility) and spatially separate BAM from CDN. Thus, its presence may facilitate enzymatic cleavage and so enhance the kinetics of drug release.

The spacer can e.g. be linked directly to the specifier or to the connector. Alternatively the spacer can be connected to the specifier or the connector via an additional linking group, such as a carbonyl, an amide, an ester, a urea, a disulfide bridge, a carbamate, a hydrazone, an imine, an oxime, a triazole group, a maleimide, a carbon-carbon double or triple bond or an alkylene.

In one embodiment of the invention, the spacer is a polyamine including: polyethylenimine, polylysine (PLL), spermine, spermidine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In another embodiment of the Invention, the spacer is a polyethylene glycol (PEG).

In another embodiment, the spacer is a compound of Formula (IV$_a$):

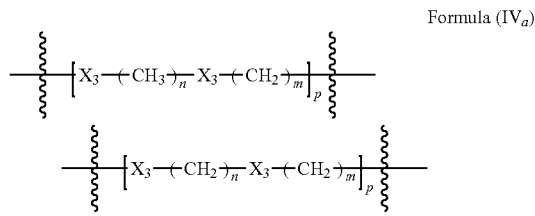

wherein: X$_3$ is —O— or —NH—, m, n and p are an integer ranging from 0 to 12 (i.e. 0, 1, 2, 3, 4, 5, 6, 7, 8, 9, 10, 11 or 12).

In another embodiment, the spacer is a compound of Formula (IV$_b$):

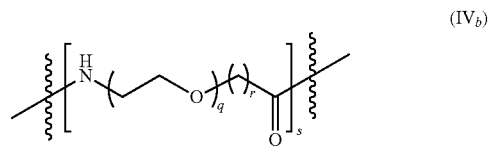

wherein q is an integer ranging from 1 to 6 (i.e. 1, 2, 3, 4, 5, 6), more preferably 2 to 4;

r is an integer ranging from 1 to 6 (i.e. 1, 2, 3, 4, 5, 6), more preferably 1 to 2;

s is an Integer ranging from 1 to 6 (i.e. 1, 2, 3, 4, 5, 6), more preferably 1 to 4.

In particular, the spacer may be a compound of Formula (IV$_b$), wherein
q is 2;
r is 1; and
s is 4.

Alternatively, the spacer may be a compound of Formula (IV$_b$), wherein
q is 4;
r is 2; and
s is 1.

The spacer of formula (IV$_b$) may in particular be used to establish a link between a BAM comprising a group than can react with an amine (i.e. a carboxylic acid, an activated acid, an acyl chloride, an anhydride, an isothiocyanate, a ketone, an aldehyde) and the connector or the specifier as shown in the figure below:

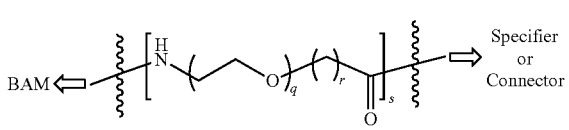

In another embodiment, the spacer is a compound of Formula (IV$_c$)

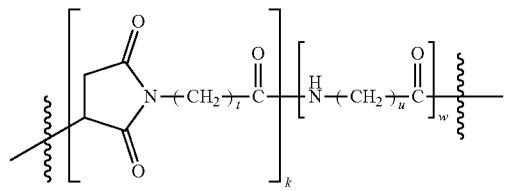
(IV$_c$)

wherein each t and u are independently an integer ranging from 1 to 10 (i.e. 1, 2, 3, 4, 5, 6, 7, 8, 9, 10), preferably 3 to 7, more preferably 5;

k is 0 or 1, preferably 1;

w is an Integer ranging from 0 to 6 (i.e. 0, 1, 2, 3, 4, 5, 6), preferably 0 or 1.

The spacer of formula (IV) may in particular be used as a link between a BAM that is an antibody and the connector or the specifier according to the figure below. Indeed, the disulfide bonds of two cysteines of the antibody can be reduced to a free cysteine having a thiol group which can react with a maleimide on the spacer.

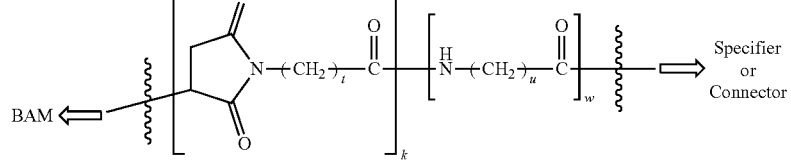

In another embodiment, the spacer is a compound of Formula (IV$_d$)

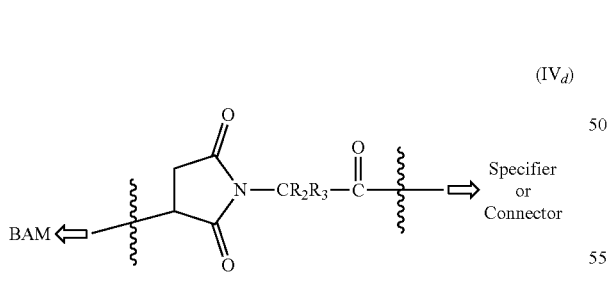
(IV$_d$)

wherein R$_2$ and R$_3$ are Independently selected from H and an alkyl optionally substituted with an amino group, preferably from H and —CH$_2$—NH$_2$.

CDNs

The CDN unit of the present invention is a compound of Formula (II$_a$), including its pharmaceutically acceptable salts, esters, stereoisomers, tautomers, solvates or prodrugs, and more specifically is a CDN with at least one phosphorothioate linkage:

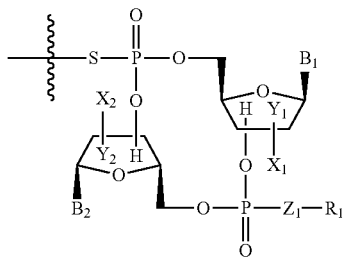
Formula (II$_a$)

wherein:

X$_1$ and Y$_1$ are independently H or F;

X$_2$ and Y$_2$ are independently H or F;

Z$_1$ is O or S;

R$_1$ is H when Z$_1$ is O;

R$_1$ is H or a linker system when Z$_1$ is S;

B$_1$ and B$_2$ are purine bases chosen from:

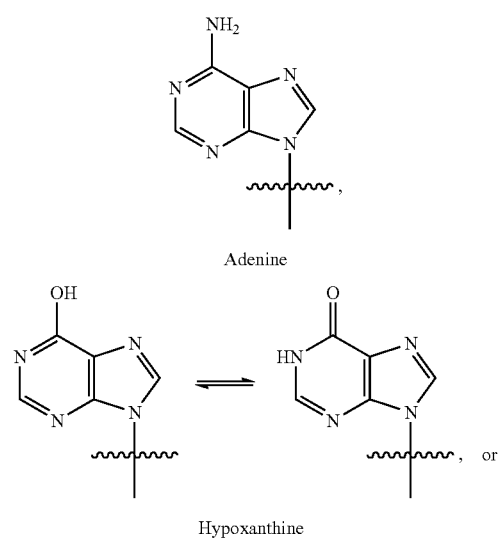

Adenine

Hypoxanthine

-continued

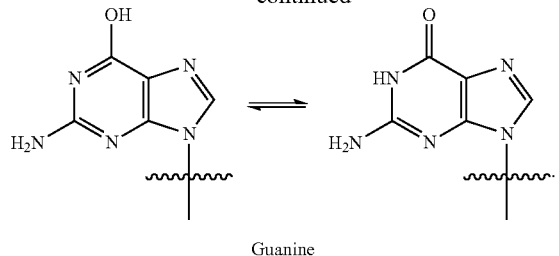

Guanine or pharmaceutically acceptable salts, stereoisomers, tautomers or solvates thereof.

In one embodiment, $X_2$ and $Y_2$ are H.
In one embodiment, $X_2$ is H and $Y_2$ is F.
In one embodiment, $X_2$ is F and $Y_2$ is H.
In one embodiment, $X_2$ and $Y_2$ are F.
In one embodiment, $X_1$ and $Y_1$ are H.
In one embodiment, $X_1$ is H and $Y_1$ is F.
In one embodiment, $X_1$ is F and $Y_1$ is H.
In one embodiment, $X_1$ and $Y_1$ are F.
In a particularly preferred embodiment, $Y_1$ and $Y_2$ are both H, one of $X_1$ and $X_2$ is F and the other is H.
In a particularly preferred embodiment, $Y_1$ and $Y_2$ are both H and $X_1$ and $X_2$ are both F.
In one embodiment, $B_1$ and $B_2$ are independently chosen from Guanine or Adenine.
In one embodiment, $B_1$ and $B_2$ are independently chosen from Adenine or Hypoxanthine.
In one embodiment, $B_1$ and $B_2$ are independently chosen from Guanine or Hypoxanthine.
In a particularly preferred embodiment, one of $B_1$ and $B_2$ is Adenine and the other is Hypoxanthine.

The CDN unit comprises at least one phosphorothioate linkage and the second linkage may be a phosphodiester linkage or a phosphorothiate linkage. When the second linkage is a phosphodiester linkage, i.e. when $Z_1$ is O, $R_1$ is H. When the second linkage is a phosphodiester linkage, i.e. when $Z_1$ is S, $R_1$ is H or a linker system. Said linker system may be the same as the linker system described above, i.e. a $R_1$ may be linked to a connector which is linked to a specifier.

It is to be understood that the CDN unit of formula ($II_a$) encompasses pharmaceutically acceptable salts thereof. Suitable salts include for instance those derived from alkali metals such as potassium and sodium or from alkaline earth metals such as calcium and magnesium or from organic bases such as triethylamine. The salts may in particular be introduced on the second phosphorothioate linkage or the second phosphodiester linkage. As such, R1 may be a positively charged counter-Ion.

As used herein the term "the CDN of compounds of Formula ($II_a$)" refers to the CDN unit of the Pro-CDN compound of formula (I) that is connected to the linker system. The CDN of compounds of Formula ($II_a$) is connected to the linker system after reaction with the linker system via a —SH group.

In some embodiments, the CDN of compounds of Formula ($II_a$) is a monophosphorothioate molecule and can be selected from (3',3') CDNs of Formula ($II_b$), including its pharmaceutically acceptable salts, esters, stereoisomers, tautomers, solvates or prodrugs:

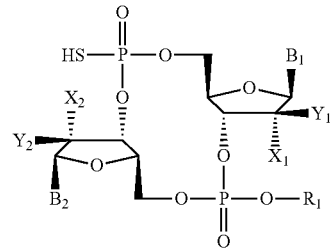

Formula ($II_b$)

wherein $X_1$, $Y_1$, $X_2$, $Y_2$, $B_1$, $B_2$, and $R_1$ are as defined above.

In some embodiments, the CDN of compounds of Formula ($II_a$) is a monophosphorothioate molecule and can be selected from (2',3') CDNs of Formula ($II_c$) and CDNs of Formula ($II_d$), including their pharmaceutically acceptable salts, esters, stereoisomers, tautomers, solvates or prodrugs:

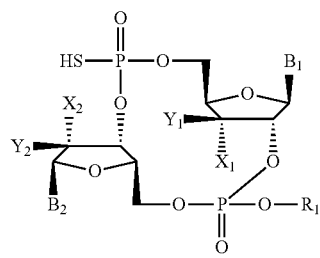

Formula ($II_c$)

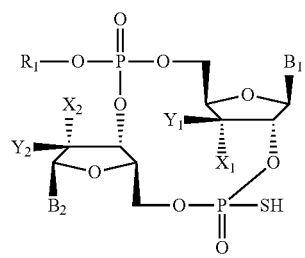

Formula ($II_d$)

wherein $X_1$, $Y_1$, $X_2$, $Y_2$, $B_1$, $B_2$ and $R_1$ are as defined above.

In some embodiments, the CDN of compounds of Formula ($II_a$) is a monophosphorothioate molecule and can be selected from (3',2') CDNs of Formula ($II_e$) and CDNs of Formula ($II_f$), including their pharmaceutically acceptable salts, esters, stereoisomers, tautomers, solvates or prodrugs:

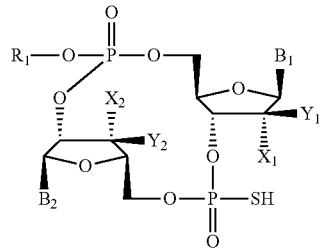

Formula ($II_e$)

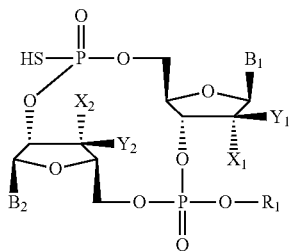
Formula (II$_f$)

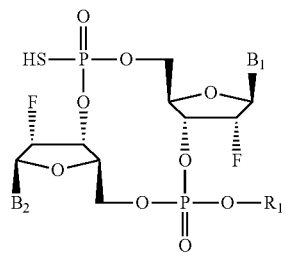
Formula (II$_g$)

wherein $X_1$, $Y_1$, $X_2$, $Y_2$, $B_1$, $B_2$ and $R_1$ are as defined above.

In the present invention, the presence of Fluoride (F) or hydrogen (H) atoms at the 2' or 3' position of the sugar is indispensable for the esterification of the phosphorothioate. When a hydroxyl group (OH) is present on 2' or 3', the esterification reaction provides a large scale of acyclic dinucleotide.

In one embodiment, the preferred sugar residues of the nucleoside are pentofuranosyl sugars selected from the group consisting of D-enantiomers of ribose or xylose and their modified derivatives on position 2' Formula (VIII$_a$) or 3' Formula (VIII$_b$):

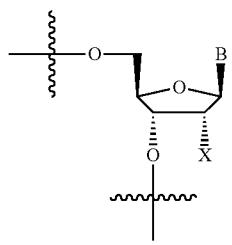
Formula (VIII$_a$)

β-D-ribofuranosyl nucleoside

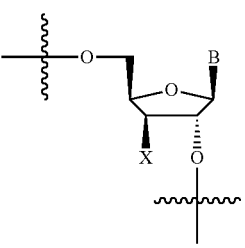
Formula (VIII$_b$)

β-D-xylofuranosyl nucleoside wherein is F or H.

In some embodiments, the CDN of compounds of Formula (II$_a$) is a monophosphorothioate molecule and can be selected from (3',3') CDNs of Formulae (II$_g$), including their pharmaceutically acceptable salts, esters, stereoisomers, tautomers, solvates or prodrugs, with $X_1$ and $X_2$ are fluoride atom, $Y_1$ and $Y_2$ are hydrogen atom:

wherein $B_1$, $B_2$, and $R_1$ are as defined above.

In some embodiments, the CDN of compounds of Formula (II$_a$) is a monophosphorothioate molecule and can be selected from (2',3') CDNs of Formula (II$_h$) and CDNs of Formula (II$_i$) including their pharmaceutically acceptable salts, esters, stereoisomers, tautomers, solvates or prodrugs, with $Y_1$ and $X_2$ are fluoride atom, $X_1$ and $Y_2$ are hydrogen atom:

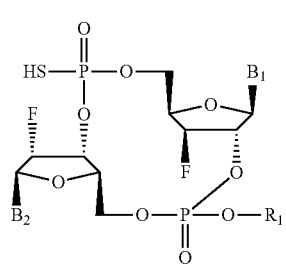
Formula (II$_h$)

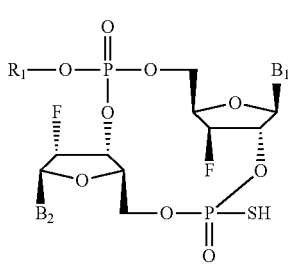
Formula (II$_i$)

wherein $B_1$, $B_2$ and $R_1$ are as defined above.

In some embodiments, the CDN of compounds of Formula (II$_a$) is a monophosphorothioate molecule and can be selected from (3',2') CDNs of Formula (II$_j$) and CDNs of Formula (II$_k$), including their pharmaceutically acceptable salts, esters, stereoisomers, tautomers, solvates or prodrugs, with $Y_2$ and $X_1$ are fluoride atom, $X_2$ and $Y_1$ are hydrogen atom:

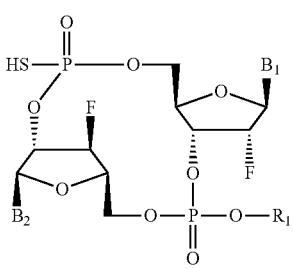
Formula (II$_j$)

Formula (II$_k$)

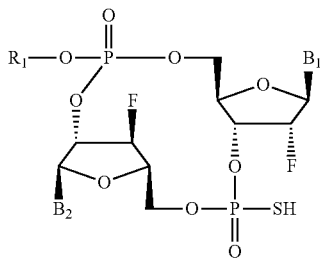

wherein B$_1$, B$_2$ and R$_1$ are as defined above.

In one embodiment, the CDN of compounds of Formula (II$_a$) is selected from one of the following formulas:

CL797

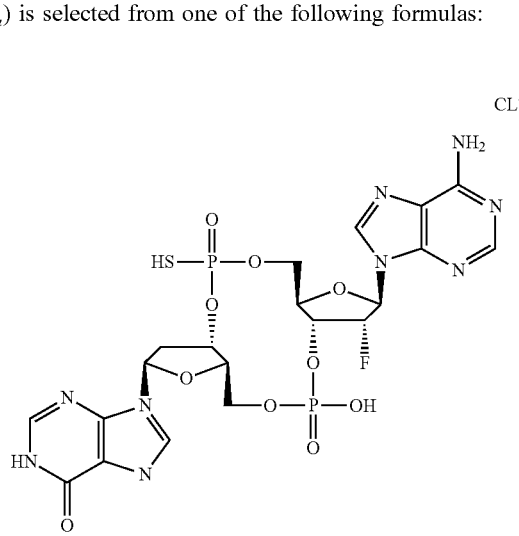

CL702

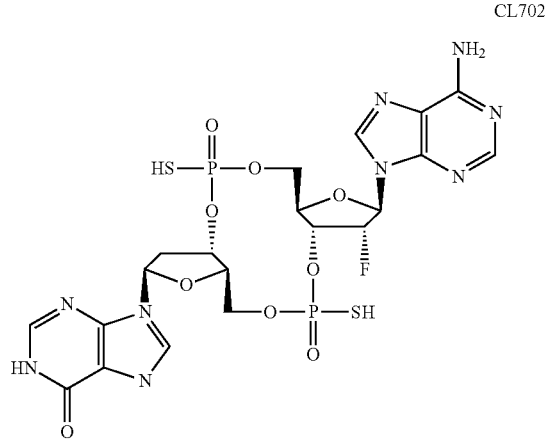

CL 656

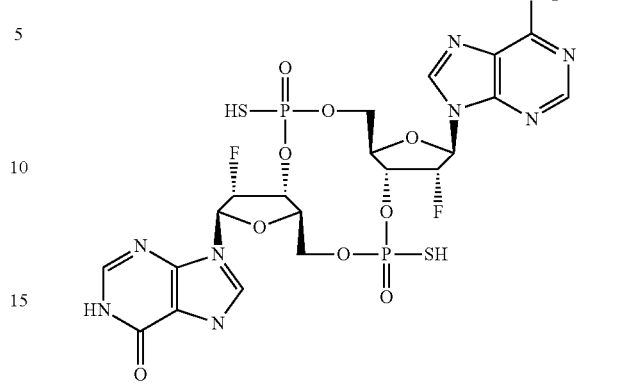

CL845

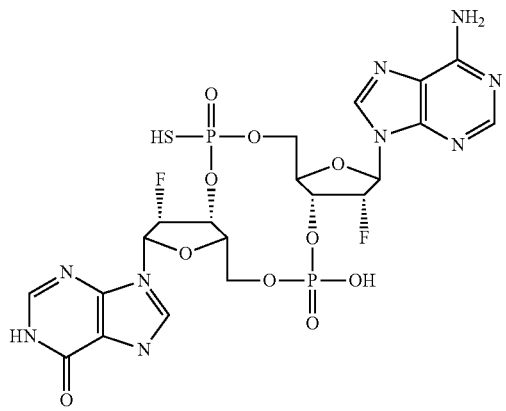

Compounds bearing a phospho or phosphorothioate diester group have a negatively charged ionic nature at physiological pH. The therapeutic activity of such compounds is consequently limited, on account of the low diffusion of negatively charged compounds across biological lipid membranes. In particular, charged compounds do not diffuse efficiently across cell membranes, or Indeed across the cerebral barrier. The coupling to a cleavable Linker system via the phosphorothioate diester link of compound of Formulae (II$_a$) to (II$_k$) is one solution to drug delivery and/or bioavailability issues.

In the present invention, the phosphorothioate modification acts as a prodrug by masking the polar functional group according to previously published data (Gong-Xin et al: «Chapter 3.6. Prodrugs of Phosphonates, Phosphinates and Phosphates», Prodrugs Challenges and Reward Part 1. Springer New York, US, vol. 5.1, 2007, p. 923-964). The mission of such prodrug was to mask the sulfur atoms of phosphorothioate groups in CDN analogues so that they are neutral at physiological pH and hence have a better uptake into cells.

In the present invention, the phosphorothioate moiety is a mandatory element to couple the CDN to the connector.

Additional Linking Groups

The linker system of the invention may further comprise additional linking groups between the different elements, i.e. the connector, the specifier and the spacer, or end-capping one of the elements. For example the linker system may comprise an additional linking group between the connector and the specifier and/or between the specifier and the spacer and/or between the connector and the spacer and/or one end of the spacer, the connector or the specifier. The term "additional linking group" is intended to mean a functional group used to establish a link between two elements, such as a carbonyl, an amide, an ester, a urea, a disulfide bridge, a carbamate, a hydrazone, an imine, an oxime, a triazole group, a maleimide, a carbon-carbon double or triple bond, an alkylene. Examples of suitable additional linking groups are described below; see for example $W_1$, $W_2$ and $W_3$. $W_1$ results from the reaction between $X_5$ and $X_6$; $W_2$ results from the reaction between $X_7$ and $X_8$; $W_3$ results from the reaction between $X_3$ and $X_8$.

Synthesis

The Pro-CDN can be synthetized as described in scheme 2.1, as represented in FIG. 24, wherein:
$P_1$ is a protecting group:
$P_1$ can be a BOC, Fmoc, Z, TFA for an amine,
$P_1$ can be a TBDMS a trityl group for an alcohol,
$P_1$ is a trityl group for a Thio-alcohol,
$P_1$ is an alkyl or an aryl group for an acid function;
The Specifier is as defined above;
$X_3$ can be OH or $NH_2$;
$X_4$ is a halogen atom: I, Br, Cl, F;
$X_5$ can be:
An acid or activated acid —$COOR_3$ with $R_3$ is H, N-hydroxysuccinimide ....
An amine: —$NH_2$,
An alcohol or thio-alcohol: —OH, —SH.
$X_6$ can be —OH, —$NH_2$, or a group of Formula (XIV):

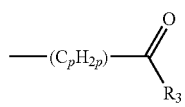

Formula (XIV)

with p is as defined above and $R_3$ is:
—H,
—OH;
an activated acid function:

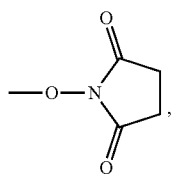 , 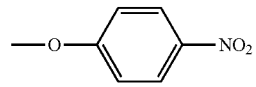

an halogen —Cl, —Br, —I, —F $W_1$ is link between of the specifier and the connector the nature of $W_1$ depends of $X_5$ and $X_6$ function. $W_1$ can be an amide, an ester, an ether, a thio-ether or a disulfide bridge;

$X_1$, $Y_1$, $X_2$, $Y_2$, $Z_1$, $R_1$, $B_1$ and $B_2$ are as defined above.

The synthesis of the conjugate of Formula ($I_d$) requires first preparation of the Specifier-Connector of Formula (XII). This intermediate can be prepared in 2 steps.

The Specifier-Connector of Formula (XII) can be connected to the STING agonist of Formula ($II_a$) by a direct esterification of a phosphorothloate diester link between two nucleosides of the CDN. The reaction can be realized in a mix of water and acetone to reach the compound of Formula (XIII) which can be deprotected to give the Pro-CDN of Formula ($I_b$).

Scheme 2.2, as represented in FIG. 25, wherein:
$P_1$, BAM, Specifier, $X_3$, $X_4$, $X_5$, $X_6$, $X_1$, $Y_2$, $X_2$, $Y_2$, $Z_1$, $R_1$, $B_1$ and $B_2$ are as defined above;
$X_7$ and $X_8$ can be independently:
An acid or activated acid —$COOR_3$ with $R_3$ is H, N-hydroxysuccinimide ...
An amine: —$NH_2$,
An alcohol or thio-alcohol: —OH, —SH.
An azide function: —$N_3$;
a maleimide group of Formula (XX):

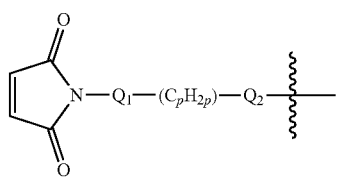

Formula (XX)

With:
p is an integer ranging from 0 to 12,
$Q_1$ is —$CH_2$— or —CO—,
$Q_2$ is —$CH_2$—, —NH— or —CO—;
a 3-arylpropionitrile (APN) group of Formula (XXI):

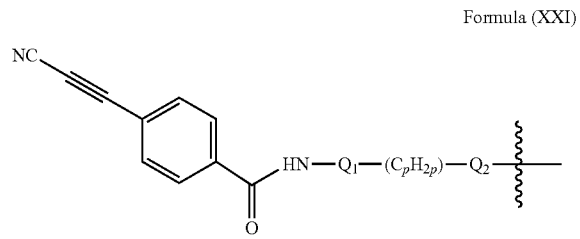

Formula (XXI)

With:
p is an integer ranging from 0 to 12,
$Q_1$ is —$CH_2$— or —CO—;
$Q_2$ is —$CH_2$—, —NH—, —O—, —S—, or —CO—;
a halogen: F, I, Br, Cl;
a group of Formula (XXII):

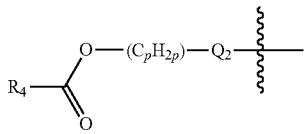

Formula (XXII)

With: $R_4$ is an halogen (Cl, Br, I, F), a 4-nitrophenoxy group;
an aldehyde group of Formula (XXIII):

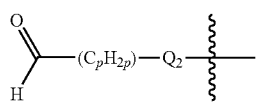

Formula (XXIII)

With p and $Q_2$ are as defined above;
a cyclo-octyl group of Formula (XXIV):

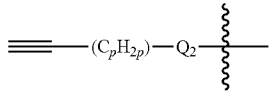

Formula (XXIV)

With p and $Q_2$ are as defined above;
a cyclo-octyl group of Formula (XXV):

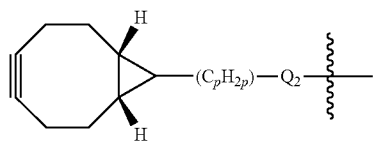

with p and $Q_2$ are as defined above; a dibenzocyclooctyne (DBCO) group of Formula (XXVI):

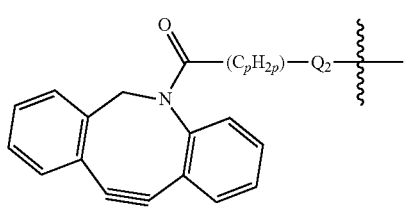

Formula (XXVI)

With p and $Q_2$ are as defined above;
$W_2$ is link between of the specifier and the connector the nature of $W_2$ depends of $X_7$ and $X_8$ functions and is described below.

$W_1$ can be an amide, an ester, a urea, a disulfide bridge, a carbamate, a hydrazone, an imine, an oxime, a triazole group;

The synthesis of the conjugate BAM-Pro-CDN requires the preparation of compound of Formula (XIX), then the coupling of this compound with the CDN of Formula ($II_a$) can provide the desired conjugate of Formula (V) by esterification of phosphorothioate link as defined above.

Scheme 2.3, as represented in FIG. 26, wherein $P_1$, BAM, Specifier, $X_3$, $X_4$, $X_5$, $X_6$, $X_1$, $Y_1$, $X_2$, $Y_2$, $Z_1$, $R_1$, $B_1$, $B_2$, $X_7$, $X_8$, $W_2$ and $W_3$ are as defined above.

$W_3$ is link between of the BAM and the connector the nature of $W_3$ depends of $X_8$ and $X_3$ function. $W_3$ can be an amide, an ester, a disulfide bridge.

The functions $X_7$ and $X_8$ must be reactive to form $W_2$ link, $W_2$ can be:

An amide

Forming amides is one of the most important reactions for conjugation between a Biologically Active Molecule of Formulae (VIIa) or (XXXII) and the compound of Formulae (XVI) or (XXX).

Typically, amines can react with carboxyl acid via some familiar activating reagents, such as N-hydroxysuccinimide (NHS), 2-Succinimido-1,1,3,3-tetra-methyluronium tetrafluoroborate (TSTU), and Benzotriazol-1-yloxytripyrrolidinophosphonium hexafluorophosphate (PyBOP).

In the case of peptides or proteins, like antibodies, amines of lysines are commonly used for linking the acid terminal of spacer of compound of Formula (I) because lysines are usually exposed on the surface of the antibodies and therefore are easily accessible. On the other hand, acid functions of glutamic acid (Glu) or Aspartic acid (Asp) can be used for linking the amine terminal of spacer of compound of Formula (I).

An Ester:

In same manner alcohol derivatives can react with carboxylic acid derivatives with known method.

An Urea or thiourea:

Urea or thiourea can be obtained from isocyanate or isothiocyanate derivative and an amine derivative.

A Disulfite bridge

Employing the thiols for example, interchain cysteine residues in monoclonal antibodies or thiol of the Biologically Active Molecule, as attachment sites for drug molecules is one of the most used conjugation methods.

In some case, disulfide bonds can be used as potential conjugation sites. The disulfide bonds can be reduced by tris(2-carboxyethyl) phosphine (TCEP) or dithiothreitol (DTT), which results in thiol groups that are available for conjugating with CDN-linker molecules.

A substituted Maleimide

Classically, cysteine residues can be modified through addition of thiols to electrophiles such as maleimides.

The conjugate could be achieved by reducing the disulfide bonds of the Biologically Active Molecule and then adding to maleimides. Addition to maleimides is the most common method for attaching drugs to antibodies. Adcetris®, which was approved by the FDA for the treatment of patients with Hodgkin's lymphoma after failed autologous stem cell transplantation or patients with systemic anaplastic large-cell lymphoma after the failure of at least one prior multi-agent chemotherapy regimen, was produced by this method in which a maleimide-functionalized drug was conjugated to the interchain cysteine residues of an anti-CD30 antibody. Maleimide-based antibody-drug conjugates were recently found to have limited stability in blood circulation, which would lower the efficacy of the conjugates and damage healthy tissue. Succinimide or maleimide hydrolysis is a promising method to get around this problem. Once hydrolyzed, the BAM-CDN conjugates were no longer subject to elimination reactions of maleimides through retro-Michael reactions, thus improving the stabilities and potencies of BAM-CDN conjugates.

An Addition Alkynes

To avoid the maleimide instability issue, Kolodych et al. developed a heterobifunctional reagent, sodium 4-((4-(cyanoethynyl)benzoyl)oxy)-2,3,5,6-tetrafluorobenzenesulfonate (CBTF), for amine-to-thiol coupling.

This reagent comprises a 3-arylpropionitrile (APN) group that replaces the maleimide and allows for the preparation of remarkably stable conjugates. Addition of thiols in the Biologically Active Molecule to the 3-arylpropionitriles predominantly produced Z-isomers of the addition products.

A carbamate

Amines of the Biologically Active Molecule could react with the hydroxyls that derived from the linkers in the effect of phosgene, 4-nitrophenyl chloroformate, etc. and form the carbamate containing CDN-linkers.

Similar with amines, alcohols can react with chloroformates to form carbonates. For example, Moon et al. conjugated 7-ethyl-10-hydroxycamptothecin (SN-38) derivatives to hMN-14, a humanized anti-CEACAMS mAb, via a carbonate bond.

An imine, a hydrazine, an oxime

Conjugation via aldehydes is another method for linking CDN-linker to a Biologically Active Molecule with an amine, a hydrazine or a hydroxylamine function.

A triazole:

Azides can react with alkynes to form triazoles through click chemistries, such as copper-catalyzed azide-alkyne cycloaddition (CuAAC).

This approach can be used when an azide or an alkyne function is present or can be introduced on the Linker or on the BAM moeity.

The azide function present on the BAM could react with a dibenzylcyclooctyne (DBCO) containing on CDN-linker without any catalytic agent.

This strategy could expand the extent of bioactive drugs that can be linked to monoclonal antibodies.

Definitions

Stimulator of interferon genes (STING) can act as a cytosolic DNA sensor wherein cytosolic DNA and unique bacterial nucleic acids called cyclic dinucleotides (CDN) are recognized by STING, and therefore STING agonists.

In the present invention, the term "cyclic dinucleotide" (abbreviated as "CDN") represents a class of cyclic molecules with one phosphodiester linkage and one phosphorothioate diester linkage, between two nucleosides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')).

The term "Pro-CDN" refers to a CDN coupled to a linker system. The Pro-CDNs of the present invention need to be metabolized at their targeted sites into CDNs to exert their full immunomodulatory effects.

The term "linker system" refers to a connector linked to a specifier.

The terms "linked", "coupled" or "connected" means attached by a covalent bond.

The term "connector" refers to a spontaneous self-eliminating group linking a molecule (CDN or BAM) to the specifier.

The term "specifier" refers to an enzymatically cleavable unit.

The term "SAM Biologically active molecule" refers to any moiety that can be coupled to a Pro-CDN via notably a spacer.

The term "spacer" refers to a hydrophilic group.

The term "nucleoside" refers to a glycosylamine comprising a nitrogenous base and a five-carbon sugar, wherein the nitrogenous base is bound to the five-carbon sugar via a beta-glycosidic linkage.

The term "nucleotide" refers to any nucleoside linked to a phosphate group at position 5', 3' or 2' of the sugar moiety.

"Pharmaceutically acceptable salts" include those salts derived from pharmaceutically acceptable inorganic or organic bases. Suitable salts include for instance those derived from alkali metals such as potassium and sodium or from alkaline earth metals such as calcium and magnesium or from organic bases such as triethylamine. Due to the negatively charged ionic nature of the phospho or phosphorothioate diester linkage, the counter-ion forming the salt is positively charged.

"Stereoisomers" include in particular enantiomers. Thus, the compounds of the invention may be enantiomerically pure or provided as a mixture of enantiomers.

Likewise, all tautomeric forms of the compounds of the invention are also intended to be included.

For example, the tautomers of the compounds of the invention include compounds deriving from tautomerisation of a hypoxanthine moiety or a guanine moiety as follows:

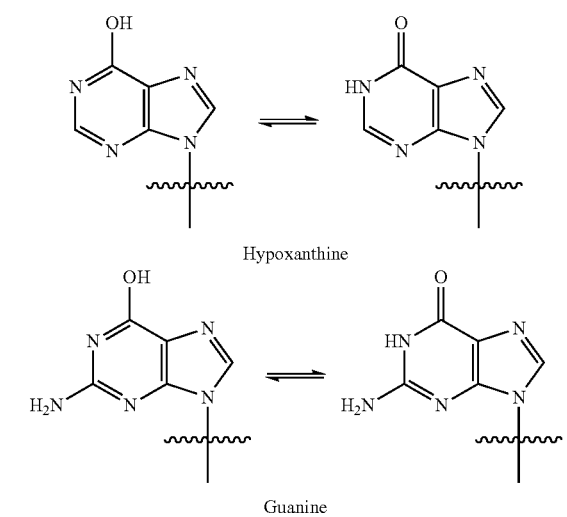

Hypoxanthine

Guanine

The term "solvate" denotes a compound formed by solvation, for example as a combination of solvent molecules with molecules or ions of a solute. Well known solvent molecules include water, alcohols and other polar organic solvents. Alcohols include methanol, ethanol, n-propanol, isopropanol, n-butanol, isobutanol, and t-butanol. Alcohols also include polymerized alcohols such as polyalkylene glycols (e.g., polyethylene glycol, polypropylene glycol). The best-known and preferred solvent is typically water, and solvate compounds formed by solvation with water are termed hydrates.

Pharmaceutical Compositions

Another object of the invention is a pharmaceutical composition comprising a Pro-CDN or a BAM-CDN conjugate of the invention and a pharmaceutically acceptable excipient. In one embodiment, the pharmaceutical composition is an immunogenic composition or vaccine adjuvant comprising a Pro-CDN or a BAM-CDN conjugate of the invention.

In one embodiment, the pharmaceutical composition is a composition comprising a Pro-CDN or a BAM-CDN conjugate of the invention and one or more immunostimulatory agents.

In one embodiment, the pharmaceutical composition is a vaccine or immunogenic composition comprising an antigen or antigen composition and a Pro-CDN or a BAM-CDN conjugate of the invention.

The pharmaceutical composition may comprise conventional excipients in conventional proportions, with or without additional active compounds or principles, and the unit dosage forms may contain any suitable effective amount of the active ingredient commensurate with the intended daily dosage range to be employed. The excipient(s) must be acceptable in the sense of being compatible with the other ingredients of the composition and not deleterious to the recipient thereof.

Generally, the compound of the invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or injectable (including subcutaneous, intramuscular, parenteral, intravenous or intradermal) route. Such compositions may be prepared by any method known in the art of pharmacy, for example by bringing into association the active ingredient with the carrier(s) or excipient(s).

Use of the Compounds of the Invention

Another object of the present invention is Pro-CDN or a BAM-CDN conjugate of the invention for use in a therapeutic treatment in humans or animals.

The Pro-CDN or a BAM-CDN conjugate of the invention may be used as therapeutic agents in a monotherapy or in a combination therapy, such as chemoimmunotherapy.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

One object of the invention is the Pro-CDN or a BAM-CDN conjugate of the invention for use in the treatment of a disease that may be alleviated by the induction of an immune response via the STING pathway.

One particular aspect of the invention is a Pro-CDN or a BAM-CDN conjugate of the invention for use as an immunomodulatory agent.

Indeed, the Pro-CDN or a BAM-CDN conjugate of the invention can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of, infection or disease in that human or animal, and/or to modulate the immune system of that human or animal to achieve some other therapeutic benefit.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both. "Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

In one embodiment, the Pro-CDN or a BAM-CDN conjugate of the invention are used for cytokine induction as immunotherapy of immunosuppressed individuals.

The present invention thus discloses a method for inducing cytokine in immunosuppressed individuals, said method comprising administering to a patient in need thereof a Pro-CDN or a BAM-CDN conjugate of the invention.

Another aspect of the invention is a Pro-CDN or a BAM-CDN conjugate of the invention for use as immunoadjuvant.

In particular, the Pro-CDN or a BAM-CDN conjugate of the invention can be used for cytokine induction immunotherapy as vaccine adjuvant therapy.

In this example, a Pro-CDN or a BAM-CDN conjugate of the invention would be administered to a human or animal subject that has received, is receiving or will receive a vaccination. The benefits provided by the present invention might include enhanced efficacy of the vaccination against the target antigen, reduced toxicity of the vaccination, reduced adverse side effects of the vaccination, or enhanced immune protection of the human or animal subject.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" or "immunoadjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

Another object of the present invention is a Pro-CDN or a BAM-CDN conjugate of the invention for use in the treatment of cancer or pre-cancerous syndromes, bacterial infection or infectious diseases, such as viral infection, in particular an AIDS Infection or an HIV infection.

As used herein, "cancer" refers to the physiological condition in subjects that is characterized by unregulated or dysregulated cell growth or death. The term "cancer" includes solid tumors and blood-born tumors, whether malignant or benign.

In one embodiment, the cancer is acinar adenocarcinoma, acinar carcinoma, acral-lentiginous melanoma, actinic keratosis, adenocarcinoma, adenocystic carcinoma, adenosquamous carcinoma, adnexal carcinoma, adrenal rest tumor, adrenocortical carcinoma, aldosterone secreting carcinoma, alveolar soft part sarcoma, amelanotic melanoma, ameloblastic thyroid carcinoma, angiosarcoma, apocrine carcinoma, Askin's tumor, astrocytoma, basal cell carcinoma, basaloid carcinoma, basosquamous cell carcinoma, biliary cancer, bone cancer, bone marrow cancer, botryoid sarcoma, brain cancer, breast cancer, bronchioalveolar carcinoma, bronchogenic adenocarcinoma, bronchogenic carcinoma, carcinoma ex pleomorphic adenoma, cervical cancer, chloroma, cholangiocellular carcinoma, chondrosarcoma, choriocarcinoma, choroid plexus carcinoma, clear cell adenocarcinoma, colon cancer, colorectal cancer, comedocarcinoma, cortisol-producing carcinoma, cylindrical cell carcinoma, dedifferentiated liposarcoma, ductal adenocarcinoma of the prostate, ductal carcinoma, ductal carcinoma in situ, duodenal cancer, eccrine carcinoma, embryonal carcinoma, endometrial carcinoma, endometrial stromal carcinoma, epithelioid sarcoma, esophageal cancer, Ewing's sarcoma, exophytic carcinoma, fibroblastic sarcoma, fibrocarcinoma, fibrolamellar carcinoma, fibrosarcoma, follicular thyroid carcinoma, gallbladder cancer, gastric adenocarcinoma, giant cell carcinoma, giant cell sarcoma, giant cell tumor of bone, glioma, glioblastoma multiforme, granulose cell carcinoma, head & neck cancer, hemangioma, hemangiosarcoma, hepatoblastoma, hepatocellular carcinoma, Hurthle cell carcinoma, ileal cancer, infiltrating lobular carcinoma, inflammatory carcinoma of the breast, intraductal carcinoma, intraepidermal carcinoma, jejuna cancer, Kaposi's sarcoma, Krukenberg's tumor, Kulchitsky cell carcinoma, Kupffer cell sarcoma, large cell carcinoma, larynx cancer, lentigo maligna melanoma, liposarcoma, liver cancer, lobular carcinoma, lobular carcinoma in situ, lung cancer, lymphoepithelioma, lymphoepithelioma, lymphosarcoma, malignant melanoma, medullary carcinoma, medullary thyroid carcinoma, medulloblastoma, meningeal carcinoma, Merkel cell carcinoma, micropapillary carcinoma, mixed cell sarcoma, mucinous carcinoma, mucoepidermoid carcinoma, mucosal melanoma, myxoid liposarcoma, myxosarcoma, nasopharyngeal carcinoma, nephroblastoma, neuroblastoma, nodular melanoma, nonclear cell renal cancer, non-small cell lung cancer, oat cell carcinoma, ocular melanoma, oral cancer, osteoid carcinoma, osteosarcoma, ovarian cancer, Paget's carcinoma, pancreatic cancer, pancreatoblastoma, papillary adenocarcinoma, papillary carcinoma, papillary thyroid carcinoma, pelvic cancer, periampullary carcinoma, phyllodes tumor, pituitary cancer, pleomorphic liposarcoma, pleuropulmonary blastoma, primary intraosseous carcinoma, prostate cancer, rectal cancer, renal cell carcinoma, retinoblastoma, rhabdomyosarcoma, round cell liposarcoma, scar cancer, schistosomal bladder cancer, schneiderian carcinoma, sebaceous carcinoma, signet-ring cell carcinoma, skin cancer, small cell lung cancer, small cell osteosarcoma, soft tissue sarcoma, splindle cell carcinoma, spindle cell sarcoma, squamous cell carcinoma, stomach cancer, superficial spreading melanoma, synovial sarcoma, telangiectatic sarcoma, terminal duct carcinoma, testicular cancer, thyroid cancer, transitional cell carcinoma, tubular carcinoma, tumorigenic melanoma, undifferentiated carcinoma, urachal adenocarcinoma, urinary bladder cancer, uterine cancer, uterine corpus carcinoma, uveal melanoma, vaginal cancer, cerrucous carcinoma, villous carcinoma, well-differentiated liposarcoma, Wilm's tumor or yolk sac tumor.

In a particular embodiment, the cancer is chosen from the following group: melanoma, prostate cancer, hepatocarcinoma, colon cancer, bladder cancer, breast cancer, cholangiocellular cancer, leukemia, lung cancer, lymphoma, nasopharyngeal cancer, ovarian cancer, pancreatic cancer and urothelial cancer.

In a particular embodiment, the cancer is from the following group: melanoma, lymphoma colon and pancreatic cancer.

The present invention thus discloses a method for treating a cancer or pre-cancerous syndromes, a bacterial Infection or infectious diseases, such as viral infection, in particular an AIDS Infection or an HIV infection, said method comprising administering to a patient in need thereof a Pro-CDN or a BAM-CDN conjugate of the invention.

Another object of the invention is a therapeutic combination comprising a Pro-CDN or a BAM-CDN conjugate of the invention and a therapeutic agent.

Another object of the invention is a kit-of-parts comprising a Pro-CDN or a BAM-CDN conjugate of the invention and a chemotherapeutic agent, for use in the treatment of cancer.

By "kit-of-parts", it is meant a combined preparation wherein the active ingredients are combined together or physically separated for use in a combined therapy by simultaneous administration or sequential administration to the patient.

The Pro-CDN or a BAM-CON conjugate of the present invention can be used for cytokine induction immunotherapy in combination with chemotherapy.

In this example, a Pro-CDN or a BAM-CDN conjugate of the invention would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, Provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The present invention thus discloses a method for treating cancer, said method comprising administering to a patient in need thereof:
  a Pro-CDN or a BAM-CDN conjugate of the invention and
  a chemotherapeutic agent.

When both compounds are administered simultaneously, the kit-of-parts can contain both compounds in a single pharmaceutical composition, such as a tablet, or in separate pharmaceutical compositions. When the compounds are not administered simultaneously, the kit-of-parts will contain each compound in separate pharmaceutical compositions either in a single package or in separate pharmaceutical compositions in separate packages. The kit-of-parts can also be provided by instruction, such as dosage and administration instructions. Such dosage and administration instructions can be of the kind that are provided to a doctor, for example by a drug product label, or they can be of the kind that are provided by a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, For example, one agent may be administered once a day, and the other agent may be administered 2 or 3 times a day, or one agent may be administered once a week, and the other agent may be administered once a day and the like.

In this example, a Pro-CDN or a BAM-CDN conjugate of the invention would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

EXAMPLES

Figure 1:
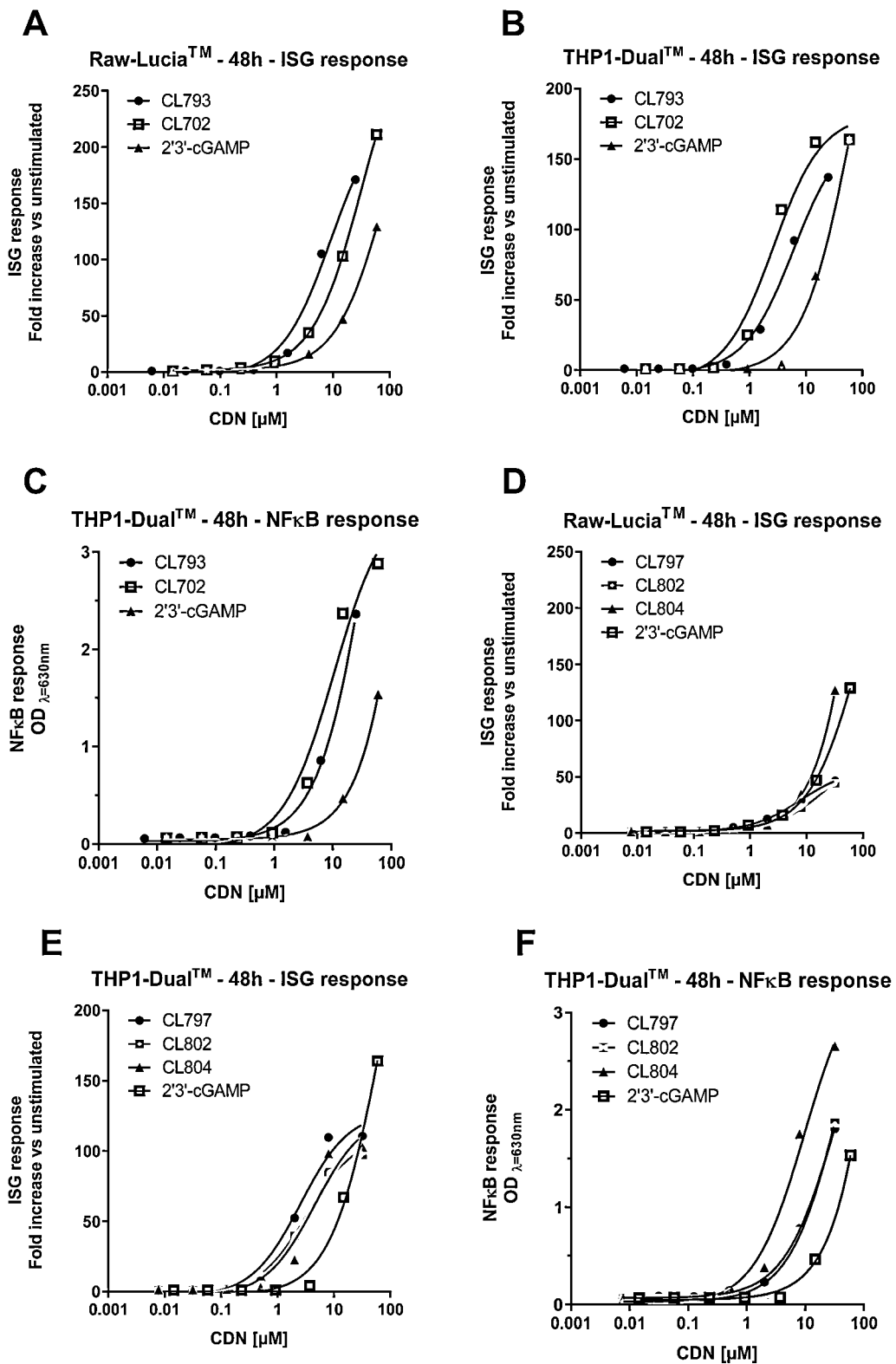
FIG. 1. Comparison of ISG54 (A-B, D-E) and NFκB (C and F) activity induced (time indicated above) by Pro-CDN (CDN-linker system: CL793 vs CL702, CL802 and CL804 vs CL797) of the present invention in a murine (A, D) or a human (B-C and E-F) reporter cell.

Specific compounds that are representative of this invention were prepared as per the following examples and are offered by way of illustration to aid in the understanding of the invention. They should not be construed to limit in any way the Invention set forth in the claims that follow thereafter. The present compounds can also be used as intermediates in subsequent examples to produce additional compounds of the present invention. No attempt has necessarily been made to optimize the yields obtained in any of the reactions. One skilled in the art would know how to Increase such yields through routine variations in reaction times, temperatures, solvents, reagents and chemical synthesis other parameters.

The present invention is further illustrated in Example 1, which shows preparative methods for synthesizing the conjugates, and in Example 2, which shows methods for the biological evaluation of these conjugates. It will be understood by one of ordinary skill in the art that these examples are in no way limiting and that variations of details can be made without departing from the spirit and scope of the present invention.

The terms used in describing the invention are commonly used and known to those skilled in the art. As used herein, the following abbreviations have the indicated meanings:

° C. for degrees Celsius; A for adenosine; Aca for 6-Aminocaproic acid; ACN for acetonitrile; AEEA for [2-(2-aminoethoxy)ethoxy]acetic acid; AEEEEP for 3-[2-[2-[2-(2-aminoethoxy)ethoxy]ethoxy]ethoxy]propanoic acid; Ala for Alanine; AP-1 for Activator protein 1; Arg for arginine; AU for Arbitrary Unit; $BF_3·Et_2O$ for Boron trifluoride ethyl etherate; Boc for tert-butoxycarbonyl; Bz for benzoyl; CE for cyanoethyl; $C_{18}$ for octadecyl carbon chain bonded silica; $C_{14}/C_{14}$—CO— for 3-(tetradecanoyloxy)tetradecanoate; $CHCl_3$ for chloroform; Cit for citrulline; CMV for cytomegalovirus; $CO_2$ for carbon dioxide; 2-CTC resin for 2-Chlorotrityl chloride resin; CTLA4 for cytotoxic T-lymphocyte-associated protein 4; Da for Dalton; dA for deoxyadenosine; Dap for 2,3-diaminopropionic acid; dAMP for deoxyadenosine monophosphate; DAR for Drug Antibody Ratio; ICI for immune checkpoint inhibitors; di for deoxyinosine; dIMP for deoxyinosine monophosphate; $D_2O$ for deuterium oxide; DCA for dichloroacetic acid; DCM (or $CH_2Cl_2$) for dichloromethane; DIEA for diisopropyl-ethylamine; DMAP for Dimethyl aminopyridine; DMF for dimethyl formamide, DMSO for dimethylsulfoxide; DMSO-$d_6$ for deuterated dimethylsulfoxide; DMTrCl for 4; 4'-dimethoxytrityl chloride; DTT for Dithiothreitol; $EC_{50}$ for Half maximal effective concentration; equiv. for equivalent; EDCl for N-Ethyl-N'-(3-dimethylaminopropyl)carbodiimide hydrochloride; ES for electrospray ionization; $Et_2O$ for diethyl ether; EtOAc for ethyl acetate; EtOH for ethanol; FITC for Fluorescein isothiocyanate; Fmoc for fluorenylmethyloxycarbonyl; βGAL for beta-galactosidase; g for grams; Gp75 for glycoprotein 75; $^1H$ for proton; h for hours; HATU for 1-[Bis(dimethylamino)methylene]-1H-1,2,3-triazolo[4,5-b]pyridinium-3-oxid-hexafluoro-phosphate; HBV for hepatitis B virus; HCV for hepatitis C virus; HEK for Human embryonic kidney cells; Hz for Hertz; HER2 for human epidermal growth factor receptor 2; HPLC for high-performance liquid chromatography; I for inosine; HIV for human immunodeficiency virus; HTLV for Human T cell Leukemia/lymphoma Virus; IFNAR1 for interferon alpha receptor 1; IFNAR2 for interferon alpha receptor 2; IFN for interferon; IFN-α for Interferon alpha; IFN-β for interferon beta; IL for Interleukin; IRF3 for interferon regulatory factor 3; ISG (or ISG54) for interferon-stimulated gene; ISAC for immunostimulatory antibody conjugate; ISRE for interferon-stimulated response element; JAK1 for Janus kinase 1; kD for kilo Dalton; Lev for levulinic; LC for liquid chromatography; Luc for luciferase; m for multiplet; M for molar; mAb for monoclonal antibody; Mal for maleimide; m/z for mass-to-charge ratio; MeOH for methanol; mg for milligrams; Me-Su- for 4-methoxy-4-oxobutanoic acid; $MgSO_4$ for magnesium sulfate; MHz for megahertz; min for minutes; mL (or ml) for milliliters; mmol for millimoles; mol/L for mole/liter; MS for mass spectrometry; MSNT for 1-(Mesitylene-2-sulfonyl)-3-nitro-1,2,4-triazole; MyD for Myeloid differentiation primary response; NaCl for sodium chloride; $NaHCO_3$ for sodium bicarbonate; $Na_2HPO_4$ for disodium hydrogen phosphate; $NaHSO_3$ for sodium thiosulfate; NaI for sodium iodide; NEM for N-ethyl maleimide; NF-κB for nuclear factor kappa-light-chain-enhancer of activated B cells; NMR for nuclear magnetic resonance; Ova for ovalbumin; $^{31}P$ for phosphorus; PAB for para-aminobenzyl; PADS for phenylacetyl disulfide; Pd for Palladium; PdI for polydispersity index determination; PD-1 for Programmed cell death 1; PDL1 for Programmed death-ligand 1; PEG for polyethylene glycol; Phe for phenylalanine; ppm for parts per million; Piv for pivaloyl; POM for pivaloyl-oxy-methyl; PS for phosphorothioate; rt or RT for room temperature; Rt for retention time; SEAP for secreted embryonic alkaline phosphatase; s for singlet; KO for knockout; SPPS for solid phase peptide synthesis; STAT1 for Signal transducer and activator of transcription 1; STING for stimulator of interferon genes; $SOCl_2$ for thionyl chloride; TEAB for triethyl ammonium carbonate; THF for tetrahydrofuran; TBDMSCl for tert-butyldimethylsilyl chloride; TFA for trifluoroacetic acid; TLR for toll like receptor; TNF for tumor necrosis factor; TyK2 for Tyrosine Kinase 2; UV for ultra-violet; Val for valine; µg for microgram; µL (or µl) for microliter; µm for micrometer; µmol for micromole; δ for chemical shift; ε for extinction coefficients, Amax for maximum absorbance wavelengths.

Anhydrous solvents and reagents suitable for nucleoside and nucleotide synthesis were purchased and were handled under dry argon or nitrogen using anhydrous technique. Amidite coupling reactions and cyclizations were performed in anhydrous acetonitrile or pyridine under dry argon or nitrogen. The starting materials for all reactions in dry pyridine were dried by concentration (three times) from pyridine. Preparative silica-gel flash chromatography was performed using Fluka 60 Å high-purity grade or Merck Grade 9385 silica using gradients of methanol in dichloromethane. Analytical LC/ES MS was performed on an Agilent 1290 Infinity UHPLC system coupled to a diode array detector (DAD) Agilent 1260 Infinity and an Agilent 6130 Quadrupole mass spectrometer equipped with an electrospray ionization source (ESI) and controlled by Chemstation software. The LC system was equipped with an Aquity CSH C18 50×2.1 mm 1.7 µm column using gradients of 10 mM ammonium formate and acetonitrile at 300 µl/min flow. The UV detection wavelength was 254 nm. The mass spectrometer was operated in positive and negative ESI modes Preparative HPLC was performed on a Waters preparative 150Q HPLC system monitoring at 254 nm on a SunFire Prep C18 5 µm OBD 30×150 mm column using gradients of 10 mM ammonium formate and acetonitrile at a flow rate 60 ml/min. The $^1$H NMR spectra were acquired on either a Bruker 300 MHz (Fourrier 300) at room temperature and reported in ppm downfield. Molecular sieves (MS) 3 Å were employed after drying the commercially supplied product at 250° C. for 12 h under vacuum. The commercial nucleoside phosphoramidites were supplied from Chemgenes.

The following examples serve to illustrate the present invention. These examples are in no way intended to limit the scope of the invention.

Example 1: Synthesis of the Compounds of the Invention

Example 1.1: Synthesis of CDNs of the Invention

Intermediate 1.1: 3'-O-(Allyl,CE)phosphotriester-$N^6$-(Bz)-2'-fluoro-2'-deoxy-Adenosine Commercially available 2'-fluoro-2'-deoxy-Adenosine phosphoramidite (30.0 g, 34.2 mmol) was co-evaporated with dry ACN three times, and the resulting solid was dissolved in a solution of Activator 42® (0.1 M in ACN) (685.0 ml, 22.8 mmol) in the presence of molecular sieves (3 Å). Allyl alcohol (4.66 mL, 68.5 mmol) was added, and the resulting mixture was stirred for 30 min. Then, 5.5 M tert-butyl hydroperoxide in decane (12.45 ml, 68.5 mmol) was added, and the mixture was stirred for 40 min. The solution was filtered, the molecular sieves were washed with DCM, and the filtrate was concentrated in vacuo. The residue was treated with 3% DCA in $CH_2Cl_2$ (750 ml), and water (10 equiv.), for 15 min. The reaction was quenched with MeOH and pyridine. The solvents were removed in vacuo, and the residue was purified by silica-gel column chromatography, using $CH_2Cl_2$/MeOH (5% to 20%) as eluent, to give 13.0 g (69% yield) of Intermediate 1.1 LC-MS: Rt=4.50 min, m/z=547 [M+H]$^+$, m/z=545 [M−H]$^-$.

Intermediate 1.2: [3'-O-(CE)phosphorothioate triester-2'-deoxy-Inosine]-(3',5')-[3'-O-(Allyl,CE) phosphotriester-$N^6$-(Bz)-2'-fluoro-2'-deoxy-Adenosine]

Intermediate 1.1 (13.0 g, 23.79 mmol) was dissolved in a solution of Activator 42® (0.1 M in ACN) (476 ml, 47.6 mmol) in the presence of molecular sieves (3 Å). Commercially available phosphoramidite of 2'-deoxy-Inosine (18.85 g, 38.91 mmol) was added to the solution in one portion. The mixture was stirred for 30 min at RT. Then, a solution of PADS (23.8 g, 47.6 mmol) in dry pyridine (23.8 ml) was added, and the mixture was stirred for 1 h. The resulting solution was filtered, the molecular sieves were washed with $CH_2Cl_2$, and the filtrate was concentrated in vacuo. The residue was treated with 3% DCA in $CH_2Cl_2$ (500 mL) and water (10 equiv.), for 15 min. The reaction was quenched with MeOH and pyridine. The solvents were removed in vacuo, and the residue was purified by silica-gel column chromatography, using $CH_2Cl_2$/MeOH (5% to 20%) as eluent, to provide 10.62 g (59% yield) of Intermediate 1.2. Rt=4.12 min, m/z=930 [M+H]$^+$, m/z=928 [M−H]$^-$.

Intermediate 1.3: [3'-O-(CE)phosphorothioate triester-2'-fluoro-2'-deoxy Inosine]-(3',5')-[3'—O-(CE) phosphodiester-$N^6$-(Bz)-2'-deoxyAdenosine]

To a solution of Intermediate 1.2 (10.6 g, 15.42 mmol) in dry THF (100 ml) N-methyl aniline (3.70 g, 34.26 mmol) and tetrakis(triphenylphosphine)palladium(0) (2.64 g, 2.28 mmol) were added. The resulting suspension was stirred at rt for 2 h. Then, the solvent was removed in vacuo, and the residue was triturated with diethyl ether. The resulting colorless precipitate was collected by filtration, and then washed with chilled diethyl ether. The crude product was purified by silica-gel column chromatography, using DCM/MeOH (0% to 10%) as eluent, to give 8.18 g (80% yield) of Intermediate 1.3. LC-MS: Rt=2.92 min, m/z=890 [M+H]$^+$, m/z=888 [M−H]$^-$ Intermediate 1.4: (3',3')Cyclic-[3'-O-(CE)phosphotriester-$N^6$-(Bz)2'-deoxy-Adenosine]-[3'-O-(CE)phosphorothioate triester-2'-fluoro-2'-deoxy-Inosine]

Intermediate 1.3 (10.74 g, 12.08 mmol) was co-evaporated with dry pyridine three times. The residue was suspended in dry pyridine (1320 ml), and 1-(mesitylene-2-sulfonyl)-3-nitro-1,2,4-triazole (MSNT) (17.88 g, 60.4 mmol) was added to the resulting solution. The resulting mixture was stirred at 25° C. for 1 h. Then, the solvent was removed in vacuo the residue was suspended in EtOAc and was washed with water and brine. The organic layer was dried over $MgSO_4$, filtered and concentrated in vacuo. The crude product was purified by silica-gel column chromatography, using DCM/MeOH (0% to 10%) as eluent, to give 4.20 g (40% yield) of Intermediate 1.4. LC-MS: Rt=3.59 and 3.80 min, m/z=872 [M+H]⁺, m/z=870 [M−H]⁻.

Intermediate 1.5

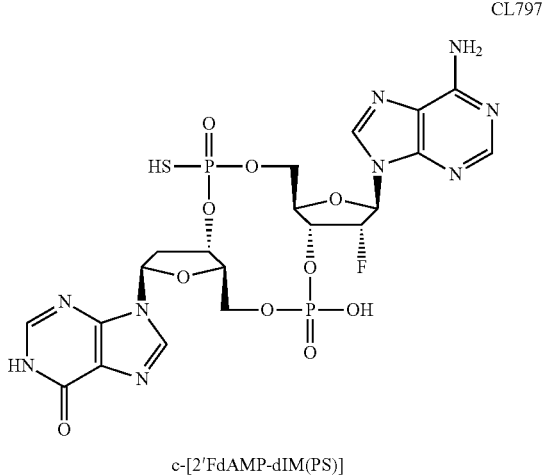 [SMILES: Nc1ncnc2c1ncn2[C@@H]1O[C@@H]2COP(=O)(S)O[C@H]3C[C@H](n4cnc5c(=O)[nH]cnc54)O[C@@H]3COP(=O)(O)O[C@H]2[C@H]1F]

c-[2'FdAMP-dIM(PS)]

Intermediate 1.4 (1.0 g, 1.15 mmol) was treated with a solution of methylamine in EtOH (33%), and the resulting mixture was stirred at rt for 4 h. The reaction mixture was concentrated. The crude was subjected to preparative HPLC using a $C_{13}$ Sunfire column (19×150 mm, 5 μm) and ammonium formate/ACN as eluent. The fractions containing the desired compound were pooled and lyophilized to provide 0.68 g; (89% yield) of Intermediate 1.5. LC-MS: Rt=0.590 and 0.501 min, m/z=662 [M+H]⁺, m/z=660 [M−H]⁻. ¹H NMR (D₂O, 300 MHz) δ (ppm) 7.79-8.44 (m, 5H), 6.23-6.34 (m, 2H), 5.55 (m, 1H), 5.36-4.90 (m, 3H), 4.51 (m, 2H), 4.32 (m, 2H), 4.08 (m, 2H), 3.59 (m, 1H), 3.02 (m, 1H), 2.69 (m, 1H).

Intermediate 1.6: 5'-O-DMTr-2'-deoxy-Inosine

The commercially available 2'-deoxy-Inosine (10.0 g, 39.6 mmol) was co-evaporated three times with dry pyridine. The residue was suspended in dry pyridine. DMAP (7.27 g, 59.5 mmol) and DimethoxyTritryl chloride (DMTrCl; 20.15 g, 59.5 mmol) were added to the resulting solution. The resulting mixture was stirred at 40° C. overnight. Then, the reaction was stopped by addition of methanol, the reaction mixture was diluted with EtOAc and was washed with saturated NaHCO₃, water and brine. The organic layer was dried over MgSO₄, filtered and concentrated in vacuo. The crude compound was purified by silica-gel column chromatography, using DCM/MeOH with 0.5% pyridine as eluent to provide 10.0 g (45% yield) of Intermediate 1.6. LC-MS: Rt=4.91 min, m/z=555 [M+H]⁺, m/z=553 [M−H]⁻.

Intermediate 1.7: 5'-O-DMTr-3'-O-Lev-2'-deoxy-Inosine

To a solution of Intermediate 1.6 (9.79 g, 17.65 mmol) in dry DMF (100 ml) EDCl (5.08 g, 26.5 mmol), DMAP (2.59 g, 21.18 mmol) and levulinic acid (2.89 ml, 28.2 mmol) were added. The resulting mixture was stirred at rt overnight. Then, the reaction mixture was diluted with EtOAc and was washed with saturated NaHCO₃, water and brine. The organic layer was dried over MgSO₄, filtered and concentrated in vacuo. The crude compound was purified by silica-gel column chromatography, using DCM/MeOH as eluent to provide 6.16 g (53% yield) of Intermediate 1.7. LC-MS: Rt=5.37 min, m/z=653 [M+H]⁺, m/z=651 [M−H]⁻.

Intermediate 1.8: 5'-O-DMTr-3'-O-Lev-N¹-POM-2'-deoxy-Inosine

To a solution of Intermediate 1.7 (6.16 g, 9.44 mmol) in dry DMF (120 mL) K₂CO₃ (3.91 g, 28.3 mmol), and POM-Cl (1.70 g, 11.3 mmol) were added. The resulting mixture was stirred at rt overnight. Then, the reaction mixture was diluted with EtOAc and was washed with saturated NaHCO₃, water and brine. The organic layer was dried over MgSO₄, filtered and concentrated in vacuo. The crude compound was purified by silica-gel column chromatography, using DCM/MeOH as eluent to provide 5.33 g (74% yield) of Intermediate 1.8, which was used in the next step without any further purification. LC-MS: Rt=6.36 min, m/z=767 [M+H]⁺, m/z=765 [M−H]⁻.

Intermediate 1.9: 3'-O-Lev-N¹-POM-2'-deoxy-Inosine

Intermediate 1.8 (5.30 g, 6.91 mmol) was treated with a solution of DCA/DCM (3%) in the presence of water (10 equiv.) for 15 min. The reaction was quenched by addition of MeOH and pyridine. The solvents were removed in vacuo and the residue was purified by silica-gel column chromatography, using DCM/MeOH as eluent to provide 3.03 g (94% yield) of Intermediate 1.9. LC-MS: Rt=4.03 min, m/z=465 [M+H]⁺, m/z=463 [M−H]⁻.

Intermediate 1.10: [N⁶-Bz-3'-O-(CE)phosphorothioate-triester-2'-fluoro-2'-deoxy-Adenosine]-(3',5')-[N¹-POM-3'-O-Lev-2'-deoxy-Inosine]

Intermediate 1.9 (3.01 g, 6.48 mmol) and commercially available phosphoramidite of 2'-fluoro-2'-deoxy-Adenosine (5.90 g, 6.74 mmol) was co-evaporated three times with dry ACN, and the resulting solid was dissolved in a solution of Activator 42® (0.1 mol/L, 2 equiv.; 130 mL) in the presence of molecular sieves (3 Å). The resulting mixture was stirred for 45 min. Then, a solution of PADS (3.91 g, 12.96 mmol) in pyridine was added to the mixture, which was stirred for 35 min. The solution was filtered and the molecular sieves were washed with DCM. The filtrate was concentrated in vacuo. The residue was treated with a solution of DCA/DCM (3%) in the presence of water (10 equiv.) for 15 min. The reaction was quenched with addition of MeOH and pyridine. The solvents were removed in vacuo and the residue was purified by silica-gel column chromatography, using DCM/MeOH as eluent to provide 4.90 g (78% yield) of Intermediate 1.10. LC-MS: Rt=5.17 min, m/z=969 [M+H]⁺, m/z=967 [M−H]⁻.

Intermediate 1.11: [N⁶-Bz-5'-O-H-phosphonate-3'-O-(CE)phosphorothioate-triester-2'-fluoro-2'-deoxy-Adenosine]-(3',5')-[N¹-POM-3'-O-Lev-2'-deoxy-Inosine]

To a solution of Intermediate 1.10 (4.78 g, 4.93 mmol) in dry pyridine (100 ml) was added diphenyl phosphite (1.91 mL, 9.87 mmol), the resulting mixture was stirred at room temperature for 2 hours, quenched by an addition of triethylammonium acetate (3.78 ml, 4 equiv.), and then concentrated under reduced pressure. The residue was purified by silica-gel column chromatography, using DCM/MeOH as eluent to provide 2.76 g (54% yield) of Intermediate 1.11. LC-MS: Rt=4.27 min, m/z=1033 [M+H]$^+$, m/z=1031 [M−H]$^−$.

Intermediate 1.12: [N$^6$-Bz-5'-O-H-phosphonate-3'-O-(CE)phosphorothioate-triester-2'-fluoro-2'-deoxy-Adenosine]-(3',5')-[N$^1$-POM-3'-O-Lev-2'-deoxy-Inosine]

Intermediate 1.11 (2.75 g, 2.66 mmol) was treated with a solution of 0.5 M hydrazine (0.99 ml, 13.31 mmol) In a mixture of pyridine/acetic acid (3:2) (27 ml) for 15 min. The reaction was quenched by addition of pentanedione (2.73 ml, 26.62 mmol). The solvents were removed in vacuo and the residue was triturated with diethyl ether to provide 2.45 g (99% yield) of Intermediate 1.12, which was used in the next step without any further purification. LC-MS: Rt=4.02 min, m/z=935 [M+H]$^+$, m/z=933 [M−H]$^−$.

Intermediate 1.13: (3',3')Cyclic-[N$^6$-Bz-3'-O-(CE)phosphorothioate-triester-2'-fluoro-2'-deoxy-Adenosine]-[N$^1$-POM-3'-O-phosphorothioate-diester-2'-deoxy-Inosine]

Intermediate 1.12 (2.50 g, 2.67 mmol) was coevaporated with dry pyridine three times. The residue was suspended in dry pyridine (150 ml) and PivCl (1.02 ml, 8.29 mmol) was added to the resulting solution. The resulting mixture was stirred at 25° C. for 30 min. Then, sulfur (0.26 g, 8.29 mmol) was added and the new suspension was stirred for 45 min at rt. The solvent was removed in vacuo to give 2.54 g (100% yield) of crude Intermediate 1.13. This compound was used in the next step without any further purification. LC-MS: Rt=4.62 and 4.78 min, m/z=949 [M+H]$^+$, m/z=947 [M−H]−

Intermediate 1.14

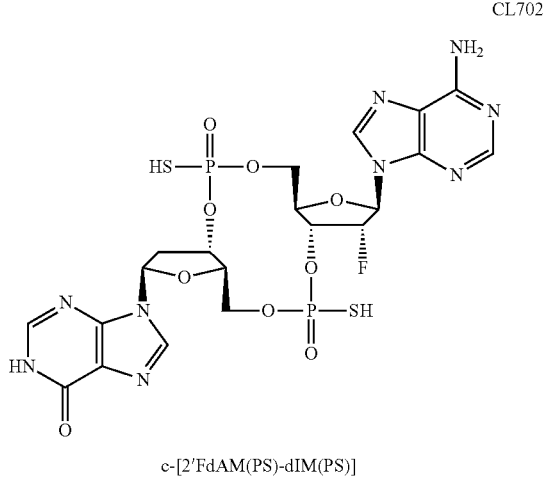 [SMILES: Nc1ncnc2c1ncn2[C@@H]1O[C@@H]2COP(=O)(S)O[C@H]3C[C@H](n4cnc5c(=O)[nH]cnc54)O[C@@H]3COP(=O)(S)O[C@H]2[C@H]1F]

CL702 c-[2'FdAM(PS)-dIM(PS)]

Intermediate 1.14 (1.68 g, 94% yield) was prepared from Intermediate 1.13 (2.50 g, 3.69 mmol) using a similar procedure to that described for Intermediate 1.5. LC-MS: Rt=0.844, 0.946, 2.28, 2.39, 2.72, 2.68 min, m/z=678 [M+H]$^+$, m/z=676 [M−H]$^−$. $^1$H NMR (D$_2$O, 300 MHz) δ (ppm) 8.48 (s, 1H), 8.24 (s, 1H), 8.21 (s, 1H), 8.04 (s, 1H), 7.96 (s, 1H), 7.90 (s, 1H), 6.30 (m, 2H), 5.70 (m, 1H), 5.53 (m, 1H), 5.02 (m, 2H), 4.45 (m, 1H), 4.21 (m, 1H), 4.09 (m, 2H), 4.02 (m, 2H), 3.94 (m, 2H), 3.10 (m, 1H), 2.90 (m, 1H). $^{31}$P NMR (D$_2$O, 202 MHz) δ (ppm) 55.95, 55.71 and 54.76, 54.29.

Intermediate 1.15: 5'-O-DMTr-2'-deoxy-2'-fluoro-Inosine

Intermediate 1.15 (52.0 g, 98% yield) was prepared from commercially available 2'-deoxy-2'-fluoro-Inosine (25.0 g, 92.5 mmol) using a similar procedure to that described for Intermediate 1.6. LC-MS: Rt=5.13 min, m/z=573 [M+H]$^+$, m/z=571 [M−H]$^−$.

Intermediate 1.16: 5'-O-DMTr-3'-O-Lev-2'-deoxy-2'-fluoro-inosine

Intermediate 1.16 (57.8 g, 95% yield) was prepared from Intermediate 1.15 (52.0 g, 91.2 mmol) using a similar procedure to that described for Intermediate 1.7. LC-MS: Rt=5.59 min, m/z=671 [M+H]$^+$, m/z=669 [M−H]$^−$.

Intermediate 1.17: 5'-O-DMTr-3'-O-Lev-N-POM-2'-deoxy-2'-fluoro-Inosine

Intermediate 1.17 (67.8 g, 99% yield) was prepared from Intermediate 1.16 (57.8 g, 86.5 mmol) using a similar procedure to that described for Intermediate 1.8. LC-MS: Rt=6.60 min, m/z=785 [M+H]$^+$, m/z=783 [M−H]$^−$.

Intermediate 1.18: 3'-O-Lev-N-POM-2'-deoxy-2'-fluoro-Inosine

Intermediate 1.18 (35.7 g, 82% yield) was prepared from Intermediate 1.17 (67.8 g 86.5 mmol) using a similar procedure to that described for Intermediate 1.9. LC-MS: Rt=4.17 min, m/z=483 [M+H]$^+$, m/z=481 [M−H]$^−$.

Intermediate 1.19: [N$_6$-Bz-3'-O-(CE)phosphorothioate-triester-2'-fluoro-2'-deoxy-Adenosine]-(3',5')-[N$^1$-POM-3'-O-Lev-2'-deoxy-2'-fluoro-Inosine]

Intermediate 1.19 (10.7 g, 99% yield) was prepared from Intermediate 1.18 (9.5 g, 10.8 mmol) and commercially available phosphoramidite of 2'-fluoro-2'-deoxy-Adenosine (5.23 g, 10.8 mmol) using a similar procedure to that described for Intermediate 1.10. LC-MS: Rt=5.28 min, m/z=987 [M+H]$^+$, m/z=985 [M−H]$^−$.

Intermediate 1.20: [N$^6$-Bz-3'-O-(CE)phosphorothioate-triester-2'-fluoro-2'-deoxy-Adenosine]-(3',5')-[N$^1$-POM-2'-deoxy-2'-fluoro-Inosine]

Intermediate 1.20 (6.46 g, 67% yield) was prepared from Intermediate 1.19 (10.7 g, 10.8 mmol) using a similar procedure to that described for Intermediate 1.11. LC-MS: Rt=4.89 min, m/z=889 [M+H]$^+$, m/z=887 [M−H]$^−$.

Intermediate 1.21: (3',3')Cyclic-[N$^6$-Bz-3'-O-(CE)phosphorothioate-triester-2'-fluoro-2'-deoxy-Adenosine]-[N$^1$-POM-3'-O-(CE)phosphorothioate-triester-2'-deoxy-2'-fluoroInosine]

Intermediate 1.20 (10.3 g, 11.6 mmol) was co-evaporated three times with dry ACN, and the resulting solid was dissolved in a solution of Activator 42® (0.1 mol/L, 2 equiv.; 460 ml) in the presence of molecular sieves (3 Å). Commercially available 2-Cyanoethyl-N,N-diisopropyl-chlorophosphoramidite (4.2 g, 13.9 mmol) was added dropwise to the solution. The resulting mixture was stirred for 45 min. Then, a solution of PADS (7.01 g, 23.2 mmol) in pyridine was added to the mixture, which was stirred for 35 min. The solution was filtered and the molecular sieves were washed with DCM. The solvents were removed in vacuo and the residue was purified by silica-gel column chromatography, using DCM/MeOH as eluent to provide 11.0 g (98% yield) of Intermediate 1.21. LC-MS: Rt=5.55, 5.77, 5.89 and 6.06 min, m/z=1020 [M+H]+, m/z=1018 [M-H]−.

Intermediate 1.22

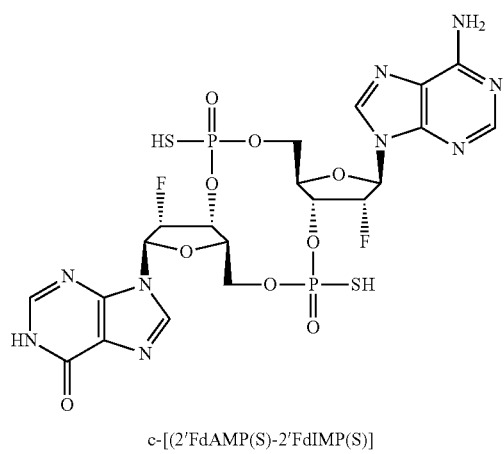

c-[(2'FdAMP(S)-2'FdIMP(S)]

Intermediate 1.22 (5.3 g, 66% yield) was prepared from Intermediate 1.21 (11.0 g, 11.0 mmol) using a similar procedure to that described for Intermediate 1.5. LC-MS: Rt=3.41 min, m/z=696 [M+H]+, m/z=694 [M-H]−. $^1$H NMR (D$_2$O, 300 MHz) δ (ppm) 8.55 (s, 1H), 8.38 (s, 1H), 8.20 (s, 1H), 7.99 (s, 1H), 6.63 (dd, 1H), 6.15 (dd, 1H), 5.16-4.95 (m, 4H), 4.52 (m, 4H), 4.07 (m, 2H).

Intermediate 1.23: (3',3')Cyclic-[N$^6$-Bz-3'-O-(CE)phosphorothioate-triester-2'-fluoro-2'-deoxy-Adenosine]-[N$^1$-POM-3'-O-(CE)phosphotriester-2'-deoxy-2'-fluoroInosine]

Intermediate 1.20 (6.2 g, 7.3 mmol) was co-evaporated three times with dry ACN, and the resulting solid was dissolved in a solution of Activator 42® (0.1 mol/L, 2 equiv.; 290 mL) in the presence of molecular sieves (3 Å). Commercially available 2-Cyanoethyl-N,N-diisopropyl-chlorophosphoramidite (2.64 g, 8.74 mmol) was added dropwise to the solution. The resulting mixture was stirred for 45 min. Then, a solution of tert-Butyl hydroperoxide (5.5 M in decane) (5 eq.) was added to the mixture, which was stirred for 35 min. The solution was filtered and the molecular sieves were washed with DCM. The solvents were removed in vacuo and the residue was purified by silica-gel column chromatography, using DCM/MeOH as eluent to provide 3.55 g (49% yield) of Intermediate 1.23. LC-MS: Rt=5.01, 5.13, 5.20, and 5.30 min, m/z=1004 [M+H]+, m/z=1002 [M-H]−.

Intermediate 1.24

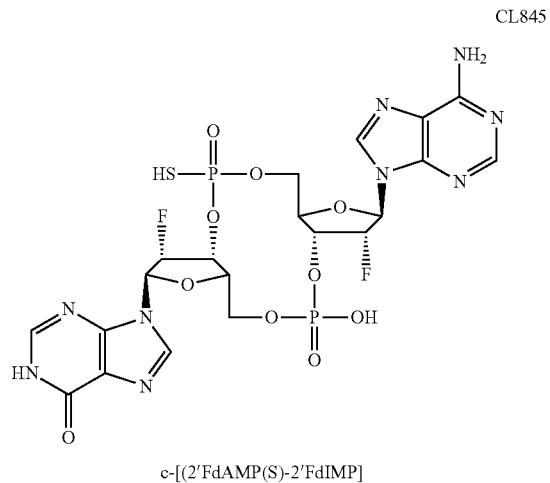 [SMILES: Nc1ncnc2c1ncn2[C@@H]1OC2COP(=O)(S)O[C@@H]3C(COP(=O)(O)O[C@H]2[C@H]1F)O[C@@H](n1cnc2c(=O)[nH]cnc21)[C@@H]3F]

c-[(2'FdAMP(S)-2'FdIMP]

Intermediate 1.24 (2.4 g, 99%) was prepared from Intermediate 1.23 (3.5 g, 3.5 mmol) using a similar procedure to that described for Intermediate 1.5. LC-MS: Rt=0.57 and 0.81 min, m/z=680 [M+H]+, m/z=678 [M-H]−. $^1$H NMR (D$_2$O, 300 MHz) δ (ppm) 8.34 (s, 1H), 8.27 (s, 1H), 8.20 (s, 2H), 7.99 (s, 1H), 7.92 (d, 1H), 6.35 (d, 1H), 6.24 (dd, 1H), 5.67 (m, 1H), 5.51 (m 1H), 5.06 (m, 4H), 4.51-4.41 (m, 8H) 4.07 (m, 4H).

Example 1.2: Synthesis of the Linkers of the Invention

Intermediate 2.1: Boc-Val-Cit-PAB-Cl

Commercially available dipeptide Boc-Val-Cit-PAB-OH (0.490 g, 1.02 mmol) was dissolved in dry Et$_2$O (20 ml) and was cooled to 0° C. SOCl$_2$ (82 µL, 1.12 mmol) was added dropwise to the solution and the mixture was stirred at rt overnight. The reaction was stopped by addition of a saturated solution of NaHCO$_3$. The layers were separated and the organic layer was dried over MgSO$_4$, filtered and concentrated in vacuo. The residue was purified by silica-gel column chromatography, using DCM/MeOH as eluent to provide 0.260 g (51% yield) of Intermediate 2.1. LC-MS: Rt=4.76 min, m/z=499 [M+H]+, m/z=497 [M-H]−.

Intermediate 2.2: Boc-Val-Cit-PAB-I

Intermediate 2.1 (0.100 g, 0.20 mmol) was dissolved in dry ACN (10 mL) and NaI (0.06 g, 0.40 mmol) was added and the mixture was stirred at rt overnight in the dark. The reaction was stopped by addition of EtOAc and a solution of NaHSO$_3$ (5%). The layers were separated and the organic layer was washed with water and brine dried over MgSO$_4$, filtered and concentrated in vacuo to provide 0.145 g (51% yield) of Intermediate 2.2. This compound was used in the next step without any further purification. LC-MS: Rt=4.99 min, m/z=590 [M+H]+, m/z=588 [M-H]−.

Intermediate 2.3: Solid Phase Synthesis of Fmoc-Val-Ala-OH

A 150 mL peptide reactor was purged with nitrogen and then charged with 2 g of 2-CTC resin and 80 mL of DCM.

The mixture was stirred for 15 min and the solvent was drained; this was repeated 2 times, then the resin was suspended in 80 mL of DMF. The resin-DMF mixture was stirred at rt for 30 min. Meanwhile, Fmoc-AlaOH (2.90 g, 9.30 mmol) in 40 ml DMF, and DIEA (162 mL, 9.30 mmol) were charged to a 100 mL flask. The contents of the flask were stirred at rt to dissolve the solid. After the DMF was drained from the reactor, the mixture containing the Fmoc-AlaOH was charged to the reactor with the resin and stirred. After 4 h the reactor was drained. Active sites on the resin were end-capped with a mixture of DIEA:MeOH (1:9 ml). This mixture was then stirred at rt for 1 h. The bed was drained, washed 2 times with 40 mL DMF, 2 times with 40 ml DCM, and one time with 40 ml DMF. The last wash demonstrated a negative UV test.

To the reactor containing Fmoc-Ala-O-2-CTC resin was charged 60 mL of 20% piperidine in DMF which was then stirred at rt for 30 min. The reactor was drained and then charged with 60 mL of 20% piperidine in DMF. The mixture was stirred for 30 min at rt and the reactor drained. The resin bed was then washed 3 times with 40 ml DMF, 3 times with 40 mL of DCM, 3 times with 40 mL of MeOH and 3 times with 40 mL of DMF. The last wash was then sampled for piperidine levels by qualitative ninhydrin test.

Then, Fmoc-Val-OH (3.16 g, 9.30 mmol), DIEA (1.62 ml, 9.30 mmol) and 15 ml DMF were charged to a flask. The contents were stirred at ambient temperature to dissolve the solid which were then cooled to 10° C. Then HATU (3.54 g, 9.30 mmol) was charged into the flask. The mixture was stirred at 10° C. to dissolve solid. The cooled solution was charged to the solid phase reactor. The flask was washed with 5 ml of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 3 times with 40 ml DMF, 3 times with 40 mL of DCM, 3 times with 40 mL of MeOH and 3 times with 40 mL of DMF.

Cleavage from resin was achieved with 5 cycles of 15 min each at rt of 15 ml of a solution 2% TFA, 1% TES in dichloromethane. This solution was charged to the solid phase reactor containing the Intermediate 2.3, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (5% MeOH/DCM) to provide 0.88 g (80% yield) of Intermediate 2.3. LC-MS: Rt=4.37 min, m/z=411 [M+H]$^+$, m/z=409 [M−H]$^−$.

Intermediate 2.4: Fmoc-Val-Ala-PAB-OH

Intermediate 2.3 (1.65 g, 4.02 mmol) was dissolved in dry DMF (10 ml). PAB-OH (0.49 g, 4.02 mmol), HATU (1.53 g, 4.02 mmol) and DIEA (2.11 ml, 12.06 mmol) were added to the solution and the mixture was stirred for 5 h. The reaction was stopped by addition of EtOAc and the mixture was washed with saturated NaHCO$_3$, water and brine. The layers were separated and the organic layer was dried over MgSO$_4$, filtered and concentrated in vacuo. The residue was purified by silica-gel column chromatography, using DCM/Acetone and DCM/MeOH as eluent to provide 1.3 g (62% yield) of Intermediate 2.4. LC-MS: Rt=5.30 min, m/z=516 [M+H]$^+$, m/z=514 [M−H]$^−$.

Intermediate 2.5: Fmoc-Val-Ala-PAB-Cl

Intermediate 2.4 (0.100 g, 0.19 mmol) was dissolved in dry CHCl$_3$ (10 ml) and was cooled to 0° C. SOCl$_2$ (16 μL, 0.213 mmol) was added dropwise to the solution and the mixture was stirred at rt for 1 h. The reaction was stopped by addition of a saturated solution of NaHCO$_3$. The layers were separated and the organic layer was dried over MgSO$_4$, filtered and concentrated in vacuo to provide 99 mg (95% yield) of crude Intermediate 2.5 which was used for the next step without any further purification. LC-MS: Rt=5.76 min, m/z=535 [M+H]$^+$, m/z=533 [M−H]$^−$.

Intermediate 2.6: Fmoc-Val-Ala-PAB-I

Intermediate 2.5 (99.0 mg, 0.18 mmol) was dissolved in acetone (10 ml). NaCl (88.0 mg, 0.584 mmol) was added dropwise to the solution and the mixture was stirred at rt for 48h in the dark. The reaction was stopped by addition of EtOAc and was washed with a 5% solution of NaHSO3 and brine. The layers were separated and the organic layer was dried over MgSO$_4$, filtered and concentrated in vacuo to provide 100 mg (82% yield) of crude Intermediate 2.6 which was used for the next step without any further purification. LC-MS: Rt=6.36 min, m/z=626 [M+H]$^+$, m/z=624 [M−H]$^−$.

Intermediate 2.7: $C_{15}H_{31}$-CO-Val-Ala-OH

The dipeptide Fmoc-Val-Ala-2CTC was prepared using a similar procedure to that described for Intermediate 2.3 with Fmoc-Ala-OH (0.682 g, 2.19 mmol) and Fmoc-Val-OH (0.743 g, 2.19 mmol). Then the Fmoc protecting group was cleaved by addition of 60 mL of 20% piperidine in DMF under stirring at rt for 30 min. The reactor was drained and then the treatment was repeated one time. The resin bed was then washed with 3 times with 40 ml DMF, 3 times with 40 mL of DCM, 3 times with 40 mL of MeOH and 3 times with 40 mL of DMF. The last wash was then sampled for piperidine levels by qualitative ninhydrin test.

Then, Palmitic acid (0.562 g, 2.19 mmol) and DIEA (0.381 mL, 2.19 mmol) in 15 ml DMF were charged to a flask. The contents were stirred at ambient temperature to dissolve the solid which were then cooled to 10° C. Then HATU (0.83 g, 2.19 mmol) was charged into the flask. The mixture was stirred at 10° C. to dissolve solid. The cooled solution was charged to the solid phase reactor. The flask was then washed with 5 ml of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 ml of DCM, 4 times with 20 mL of MeOH, 3 times with 20 mL of DMF and 8 times with 20 mL of DCM.

Cleavage from resin was achieved using a similar procedure to that described for Intermediate 2.3 to provide 0.35 g (31% yield) of Intermediate 2.7. LC-MS: Rt=7.19 min, m/z=427 [M+H]$^+$, m/z=425 [M−H]$^−$.

Intermediate 2.8: $C_{15}H_{31}$-CO-Val-Ala-PAB-OH

Intermediate 2.8 (0.14 g, 54% yield) was obtained from Intermediate 2.7 (0.215 g, 0.504 mmol) using a similar procedure to that described for Intermediate 2.4. LC-MS: Rt=7.38 min, m/z=532 [M+H]⁺, m/z=530 [M−H]⁻.

Intermediate 2.9: $C_{15}H_{31}$-CO-Val-Ala-PAB-Cl

Intermediate 2.9 (0.14 g, 99% yield) was obtained from Intermediate 2.8 (0.14 g, 0.263 mmol) using a similar procedure to that described for Intermediate 2.5. LC-MS: Rt=7.86 min, m/z=551 [M+H]⁺, m/z=549 [M−H]⁻.

Intermediate 2.10: $C_{15}H_{31}$—CO-Val-Ala-PAB-I

Intermediate 2.10 (0.14 g, 99% yield) was obtained from Intermediate 2.9 (0.14 g, 0.263 mmol) using a similar procedure to that described for Intermediate 2.6. LC-MS: Rt=8.33 min, m/z=642 [M+H]⁺, m/z=640 [M−H]⁻.

Intermediate 2.11: $CH_3$—CO-Val-Ala-OH

The dipeptide Fmoc-Val-Ala-2CTC was prepared using a similar procedure to that described for Intermediate 2.3 with Fmoc-Ala-OH (0.747 g, 2.40 mmol) and Fmoc-Val-OH (0.814 g, 2.40 mmol). Then the Fmoc protecting group was cleaved by addition of 60 mL of 20% piperidine in DMF under stirring at rt for 30 min. Then Acetic acid (0.960 mL, 2.40 mmol) and DIEA (0.417 mL, 2.40 mmol) in 15 mL DMF were charged to a flask. Then HATU (0.912 g, 2.40 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 mL of DCM, 4 times with 20 mL of MeOH, 3 times with 20 mL of DMF and 8 times with 20 mL of DCM. Cleavage from resin was achieved using a similar procedure to that described for intermediate 2.3 to provide 0.189 g (99% yield) of Intermediate 2.11. LC-MS: Rt=2.18 min, m/z=231 [M+H]⁺, m/z=229 [M−H]⁻.

Intermediate 2.12: $CH_3$—CO-Val-Ala-PAB-OH

Intermediate 2.12 (0.15 g, 56% yield) was obtained from Intermediate 2.11 (0.184 g, 0.799 mmol) using a similar procedure to that described for Intermediate 2.4. LC-MS: Rt=2.90 min, m/z=336 [M+H]⁺, m/z=334 [M−H]⁻.

Intermediate 2.13: $CH_3$CO-Val-Ala-PAB-Cl

Intermediate 2.13 (0.16 g, 99% yield) was obtained from Intermediate 2.12 (0.15 g, 0.447 mmol) using a similar procedure to that described for Intermediate 2.5. LC-MS: Rt=4.15 min, m/z=354 [M+H]⁺, m/z=352 [M−H]⁻.

Intermediate 2.14: $CH_3$CO-Val-Ala-PAB-I

Intermediate 2.14 (0.11 g, 55% yield) was obtained from Intermediate 2.13 (0.158 g, 0.447 mmol) using a similar procedure to that described for Intermediate 2.6. LC-MS: Rt=4.51 min, m/z=446 [M+H]⁺, m/z=444 [M−H]⁻.

Intermediate 2.15: $C_3H_7$—CO-Val-Ala-OH

The dipeptide Fmoc-Val-Ala-2CTC was prepared using a similar procedure to that described for Intermediate 2.3 with Fmoc-Ala-OH (0.747 g, 2.40 mmol) and Fmoc-Val-OH (0.814 g, 2.40 mmol). Then the Fmoc protecting group was cleaved by addition of 60 mL of 20% piperidine in DMF under stirring at rt for 30 min. Then butyryl chloride (0.912 ml, 2.40 mmol) and DIEA (0.420 ml, 2.40 mmol) in 15 mL DMF were charged to a flask. Then HATU (0.912 g, 2.40 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 ml of DCM, 4 times with 20 mL of MeOH, 3 times with 20 mL of DMF and 8 times with 20 mL of DCM. Cleavage from resin was achieved using a similar procedure to that described for Intermediate 2.3 to provide 0.205 g (99% yield) of Intermediate 2.15. LC-MS: Rt=3.00 min, m/z=259 [M+H]⁺, m/z=257 [M−H]⁻.

Intermediate 2.16: $C_3H_7$—CO-Val-Ala-PAB-OH

Intermediate 2.16 (0.255 g, 88% yield) was obtained from Intermediate 2.15 (0.184 g, 0.799 mmol) using a similar procedure to that described for Intermediate 2.4. LC-MS: Rt=3.49 min, m/z=364 [M+H]⁺, m/z=362 [M−H]⁻.

Intermediate 2.27: $C_3H_7$—CO-Val-Ala-PAB-Cl

Intermediate 2.17 (0.268 g, 99% yield) was obtained from Intermediate 2.16 (0.255 g, 0.702 mmol) using a similar procedure to that described for Intermediate 2.5. LC-MS: Rt=4.72 min, m/z=382 [M+H]⁺, m/z=380 [M−H]⁻.

Intermediate 2.18: $C_3H_7$—CO-Val-Ala-PAB-I intermediate 2.18 (0.4 g, 57% yield) was obtained from Intermediate 2.17 (0.268 g, 0.702 mmol) using a similar procedure to that described for Intermediate 2.6. LC-MS: Rt=5.03 min, m/z=474 [M+H]⁺, m/z=472 [M−H]⁻.

Intermediate 2.29: $C_7H_{15}$—CO-Val-Ala-OH

The dipeptide Fmoc-Val-Ala-2CTC was prepared using a similar procedure to that described for Intermediate 2.3 with Fmoc-Ala-OH (0.747 g, 2.40 mmol) and Fmoc-Val-OH (0.814 g, 2.40 mmol). Then the Fmoc protecting group was cleaved by addition of 60 mL of 20% piperidine in DMF under stirring at rt for 30 min. Then octanoyl chloride (0.150 ml, 2.40 mmol) and DIEA (0.420 ml, 2.40 mmol) in 15 ml DMF were charged to a flask. Then HATU (0.912 g, 2.40 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 mL of DCM, 4 times with 20 mL of MeOH, 3 times with 20 mL of DMF and 8 times with 20 mL of DCM. Cleavage from resin was achieved using a similar procedure to that described for Intermediate 2.3 to provide 0.250 g (99% yield) of Intermediate 2.19. LC-MS: Rt=3.19 min, m/z=315 [M+H]⁺, m/z=313 [M−H]⁻.

Intermediate 2.20: $C_7H_{15}$—CO-Val-Ala-PAB-OH

Intermediate 2.20 (0.28 g, 83% yield) was obtained from Intermediate 2.19 (0.250 g, 0.795 mmol) using a similar procedure to that described for Intermediate 2.4. LC-MS: Rt=4.90 min, m/z=420 [M+H]$^+$, m/z=418 [M−H]$^−$.

Intermediate 2.21: $C_7H_{15}$-CO-Val-Ala-PAB-Cl

Intermediate 2.21 (0.29 g, 99% yield) was obtained from Intermediate 2.20 (0.277 g, 0.660 mmol) using a similar procedure to that described for Intermediate 2.5. LC-MS: Rt=5.85 min, m/z=439 [M+H]$^+$, m/z=437 [M−H]$^−$.

Intermediate 2.22: $C_7H_{15}$-CO-Val-Ala-PAB-I

Intermediate 2.22 (0.23 g, 65% yield) was obtained from Intermediate 2.21 (0.289 g, 0.660 mmol) using a similar procedure to that described for Intermediate 2.6. LC-MS: Rt=6.11 min, m/z=530 [M+H]$^+$, m/z=528 [M−H]$^−$.

Intermediate 2.23: $C_{14}/C_{14}$—CO-Val-Ala-OH

The dipeptide Fmoc-Val-Ala-2CTC was prepared using a similar procedure to that described for Intermediate 2.3 with Fmoc-Ala-OH (0.747 g, 2.40 mmol) and Fmoc-Val-OH (0.814 g, 2.40 mmol). Then the Fmoc protecting group was cleaved by addition of 60 mL of 20% piperidine in DMF under stirring at rt for 30 min. Then 3-(tetradecanoyloxy) tetradecanoic acid (0.608 ml, 2.40 mmol) and DIEA (0.420 ml, 2.40 mmol) in 15 ml DMF were charged to a flask. Then HATU (0.912 g, 2.40 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 mL DMF, 3 times with 20 ml of DCM, 4 times with 20 mL of MeOH, 3 times with 20 mL of DMF and 8 times with 20 mL of DCM. Cleavage from resin was achieved using a similar procedure to that described for Intermediate 2.3 to provide 0.463 g (93% yield) of intermediate 2.23. LC-MS: Rt=7.78 min, m/z=625 [M+H]$^+$, m/z=623 [M−H]$^−$.

Intermediate 2.24: $C_{14}/C_{14}$—CO-Val-Ala-PAB-OH

Intermediate 2.24 (0.45 g, 61% yield) was obtained from Intermediate 2.23 (0.463 g, 0.741 mmol) using a similar procedure to that described for Intermediate 2.4. LC-MS: Rt=8.82 min, m/z=731 [M+H]$^+$, m/z=729 [M−H]$^−$.

Intermediate 2.25: $C_{14}/C_{14}$—CO-Val-Ala-PAB-Cl

Intermediate 2.25 (0.34 g, 99% yield) was obtained from intermediate 2.24 (0.330 g, 0.452 mmol) using a similar procedure to that described for Intermediate 2.5. LC-MS: Rt=9.14 min, m/z=749 [M+H]$^+$, m/z=747 [M−H]$^−$.

Intermediate 2.26: $C_4/C_{14}$—CO-Val-Ala-PAB-I

Intermediate 2.26 (0.21 g, 46% yield) was obtained from Intermediate 2.25 (0.338 g, 0.452 mmol) using a similar procedure to that described for Intermediate 2.6. LC-MS: Rt=9.33 min, m/z=840 [M+H]$^+$, m/z=838 [M−H]$^−$.

Intermediate 2.27: Me-Su-Val-Ala-OH

The dipeptide Fmoc-Val-Ala-2CTC was prepared using a similar procedure to that described for Intermediate 2.3 with Fmoc-Ala-OH (0.747 g, 2.40 mmol) and Fmoc-Val-OH (0.814 g, 2.40 mmol). Then the Fmoc protecting group was cleaved by addition of 60 mL of 20% piperidine in DMF under stirring at rt for 30 min. Then 4-methoxy-4-oxobutanoic acid (0.317 mL, 2.40 mmol) and DIEA (0.420 ml, 2.40 mmol) in 15 ml DMF were charged to a flask. Then HATU (0.912 g, 2.40 mmol) was charged into the flask. The mixture was stirred at 10° C. to dissolve solid. The cooled solution was charged to the solid phase reactor. The flask was then washed with 5 ml of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 mL of DCM, 4 times with 20 mL of MeOH, 3 times with 20 mL of DMF and 8 times with 20 mL of DCM. Cleavage from resin was achieved using a similar procedure to that described for Intermediate 2.3 to provide 0.241 g (100% yield) of Intermediate 2.27. LC-MS: Rt=4.55 min, m/z=303 [M+H]$^+$, m/z=301 [M−H]$^−$.

Intermediate 2.28: Me-Su-Val-Ala-PAB-OH

Intermediate 2.28 (0.68 g, 87% yield) was obtained from Intermediate 2.27 (0.240 g, 0.794 mmol) using a similar procedure to that described for Intermediate 2.4. LC-MS: Rt=3.38 min, m/z=731 [M+H]$^+$, m/z=729 [M−H]$^−$.

Intermediate 2.29: Me-Su-Val-Ala-PAB-Cl

The Intermediate 2.29 (0.29 g, 99% yield) was obtained from intermediate 2.28 (0.280 g, 0.687 mmol) using a similar procedure to that described for intermediate 2.5. LC-MS: Rt=4.54 min, m/z=426 [M+H]$^+$, m/z=424 [M−H]$^−$.

Intermediate 2.30: Me-Su-Val-Ala-PAB-I

Intermediate 2.30 (0.14 g, 41% yield) was obtained from Intermediate 2.29 (0.293 g, 0.688 mmol) using a similar procedure to that described for Intermediate 2.6. LC-MS: Rt=4.83 min, m/z=518 [M+H]$^+$, m/z=516 [M−H]$^−$.

Intermediate 2.31: Fmoc-(AEEA)$_4$-Val-Ala-OH

The dipeptide Fmoc-Val-Ala-2CTC was prepared using a similar procedure to that described for Intermediate 2.3 with Fmoc-Ala-OH (4.483 g, 14.4 mmol) and Fmoc-Val-OH (4.89 g, 14.4 mmol). Then the Fmoc protecting group was cleaved by addition of 60 mL of 20% piperidine in DMF under stirring at rt for 30 min. Then Fmoc-(NH—CH$_2$—CH$_2$O-CH$_2$—CH$_2$—O-CH$_2$—CO)$_4$—OH (3.70 g, 9.60 mmol) and DIEA (1.67 ml, 9.60 mmol) in 15 ml DMF were charged to a flask. Then HATU (3.65 g, 9.60 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 mL of DCM, 4 times with 20 ml of MeOH, 3 times with 20 mL of DMF and 8 times with 20 ml of DCM. This operation was repeated 4 times. Cleavage from resin was achieved using a similar procedure to that described for Intermediate 2.3 to provide 4.07 g (86% yield) of Intermediate 2.31. LC-MS: Rt=4.09 min, m/z=991 [M+H]$^+$, m/z=989 [M−H]$^−$.

Intermediate 2.32: Fmoc-(AEEA)$_4$-Val-Ala-PAB-OH

Intermediate 2.32 (2.75 g, 67% yield) was obtained from Intermediate 2.31 (4.07 g, 4.11 mmol) using a similar procedure to that described for Intermediate 2.4 LC-MS: Rt=4.79 min, m/z=1097 [M+H]$^+$, m/z=1095 [M−H]$^−$.

Intermediate 2.33: Fmoc-(AEEA)$_4$-Val-Ala-PAB-Cl

Intermediate 2.33 (0.99 g, 99% yield) was obtained from Intermediate 2.32 (0.954 g, 0.870 mmol) using a similar procedure to that described for Intermediate 2.5 LC-MS: Rt=6.24 min, m/z=1115 [M+H]$^+$, m/z=1113 [M−H]$^−$.

Intermediate 2.34: Fmoc-(AEEA)$_4$-Val-Ala-PAB-I

Intermediate 2.34 (0.69 g, 66% yield) was obtained from intermediate 2.33 (0.970 g, 0.870 mmol) using a similar procedure to that described for Intermediate 2.6 LC-MS: Rt=5.47 min, m/z=1207 [M+H]$^+$, m/z=1205 [M−H]$^−$.

Intermediate 2.35: $C_{15}H_{31}$—CO-AEEEEP-Val-Ala-OH

The dipeptide Fmoc-Val-Ala-2CTC was prepared using a similar procedure to that described for Intermediate 2.7 with Fmoc-Ala-OH (1.28 g, 4.10 mmol) and Fmoc-Val-OH (0.926 g, 4.10 mmol). Then the Fmoc protecting group was cleaved by addition of 60 mL of 20% piperidine in DMF under stirring at rt for 30 min. Then Fmoc-NH-(CH$_2$-CH$_2$-O)$_4$—CH$_2$—CH$_2$—COOH (1.0 g, 2.05 mmol) and DIEA (0.360 mL, 2.05 mmol) in 15 ml DMF were charged to a flask. Then HATU (0.780 g, 2.05 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 mL DMF, 3 times with 20 ml of DCM, 4 times with 20 mL of MeOH, 3 times with 20 mL of DMF and 8 times with 20 mL of DCM. Then the Fmoc protecting group was cleaved by addition of 60 mL of 20% piperidine in DMF under stirring at rt for 30 min. Then Palmitic acid (1.0 g, 2.05 mmol) and DIEA (0.714 ml, 0.410 mmol) in 15 ml DMF were charged to a flask. Then HATU (1.56 g, 4.10 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 ml of DCM, 4 times with 20 mL of MeOH, 3 times with 20 mL of DMF and 8 times with 20 mL of DCM. Cleavage from resin was achieved using a similar procedure to that described for intermediate 2.3 to provide 0.327 g (71% yield) of Intermediate 2.35. LC-MS: Rt=4.19 min, m/z=674 [M+H]$^+$, m/z=672 [M−H]$^−$.

Intermediate 2.36: $C_{15}H_{31}$—CO-AEEEEP-Val-Ala-PAB-OH

Intermediate 2.36 (0.3 g, 70% yield) was obtained from Intermediate 2.35 (0.320 g, 0.475 mmol) using a similar procedure to that described for Intermediate 2.4. LC-MS: Rt=6.82 min, m/z=780 [M+H]$^+$, m/z=778 [M−H]$^−$.

Intermediate 2.37: $C_{15}H_{31}$—CO-AEEEEP-Val-Ala-PAB-Cl

Intermediate 2.37 (0.26 g, 99% yield) was obtained from Intermediate 2.36 (0.260 g, 0.334 mmol) using a similar procedure to that described for Intermediate 2.5. LC-MS: Rt=7.45 min, m/z=798 [M+H]$^+$, m/z=796 [M−H]$^−$.

Intermediate 2.38: $C_{15}H_{31}$—CO-AEEEEP-Val-Ala-PAB-I

Intermediate 2.38 (0.24 g, 84% yield) was obtained from Intermediate 2.37 (0.260 g, 0.326 mmol) using a similar procedure to that described for Intermediate 2.6. LC-MS: Rt=7.63 min, m/z=889 [M+H]$^+$, m/z=887 [M−H]$^−$.

Intermediate 2.39: Fmoc-AEEA-Val-Ala-OH

The dipeptide Fmoc-Val-Ala-2CTC was prepared using a similar procedure to that described for Intermediate 2.3 with Fmoc-Ala-OH (5.98 g, 19.2 mmol) and Fmoc-Val-OH (6.52 g, 19.2 mmol). Then the Fmoc protecting group was cleaved by addition of 60 mL of 20% piperidine in DMF under stirring at rt for 30 min. Then Fmoc-NH-(CH$_2$—CH$_2$—O)$_2$—CH$_2$—COOH (4.93 g, 12.8 mmol) and DIEA (2.23 mL, 12.8 mmol) in 15 mL DMF were charged to a flask. Then HATU (4.87 g, 12.8 mmol) was charged into the flask. The mixture was stirred at 10° C. to dissolve solid. The cooled solution was charged to the solid phase reactor. The flask was then washed with 5 mL of DMF and the wash charged to the SPPS reactor. The mixture was stirred at rt for 4 h. The resin beads were then sampled for the completion of the reaction by a Keiser Test. After the reaction was complete, the reactor was drained and the resin bed washed 4 times with 20 ml DMF, 3 times with 20 mL of DCM, 4 times with 20 mL of MeOH, 3 times with 20 ml of DMF and 8 times with 20 mL of DCM. Cleavage from resin was achieved using a similar procedure to that described for Intermediate 2.3 to provide 3.25 g (91% yield) of Intermediate 2.39. LC-MS: Rt=4.15 min, m/z=556 [M+H]$^+$, m/z=554 [M−H]$^−$.

Intermediate 2.40: Fmoc-AEEA-Val-Ala-PAB-OH

Intermediate 2.40 (3.82 g, 98% yield) was obtained from Intermediate 2.39 (3.21 g, 5.78 mmol) using a similar procedure to that described for Intermediate 2.4. LC-MS: Rt=5.21 min, m/z=661 [M+H]$^+$, m/z=559 [M−H]$^−$.

Intermediate 2.41: Fmoc-AEEA-Val-Ala-PAB-Cl

Intermediate 2.41 (3.6 g, 99% yield) was obtained from Intermediate 2.40 (3.5 g, 5.30 mmol) using a similar procedure to that described for Intermediate 2.5. LC-MS: Rt=5.92 min, m/z=680 [M+H]$^+$, m/z=678 [M−H]$^−$.

Intermediate 2.42: Fmoc-AEEA-Val-Ala-PAB-I

Intermediate 2.42 (3.0 g, 73% yield) was obtained from Intermediate 2.41 (3.6 g, 5.30 mmol) using a similar procedure to that described for Intermediate 2.6. LC-MS: Rt=6.15 min, m/z=771 [M+H]$^+$, m/z=769 [M−H]$^-$.

Intermediate 2.43: Methyl (2,3,4-tri-O-acetyl-D-glucopyranosyl bromide)uronate Methyl 1,2,3,4-tetra-O-acetyl-D-glucopyranouronate (5.0 g, 13.3 mmol) was treated with a solution of hydrobromic acid in acetic acid 33% (98 mL, 597.9 mmol) at 0° C. After stirring overnight, the mixture was diluted with DCM and successively washed with cold water, saturated aqueous NaHCO$_3$ and brine. The organic layer was dried over MgSO4, filtered and concentrated in vacuo to provide 4.78 g (91% yield) of Intermediate 2.43 which is used for the next step without any further purification. $^1$H NMR (DMSOd$_6$, 400 MHz) δ 6.64 (d, 1H), 5.61 (t, 1H), 5.24 (m, 2H), 4.84 (dd, 1H), 4.56 (d, 1H), 3.76 (s, 3H), and 2.05 (m, 9H).

Intermediate 2.44: 1-(4-formyl-2-nitrophenoxy)-(Methyl-2,3,4-tri-O-acetyl)-D-glucopyranouronate For the Koenigs-Knorr reaction, the Intermediate 2.43 (4.78 g, 12.0 mmol) was coupled to 4-hydroxy-3-nitrobenzaldehyde (2.61 mg, 15.6 mmol) using Ag$_2$O (8.37 g, 36.1 mmol) in 30 mL of anhydrous ACN. The mixture was stirred under argon atmosphere at rt overnight. The reaction was filtered and diluted with EtOAc. The organic layer was washed with saturated aqueous NaHCO$_3$ and applied to flash chromatography (stepwise elution with hexane/EtOAc; 20, 30, and 40% EtOAc) to afford 5.22 g (90%, yield) of Intermediate 2.44. $^1$H NMR (DMSOd$_6$, 400 MHz) δ 9.98 (s, 1H), 8.44 (s 1H), 8.23 (d, 1H), 7.62 (d, 1H), 5.93 (d, 1H), 5.45 (t, 1H), 5.16 (q, 2H), 4.80 (d, 1H), 3.63 (s, 3H), and 2.02 (m, 9H). LC-MS: Rt=3.82 min, m/z=486 [M+H]$^+$, m/z=484 [M−H]$^-$, m/z=484 [M+H]$^+$, m/z=482 [M−H]$^-$.

Intermediate 2.45: 1-(hydroxymethyl-2-nitrophenoxy)-(Methyl-2,3,4-tri-O-acetyl)-D-glucopyranouronate Intermediate 2.44 (5.22 g, 10.1 mmol) was reduced with sodium borohydride (4.90 g, 130.0 mmol) in 65 mL of 1:5 2-propanol/CHCl$_3$ (volume ratio). The mixture was stirred under for 1h at 0° C. The reaction was filtered over Celite, the filtrate was concentrated in vacuo to afford 4.40 g (84%, yield) of Intermediate 2.45. $^1$H NMR (DMSOd$_6$, 400 MHz) δ 7.99 (s, 1H), 7.62 (d, 1H), 7.38 (d, 1H), 5.72 (m, 1H), 5.45 (m, 1H), 5.09 (q, 2H), 4.73 (d, 1H), 4.51 (s, 2H), 3.65 (s, 3H), and 2.02 (m, 9H). LC-MS: Rt=3.33 min, m/z=486 [M+H]$^+$, m/z=484 [M−H]$^-$.

Intermediate 2.46: 1-(Chloromethyl-2-nitrophenoxy)-(Methyl-2,3,4-tri-O-acetyl)-D-glucopyranouronate Intermediate 2.46 (0.5 g, 99% yield) was obtained from Intermediate 2.45 (0.5 g, 1.03 mmol) using a similar procedure to that described for Intermediate 2.5. LC-MS: Rt=4.86 min, m/z=504 [M+H]$^+$, m/z=502 [M−H]$^-$.

Intermediate 2.47: 1-(Iodomethyl-2-nitrophenoxy)-(Methyl-2,3,4-tri-O-acetyl)-D-glucopyranouronate Intermediate 2.47 (0.4 g, 72% yield) was obtained from intermediate 2.46 (0.5 g, 1.03 mmol) using a similar procedure to that described for Intermediate 2.6. LC-MS: Rt=5.62 min, m/z=596 [M+H]$^+$, m/z=594 [M−H]$^-$.

Intermediate 2.48: 1-(hydroxymethyl-2-aminophenoxy)-(Methyl-2,3,4-tri-O-acetyl)-D-glucopyranouronate Intermediate 2.45 (4.52 g 9.31 mmol) was hydrogenated in presence of Pd/Carbon (0.99 g, 0.93 mmol) in 40 mL of a mixture of EtOAc/MeOH (1/1). The mixture was stirred under for 1h at rt. The reaction was filtered over Celite, the filtrate was concentrated in vacuo to afford 2.97 g (70%, yield) of Intermediate 2.48. $^1$H NMR (DMSOd$_6$, 400 MHz) δ 6.80 (d, 1H), 6.62 (s, 1H), 6.45 (d, 1H), 5.48 (t, 1H), 5.39 (d, 1H), 5.07 (q, 2H), 4.95 (t, 1H), 4.66 (d, 2H), 4.58 (sl, 2H), 4.31 (d, 2H), 3.65 (s, 3H), and 2.02 (m, 9H). LC-MS: Rt=4.33 min, m/z=456 [M+H]$^+$, m/z=454 [M−H]$^-$.

Intermediate 2.49: 1-(hydroxymethyl-2-palmitamidophenoxy)-(Methyl-2,3,4-tri-O-acetyl)-D-glucopyranouronate To a solution of Intermediate 2.48 (0.50 g, 1.10 mmol) in dry DCM (15 ml) palmitoyl chloride (0.4 ml, 0.1.32 mmol) and DIEA (0.38 mL, 2.20 mmol) were added. The mixture was stirred at rt overnight. The reaction mixture was washed with saturated aqueous NaHCO$_3$ and brine. The organic layer was dried over MgSO$_4$, filtered and concentrated in vacuo. The residue was applied to flash chromatography to afford 0.645 g (85%, yield) of Intermediate 2.49. $^1$H NMR (DMSOd$_6$, 400 MHz) δ 8.52 (s, 1H), 7.87 (d, 1H), 7.02 (s, 2H), 5.46 (m, 2H), 5.12 (m, 3H), 4.72 (d, 1H), 4.40 (m, 2H), 3.69 (s, 3H), 2.31 (t, 2H), 2.02 (s, 9H), 1.57 (m, 2H), 1.24 (m, 24H) and 0.85 (s, 3H). LC-MS: Rt=6.33 min, m/z=694 [M+H]$^+$, m/z=692 [M−H]$^-$.

Intermediate 2.50: 1-(Chloromethyl-2-palmitamidophenoxy)-(Methyl-2,3,4-tri-O-acetyl)-D-glucopyranouronate Intermediate 2.50 (0.6 g, 99% yield) was obtained from Intermediate 2.49 (0.645 g, 0.93 mmol) using a similar procedure to that described for Intermediate 2.5. LC-MS: Rt=7.86 min, m/z=713 [M+H]$^+$, m/z=711 [M−H]$^-$.

Intermediate 2.51: 1-(Iodomethyl-2-palmitamidophenoxy)-(Methyl-2,3,4-tri-O-acetyl)-D-glucopyranouronate Intermediate 2.51 (0.6 g, 80% yield) was obtained from Intermediate 2.50 (0.6 g, 0.93 mmol) using a similar procedure to that described for Intermediate 2.6. LC-MS: Rt=8.27 min, m/z=804 [M+H]$^+$, m/z=802 [M−H]$^-$.

Intermediate 2.52: $C_{15}H_{31}$—CO-Val-Cit-OH

Intermediate 2.52, (4.2 g, 97% yield) was obtained from Fmoc-Ala-OH (8.1 g, 24.0 mmol), Fmoc-Cit-OH (9.5 g, 24.0 mmol) and Palmitic acid (6.1 g, 24.0 mmol) using a similar procedure to that described for Intermediate 2.7. $^1$H NMR (DMSOd$_6$, 400 MHz) δ 8.13 (d, 1H), 7.72 (d, 1H), 4.22 (m, 1H), 4.12 (m, 1H), 2.88 (t, 2H), 2.08 (m, 2H), 1.95 (m, 1H), 1.68 (m, 1H), 1.41 (m, 4H), 1.38 (s, 24H), and 0.85 (t, 3H). ESI-MS: m/z=694 [M+H]$^+$, m/z=692 [M−H]$^-$. ESI-MS: m/z=513 [M+H]$^+$, m/z=511 [M−H]$^-$.

Intermediate 2.53: $C_{15}H_{31}$—CO-Val-Cit-PAB-OH

Intermediate 2.53 (4.6 g, 90% yield) was obtained from Intermediate 2.52 (4.2 g, 8.2 mmol) using a similar procedure to that described for Intermediate 2.4. LC-MS: Rt=6.64 min, m/z=618 [M+H]$^+$, m/z=616 [M−H]$^−$.

Intermediate 2.54: $C_{15}H_{31}$—CO-Val-Cit-PAB-Cl

Intermediate 2.54 (1.9 g, 84% yield) was obtained from Intermediate 2.53 (0.14 g, 0.263 mmol) using a similar procedure to that described for Intermediate 2.5. LC-MS: Rt=7.38 min, m/z=637 [M+H]$^+$, m/z=635 [M−H]$^−$.

Intermediate 2.55: $C_{15}H_{31}$—CO-Val-Cit-PAB-I

Intermediate 2.55 (0.8 g, 86% yield) was obtained from Intermediate 2.54 (0.8 g, 1.25 mmol) using a similar procedure to that described for Intermediate 2.6. LC-MS: Rt=7.37 and 7.58 min, m/z=728 [M+H]$^+$, m/z=726 [M−H]$^−$.

Intermediate 2.56: 1-[hydroxy-methyl-2-(6-maleimido-hexanamido)-phenoxy]-(Methyl-2,3,4-tri-O-acetyl)-D-glucopyranouronate To a solution of Intermediate 2.48 (0.20 g, 0.4 mmol) in dry DMF (10 ml) 6-Maleimidohexanoic acid (0.1 ml, 0.48 mmol), HATU (0.18 g, 0.48 mmol) and DIEA (0.23 ml, 1.32 mmol) were added. The mixture was stirred at rt overnight. The reaction was stopped by addition of EtOAc (20 ml) and the mixture was washed with saturated aqueous NaHCO$_3$, water and brine. The organic layer was dried over MgSO$_4$, filtered and concentrated in vacuo. The residue was applied to flash chromatography to afford 0.21 g (72%, yield) of Intermediate 2.56. $^1$H NMR (DMSOd$_6$, 400 MHz) δ 8.55 (s, 1H), 7.84 (s, 1H), 7.00 (m, 1H), 5.84 (m, 2H), 5.13 (m, 3H), 4.70 (d, 1H), 3.63 (s, 3H), 3.40 (m, 2H), 2.30 (t, 2H), 2.01 (s, 9H), 1.52 (m, 2H) and 1.33 (m, 2H). ESI-MS: m/z=649 [M+H]$^+$, m/z=647 [M−H]$^−$.

Intermediate 2.57: 1-[chloro-methyl-2-(6-maleimido-hexanamido)-phenoxy]-(Methyl-2,3,4-tri-O-acetyl)-D-glucopyranouronate Intermediate 2.57 (0.21 g, 99% yield) was obtained from Intermediate 2.56 (0.21 g, 0.32 mmol) using a similar procedure to that described for Intermediate 2.5. ESI-MS: m/z=668 [M+H]$^+$, m/z=666 [M−H]$^−$.

Intermediate 2.58: 1-[iodo-methyl-2-(6-maleimido-hexanamido)-phenoxy]-(Methyl-2,3,4-tri-O-acetyl)-D-glucopyranouronate Intermediate 2.58 (0.05 g, 22% yield) was obtained from Intermediate 2.57 (0.2 g, 0.32 mmol) using a similar procedure to that described for Intermediate 2.6. $^1$H NMR (DMSOd$_6$, 400 MHz) δ 8.59 (1H, s), 7.96 (s, 1H), 7.16 (m, 1H), 7.00 (m, 3H), 5.61 (m, 1H), 5.58 (m, 1H), 5.24 (m, 1H), 5.06 (m, 1H), 4.72 (m, 1H), 4.59 (s, 2H), 3.63 (s, 3H), 3.40 (t, 2H), 2.30 (m, 2H), 2.01 (s, 9H), 1.52 (m, 4H) and 1.23 (m, 2H). ESI-MS: m/z=759 [M+H]$^+$, m/z=757 [M−H]$^−$.

Intermediate 2.59: 6-Maleimido-(hexanamido)-hexanoic acid

Intermediate 2.59 (1.84 g, 99%) was obtained from Fmoc-6-amino-hexanoic acid (5.09 g, 14.40 mmol) and 6-Maleimido-hexanoic acid (3.04 g, 14.4 mmol) using a similar procedure to that described for intermediate 2.3. LC-MS: Rt=2.44 min, m/z=325 [M+H]$^+$, m/z=323 [M−H]$^−$.

Intermediate 2.60: 1-[hydroxy-methyl-2-(6-maleimido-di-(hexanamido))-phenoxy]-(Methyl-2,3,4-tri-O-acetyl)-D-glucopyranouronate Intermediate 2.60 (92.8 mg, 28%) was obtained from Intermediate 2.48 (5.09 g, 14.40 mmol) and Intermediate 2.59 (3.04 g, 14.4 mmol) using a similar procedure to that described for Intermediate 2.56. LC-MS: Rt=4.67 min, m/z=762 [M+H]$^+$, m/z=760 [M−H]$^−$.

Intermediate 2.61: 1-[chloro-methyl-2-(6-maleimido-di-(hexanamido))-phenoxy]-(Methyl-2,3,4-tri-O-acetyl)-D-glucopyranouronate Intermediate 2.61 (95.0 mg, 99% yield) was obtained from Intermediate 2.60 (92 mg, 0.12 mmol) using a similar procedure to that described for intermediate 2.5. LC-MS: Rt=5.86 min, m/z=781 [M+H]$^+$, m/z=779 [M−H]$^−$.

Intermediate 2.62: 1-[iodo-methyl-2-(6-maleimido-di-(hexanamido))-phenoxy]-(Methyl-2,3,4-tri-O-acetyl)-D-glucopyranouronate Intermediate 2.62 (62.7 mg, 59% yield) was obtained from intermediate 2.61 (95.0 mg, 0.12 mmol) using a similar procedure to that described for Intermediate 2.6. LC-MS: Rt=6.33 min, m/z=872 [M+H]$^+$, m/z=870 [M−H]$^−$.

Intermediate 2.63: $C_{14}/C_{14}$—CO-Val-Cit-OH

Intermediate 2.63 (2.2 g, 87% yield) was obtained from Fmoc-Val-OH (3.26 g, 9.6 mmol), Fmoc-Cit-OH (3.820 g, 9.6 mmol) and 3-(tetradecanoyloxy)tetradecanoic acid (C14/C14-COOH) (2.73 g, 6.4 mmol) using a similar procedure to that described for Intermediate 2.23. $^1$H NMR (DMSOd$_6$, 400 MHz) δ 8.16 (d, 1H), 7.86 (d, 1H), 7.19 (m, 3H), 5.12 (m, 1H), 4.23 (m, 3H), 4.10 (t, 3H), 2.93 (m, 2H), 2.16 (m, 2H), 1.92 (m, 1H), 1.71 (m, 1H), 1.47 (m, 6H), 1.21 (m, 36H) and 0.83 (m, 12H). ESI-MS: m/z=711 [M+H]$^+$, m/z=709 [M−H]$^−$.

Intermediate 2.64: $C_{14}/C_{14}$—CO-Val-Cit-PAB-OH

Intermediate 2.64 (0.98 g, 50% yield) was obtained from Intermediate 2.63 (1.71 g, 2.4 mmol) using a similar procedure to that described for Intermediate 2.4. ESI-MS: m/z=817 [M+H]$^+$, m/z=815 [M−H]$^−$ Intermediate 2.65: $C_{14}/C_{14}$—CO-Val-Cit-PAB-I To a suspension of Intermediate 2.64 (0.40 g, 0.49 mmol) in dry ACN (20 ml) KI (0.134 g, 0.81 mmol) and BF$_3$·Et$_2$O (0.102 ml, 0.81 mmol) were added. The solution was stirred at RT for 1H00, then water was added to stop the reaction. The mixture was exacted 3 times with EtOAc. The organic layer was washed with a solution of NaHCO$_3$, NaHSO$_3$ and brine, dried over MgSO$_4$, filtered and concentrated in vacuo. The residue was applied to flash chromatography to afford 0.42 g (86%, yield) of Intermediate 2.65. LC-MS: Rt=9.21 min, m/z=927 [M+H]$^+$, m/z=925 [M−H]$^−$.

Intermediate 2.66: Mal-Aca-Aca-OH

Intermediate 2.66 (4.1 g, 90% yield) was obtained from Fmoc-Aca-OH (10.2 g, 28.8 mmol) and 6-Maleimido-Aca-OH (4.06 g, 19.2 mmol) using a similar procedure to that described for Intermediate 2.3. $^1$H NMR (DMSOd$_6$, 400 MHz) δ 7.69 (m, 2H), 7.17 (m, 1H), 7.00 (s, 2H), 3.36 (t, 2H), 2.98 (m, 2H), 2.18 (t, 2H), 2.00 (t, 2H), 1.48 (m, 8H), 1.35 (m, 2H) and 1.20 (m, 2H). ESI-MS: m/z=325 [M+H]$^+$, m/z=323 [M−H]$^−$.

Intermediate 2.67: Solid Phase Synthesis of Fmoc-Val-Cit-OH

Intermediate 2.67, (9.1 g, 80% yield) was obtained from Fmoc-Val-OH (8.15 g, 24.0 mmol) and Fmoc-Cit-OH (9.54 g, 24.0 mmol) using a similar procedure to that described for intermediate 2.3. $^1$H NMR (DMSOd$_6$, 400 MHz) δ 8.15 (d, 1H), 7.88 (d, 1H), 7.74 (m, 2H), 7.43-7.15 (m, 8H), 4.25-4.21 (m, 4H), 3.92 (m, 1H), 2.95 (t, 2H), 2.29 (m, 2H), 2.00 (m, 1H), 1.68 (m, 1H), 1.41 (m, 4H), 1.40 (m, 2H), and 0.87 (m, 6H). ESI-MS: m/z=711 [M+H]$^+$, m/z=709 [M−H]$^−$.

Intermediate 2.68: Fmoc-Val-Cit-PAB-OH

Intermediate 2.68 (2.79 g, 94% yield) was obtained from Intermediate 2.67 (2.45 g, 4.93 mmol) using a similar procedure to that described for intermediate 2.4. LC-MS: Rt=4.82 min, m/z=602 [M+H]$^+$, m/z=600 [M−H]$^−$.

Intermediate 2.69: Fmoc-Val-Cit-PAB-I

Intermediate 2.69 (0.96 g, 77% yield) was obtained from Intermediate 2.68 (1.06 g, 1.76 mmol) using a similar procedure to that described for Intermediate 2.65. LC-MS: Rt=577 min, m/z=712 [M+H]$^+$, m/z=710 [M−H]$^−$.

Example 1.3: Synthesis of Pro-CDNs of the Invention

Compound 1

CL793

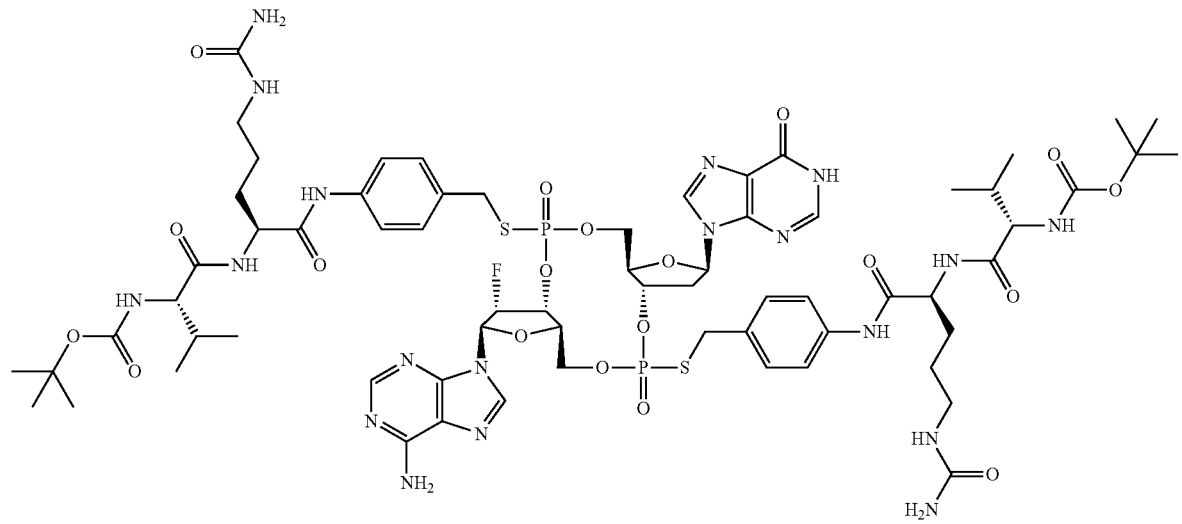

c-[2'FdAM(PS-PAB-Cit-Val-Boc)-dIM(PS-PAB-Cit-Val-Boc)]

Intermediate 1.14 (20 mg, 0.03 mmol) was dissolved in deionized water (2 ml). Intermediate 2.2 (61 mg, 0.103 mmol) in a mixture of acetone/dioxane/water (9/9/2) was added. The mixture was stirred overnight at rt. Then NaHSO$_3$ (6.14 mg, 0.06 mmol) was added and the compound was precipitated by addition of EtOAc. The precipitate was filtered, washed with EtOAc and water and dried in vacuo to provide 15 mg (32% Yield) of Compound 1. LC-MS: Rt z 4.57, 4.65 min, m/z=801 [M+2H]$^{2+}$, m/z=799 [M−2H]$^{2-}$.

Compound 2

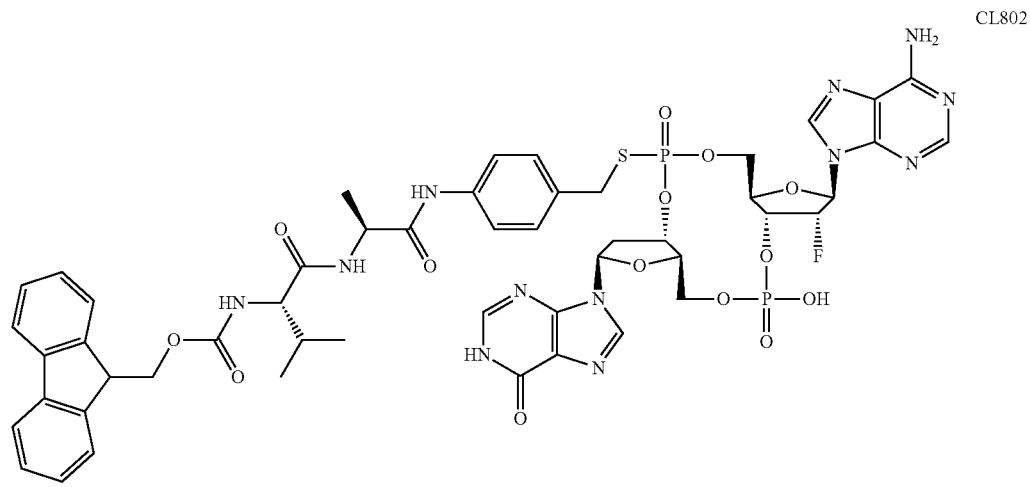

c-[2′FdAM(PS-PAB-Ala-Val-Fmoc)-dIMP]

Intermediate 1.5 (40 mg, 0.06 mmol) was dissolved in deionized water (2 ml). A solution of Intermediate 2.6 (132 mg, 0.132 mmol) in acetone was added. The mixture was stirred overnight at rt in the dark. The solvents were removed in vacuo and the residue was applied to silica-gel column chromatography, using DCM/MeOH as eluent to provide 12 mg (17% yield) of Compound 2. LC-MS: Rt=3.89, 4.11, 4.21 min, m/z=1160 [M+H]$^+$, m/z=1158 [M−H]$^-$.

Compound 3

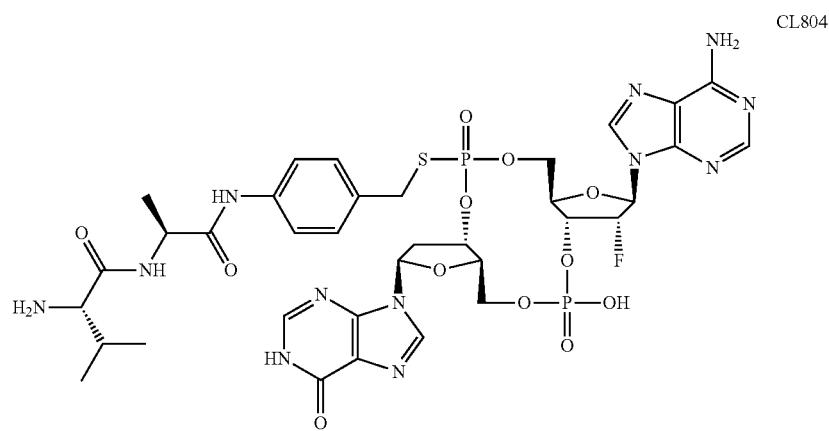

c-[2′FdAM(PS-PAB-Ala-Val)-dIMP]

Compound 2 (8 mg, 6.90 μmol) was dissolved in DMF (2 mL). A solution of piperidine 20% in DMF was added and the mixture was stirred for 1 h. Then the solvent was removed in vacuo and the residue was triturated with Et$_2$O to provide 6 mg (99% yield) of Compound 3. LC-MS: Rt=3.89, 4.11, 4.21 min, m/z=1160 [M+H]$^+$, m/z=1158 [M−H]$^-$.

Intermediate 3.1: c-[2'FdAM(PS-PAB-Ala-Val-(AEEA)$_4$-Fmoc)-dIMP]

Intermediate 1.5 (100 mg, 0.151 mmol) was dissolved in in deionized water (500 μL). A solution of Intermediate 2.34 (274 mg, 0.227 mmol) in DMF was added. The mixture was stirred overnight at rt in the dark. The solvents were removed and the residue was applied to a flash chromatography to provide 160 mg (61% yield) of Intermediate 3.1. LC-MS: Rt=4.31 min, m/z=1740 [M+H]$^+$, m/z=1738 [M−H]$^-$.

Compound 4:

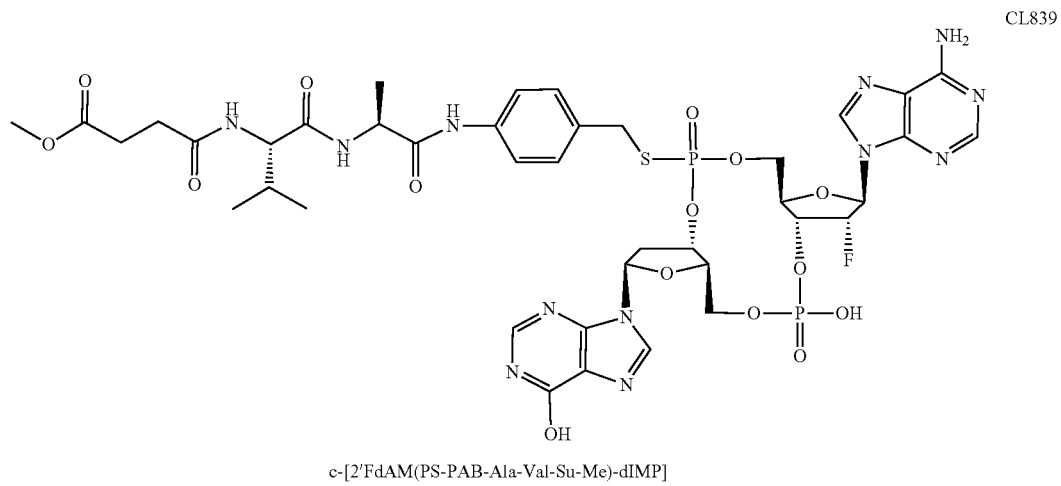

c-[2'FdAM(PS-PAB-Ala-Val-Su-Me)-dIMP]

Intermediate 1.5 (110 mg, 0.166 mmol) was dissolved in deionized water (2 mL). A solution of Intermediate 2.30 (129 mg, 0.249 mmol) in DMF was added. The mixture was stirred overnight at rt in the dark. The solvents were removed in vacuo and the residue was applied to silica-gel column chromatography, using DCM/MeOH as eluent to provide 105 mg (60% yield) of Compound 4. LC-MS: Rt=3.35 and 3.53 min, m/z=1051 [M+H]$^+$, m/z=1049 [M−H]$^-$.

Compound 5:

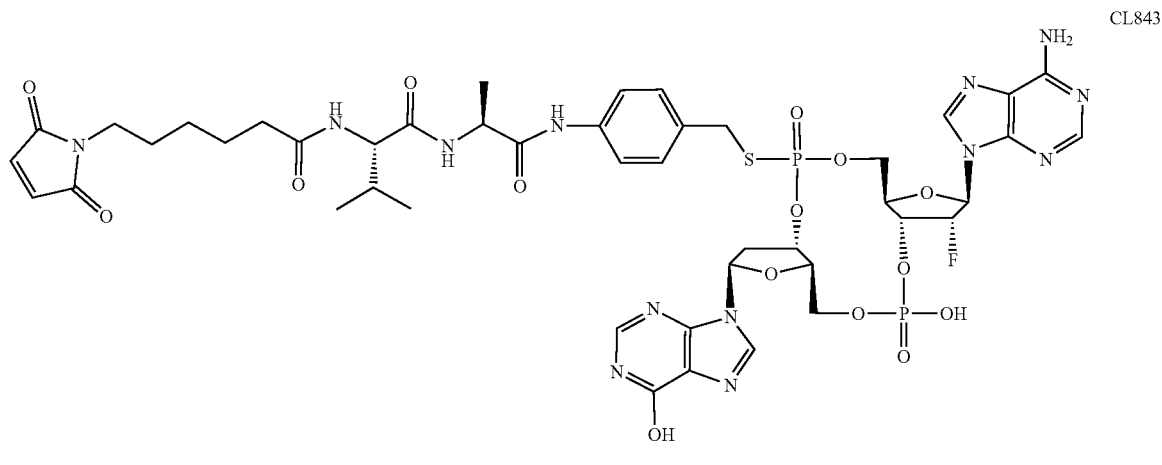

c-[2'FdAM(PS-PAB-Ala-Val-Hex-Mal)-dIMP]

To a solution of Compound 3 (45 mg, 0.048 mmol) in DMF (1 ml) at 10° C. DIEA (0.025 ml, 0.144 mmol), 6-Maleimidohexanoic acid (12 mg, 0.053 mmol) and HATU (20 mg, 0.053 mmol) were added. The mixture was stirred at rt for 4 h. Then the solvent was removed in vacuo and the residue was applied to a $C_{18}$ chromatography with TEAB/ACN as eluent to provide 33 mg (61% yield) of Compound 5. LC-MS: Rt=3.61 and 3.77 min, m/z=1131 [M+H]$^+$, m/z=1129 [M−H]$^−$.

Compound 6:

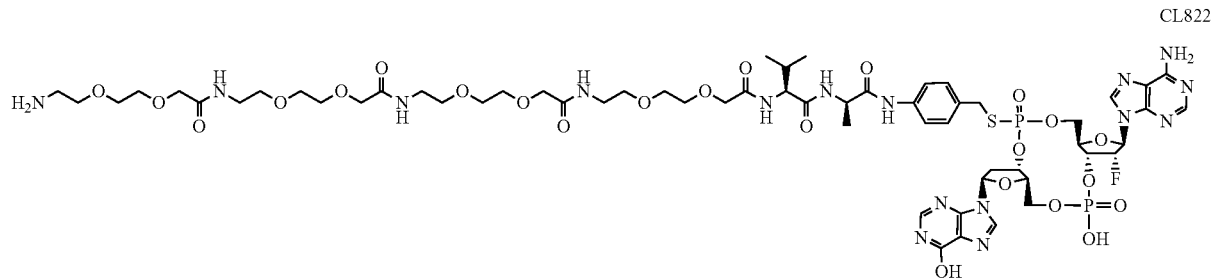

c-[2'FdAM(PS-PAB-Ala-Val-(AEEA)$_4$)-dIMP]

Compound 6 (120 mg, 92% yield) was obtained from Intermediate 3.1 (150 mg, 0.086 mmol) using a similar procedure to that described for Compound 3. LC-MS: Rt=3.34 and 3.48 min, m/z=1518 [M+H]$^+$, m/z=1516 [M−H]$^−$.

Intermediate 3.2. c-[2'FdAM(PS-PAB-Ala-Val-AEEA-Fmoc)-dIMP]

Intermediate 1.5 (200 mg, 0.302 mmol) was dissolved in in deionized water (2 ml). A solution of Intermediate 2.42 (280 mg, 0.363 mmol) in THF was added. The mixture was stirred overnight at 40° C. in the dark. The solvents were removed and the residue was applied to a flash chromatography to provide 267 mg (68% yield) of Intermediate 3.2. LC-MS: Rt=4.65 and 4.71 min, m/z=1305 [M+H]$^+$, m/z=1303 [M−H]$^−$.

Intermediate 3.3: c-[2'FdAM(PS-PAB-Ala-Val-AEEA)-dIMP]

Intermediate 3.3 was obtained from Intermediate 3.2 (267 mg, 0.205 mmol) using a similar procedure to that described for Compound 3 to provide 222 mg (100% yield) of Intermediate 3.3. LC-MS: Rt=3.20 and 3.41 min, m/z=1083 [M+H]$^+$, m/z=1081 [M−H]$^−$.

Compound 7:

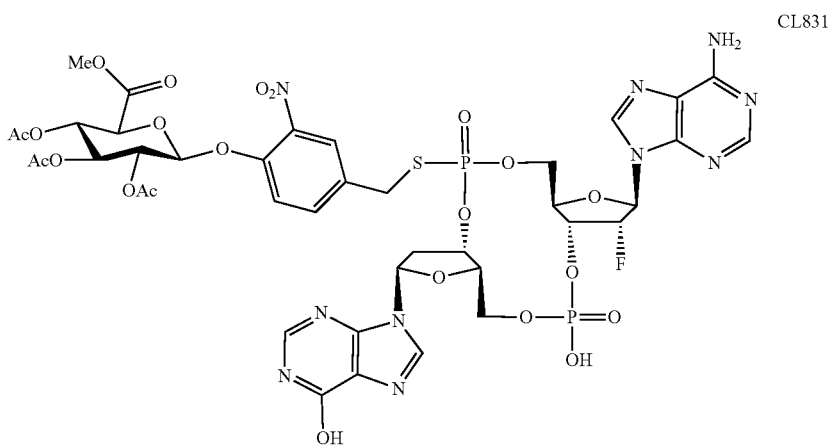

c-[2'FdAM(PS-(3-nitro-4-(Methyl-2,3,4-tri-O-acetyl-D-glucopyranouronate)-benzyl)-dIMP]

Compound 7 (97 mg, 90% yield) was obtained from Intermediate 1.5 (63 mg, 0.095 mmol) and Intermediate 2.47 (85 mg, 0.140 mmol) in THF using a similar procedure to that described for Compound 4. LC-MS: Rt=3.78 and 3.88 min, m/z=1129 [M+H]$^+$, m/z=1127 [M−H]$^-$.

Compound 8:

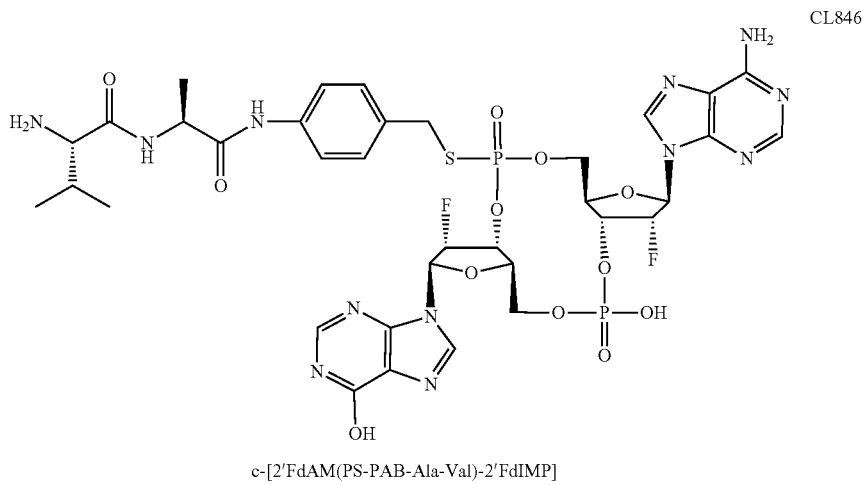

c-[2'FdAM(PS-PAB-Ala-Val)-2'FdIMP]

Intermediate 1.24 (1.0 g, 1.4 mmol) was dissolved in deionized water (2 ml.). A solution of Intermediate 2.6 (1.4 g, 2.2 mmol) in THF was added. The mixture was stirred overnight at rt in the dark. The solvents were removed in vacuo and the residue was treated with 60 mL of 20% piperidine in DMF and stirred at rt for 30 min. The solvent was removed in vacuo and applied to silica-gel column chromatography, using DCM/MeOH as eluent, to provide 0.921 g (68% yield) of Compound 8. LC-MS: Rt=3.11 and 3.16 min m/z=955 [M+H]$^+$, m/z=957 [M−H]$^-$.

Compound 9:

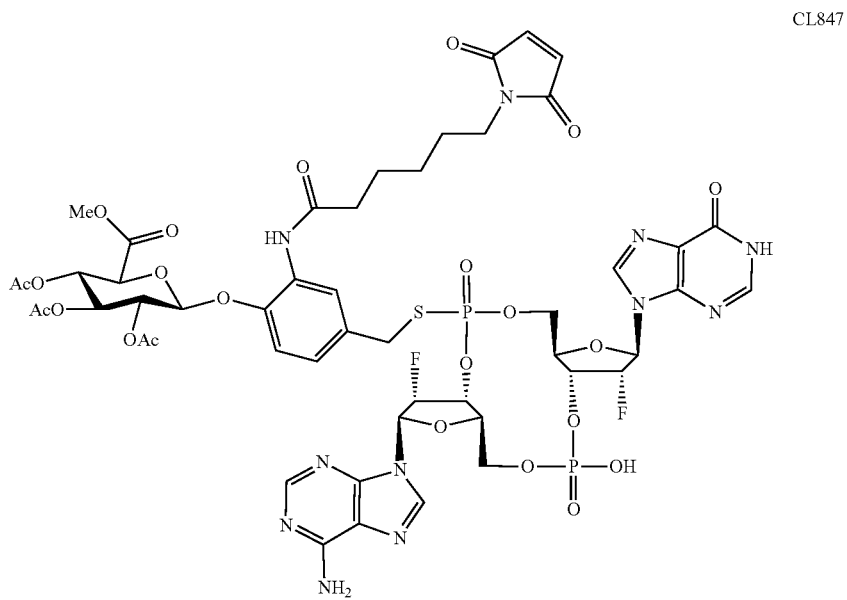

c-[2'FdAM(PS-(3-Maleimido-hexanamido-4-(Methyl-2,3,4-tri-O-acetyl-D-glucopyranouronate)-benzyl)-2'FdIMP]

Compound 9 40.0 mg (57% yield) was obtained from Intermediate 1.22 (53.0 mg, 70.0 μmol) and Intermediate 2.58 (53.0 mg, 54 μmol) in THF using a similar procedure to that described for Compound 4. LC-MS: Rt=4.08 and 4.16 min, m/z=1310 [M+H]$^+$, m/z=138 [M−H]$^−$.

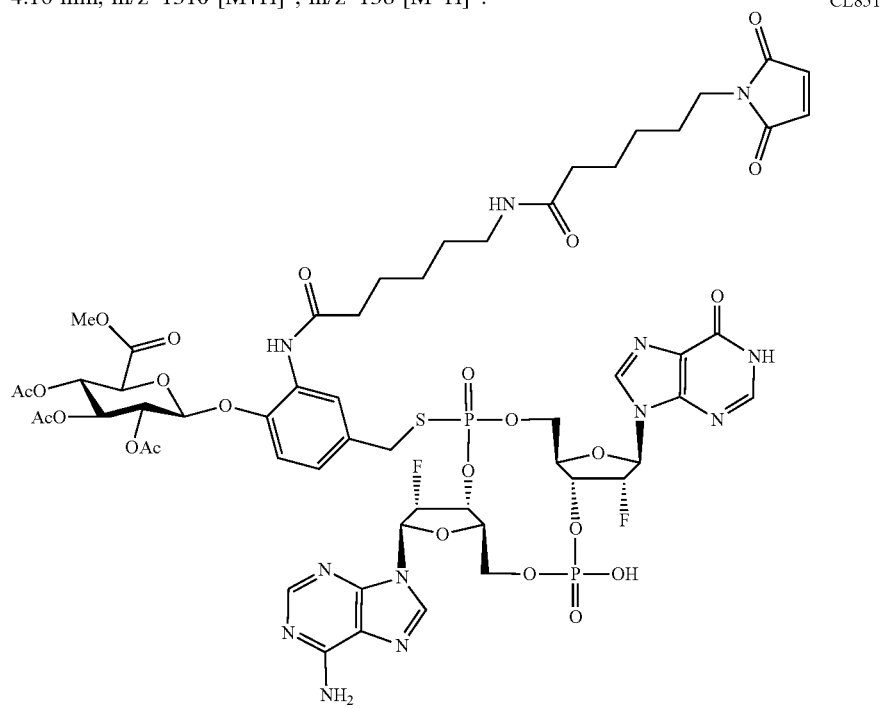

CL851

Compound 10 (4.0 mg, 5% yield) was obtained from Intermediate 1.24 (62.7 mg, 71.9 μmol) and Intermediate 2.62 (37.6 mg, 55.3 μmol) in THF using a similar procedure to that described for Compound 4. LC-MS: Rt=4.09 min, m/z=1423 [M+H]$^+$, m/z=1421 [M−H]$^−$.

Compound 11

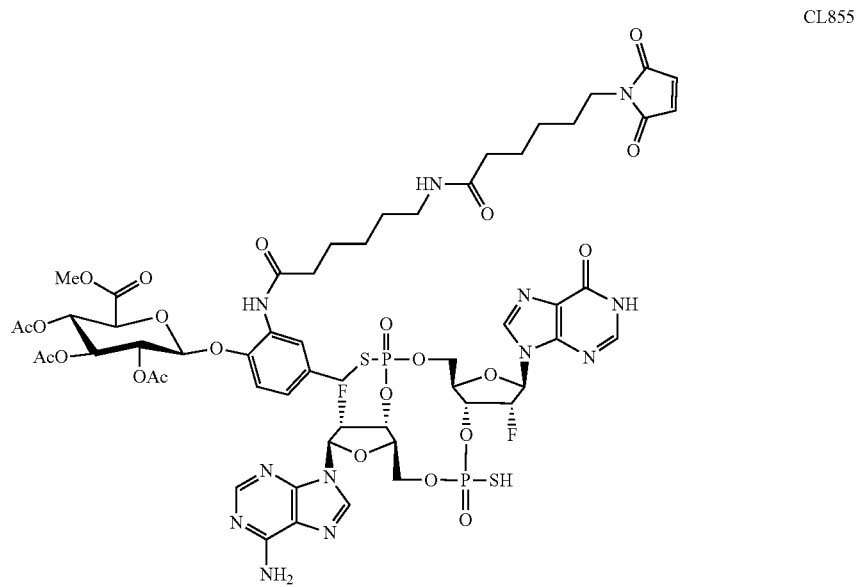

CL855 c-[2'FdAM(PS-(3-(Maleimido-di-hexanamido)-4-(Methyl-2,3,4-tri-O-acetyl-D-glucopyranouronate)-benzyl)-2'FdIMPS]

Compound 12

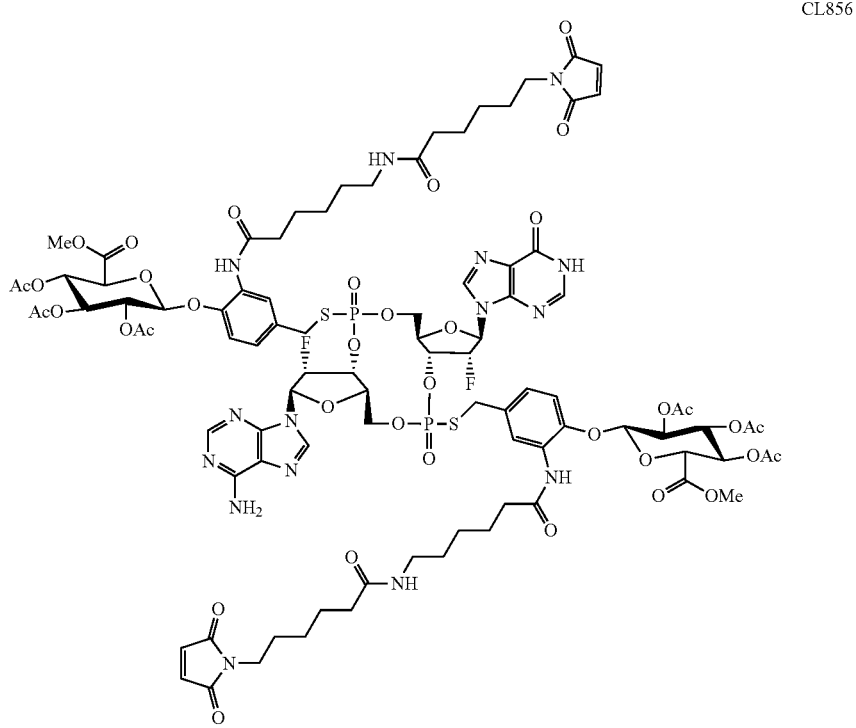

c-[2'FdAM(PS-(3-(Maleimido-hexanamido)-4-(Methyl-2,3,4-tri-O-acetyl-D-glucopyranouronate)-
benzyl)-2'FdIM(PS-(3-(Maleimido-hexanamido)-4-(Methyl-
2,3,4-tri-O-acetyl-D-glucopyranouronate)-benzyl)]

Compounds 11 and 12 were obtained from Intermediate 1.22 (72.0 mg, 0.10 mmol) and Intermediate 2.62 (90.0 mg, 0.10 mmol) in DMF using a similar procedure to that described for Compound 4 to provide: 23.0 mg (15% yield) of Compound 11. LC-MS: Rt=4.32 min, m/z=1439 [M+H]$^+$, m/z=1437 [M−H]$^-$; 24.0 mg (12% yield) of Compound 12. LC-MS: Rt=5.41 min, m/z=2182 [M+H]$^+$, m/z=2180 [M−H]$^-$ Compound 13:

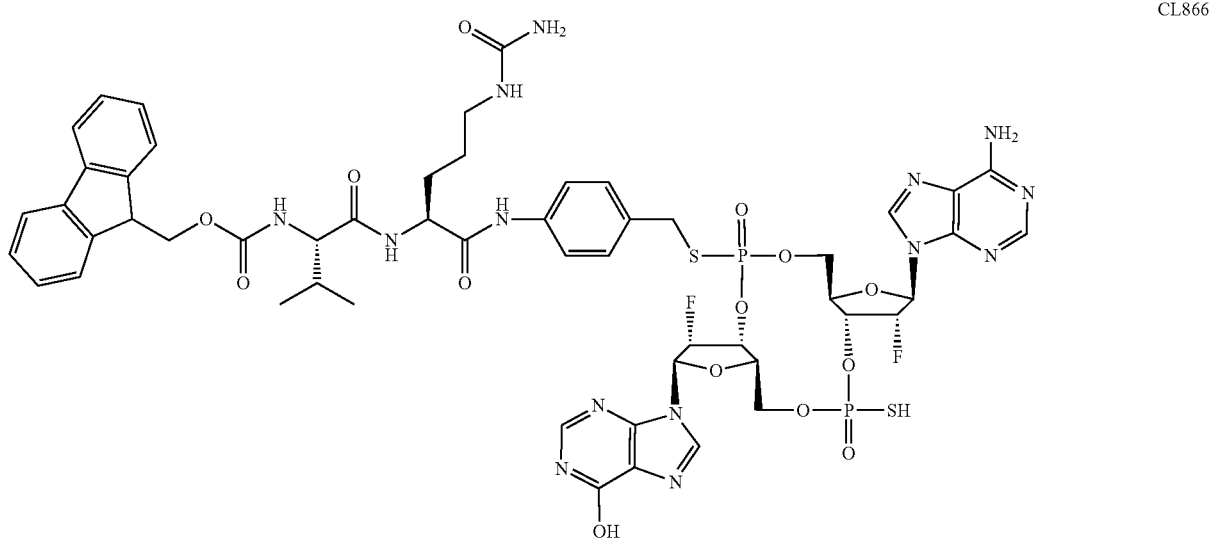

c-[2'FdAM(PS-PAB-Cit-Val-Fmoc)-2'FdIM(PS)]

Compound 14

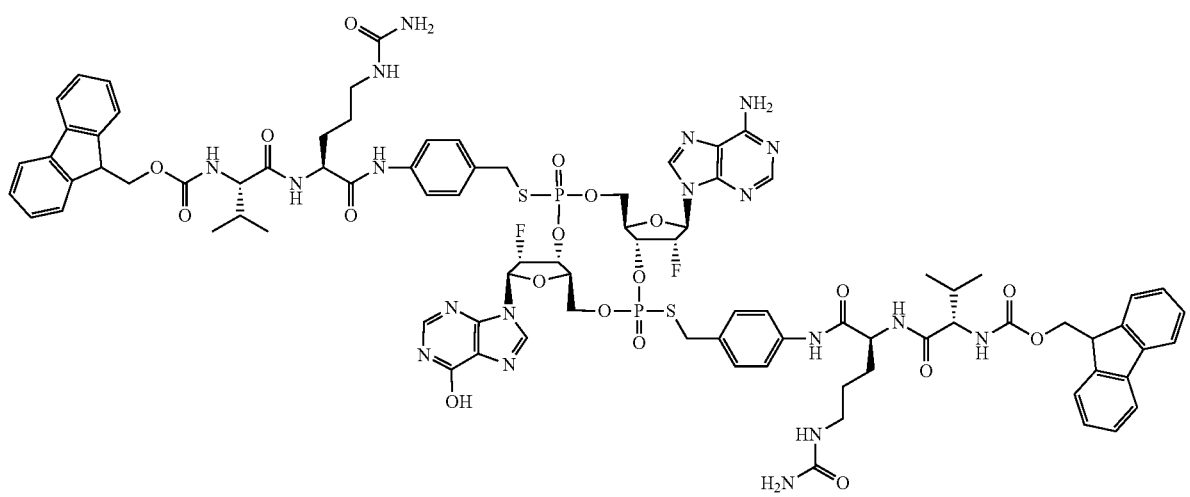

c-[2'FdAM(PS-PAB-Cit-Val-Fmoc)-2'FdIM(PS-PAB-Cit-Val-Fmoc)]

Compounds 13 and 14 were obtained from Intermediate 1.22 (300 mg, 0.431 mmol) and Intermediate 2.69 (338 mg, 0.474 mmol) in DMF using a similar procedure to that described for Compound 2 to provide 287.0 mg (52% yield) of Compound 13: LC-MS: Rt=4.65, 4.50 and 4.83 min, m/z=1279 [M+H]$^+$, m/z=1277 [M−H]$^-$, and 130 mg (16% yield) of Compound 14: LC-MS: Rt=5.66 min, m/z=1863 [M+H]$^+$, m/z=1861 [M−H]$^-$.

Compound 15

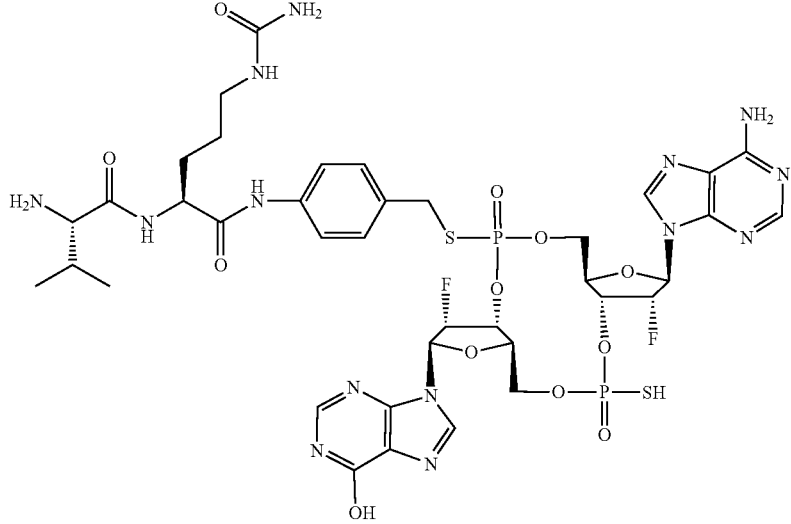

c-[2'FdAM(PS-PAB-Cit-Val)-2'FdIM(PS)]

Compound 15 (115 mg, 50% yield) was obtained from Compound 13 (280 mg, 0.219 mmol) using a similar procedure to that described for Compound 3. LC-MS: Rt=4.48, 4.65 and 4.77 min, m/z=1057 [M+H]⁺, m/z=1055 [M−H]⁻.

Compound 16

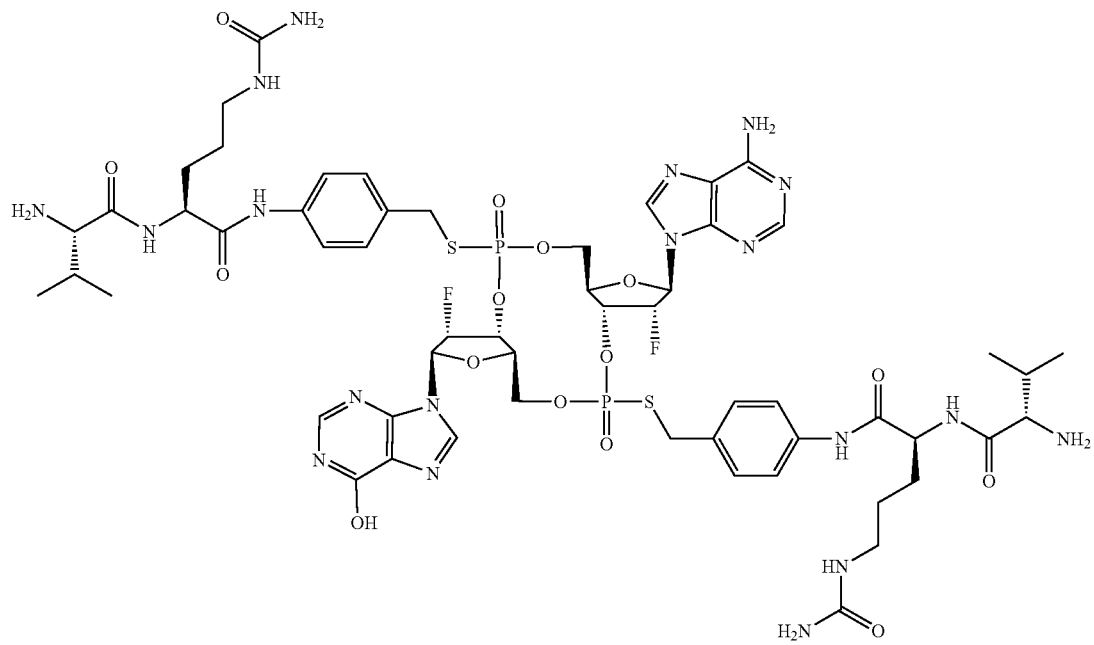

c-[2′FdAM(PS-PAB-Cit-Val)-2′FdIM(PS-PAB-Cit-Val)]

Compound 16 (55 mg, 58% yield) was obtained from Compound 14 (125 mg, 0.067 mmol) using a similar procedure to that described for Compound 3. LC-MS: Rt=4.91, 5.07 and 5.21 min, m/z=1419 [M+H]⁺, m/z=1417 [M−H]⁻.

Compound 17

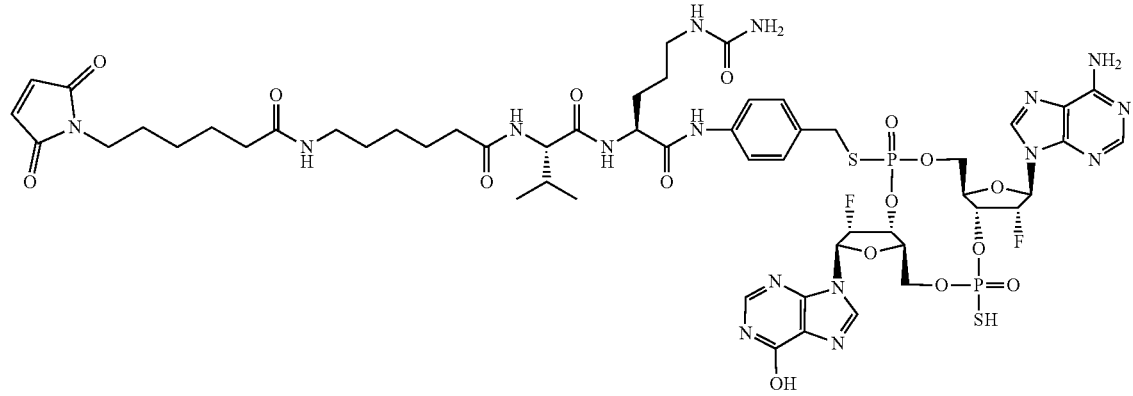

c-[2′FdAM(PS-PAB-Cit-Val)-Aca-Aca-MaI)-2′FdIM(PS)]

Compound 17 (16 mg, 30% yield) was obtained from Compound 15 (40 mg, 0.038 mmol) and Intermediate 2.66 (14 mg, 0.042 mmol) using a similar procedure to that described for Compound S. LC-MS: Rt=4.48, 4.65 and 4.77 min, m/z=1057 [M+H]+, m/z=1055 [M–H]−.

Compound 18

CL870

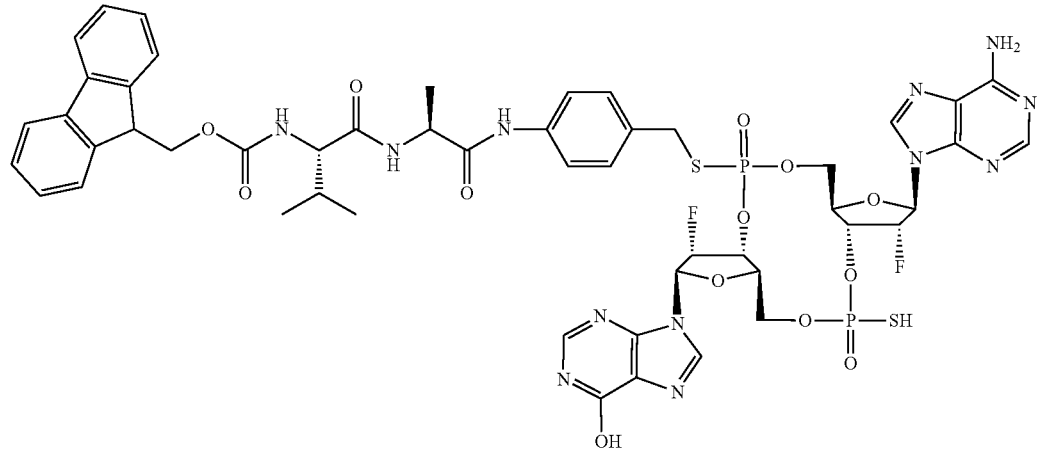

c-[2′FdAM(PS-PAB-Ala-Val-Fmoc)-2′FdIM(PS)]

Compound 19

CL871

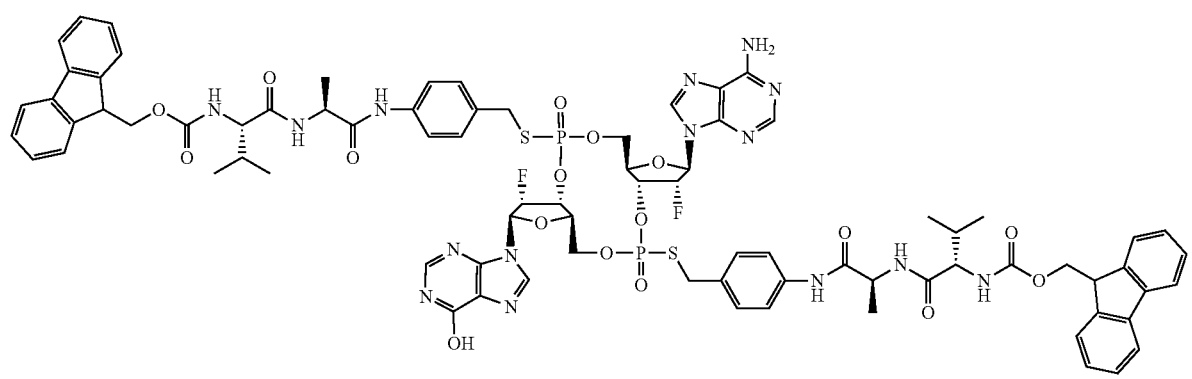

c-[2′FdAM(PS-PAB-Ala-Val-Fmoc)-2′FdIM(PS-PAB-Ala-Val-Fmoc)]

Compounds 18 and 19 were obtained from Intermediate 1.22 (300 mg, 0.431 mmol) and Intermediate 2.6 (351 mg, 0.561 mmol) in DMF using a similar procedure to that described for Compound 2 to provide 150.0 mg (50% yield) of Compound 18: LC-MS: Rt=4.62, 4.73 and 4.90 min, m/z=1194 [M+H]+, m/z=1192 [M–H]−, and 170 mg (45% yield) of Compound 19: LC-MS: Rt=6.17, 6.32 and 6.33 min, m/z=1691 [M+H]+, m/z=1689[M–H]−.

Compound 20

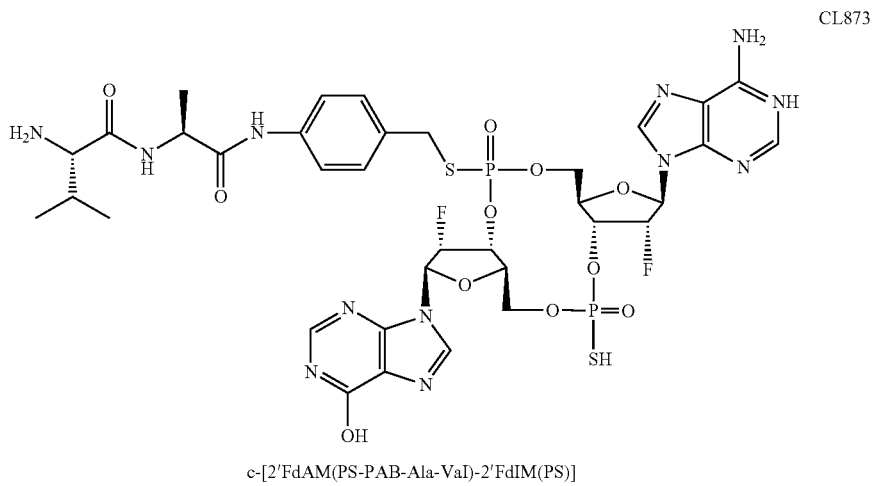

c-[2'FdAM(PS-PAB-Ala-Val)-2'FdIM(PS)]

Compound 20 (95 mg, 76% yield) was obtained from Compound 18 (150 mg, 0.127 mmol) using a similar procedure to that described for Compound 3. LC-MS: Rt=3.23, 3.39 and 3.62 min, m/z=971 [M+H]$^+$, m/z=969 [M−H]$^-$.

Compound 21

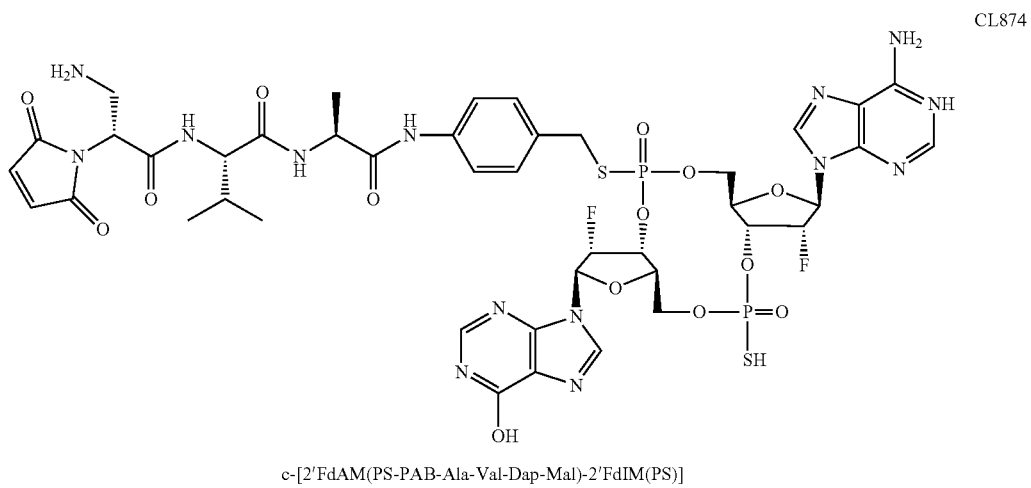

c-[2'FdAM(PS-PAB-Ala-Val-Dap-Mal)-2'FdIM(PS)]

To a solution Compound 20 (58 mg, 0.060 mmol) in dry DMF, Mal-L-Dap(Boc)-OH (28 mg, 0.060 mmol), DIEA (31 µL, 0.18 mmol) and HATU (25 mg, 0.066 mmol) were added. The solution was stirred for 3h at rt. Then the solution was diluted with AcOEt washed with water, NaHCO$_3$ and brine. The organic layer was dried over MgSO$_4$, filtered and concentrated in vacuo. The crude was treated with a solution of TFA and p-toluenethiol (16 mg, 0.128 mmol). The solution was stirred 5 min at rt, the solution was concentrated, the residue was triturated with acetone. The crude was purified on Cia column to provide Compound 21 (6.7 mg, 46% yield). LC-MS: Rt=3.72, 3.53 and 3.37 min, m/z=1137 [M+H]$^+$, m/z=1135 [M−H]$^-$.

Example 1.4: Synthesis of BAM-CDN Conjugates of the Invention

Compound 22

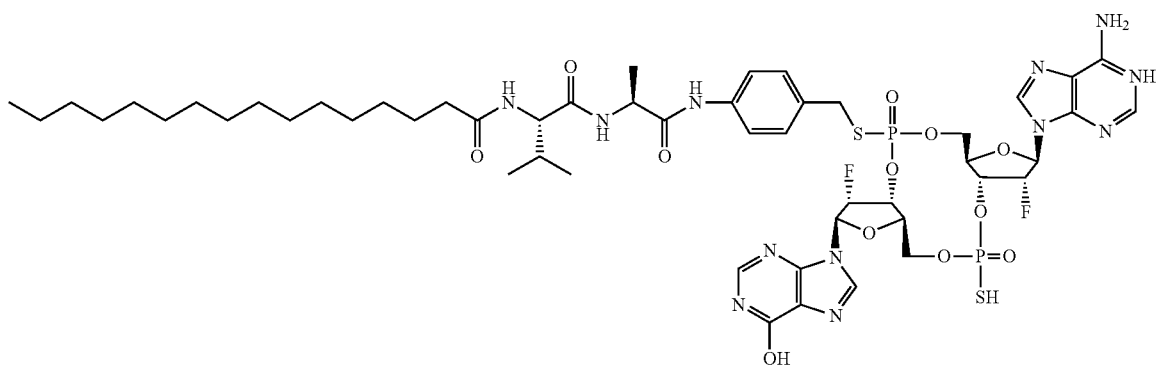

c-[2'FdAM(PS-PAB-Ala-Val-C$_{16}$)-dIMP]

Intermediate 1.5 (40 mg, 0.06 mmol) was dissolved in deionized water (2 ml.). A solution of Intermediate 2.10 (85 mg, 0.132 mmol) in acetone was added. The mixture was stirred overnight at rt in the dark. The solvents were removed in vacuo and the residue was applied to silica-gel column chromatography, using DCM/MeOH as eluent to provide 12 mg (25% yield) of Compound 22. LC-MS: Rt=7.97 min, m/z=1176 [M+H]$^+$, m/z=1174 [M−H]$^−$.

Compound 22 (CL808) belongs to Formula (V$_a$) and comprises a monophosphorothioate CDN (CL797), a PAB moiety as a connector, a Val-Ala specifier and a BAM consisting of a saturated fatty acid (C$_{16}$ carbon chain) to facilitate CDN penetration into cell.

Compound 23:

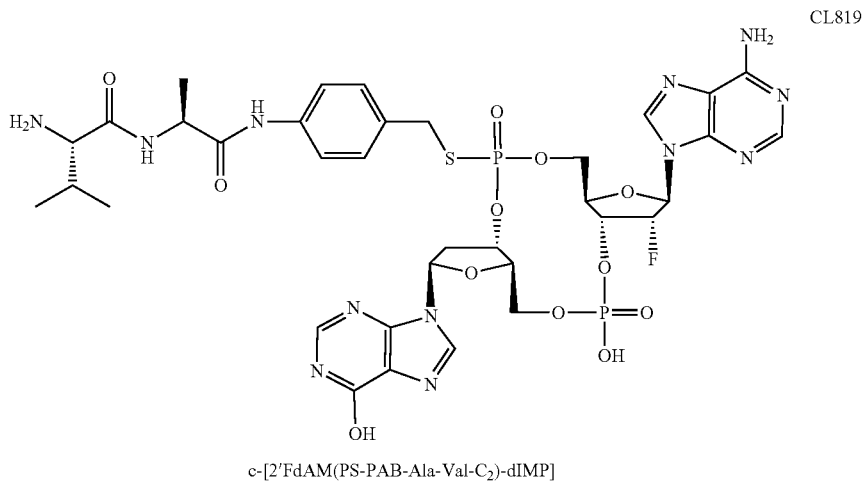

c-[2'FdAM(PS-PAB-Ala-Val-C$_2$)-dIMP]

Compound 23 was obtained from Intermediate 1.5 (60 mg, 0.091 mmol) and Intermediate 2.14 (101 mg, 0.227 mmol) in DMF using a similar procedure to that described for Compound 4 to provide 12.8 mg (14% yield) of Compound 23. LC-MS: Rt=3.22 min, m/z=979 [M+H]$^+$, m/z=977 [M−H]$^−$.

Compound 24:

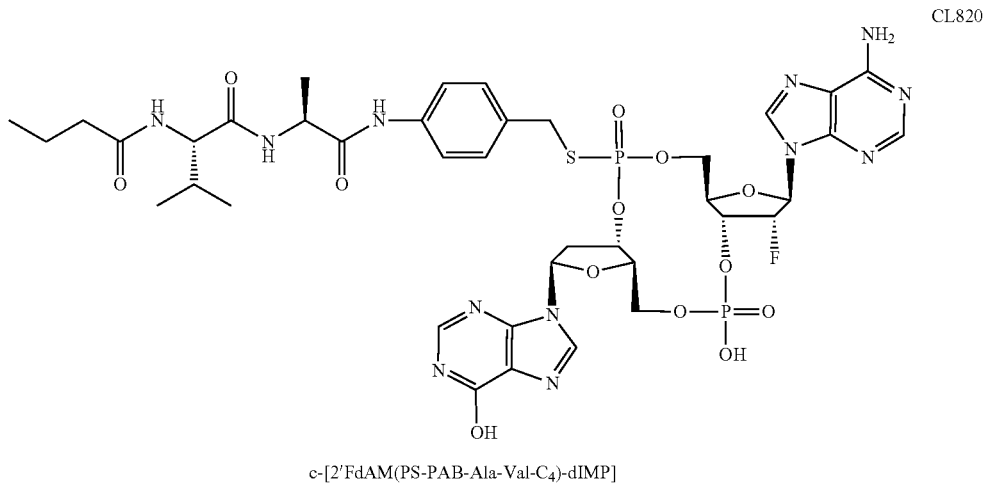

c-[2'FdAM(PS-PAB-Ala-Val-C₄)-dIMP]

Compound 24 was obtained from Intermediate 1.5 (60 mg, 0.091 mmol) and Intermediate 2.18 (107 mg, 0.227 mmol) In DMF using a similar procedure to that described for Compound 4 to provide 12.0 mg (13% yield) of Compound 24. LC-MS: Rt=3.46 min, m/z=1007 [M+H]$^+$, m/z=1005 [M−H]$^-$.

Compound 25:

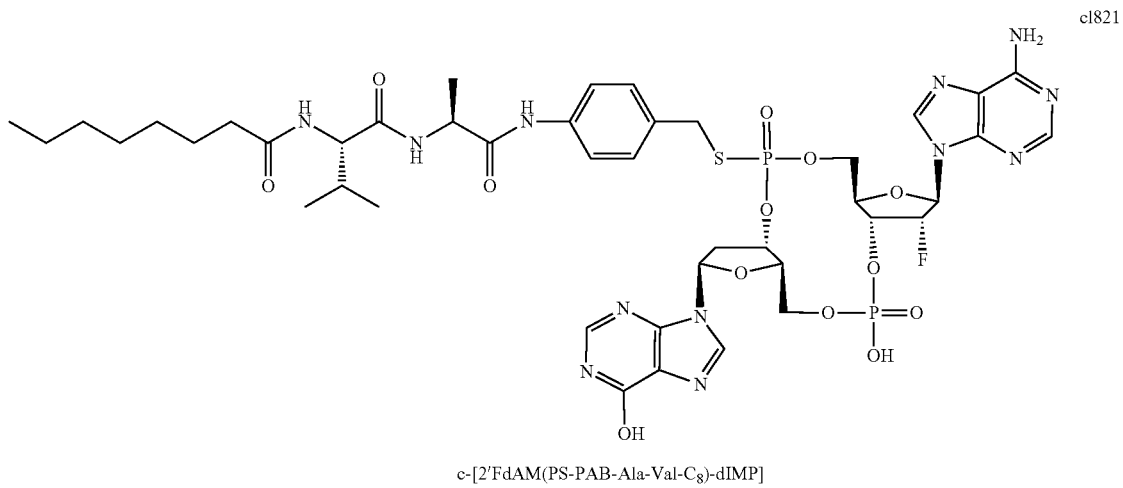

c-[2'FdAM(PS-PAB-Ala-Val-C₈)-dIMP]

Compound 25 was obtained from Intermediate 1.5 (60 mg, 0.091 mmol) and Intermediate 2.22 (120 mg, 0.227 mmol) in DMF using a similar procedure to that described for Compound 4 to provide 12.0 mg (12% yield) of Compound 25. LC-MS: Rt=4.35 min, m/z=1064 [M+H]$^+$, m/z=1065 [M−H]$^-$.

Compound 26
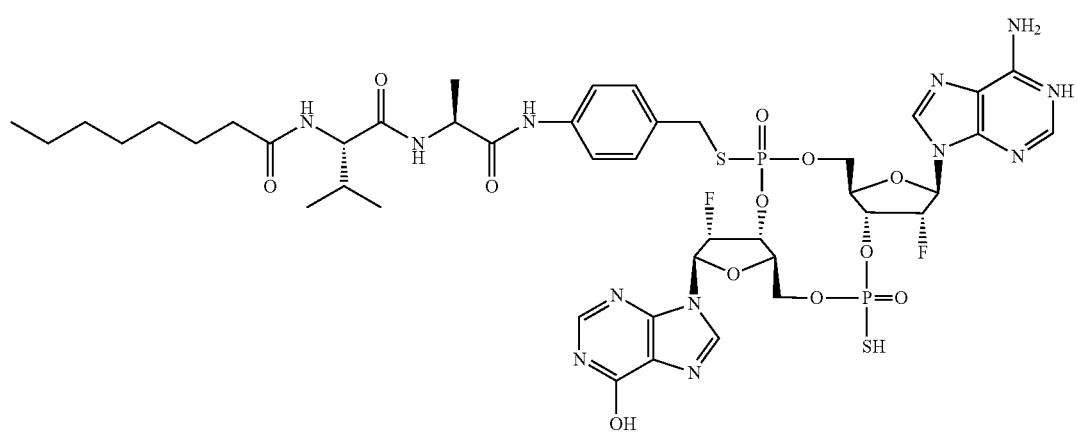
c-[2′FdAM(PS-PAB-Ala-Val-C$_8$)-2′FdIMPS]
Compound 27
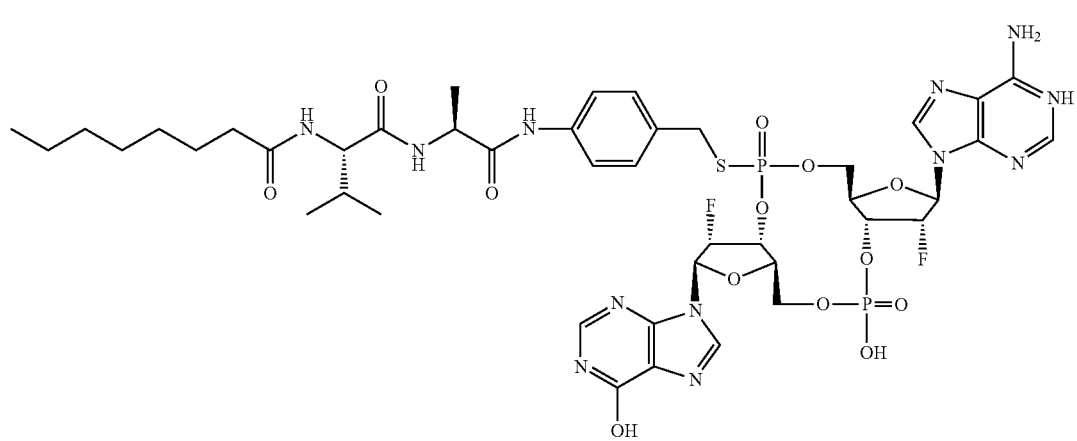
c-[2′FdAM(PS-PAB-Ala-Val-C$_8$)-2′FdIMP]
Compound 28
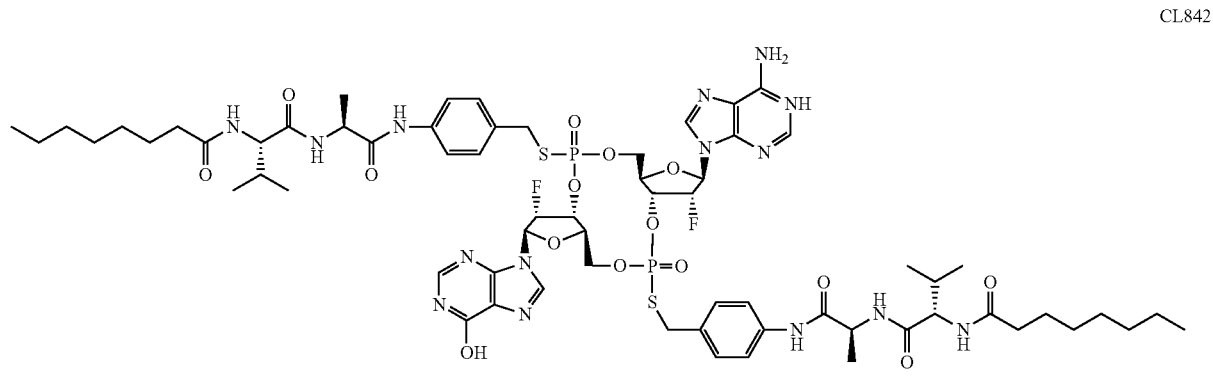
c-[2′FdAM(PS-PAB-Ala-Val-C$_8$)-2′FdIM(PS-PAB-Ala-Val-C$_8$)]

Compounds 26, 27 and 28 were obtained from Intermediate 1.22 (51 mg, 0.073 mmol) and Intermediate 2.22 (39 mg, 0.073 mmol) in DMF using a similar procedure to that described for Compound 4 to provide: 5.0 mg (6% yield) of Compound 26. LC-MS: Rt=4.44 min, m/z=1098 [M+H]$^+$, m/z=1096 [M−H]$^−$; 1.4 mg (1.8% yield) of Compound 27. LC-MS: Rt=4.27 min, m/z=1081 [M+H]$^+$, m/z=1079 [M−H]$^−$; 8.4 mg (10% yield) of Compound 28. LC-MS: Rt=6.05 min, m/z=1498 [M+H]$^+$, m/z=1496 [M−H]$^−$ Compound 29

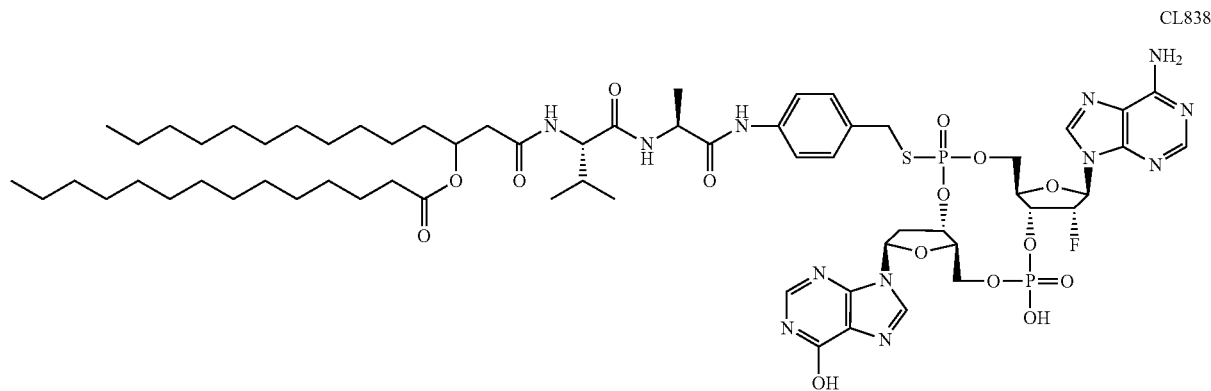

c-[2'FdAM(PS-PAB-Ala-Val-C$_{14}$/C$_{14}$)-dIMP]

Compound 29 was obtained from Intermediate 1.5 (80 mg, 0.121 mmol) and Intermediate 2.26 (152 mg, 0.181 mmol) in DMF using a similar procedure to that described for Compound 4 to provide 17.0 mg (10% yield) of Compound 29. LC-MS: Rt=7.05 and 7.26 min, m/z=1374 [M+H]$^+$, m/z=1372 [M−H]$^−$.

Compound 30

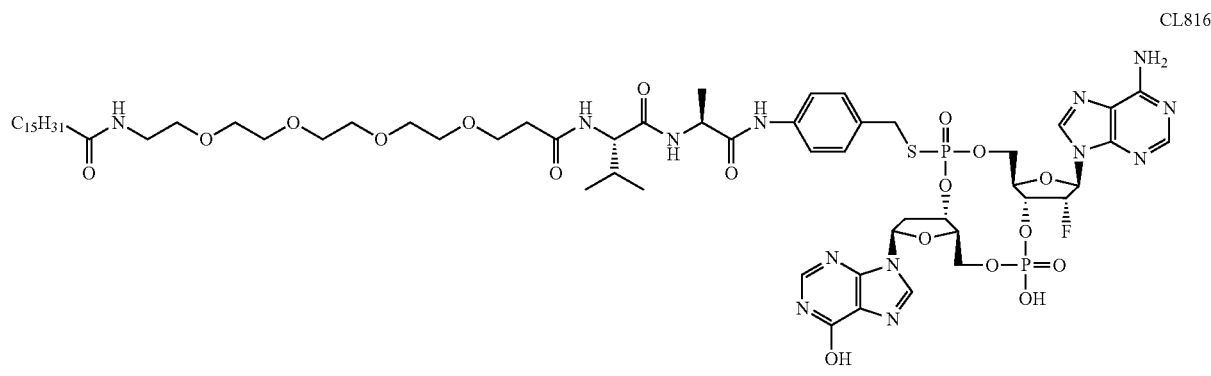

c-[2'FdAM(PS-PAB-Ala-Val-AEEEEP-C$_{16}$)-dIMP]

Compound 30 was obtained from Intermediate 1.5 (30 mg, 0.045 mmol) and Intermediate 2.38 (121 mg, 0.136 mmol) in Acetone using a similar procedure to that described for Compound 4 to provide 33 mg (51% yield) of Compound 30. LC-MS: Rt=5.66 min, m/z=1423 [M+H]$^+$, m/z=1421 [M−H]$^−$.

Compound 31
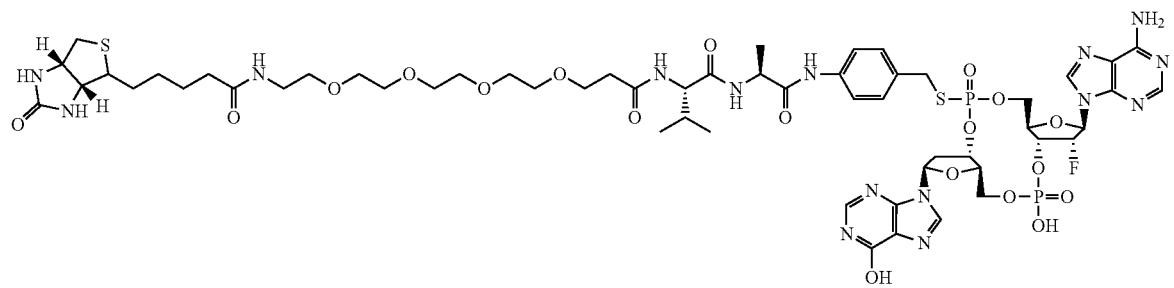
c-[2′FdAM(PS-PAB-Ala-Val-(AEEA)₄-Biotin)-dIMP]
To a solution of Compound 6 (66 mg, 0.043 mmol) in DMF (1 mL) DIEA (0.023 ml, 0.130 mmol), D-Biotin (12 mg, 0.053 mmol) and HATU (18 mg, 0.048 mmol) were added. The mixture was stirred at rt overnight. Then the solvent was removed in vacuo and the residue was applied to a flash chromatography to provide 57 mg (75% yield) of Compound 31. LC-MS: Rt=3.48 and 3.59 min, m/z=1744 [M+H]⁺, m/z=1742 [M−H]⁻.

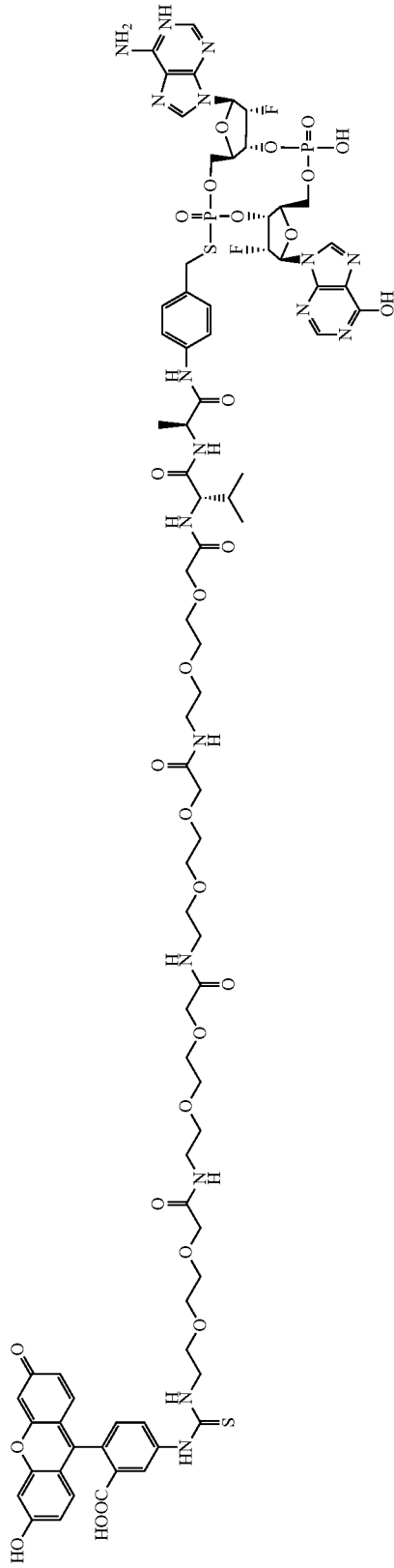
CL825
c-[2'FdAM(PS-PAB-Ala-Val-(AEEA)-FITC)-dIMP]
Compound 32

To a solution of Compound 6 (40 mg, 0.026 mmol) in DMF (1 ml) TEA (21.7 μL, 0.156 mmol), FITC (20.6 mg, 0.052 mmol) were added. The mixture was stirred at rt overnight. Then the solvent was removed in vacuo and the residue was applied to a flash chromatography to provide 34 mg (68% yield) of Compound 32. LC-MS: Rt=3.60 and 3.65 min, m/z=1907 [M+H]+, m/z=1905 [M−H]−.

Compound 33

CL826

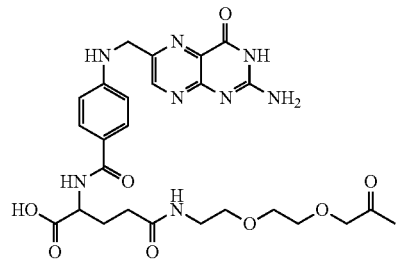

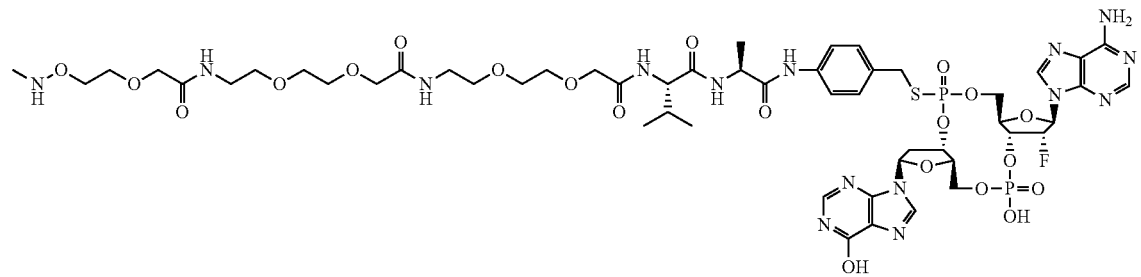

c[2′FdAM(PS-PAB-Ala-Val-(AEEA)4-Folic Acid)-dIMP]

To a solution of Compound 6 (40 mg, 0.026 mmol) in DMF (1 ml) DIEA (14.0 μL, 0.079 mmol), N-hydroxysuccinyl folate (21.0 mg, 0.040 mmol) were added. The mixture was stirred at rt for 4h. Then the solvent was removed in vacuo and the residue was applied to a flash chromatography with to provide 36 mg (70% yield) of Compound 33. LC-MS: Rt=3.20 and 3.31 min, m/z=1941 [M+H]+, m/z=1939 [M−H]−.

Compound 34

CL832

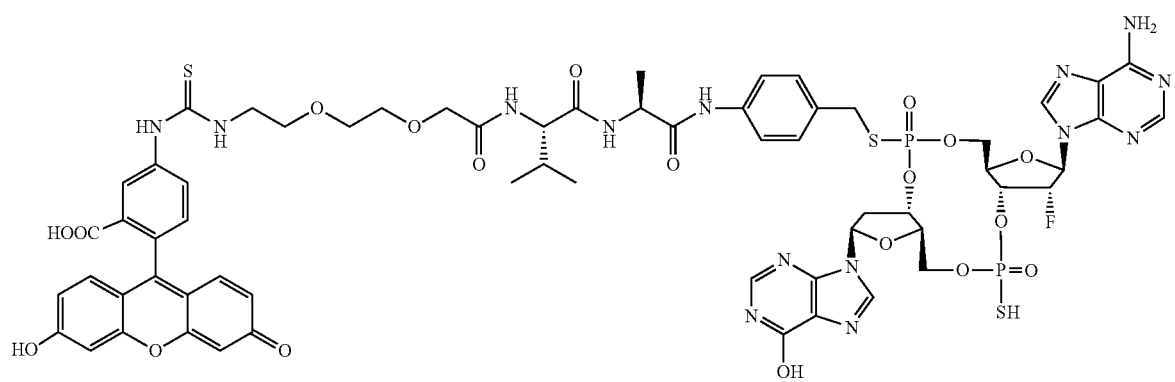

c-[2′FdAM(PS-PAB-Ala-Val-AEEA-FITC)-dIMP]

To a solution of Intermediate 3.3 (55 mg, 0.051 mmol) in DMF (1 ml) TEA (42.5 μL, 0.306 mmol), FITC (40.0 mg, 0.102 mmol) were added. The mixture was stirred at rt overnight. Then the solvent was removed in vacuo and the residue was applied to a flash chromatography with to provide 25 mg (33% yield) of Compound 34. LC-MS: Rt=3.02 min, m/z=1472 [M+H]$^+$, m/z=1470 [M−H]$^−$.

Compound 35

CL833

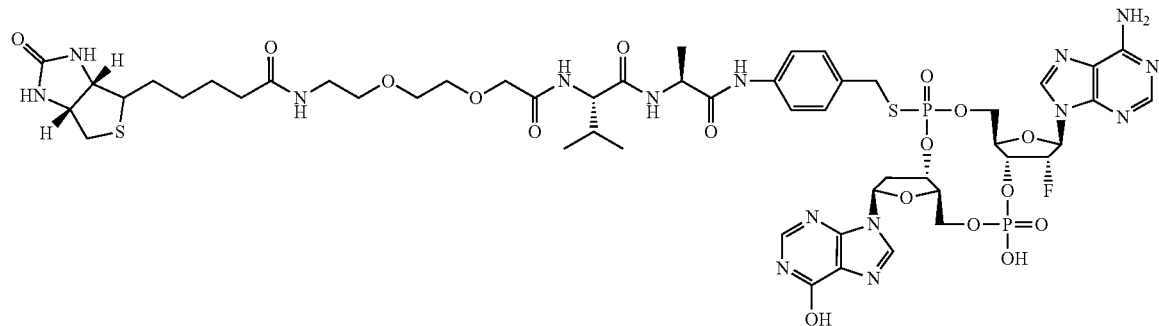

c-[2′FdAM(PS-PAB-Ala-Val-AEEA-Biotin)-dIMP]

To a solution of Intermediate 3.3 (55 mg, 0.051 mmol) in DMF (1 mL) DIEA (27 μL, 0.153 mmol), D-Biotin (14 mg, 0.053 mmol) and HATU (21 mg, 0.056 mmol) were added. The mixture was stirred at rt overnight. Then the solvent was removed and the residue was applied to a flash chromatography to provide 12 mg (18% yield) of Compound 35. LC-MS: Rt=3.45 and 3.58 min, m/z=1309 [M+H]$^+$, m/z=1307 [M−H]$^−$.

Compound 36

CL834

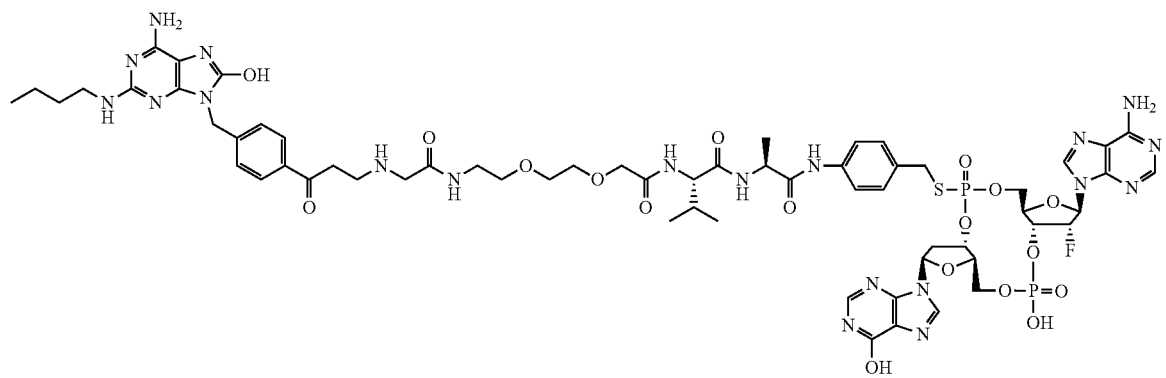

c-[2′FdAM(PS-PAB-Ala-Val-AEEA-CL264)-dIMP]

To a solution of Intermediate 3.3 (55 mg, 0.051 mmol) In DMF (1 ml) DIEA (27 μL, 0.153 mmol), CL264 (Invivo-Gen) (21 mg, 0.051 mmol) and HATU (21 mg, 0.056 mmol) were added. The mixture was stirred at rt overnight. Then the solvent was removed and the residue was applied to a flash chromatography to provide 60 mg (83% yield) of Compound 36. LC-MS: Rt=3.94 min, m/z=1478 [M+H]$^+$, m/z=1476 [M−H]$^−$.

Compound 37

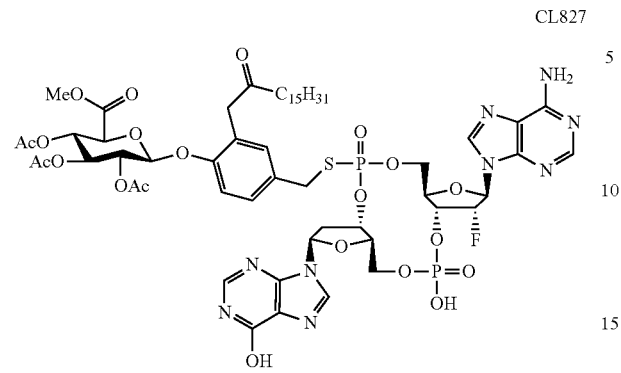

c-[2'FdAM(PS-(3-palmitamido-4-(Methyl-2,3,4-tri-O-acetyl-D-glucopyranouronate)-benzyl)-dIMP]

Compound 37 (85 mg, 77% yield) was obtained from Intermediate 1.5 (55 mg, 0.082 mmol) and Intermediate 2.51 (100 mg, 0.124 mmol) in THF using a similar procedure to that described for Compound 4. LC-MS: Rt=6.03 and 6.14 min, m/z=1337 [M+H]$^+$, m/z=1335 [M−H]$^-$.

Compound 38

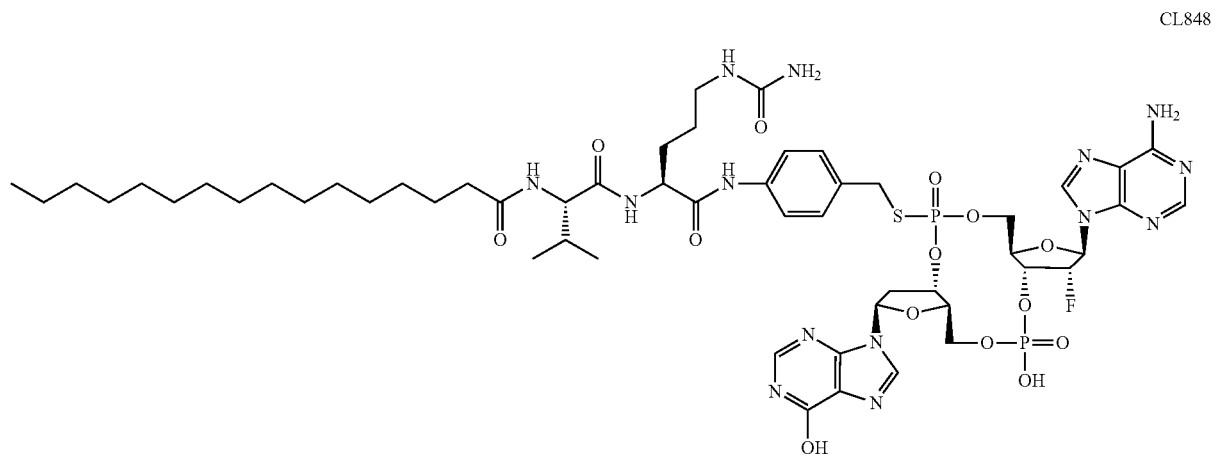

c-[2'FdAM(PS-PAB-Cit-Val-C$_{16}$)-dIMP]

Compound 38 (2.5 mg, 2.2% yield) was obtained from Intermediate 1.5 (60.0 mg, 91.0 μmol) and Intermediate 2.55 (60.0 mg, 0.140 mmol) in THF using a similar procedure to that described for Compound 4. LC-MS: Rt=5.46 and 5.53 min, m/z=1262 [M+H]$^+$, m/z=1260 [M−H]$^-$.

Compound 39

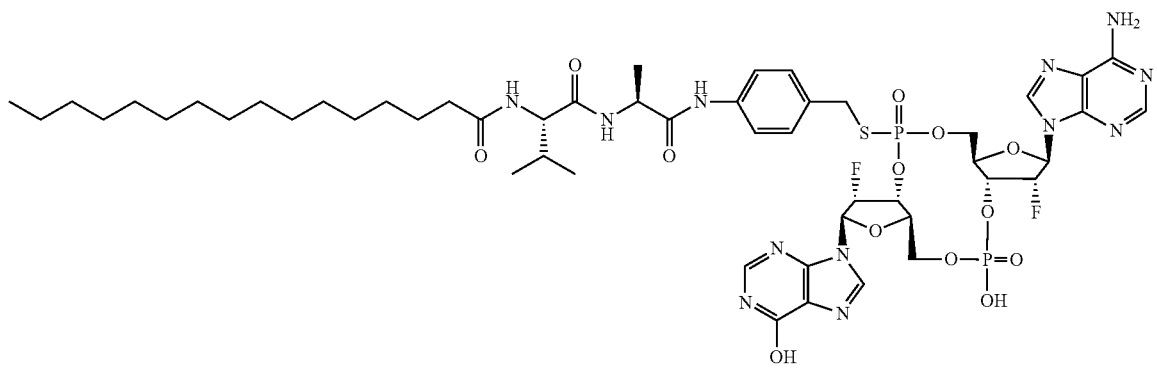

c-[2'FdAM(PS-PAB-Ala-Val-C$_{16}$)-2'FdIMP]

To a solution of Compound 8 (100.0 mg, 0.105 mmol) in DMF (1 ml) DIEA (55.0 µL, 0.314 mmol), Palmitic acid (29.5 mg, 0.115 mmol) and HATU (43.8 mg, 0.115 mmol) were added. The mixture was stirred at rt overnight. Then the solvent was removed and the residue was applied to a flash chromatography to provide 11 mg (9% yield) of Compound 39. LC-MS: Rt=5.67 and 5.73 min, m/z=1193 [M+H]$^+$, m/z=1191 [M−H]$^−$.

Compound 40

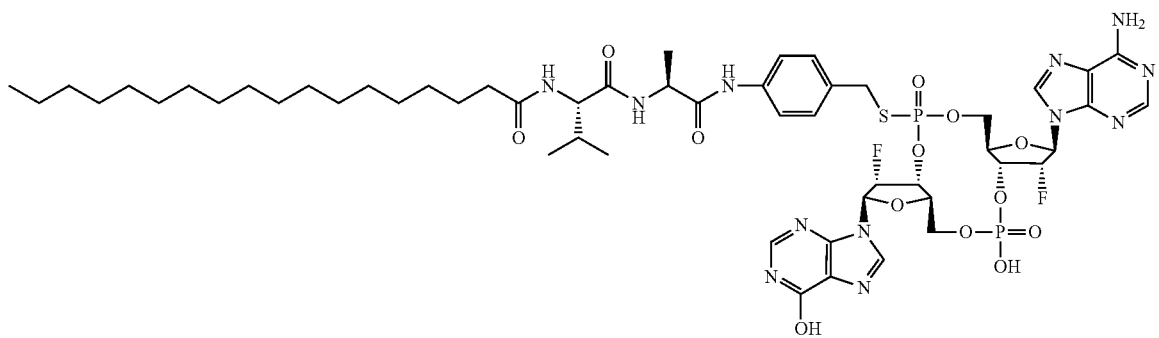

c-[2'FdAM(PS-PAB-Ala-Val-C$_{18}$)-2'FdIMP]

To a solution of Compound 8 (100.0 mg, 0.105 mmol) in DMF (1 ml) DIEA (55.0 µL, 0.314 mmol), Stearic acid (32.8 mg, 0.115 mmol) and HATU (43.8 mg, 0.115 mmol) were added. The mixture was stirred at rt overnight. Then the solvent was removed and the residue was applied to a flash chromatography to provide 1.9 mg (2% yield) of Compound 40. LC-MS: Rt=6.15 and 6.21 min, m/z=1121 [M+H]$^+$, m/z=1119 [M−H]$^−$.

Compound 41

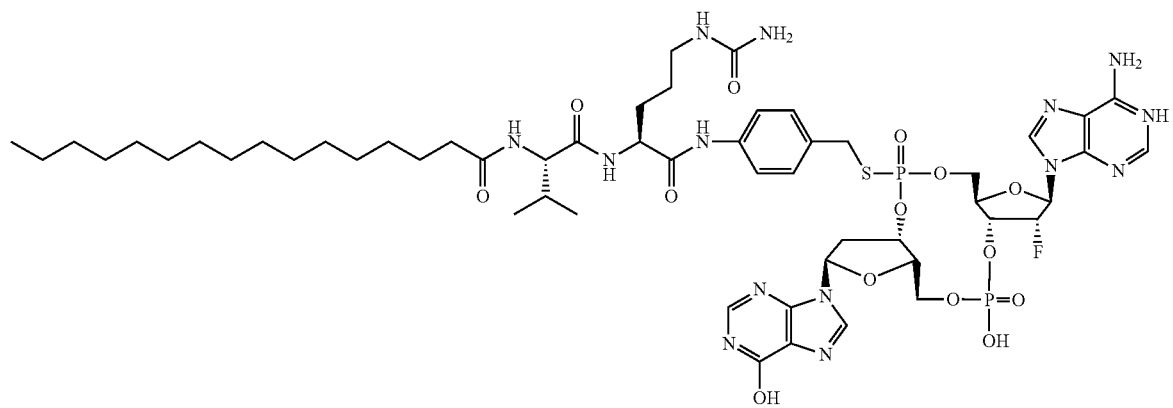

c-[2'FdAM(PS-(PAB-Cit-Val-C₁₆)-2'FdIMP]

Compound 41 12.5 mg (13% yield) was obtained from Intermediate 1.24 (50.0 mg, 74.0 μmol) and Intermediate 2.55 (80.0 mg, 110.0 μmol) in THF using a similar procedure to that described for Compound 4. LC-MS: Rt=5.49 and 5.59 min, m/z=1280 [M+H]⁺, m/z=1281 [M−H]⁻.

Compound 42

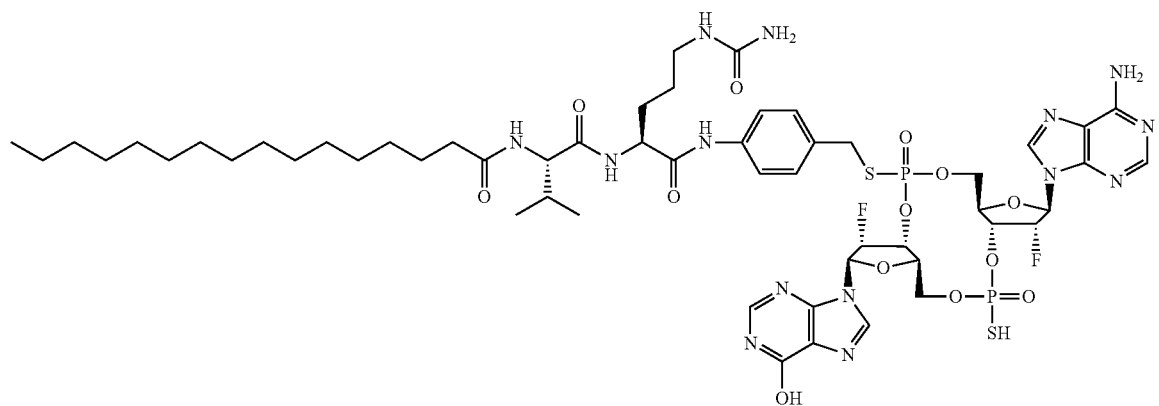

c-[2'FdAM(PS-(PAB-Cit-Val-C₁₆)-2'FdIM(PS)]

Compound 42 7.1 mg (10% yield) was obtained from Intermediate 1.22 (50.0 mg, 72.0 μmol) and Intermediate 2.55 (105.0 mg, 144.0 μmol) in THF using a similar procedure to that described for Compound 4. LC-MS: Rt=5.62 and 5.70 min, m/z=1296 [M+H]⁺, m/z=1294 [M−H]⁻.

Compound 43

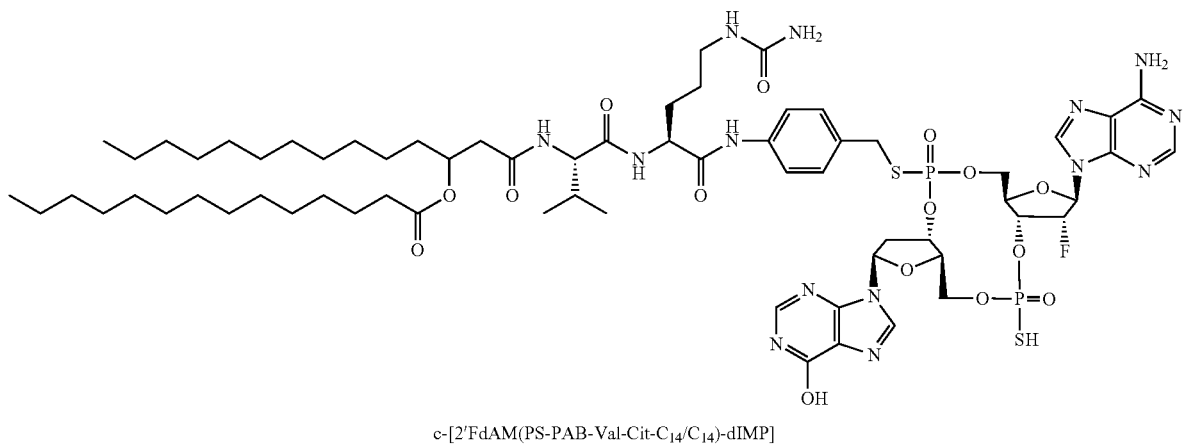

c-[2'FdAM(PS-PAB-Val-Cit-C14/C14)-dIMP]

Compound 43 (12.0 mg, 36% yield) was obtained from Intermediate 1.5 (15 mg, 0.023 mmol) and Intermediate 2.65 (42 mg, 0.042 mmol) in DMF using a similar procedure to that described for Compound 4. LC-MS: Rt=7.23 and 7.12 min, m/z=1460 [M+H]$^+$, m/z=1458 [M−H]$^−$.

Compound 44

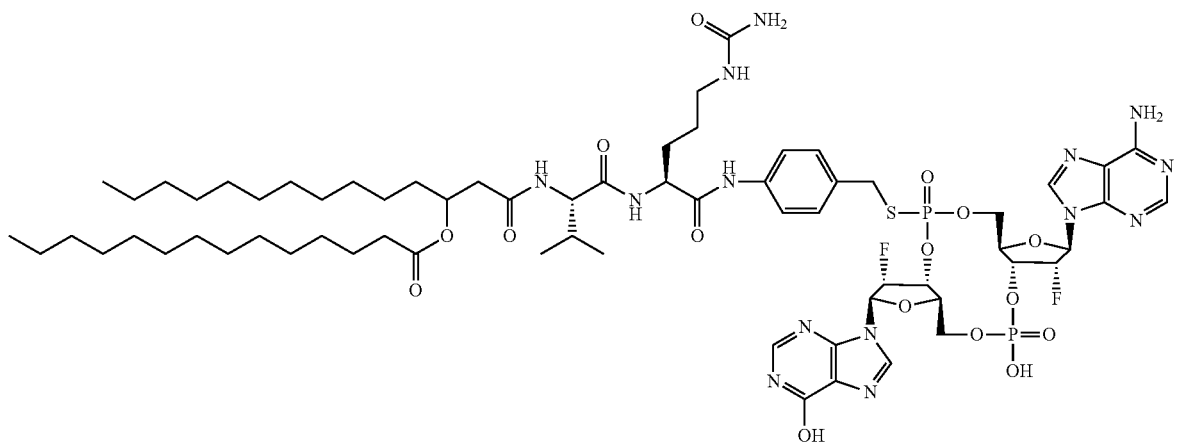

c-[2'FdAM(PS-PAB-Val-Cit-C14/C14)-2'FdIMP]

Compound 44 (24.0 mg, 26% yield) was obtained from Intermediate 1.24 (40 mg, 0.059 mmol) and intermediate 2.65 (109 mg, 0.118 mmol) in DMF using a similar procedure to that described for Compound 4. LC-MS: Rt=7.07 and 7.17 min, m/z=1478 [M+H]$^+$, m/z=1476 [M−H]$^−$.

Compound 45

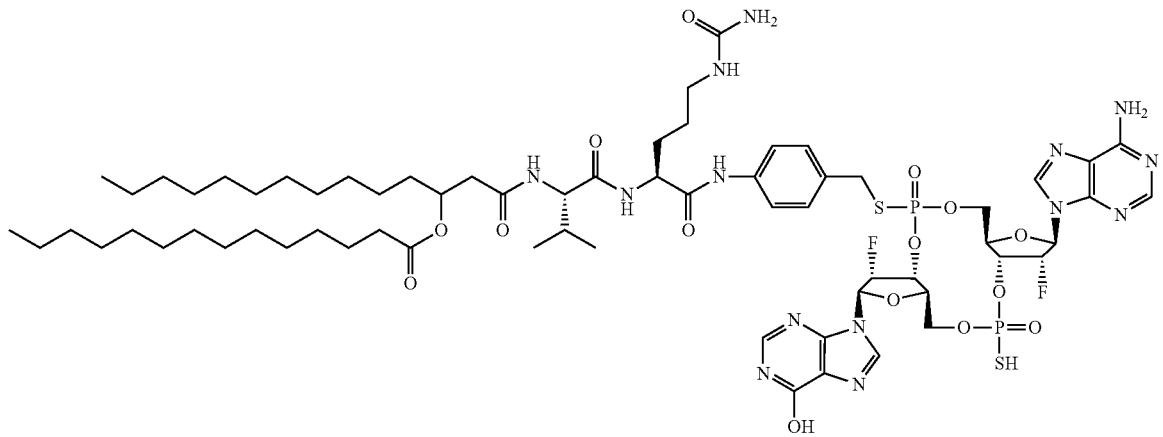

c-[2'FdAM(PS-PAB-Val-Cit-C₁₄/C₁₄)-2'FdIM(PS)]

Compound 45 (30.0 mg, 35% yield) was obtained from Intermediate 1.22 (40 mg, 0.059 mmol) and Intermediate 2.65 (80 mg, 0.086 mmol) in DMF using a similar procedure to that described for Compound 4. LC-MS: Rt=7.19 and 7.31 min, m/z=1494 [M+H]⁺, m/z=1492 [M−H]⁻.

Compound 46

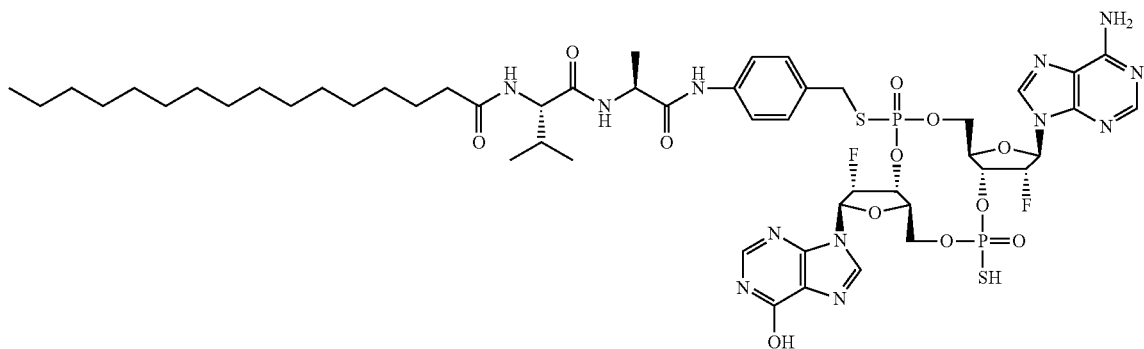

c-[2'FdAM(PS-PAB-Val-Cit-C₁₆)-2'FdIM(PS)]

Compound 46 (21.0 mg, 24% yield) was obtained from Intermediate 1.22 (72 mg, 0.050 mmol) and Intermediate 2.10 (60 mg, 0.093 mmol) in DMF using a similar procedure to that described for Compound 4. LC-MS: Rt=5.83, 5.92, 6.09 and 6.20 min, m/z=1210 [M+H]⁺, m/z=1208 [M−H]⁻.

General Procedure for Coupling CDN to an Antibody:

Intact and reduced antibody, with or without deglycosylation, were processed using the procedure as follow:

An antibody solution in phosphate buffer (Na₂HPO₄ 0.1 M+0.1 M NaCl+50 mM borax pH8) was reacted with 0.5 M dithiothreitol (DTT) Ratio DTT/Ac 250/1, the mixture was incubated at 37° C. for 35 min. The reduced antibody solution was cooled in an ice-bath at around 0° C. for 15 minutes. Then stock solution of Pro-CDN with a maleimido group in DMSO was added (Ratio Pro-CDN/Ac 15/1) and incubated on a roller-plate in a refrigerator at 4° C. for 3 hours. A solution of N-ethyl maleimide NEM (20 equiv.) in water was added and was incubated at RT for 35 min. The crude coupled antibody was purified using Zeba™ Spin desalting Columns (7 kD) with phosphate buffer (Phosphate buffer 0.05 M+0.15 M NaCl pH7.2). The coupled antibody concentration was obtained via the NanoDrop spectrophotometer. The coupled antibody was stored at 4° C.

The reduced coupled Antibody (i.e the de-glycosylated coupled Antibody) can be analyzed using LC/MS spectrometry. The Payload Distribution Analysis can be then determined with the DAR (Drug Antibody Ratio) calculator. Raw data obtained from LC/MS were deconvoluted.

For complete coupled Antibody (i.e glycosylated coupled Antibody), UV spectroscopy is the simplest and most convenient approach for DAR determination and works well with a wide range of conjugation methods, including cysteine-linked ISAC. As the UV spectrum of the antibody and the payload (here the CDN) have different maximum absorbance wavelengths (λmax) this method can be used to approximate the DAR. After measuring the extinction coefficients (E) of the antibody at λ=280 nm and that of the Pro-CDN at λ=260 nm, the individual concentrations of mAb and Pro-CDN can be determined by the solution of two simultaneous equations, from which the molar ratio (moles of Pro-CDN per mole of antibody) can be calculated.

| Antibody | Isotype |
|---|---|
| mAb1 | hIgG1 N298A |
| mAb2 | mIgG2a |
| mAb3 | mIgG1 |
| mAb4 | hIgG1 |

Figure 27:
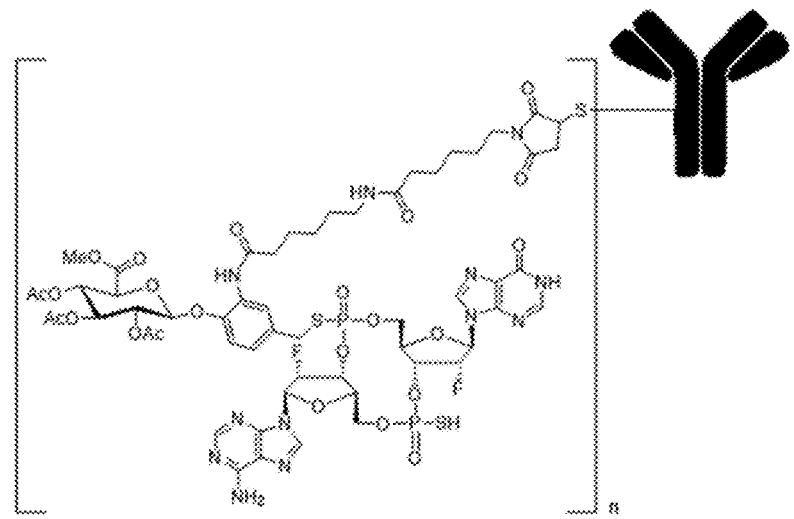
FIG. 27: Compound 47: Anti-PDL-1-mAb1-CL855

Compound 47: Anti-PDL-1-mAb1-CL855, as represented in FIG. 27, was obtained from Anti-PDL1-mAb1 (32.7 nmol) and Compound 11 (491.25 nmol) using the general procedure described above to obtain 21.3 nmol (65% Yield) of the conjugate.
DAR Determination:
The deconvolution parameters for this conjugate were set as follows:

| | Mass (Da) | Payload Distribution analysis |
|---|---|---|
| CL855 | 1 438.0 | |
| Reduced Antibody | 144 518.0 | |
| Coupled Reduced Antibody | 155 783.0 | 7.8 |
| | 157 259.0 | 8.8 |

| | UV | | |
|---|---|---|---|
| | 260 nm | 280 nm | DAR |
| Anti-PDL1-mAb3 | 0.152 | 0.283 | |
| Anti-PDL1-mAb3-CL855 | 0.436 | 0.418 | 7.2 |

Figure 28:
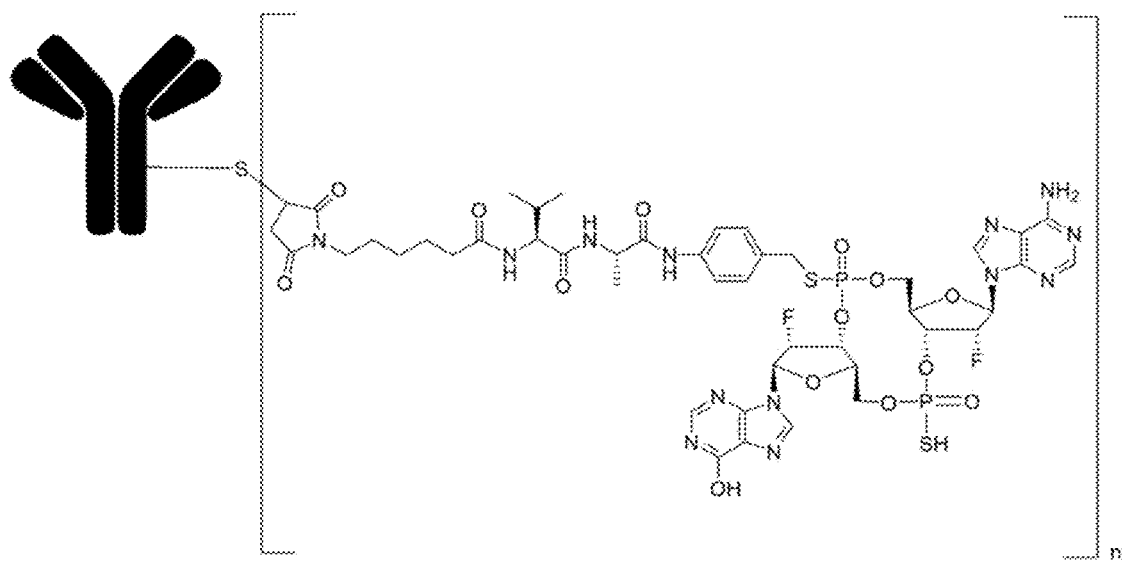
FIG. 28: Compound 48: Anti-GP7S-mAb2-CL843

Compound 48: Anti-GP75-mAb2-CL843, as represented in FIG. 28, was obtained from Anti-GP75-mAb2 (23.4 nmol) and Compound 5 (250 nmol) using the general procedure described above to obtain 15.1 nmol (64% Yield) of the conjugate.
DAR Determination:

| | UV | | |
|---|---|---|---|
| | 260 nm | 280 nm | DAR |
| Anti-PDL1-mAb3 | 2.220 | 3.930 | |
| Anti-PDL1-mAb3-CL843 | 3.204 | 4.387 | 1.81 |

Figure 29:
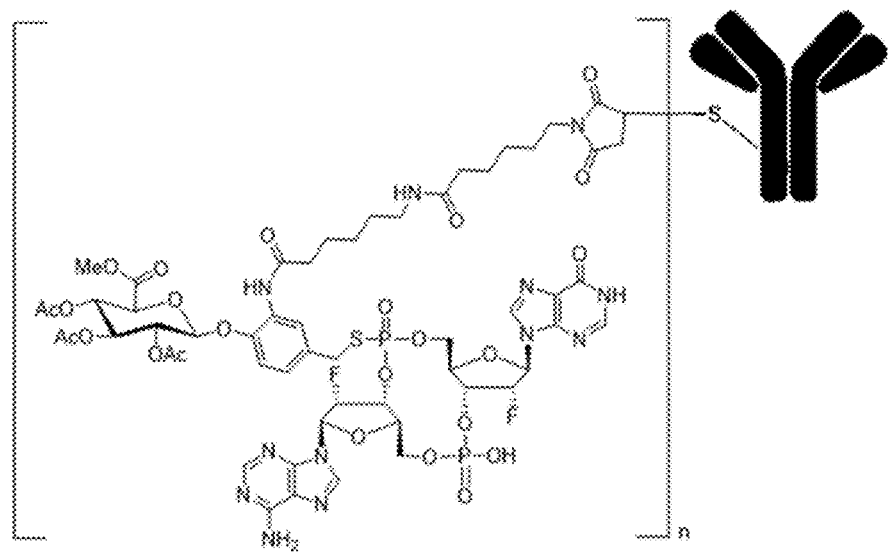
FIG. 29: Compound 49: Anti-GP75-mAb2-CL851

Compound 49: Anti-GP7S-mAb2-CL851, as represented in FIG. 29, was obtained from Anti-GP75-mAb2 (11.5 nmol) and Compound 10 (145 nmol) using the general procedure described above to obtain 7.1 nmol (62% yield) of the conjugate.
DAR Determination:

| | UV | | |
|---|---|---|---|
| | 260 nm | 280 nm | DAR |
| Anti-PDL1-mAb3 | 0.171 | 0.312 | |
| Anti-PDL1-mAb3-CL851 | 0.406 | 0.414 | 8.7 |

Figure 30:
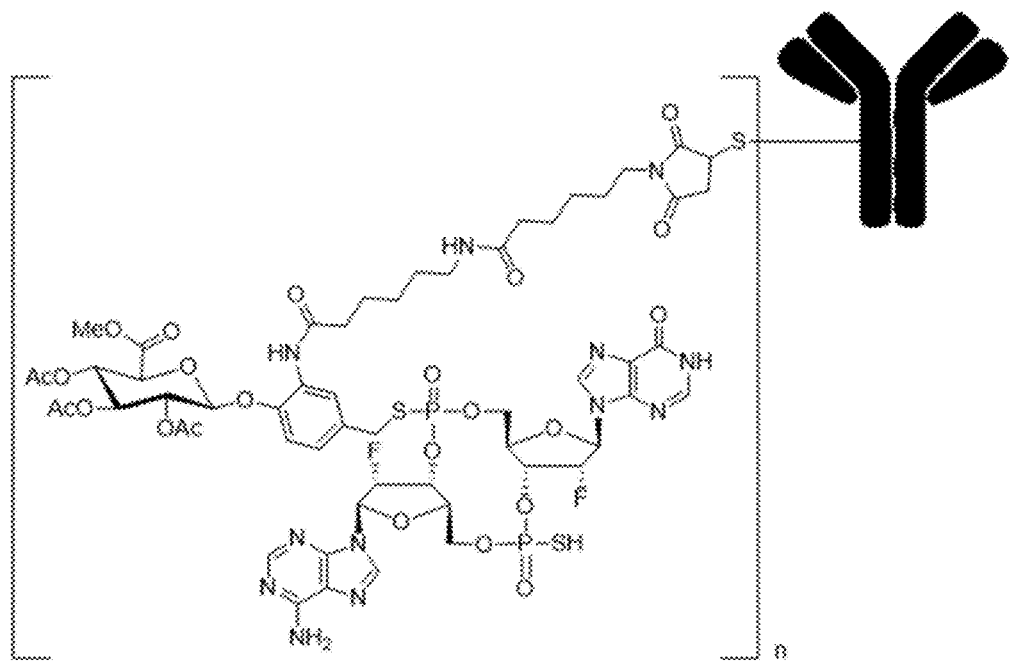
FIG. 30: Compound 50: Anti-CTLA4-mAb2-CL855

Compound 50: Anti-CTLA4-mAb2-CL8SS, as represented in FIG. 30, was obtained from Anti-CTLA4-mAb2 (26.5 nmol) and Compound 11 (422 nmol) using the general procedure described above to obtain 12.5 nmol (47% yield) of the conjugate.
DAR Determination:

| | UV | | |
|---|---|---|---|
| | 260 nm | 280 nm | DAR |
| Anti-PDL1-mAb3 | 0.139 | 0.264 | |
| Anti-PDL1-mAb3-CL855 | 0.506 | 0.457 | 9.8 |

Figure 31:
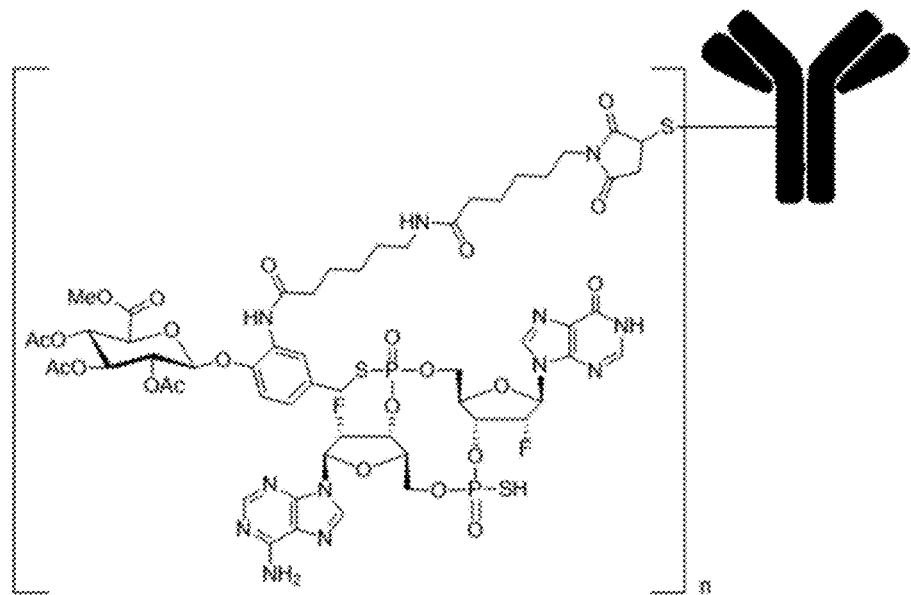
FIG. 31: Compound 51: Anti-PDL1-mAb3-CL855

Compound 51: Anti-PDL1-mAb3-CL8SS, as represented in FIG. 31, was obtained from Anti-PDL1-mAb3 (61.4 nmol) and Compound 11 (1242 nmol) using the general procedure described above to obtain 10 nmol (16% yield) of the conjugate.

Figure 32:
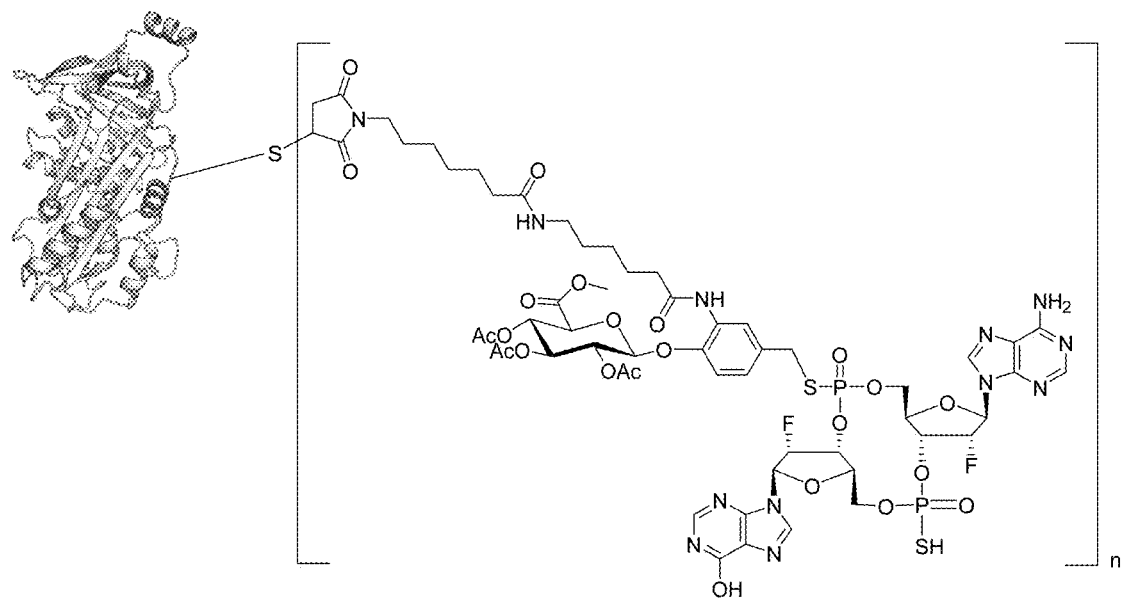
FIG. 32: Compound 52: Ova-CL855

Compound 52: Ova-CL855, as represented in FIG. 32, was obtained from Ova (16.1 nmol) and Compound 11 (226.8 nmol) using the general procedure described above to obtain 15.41 nmol (95% yield) of the conjugate.
DAR Determination:

| | UV | | |
|---|---|---|---|
| | 260 nm | 280 nm | DAR |
| Ova | 0.233 | 0.394 | |
| Ova-CL855 | 1.961 | 0.997 | 7.1 |

Figure 33:
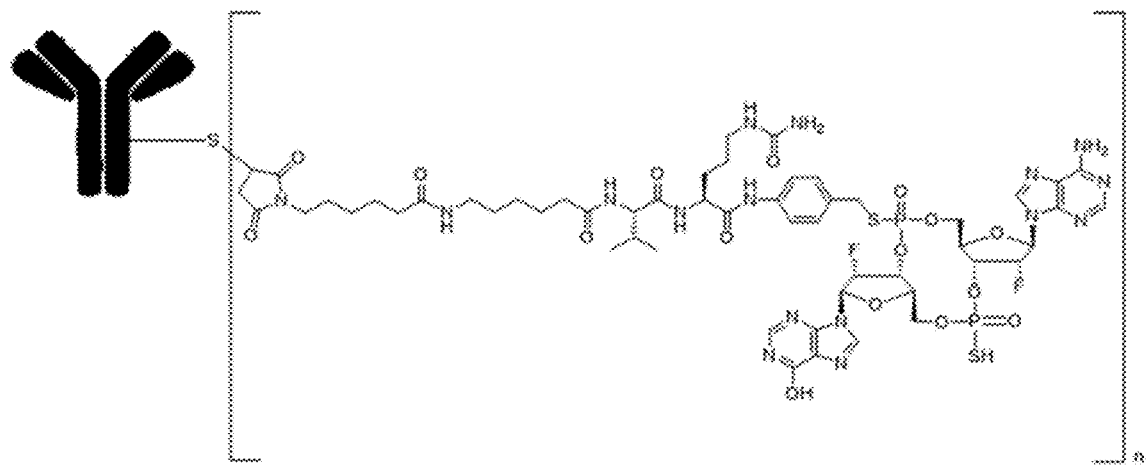
FIG. 33: Compound 53: Anti-PDL1-mAb1-CL862

Compound 53: Anti-PDL1-mAb1-CL862, as represented in FIG. 33, was obtained from Anti-PDL1-mAb1 (4.4 nmol) and Compound 17 (61.98 nmol) using the general procedure described above to obtain 3.79 nmol (86% Yield) of the conjugate.
DAR Determination:

| | UV | | |
|---|---|---|---|
| | 260 nm | 280 nm | DAR |
| Anti-PDL1-mAb1 | 0.530 | 0.933 | |
| Anti-PDL1-mAb1-CL862 | 0.712 | 0.793 | 4.3 |

Figure 34:
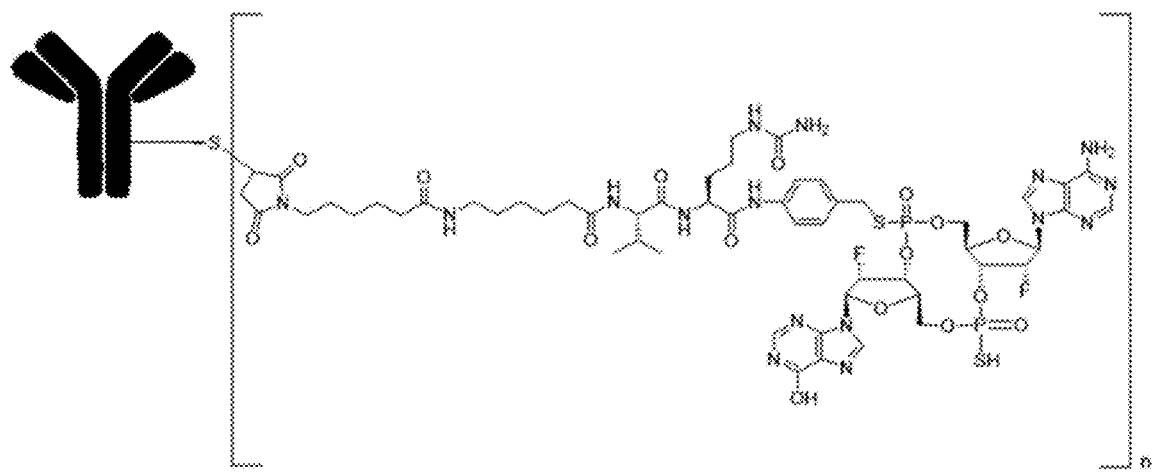
FIG. 34: Compound 54: Anti-PDL1-mAb3-CL862

Compound 54: Anti-PDL1-mAb3-CL862, as represented in FIG. 34, was obtained from Anti-PDL1-mAb3 (6.79 nmol) and Compound 17 (60.07 nmol) using the general procedure described above to obtain 4.25 nmol (73% yield) of the conjugate.
DAR Determination:

| | UV | | |
|---|---|---|---|
| | 260 nm | 280 nm | DAR |
| Anti-PDL1-mAb3 | 0.573 | 0.983 | |
| Anti-PDL1-mAb3-CL862 | 0.550 | 0.674 | 3.0 |

Figure 35:
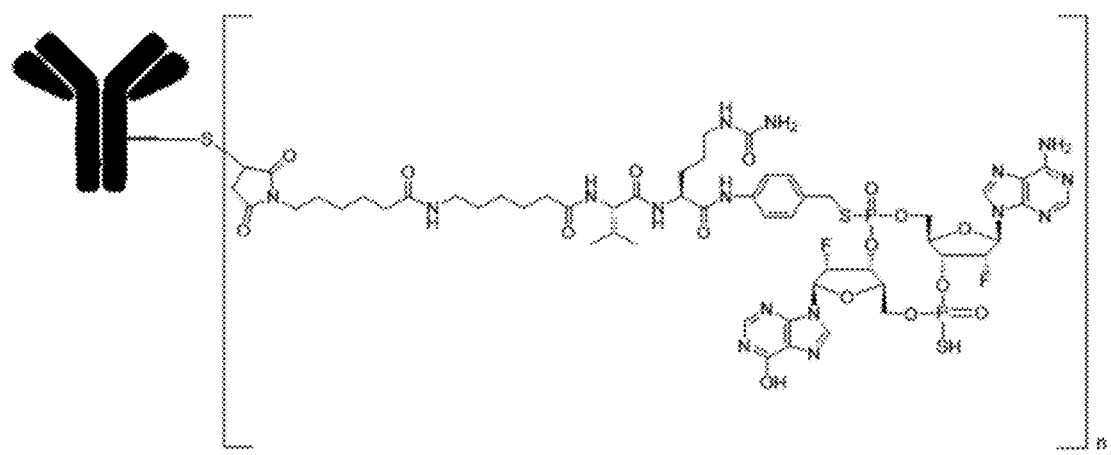
FIG. 35: Compound 55: Anti-GP75-mAb2-CL862

Compound 55: Anti-GP75-mAb2-CL862, as represented in FIG. 35, was obtained from Anti-GP7S-mAb2 (6.73 nmol) and Compound 17 (62.52 nmol) using the general procedure described above to obtain 4.78 nmol (79% yield) of the conjugate.

DAR Determination:

| | UV | | |
|---|---|---|---|
| | 260 nm | 280 nm | DAR |
| Anti-GP75-mAb2 | 0.545 | 0.975 | |
| Anti-GP75-mAb2-CL862 | 0.577 | 0.750 | 2.7 |

Figure 36:
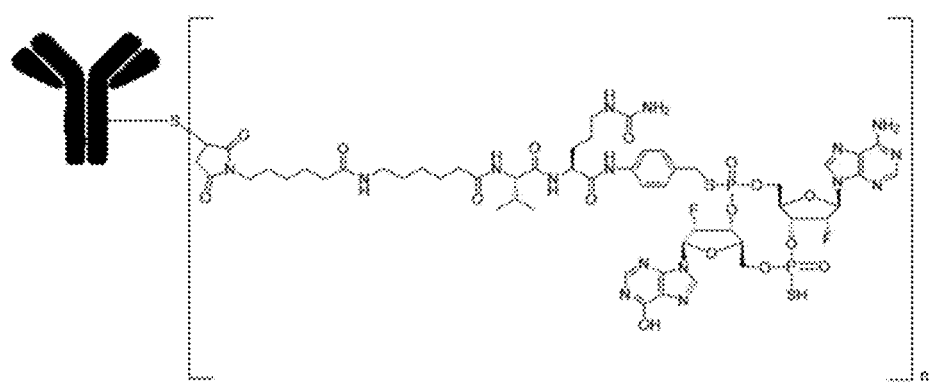
FIG. 36: Compound 56: Anti-CTLA4-mAb2-CL862

Compound 56: Anti-CTLA4-mAb2-CL862, as represented in FIG. 36, was obtained from Anti-CTLA4-mAb2 (6.56 nmol) and Compound 17 (61.08 nmol) using the general procedure described above to obtain 4.88 nmol (82% yield) of the conjugate.
DAR Determination:

| | UV | | |
|---|---|---|---|
| | 260 nm | 280 nm | DAR |
| Anti-CTLA4-mAb2 | 0.528 | 0.950 | |
| Anti-CTLA4-mAb2-CL862 | 0.639 | 0.782 | 3.4 |

Figure 37:
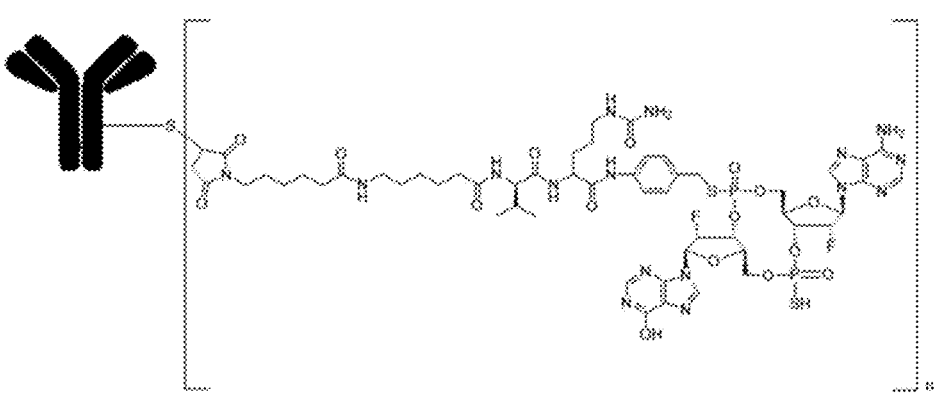
FIG. 37: Compound 57: Anti-HER2-mAb4-CL862

Compound 57: Anti-HER2-mAb4-CL862, as represented in FIG. 37, was obtained from Anti-HER2-mAb4 (7.10 nmol) and Compound 17 (65.42 nmol) using the general procedure described above to obtain 5.04 nmol (82% yield) of the conjugate.
DAR Determination:

| | UV | | |
|---|---|---|---|
| | 260 nm | 280 nm | DAR |
| Anti-HER2-mAb4 | 0.577 | 1.028 | |
| Anti-HER2-mAb4-CL862 | 0.649 | 0.803 | 3.2 |

Figure 38:
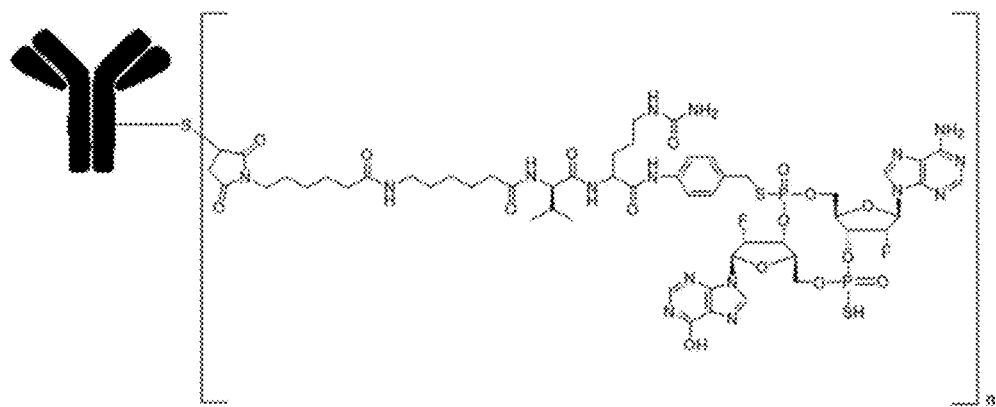
FIG. 38: Compound 58: Anti-βGAL-mAb4-CL862

Compound 58: Anti-βGAL-mAb4-CL862, as represented in FIG. 38, was obtained from Anti-βGAL-mAb4 (6.70 nmol) and Compound 17 (61.17 nmol) using the general procedure described above to obtain 4.07 nmol (68% yield) of the conjugate.
DAR Determination:

| | UV | | |
|---|---|---|---|
| | 260 nm | 280 nm | DAR |
| Anti-βGAL-mAb4 | 0.531 | 0.970 | |
| Anti-βGAL-mAb4-CL862 | 0.786 | 0.865 | 4.5 |

Figure 39:
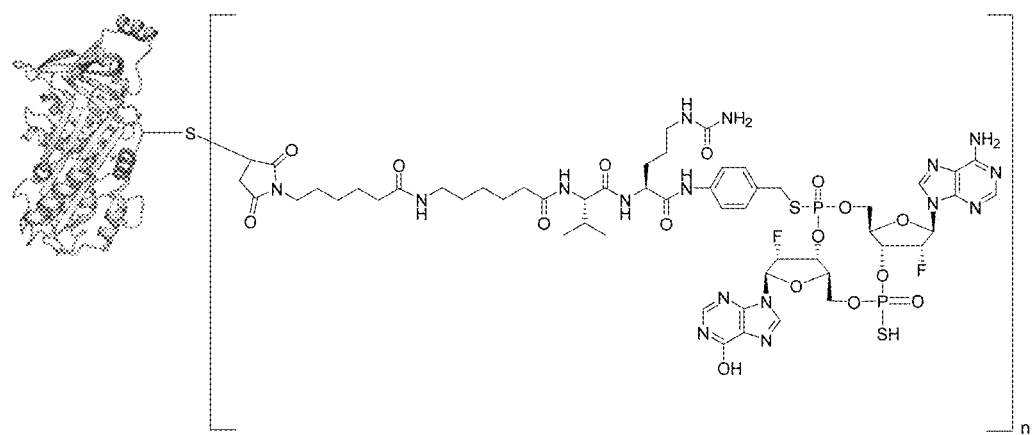
FIG. 39: Compound 59: Ova-CL862

Compound 59: Ova-CL862, as represented in FIG. 39, was obtained from Ova (7.89 nmol) and Compound 17 (198.0 nmol) using the general procedure described above to obtain 4.30 nmol (79% yield) of the conjugate.
DAR Determination:

| | UV | | |
|---|---|---|---|
| | 260 nm | 280 nm | DAR |
| Ova | 0.348 | 0.584 | |
| Ova-CL862 | 0.690 | 0.471 | 2.3 |

Figure 40:
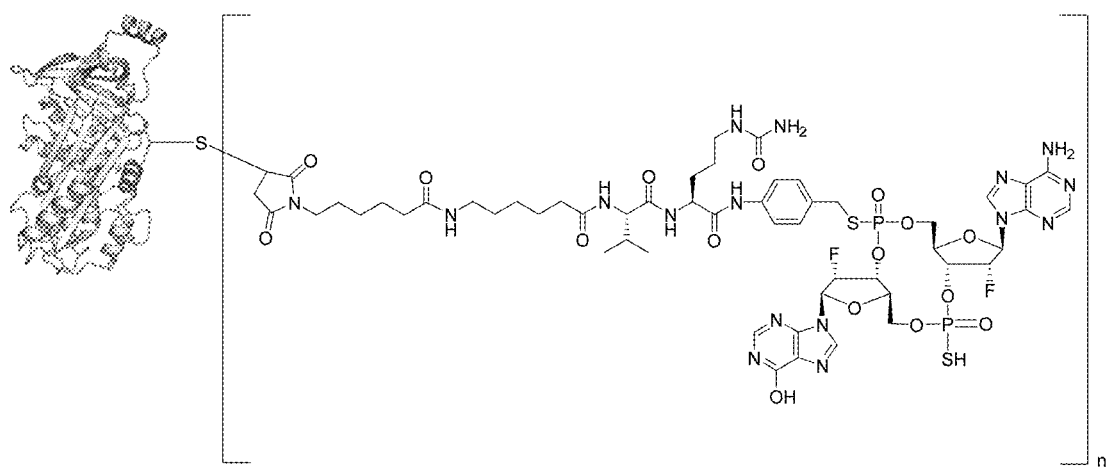
FIG. 40: Compound 60: PE-CL862

Compound 60: PE-CL862, as represented in FIG. 40, was obtained from PE (7.89 nmol) and Compound 17 (198.0 nmol) using the general procedure described above to obtain 4.30 nmol (79% yield) of the conjugate.

Example 2: Biological Assays for Linked CDNs

In the present invention, the immunomodulatory activity of CDN analogs modified with linker systems (Pro-CDN) and the CDN-BAM conjugates described in Formula (I) and in Formulae ($V_a$) to ($V_f$), was ascertained in in vitro-cell based assay and in live mammalian cells. These compounds induced the production of multiple cytokines, specifically the production of Type I interferons and/or pro-inflammatory cytokines, as indirectly determined by an ISG54 (interferon-stimulated gene) reporter assay (Fensteri et al., 2008).

The in vitro cytokine-induction activity of a representative set of both Pro-CDN and BAM-CDN conjugates is reported here to require the presence of the eukaryotic cellular receptor known as "stimulator of interferon genes" (STING).

These experiments were performed as described below.

Example 2.1: Evaluation of Pro-CDN for their Ability to Activate STING-Dependent Cytokine Induction In Vitro in a Human or Murine Reporter Cell Line Cytokine reporter cell line used: THP1-Dual™ and RAW-Lucia™ ISG cells (InvivoGen cat code: thpd-nfis, rawl-isg)
Compounds tested:
CL793 (Compound 1) vs CL702 (Intermediate 1.14)
CL802 (Compound 2) and CL804 (Compound 3) vs CL797 (Intermediate 1.5)
Reference compounds: 2'3'-cGAMP (InvivoGen catalog code: tlrl-nacga23-5)
Cytokines evaluated: IFN-α/β and NF-κB activity
The in vitro STING agonist activity disclosed in the present invention has been measured by monitoring of the IRF pathway. The IRF pathway has been investigated by using the two following ISG reporter cell lines (described here and provided with their corresponding InvivoGen catalog code).
RAW-Lucia™ ISG (InvivoGen catalog code: rawl-isg): These cells were generated from the RAW 264.7 murine macrophage cell line (ATCC® TIB-71™). They enable study of IRF signaling pathway, by assessing the activity of a secreted luciferase (Lucia), measured in cell culture supernatant by using QUANTI-Luc™ (InvivoGen; catalog code: rep-qlc1), a luminometric enzyme assay that measures luciferase expression.
THP1-Dual™ (InvivoGen catalog code: thpd-nfis): These cells were derived from the human monocytic cell line THP-1 by stable integration of two inducible reporter constructs. They enable simultaneous study of two signaling pathways: the NF-κB pathway, by monitoring the activity of secreted embryonic alkaline phosphatase (SEAP); and the IRF pathway, by assessing the activity of a secreted luciferase (Lucia). Both reporter proteins can be readily measured in the cell culture supernatant by using QUANTI-Blue™ (InvivoGen catalog code: rep-qb1), a SEAP detection reagent that turns purple/blue in the presence of SEAP (quantified by measuring the optical density from 620 nm to 655 nm), and QUANTI-Luc™ (InvivoGen; catalog code: rep-qlc1), a luminometric enzyme assay that measures luciferase expression to report on ISG54 expression (as an indicator of IFN-α/β production).

To each well of a flat-bottom 96-well plate were added 20 µL of a solution a CDN (50 µM in saline solution), followed by 180 µL of a suspension of a single cell line (100,000 cells per well). The plate was incubated for 18 h to 48 h at 37° C. in 5% $CO_2$. The level of ISG response in each well was indirectly quantified using QUANTI-Luc™ (as an indicator of ISG/IFN-β production), which was prepared and used according to the manufacturer's instructions (InvivoGen).

The results from this experiment are shown above in FIG. 1(A-F). FIGS. 1A and 1D illustrate the fold induction for tested compound (CL793, CL802 and CL804) relative to untreated cells and compared to the reference compound (2'3'-cGAMP and unmodified CDN CL702 or CL797) when used at the same concentration in an ISG murine reporter cell line. FIGS. 1B and 1E depict the ISG response in a human reporter cell line while FIGS. 1C and 1F the STING-dependent NF-κB response. The different dose response curves show that for each one of the read out (ISG or NF-κB), the tested CDNs (CL793, CL802 or CL804) induce a similar to a greater response than the 2'3'-cGAMP (the endogenous STING agonist in mammals) does. The modified Pro-CDN compounds display the same activity than the unmodified CDN CL702 or CL797. This findings demonstrate that modification of STING ligands to promote their binding to any biologically active molecules are able to keep on their ability to induce ISG and NF-κB pathways.

Example 2.2: Evaluation of Pro-CDNs for their Ability to Induce Cytokines Ex Vivo in Whole Blood from Healthy Human Donors Compounds tested:
CL793 (Compound 1) vs CL702 (Intermediate 1.14)
CL802 (Compound 2) and CL804 (Compound 3) vs CL797 (Intermediate 1.5)
Reference compound: 2'3'-cGAMP (InvivoGen catalog code: tlrl-nacga23-5)
Cytokines evaluated: Type I IFNs (using HEK-Blue™ IFN-α/β cells KO STING)
Reporter Cell Lines:
Type I IFNs: HEK-Blue™ IFN-α/β-KO-STING: These cells, in which the STING gene has been inactivated, are derived from HEK293 cell line known as HEK-Blue™ IFN-α/β (InvivoGen catalog code: hkb-ifnab). HEK-Blue™ IFN-α/β cells enable detection of bioactive human type I IFNs through monitoring of activation of the ISG3 pathway. These cells were generated by stable transfection of HEK293 cells with the human STAT2 and IRF9 genes to obtain a fully active Type-I IFN signaling pathway. The other genes of the pathway (IFNAR1, IFNAR2, JAK1, TyK2 and STAT1) are naturally expressed in sufficient amounts. The cells were further transfected with a SEAP reporter gene under control of an IFNα/β-inducible ISG54 promoter. This promoter comprises five IFN-stimulated response elements (ISREs) fused to a minimal promoter of the human ISG54 gene, which is unresponsive to activators of the NF-κB or AP-1 pathways. Stimulation of HEK-Blue™ IFN-α/β cells with human IFN-α or IFN-β activates the JAK/STAT/ISGF3 pathway and subsequently induces production of SEAP. Production of type I IFNs in these cells is measured using QUANTI-Blue™.

Acquisition and Handling of Human Blood Samples
Human blood samples were acquired from healthy donors at the *Etablissement Français du Song* (EFS Pyrénées Méditerranée, Toulouse, France; per agreement #21/PLER/TOU/2016-0082). Briefly, the samples were collected by venipuncture into sodium heparin tubes at the time of donation. The samples were analyzed for rhesus (Rh), blood group, hematocrit and serological status (AgHBS, HIV, HCV, HTLV, HBC, CMV, Syph). The tubes were picked up on the day of collection and subsequently tested (blood analysis, and treatment with test items) on the same day.

Treatment of Human Blood Samples
Each blood sample was diluted (1:2 [v/v]) in RPMI medium and aliquoted into 96-well plates (180-µL wells) containing either CDN (√10-fold serial dilution starting from 50 µM). The plates were incubated at 37° C. in a 5% $CO_2$ incubator for 18 hours. Then, the supernatants were collected, transferred into the corresponding wells of round-bottom 96-well plates, and either stored at −80° C., or immediately tested in the appropriate reporter cell line.

Testing of Human Blood Samples
A new 96-wells plate was prepared for each reporter cell lines tested, as follows: 10 µL of supernatant from the previous plate were added to the corresponding well in the new reporter cell plate. Then, a 190-µL aliquot of cells of the desired reporter cell line, previously harvested in medium containing heat-inactivated serum and counted, was added to each well (approximately 50,000 cells/well), and the plate was incubated for approximately 20 hours. The desired cytokine induction activity was determined using the QUANTI-Blue™ assay, as previously described. Briefly, 20 µL of supernatant from the previously incubated plate was transferred to the corresponding well of a new 96-well plate in which 180 µL of QUANTI-Blue™ reagent had previously been added.

Figure 2:
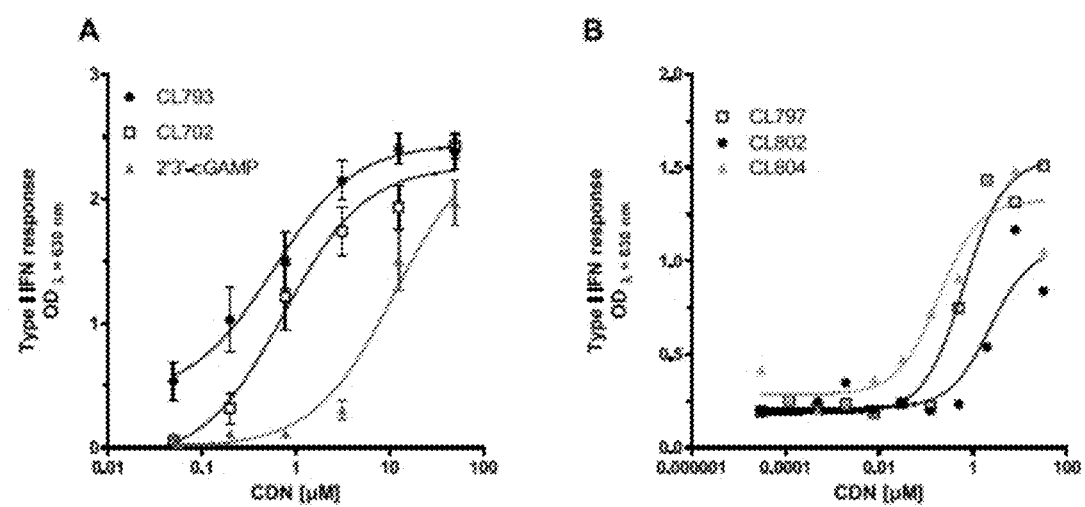
FIG. 2: Dose-response curves representing induction of Type I IFN for Pro-CDNs compounds CL793 (A) or CL802 and CL804 (B) in whole-blood assay in comparison to parental molecules CL702 or CL797 and the endogenous STING agonist 2'3'-cGAMP. The data represent the mean OD±sem from ten healthy donors (FIG. 2A) or the mean OD from two healthy donors (FIG. 2B).

Results presented in FIG. 2 summarize the induction of type I IFNs for CDN-linker system compounds (CL793, CL802 and CL804) relative to the reference compound (2'3'-cGAMP) or unmodified CDN (CL702 or CL797 respectively) in the whole-blood assay for each compound in this assay. As shown in FIG. 2A, the tested Pro-CDN CL793 provides, like the unmodified corresponding CDN (CL702), superior induction of type I interferons compared to the reference compound 2'3'-cGAMP. The dose-response curve in FIG. 2B shows that the tested Pro-CDN CL804 induce a type I IFNs production similar to the one induced by the unmodified corresponding CDN, CL797. This findings corroborate in vitro observations presented in FIG. 1 and demonstrate that modifications of STING ligands to promote their linkage to any biologically active molecules are able to keep on their ability to induce type I IFN pathway.

Example 2.3: Evaluation of BAM-CDN Conjugates for their Ability to Activate STING-Dependent Cytokine Induction In Vitro in a Human or Murine Reporter Cell Line Cytokine reporter cell line used: THP1-Dual™ and RAW-Lucia™ ISG cells
Compounds tested: CL808 (Compound 22) vs CL797 (Intermediate 1.5)
Reference compounds: 2'3'-cGAMP (InvivoGen catalog code: tirl-nacga23-5)
Cytokines evaluated: IFN-α/β and NF-κB activity The in vitro STING agonist activity of BAM-CDN conjugates has been measured by monitoring of the IRF pathway as described above in Example 2.1.

Figure 3:
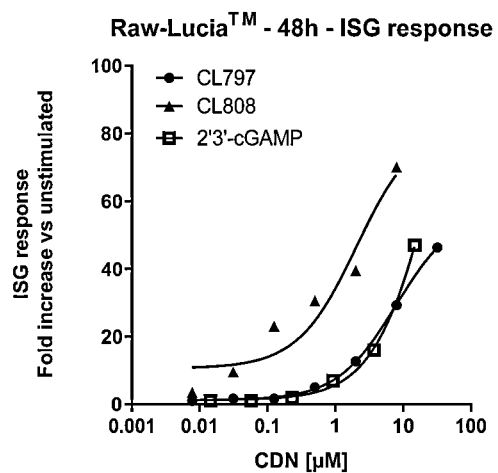
FIG. 3: Comparison of ISG54 (A-B) and NF-κB (C) activity induced (time indicated above) by a BAM-CDN (CL808) of the present invention in a murine (A) or a human (B and C) reporter cell.
Figure 3:
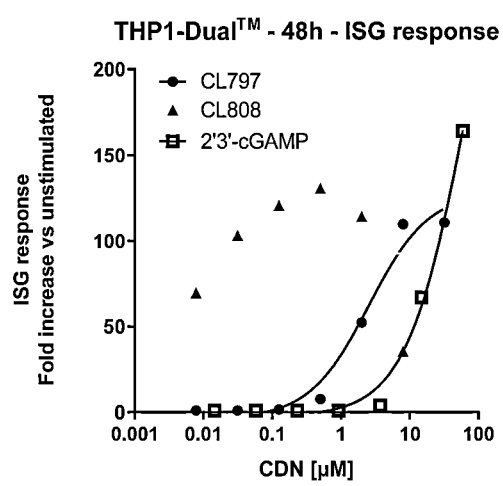
Figure 3:
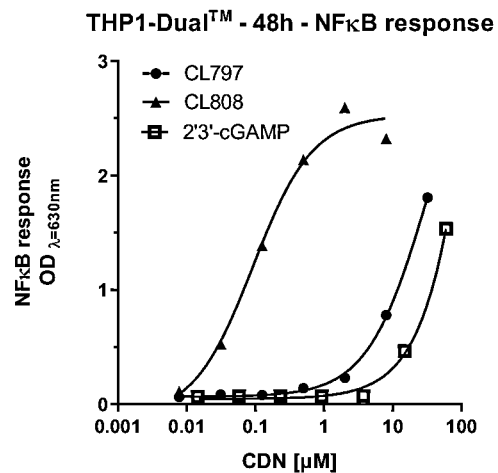

The results from this experiment are shown above in FIG. 3(A-C). FIG. 3A illustrates the fold induction for tested compounds (CL794 and CL808) relative to untreated cells and compared to the reference compound (2'3'-cGAMP and unmodified corresponding CDN CL797) when used at the same concentration in an ISG murine reporter cell line. FIG.

4B shows the ISG response in a human reporter cell line while FIG. 3C the STING-dependent NF-κB response. The different dose response curves (FIGS. 3A-C) show that the BAM-CDN CL808 induces an ISG or NF-κB response to a greater extent than does 2'3'-cGAMP, the endogenous STING agonist in mammals. The BAM-CDN compound CL808 displays a much higher activity compared to the unmodified corresponding CDN, CL797. It has to be noted that we observed toxicity at higher concentration of CL808 for both cell lines.

This finding demonstrates that the coupling of STING ligands to a biologically active molecules does not modify their ability to induce ISG and NF-κB pathways. In this example, BAM is a lipid moiety that is able to form liposomal structure with CDN or a nanoparticle to protect and to increase the uptake of CDN. The strong gain in activity compare to unmodified CDN could be explained by a better penetration of the CDN to reach its intracellular target.

Example 2.4: Evaluation of BAM-CDNs for their Ability to Induce Cytokines Ex Vivo in Whole Blood from Healthy Human Donors Compound tested: CL808 (Compound 22)
Reference compound: unmodified CDN CL797 (Intermediate 1.5)
Cytokines evaluated: Type I IFNs, IL1α/β, IL6 and TNFα (using HEK cytokine reporter cell lines)
Reporter Cell Lines:
Type I IFNs: HEK-Blue™ IFN-α/β-KO-STING: These cells, in which the STING gene has been inactivated, are derived from HEK293 cell line known as HEK-Blue™ IFN-α/β (InvivoGen catalog code: hkb-ifnab). HEK-Blue™ IFN-α/β cells enable detection of bioactive human type I IFNs through monitoring of activation of the ISG3 pathway. These cells were generated by stable transfection of HEK293 cells with the human STAT2 and IRF9 genes to obtain a fully active Type-I IFN signaling pathway. The other genes of the pathway (IFNAR1, IFNAR2, JAK1, TyK2 and STAT1) are naturally expressed in sufficient amounts. The cells were further transfected with a SEAP reporter gene under control of an IFN-α/β-inducible ISG54 promoter. This promoter comprises five IFN-stimulated response elements (ISREs) fused to a minimal promoter of the human ISG54 gene, which is unresponsive to activators of the NF-κB or AP-1 pathways. Stimulation of HEK-Blue™ IFN-α/β cells with human IFN-α or IFN-β activates the JAK/STAT/ISGF3 pathway and subsequently induces production of SEAP. Production of type I IFNs in these cells is measured using QUANTI-Blue™.
IL1α/β: HEK-Blue™ IL-1R (InvivoGen catalog code: hkb-il1r): The HEK293 cell line known as HEK-Blue™ IL-1R was designed to detect bioactive human and murine IL-1 through monitoring of activation of the NF-κB and AP-1 pathways. Additionally, these cells detect bioactive IL-1 from cynomolgus monkeys, dogs, hamsters and rats. In fact, HEK-Blue™ IL-1R cells can detect IL-1α and IL-1β, as these cytokines bind to the same receptor, IL-1R. These cells derive from HEK-Blue™ IL-1α cells (InvivoGen catalog code: hkb-il1b), in which the TNF-α response is blocked. Therefore, HEK-Blue™ IL-1R cells respond specifically to IL-1. These cells endogenously express the human IL-1 receptor and were stably transfected with the murine IL-1 receptor, rendering them sensitive to both human and murine IL-1β. HEK-Blue™ IL-1R cells express a SEAP reporter gene under control of an IFN-β minimal promoter fused to five NF-κB and five AP-1 binding sites. Binding of IL-1β to IL-1R on the surface of HEK-Blue™ IL-1R cells triggers a signaling cascade that leads to the activation of NF-κB and subsequent production of SEAP. Production of IL-1β in these cells is measured using QUANTI Blue™.

IL6: HEK-Blue™ IL-6 (InvivoGen catalog code: hkb-hil6): HEK-Blue™ IL-6 cells allow the detection of bioactive human IL-6 by monitoring the activation of the STAT-3 pathway. These cells were generated by stable transfection of HEK293 cells with the human IL-6R gene and a STAT3-inducible SEAP reporter gene. Upon IL-6 stimulation, HEK-Blue™ IL-6 cells trigger the activation of STAT3 and the subsequent secretion of SEAP. Levels of STAT3-induced SEAP can be readily monitored using QUANTI-Blue™.

TNFα: HEK-Blue™ TNF-α (InvivoGen catalog code: hkb-tnfdmyd): HEK-Blue™ TNF-α cells are a HEK293 cell line that enables detection of bioactive human and murine TNF-α through monitoring of activation of the NF-κB pathway. These cells were generated by stable transfection of HEK293 cells with a SEAP reporter gene under control of an IFN-β minimal promoter fused to five NF-κB and five AP-1 binding sites. They were further rendered unresponsive to IL-1β by knocking out the MyD88 gene. Stimulation of HEK-Blue™ TNF-α cells with TNF-α triggers activation of the NF-κB-inducible promoter and production of SEAP. Production of TNF-α in these cells is measured using QUANTI-Blue™.

The ex vivo activity of BAM-CDN conjugates has been measured by monitoring the production of type I IFNs, and pro-inflammatory cytokines IL1α/β, IL6 and TNFα in whole blood assays as described above in Example 2.2.

Figure 4:
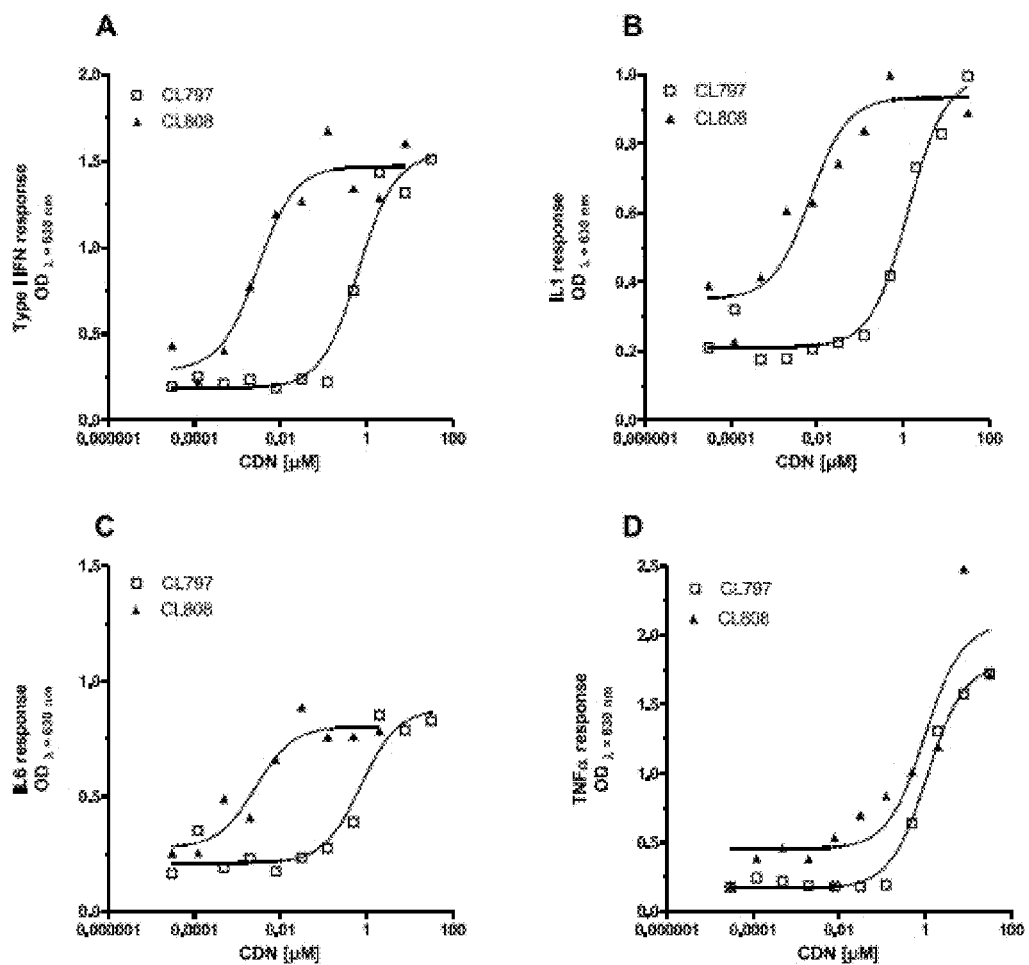
FIG. 4: Dose-response curves representing induction of type I IFN (A), IL1α/β (B), IL6 (C) and TNFα (D) for BAM-CDN compound (CL808 full black triangle) relative to the unmodified corresponding CDN (CL702 empty square) in whole-blood assay. The data represent the mean OD±sem from two healthy donors.

The results presented in FIG. 4 confirms findings observed in previous Example 2.3. Whatever the cytokine tested, CL808 displays a stronger activity than the unmodified corresponding CDN CL797 (significant shift of the dose-response curve to the left). Of note the $C_{16}$ carbon chain moiety by itself doesn't have ISG or NFκB activity. The chemistry coupling of a biologically active molecule (here a lipid) on the parent CDN CL797 does not alter the STING-dependent cytokine induction and strongly increase the basal activity due to a better penetration/uptake of the CDN.

Example 3: Biological Assays for Pro-CDNs

In the present invention, the immunostimulatory activity of these CDN analogs modified with linker systems (Pro-CDN) described in Formula (I) and in Formulae ($V_a$) to ($V_f$), was ascertained in in vitro-cell based assays. These compounds induced the production of multiple cytokines specifically the production of Type I interferons, as determined by a proprietary IRF (interferon regulatory factor) reporter cell based assay. The in vitro cytokine-induction activity of a representative set of Pro-CDN is depicted here after.

Cytidine reporter cell line used: THP1-Dual™ cells (InvivoGen catalog code: thpd-nfis)
Compounds tested: CL804 (Compound 3), CL822 (Compound 6), CL831 (Compound 7), CL843 (Compound 5), CL846 (Compound 8), CL847 (Compound 9), CL851 (Compound 10), CL750 (see formula below), CL855 (Compound 11), CL856 (Compound 12), CL862 (Compound 17), CL868 (Compound 15), CL869 (Compound 16), CL 873 (Compound 20) and CL 874 (Compound 21)

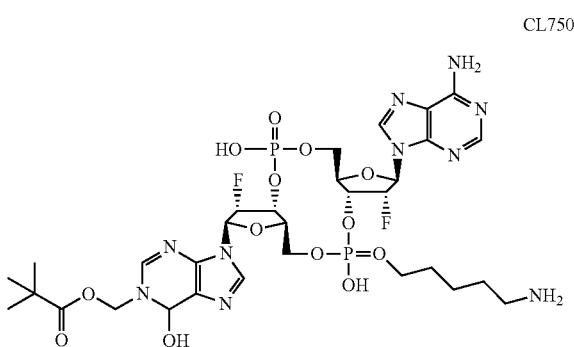

CL750

Reference compounds: 2'3'-cGAMP (InvivoGen catalog code: tlrl-nacga23-5), CL797 (Intermediate 1.5), CL845 (Intermediate 1.24), CL656 (Intermediate 1.22) also known as 3'3'-cAIM(PS)2 Difluor (Rp/Sp) (InvivoGen catalog code: tirl-nacairs)

Cytokines evaluated: IFN-α/β

The in vitro STING agonist activity disclosed in the present invention has been measured by monitoring of the IRF pathway. The IRF pathway has been investigated by using InvivoGen's THP1-Dual reporter cell line as described in Example 2.

the pro-CDNs derived from unmodified CL797 or CL845, as observed with the CDN from which they are derived. Lastly, we can conclude that in order to have an ISG activity, the moiety added to the CDN phosphorous group to transform it into a pro-CDN has to be cleavable as the CL750 which comprises an uncleavable moiety does not display any activity.

In the present invention we also describe the use of two types of maleimide group to form pro-CDNs.

Figure 5:
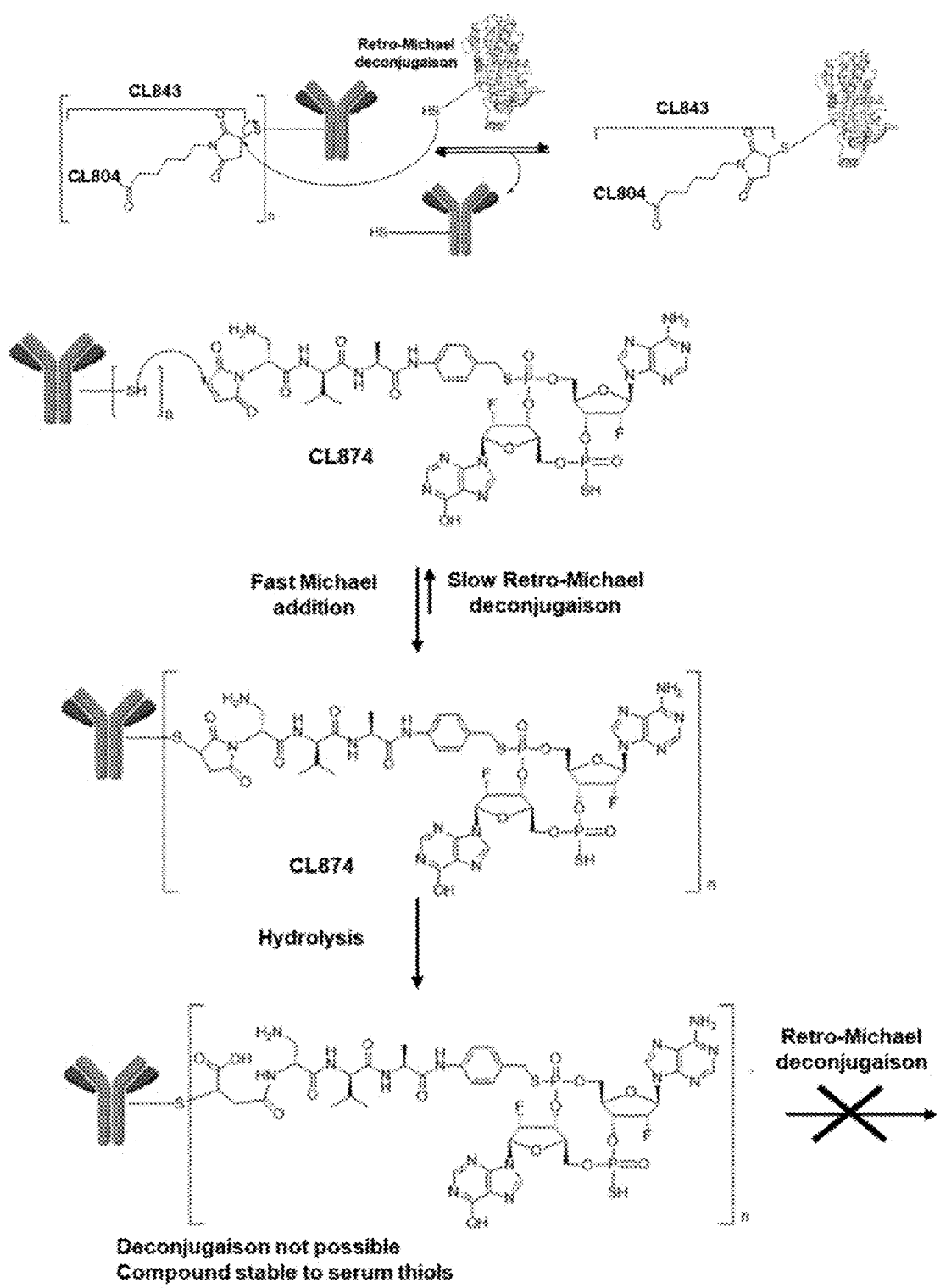
FIG. 5: Theoretical example of deconjugation through a retro-Michael pathway and comparison with CL874 pro-CDN compound.

Maleimide groups have been extensively used for coupling on cysteine because they react rapidly and selectively with thiols. It has recently come to light that the thioether linkage undergoes deconjugation through a retro-Michael pathway, leading to loss of cargo and reduction in efficacy (FIG. 5). The maleimide-cargo conjugate can then be bound to other plasma thiols (e.g. human serum albumin) leading to off-site toxicity and reduced efficacy.

'Selfhydrolysing maleimide reagents undergo rapid hydrolysis to the corresponding succinamic acid post-conjugation, thus eliminating the retro-Michael deconjugation pathway and resulting in more effective/stable bioconjugates. Pro-CDN CL874 is an example of compounds that can be coupled to a thiol of a cystein present in an antibody or protein and can be rapidly hydrolyzed to obtain a stable conjugated compound. This pro-CDN retains full 15G activity.

TABLE

ISG activity of pro-CDN described in the present invention.

| Pro-CDN/ Compound | CDN | LINKER | | | EC50 (μM) | % activity (vs cGAMP) | Fold ISG induction vs unstimulated @10 μM |
|---|---|---|---|---|---|---|---|
| | | Connector | Specifier | Spacer | | | |
| CL804 | CL797 | PAB | Val-Ala | / | 11.77 | 174 | 110 |
| CL822 | CL797 | PAB | Val-Ala | (AEEA)4 | n/a | | 29 |
| CL831 | CL797 | PHMNB | GLU | / | n/a | | 6 |
| CL843 | CL797 | PAB | Val-Ala | Mal-Aca | n/a | | 16 |
| | CL797 (Reference) | / | / | / | 8.15 | 251 | 181 |
| CL846 | CL845 | PAB | Val-Ala | | 4.21 | 486 | 269 |
| CL847 | CL845 | PHMAB | GLU | Mal-Aca | n/a | | 132 |
| CL851 | CL845 | PHMAB | GLU | Mal-Aca-Aca | 12.83 | 160 | 37 |
| | CL845 (Reference) | / | / | / | 4.57 | 448 | 227 |
| CL750 (Comparative) | CL614 (POM) | 1-Amino-pentanol | | | n/a | n/a | 1 |
| CL855 | CL656 | PHMAB | GLU | Mal-Aca-Aca | 7.136 | 287 | 115 |
| CL856 | CL656 | PHMAB × 2 | GLU | Bis(Mal-Aca-Aca) | 3.097 | 661 | 59 |
| CL862 | CL656 | PAB | Val-Cit | Mal-Aca-Aca | 6.688 | 306 | 198 |
| CL868 | CL656 | PAB | Val-Cit | / | 1.764 | 1161 | 291 |
| CL869 | CL656 | PAB × 2 | Bis(Val-Cit) | / | 1.359 | 1507 | 231 |
| CL873 | CL656 | PAB | Val-Ala | / | 1.025 | 1998 | 211 |
| CL874 | CL656 | PAB | Val-Ala | Dap-Mal | 6.812 | 297 | 156 |
| | CL656 (Reference) | / | / | / | 1.004 | 2040 | 215 | n/a: not applicable, AEEA for [2-(2-aminoethoxy)ethoxy]acetic acid, GLU = Methyl-2,3,4-tri-O-acetyl)-D-glucopyranouronate, Aca = Aminocaproate, Mal = Maleimido, Dap = 2,3-diaminopropionic acid.
$EC_{50}$ 2'3'cGAMP = 20.48 μM (Lioux et al., 2016) (48 h post-stimulation).
% activity (vs cGAMP) = ($EC_{50}$ 2'3'cGAMP/$EC_{50}$ compound) × 100
Fold ISG induction vs unstimulated 2'3'-cGAMP at 10 μM = 93.

The results from this experiment are summarized above in Table above. First, each CDN-linker system or Pro-CDN described in the present invention displayed a significant ISG response from a fold of 6 to 291 versus unstimulated, when they are used at 10 μM. Then, in comparison with 2'3'-cGAMP, most of pro-CDNs have a greater ISG activity and those derived from CL656 display a better potency than Example 4: Biological Assays for BAM-CDNs Example 4.1: BAM=Lipid The in vitro STING agonist activity of BAM-CDN conjugates (with BAM=lipid) has been measured by monitoring the IRF pathway as described above in Example 2.3.

Cytokine reporter cell lines used: THP1-Dual™ cells and RAW-ISG Lucia™ (InvivoGen catalog code: thpd-nfls and rawl-isg)

Compounds tested: CL808 (Compound 22), CL821 (Compound 25), CL820 (Compound 24), CL819 (Compound 23), CL850 (Compound 40), CL849 (Compound 39), CL841 (Compound 27), CL840 (Compound 26), CL842 (Compound 28), CL863 (Compound 46)

Reference compounds: CL797 (Intermediate 1.5), CL845 (Intermediate 1.24) and CL656 (Intermediate 1.22) also known as 3'3'-cAIM(PS)2 Difluor (Rp/Sp) (InvivoGen catalog code: tirl-nacairs)

Cytokines evaluated: IFN-α/β

The results shown in FIG. 3(A-C) in Example 2.3 show that the BAM-CDN compound CL808 displays a much higher activity compared to the unmodified corresponding CDN, CL797. This finding demonstrates that lipid moiety is able to form liposomal structure with CDN or a nanoparticle to protect and to increase the uptake of CDN. In this example and as described in Example 2.3., we further evaluated the role of the lipid chain in terms of IRF pathway and particle formation.

Figure 6:
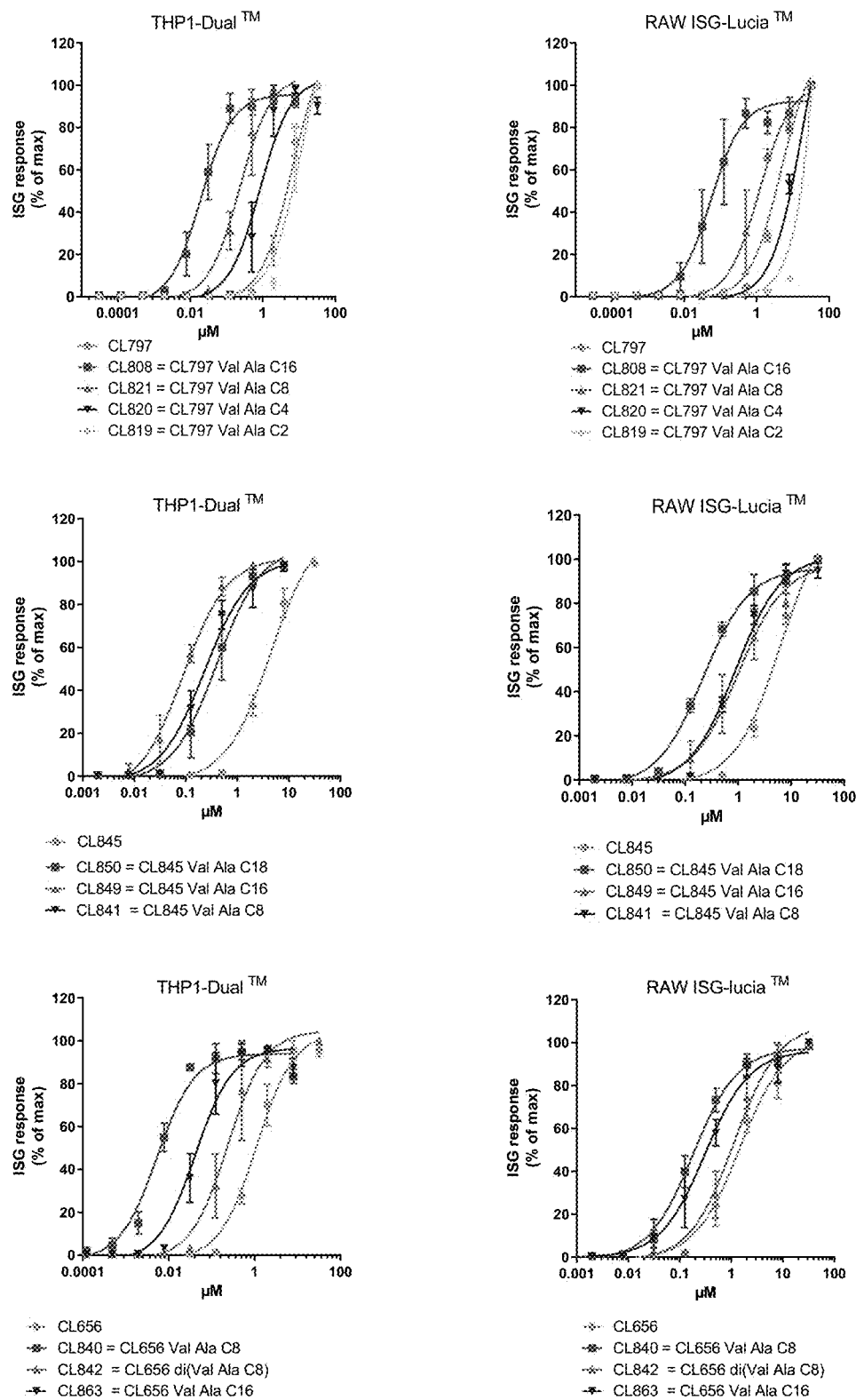
FIG. 6: Comparison of ISG54 activity induced by lipidated-CDN with the unmodified CDNs (CL797 left part, CL845 in the middle section and CL656 right part) in a human (above panel) or a murine (below panel) reporter cell.

The results presented in FIG. 6 confirm findings observed in previous Example 2.3. CL808 displays a stronger activity than the unmodified corresponding CDN CL797 (significant shift of the dose-response curve to the left). The chemistry coupling of a biologically active molecule (here a lipid) on the parent CL797, CL845 or CL656 strongly increases the basal activity due to a better penetration/uptake of the CDN and the improvement in potency is significant with C8 or longer chain (e.g. EC50 (CL808=C16-CL797)<EC50 (CL821=C8-CL797)<EC50 (CL820=C4-CL797)=EC50 (CL819=C2-CL797)=EC50 (CL797)).

As shown in the Table below, using hydrophobic lipid chains as a BAM (a C14 C14 for example), the modified CDN can self-organize/assemble in lipid-based nanoparticles (CL838, CL859, CL860, CL842 or CL861). Then, when the specifier is the dipeptide Valine-Citrulline (CL860 or CL861) the size tends to be smaller, around the size of Small Unilamellar Vesicle (aka SUV<40 nm).

This organization in lipid-based particles suggests that the CDN is protected from the environment and allows a better penetration and a sustained release mechanism into the cell.

Example 4.2: Dipeptide Specifier: Comparison Val-Citrulline Vs Val-Alanine

A general substrate for cathepsins is Z-Val/Phe-Arg-X (Barrett, A. J. Biochem. J. 1980, 187, 909-912). Over decades, protected substrates have been developed and substrates containing citrulline (Cit), which is isosteric and isoelectronic like Arg but much less basic, display a superior systemic stability over other cleavable linkers (Dubowchik et al, Bioorganic & Medicinal Chemistry Letters 1998, 3341-3346). The widely used Val-Cit dipeptide linker has been popularized as a way to maintain a stable covalent attachment of the drug to the antibody that could be preferentially cleaved by intracellular protease(s) of the lysosomal degradation pathway (Dubowchik G M et al Bioconjug Chem 2002,13:855-69 or Junutula J R et al Nat Biotechnol 2008; 26:925-32). Based on this literature, in this application we describe the use of Val-Cit as a specifier to connect CDN to a RAM (a $C_{16}$ lipid chain in this example) using the methodology described in Example 2.1 and we compare it to the Val-Ala specifier described in patent WO2018/100558.

Cytokine reporter cell lines used: RAW-ISG Lucia™ (InvivoGen ca code: rawl-isg)

Compounds tested: CL848 (Compound 38), CL808 (Compound 22), CL852 (Compound 41), CL849 (Compound 39), CL853 (Compound 42), CL863 (Compound 46)

Reference compounds: CL797 (Intermediate 1.5), CL845 (Intermediate 1.24) and CL656 (Intermediate 1.22)

Cytokines evaluated: IFN-α/β

Figure 7:
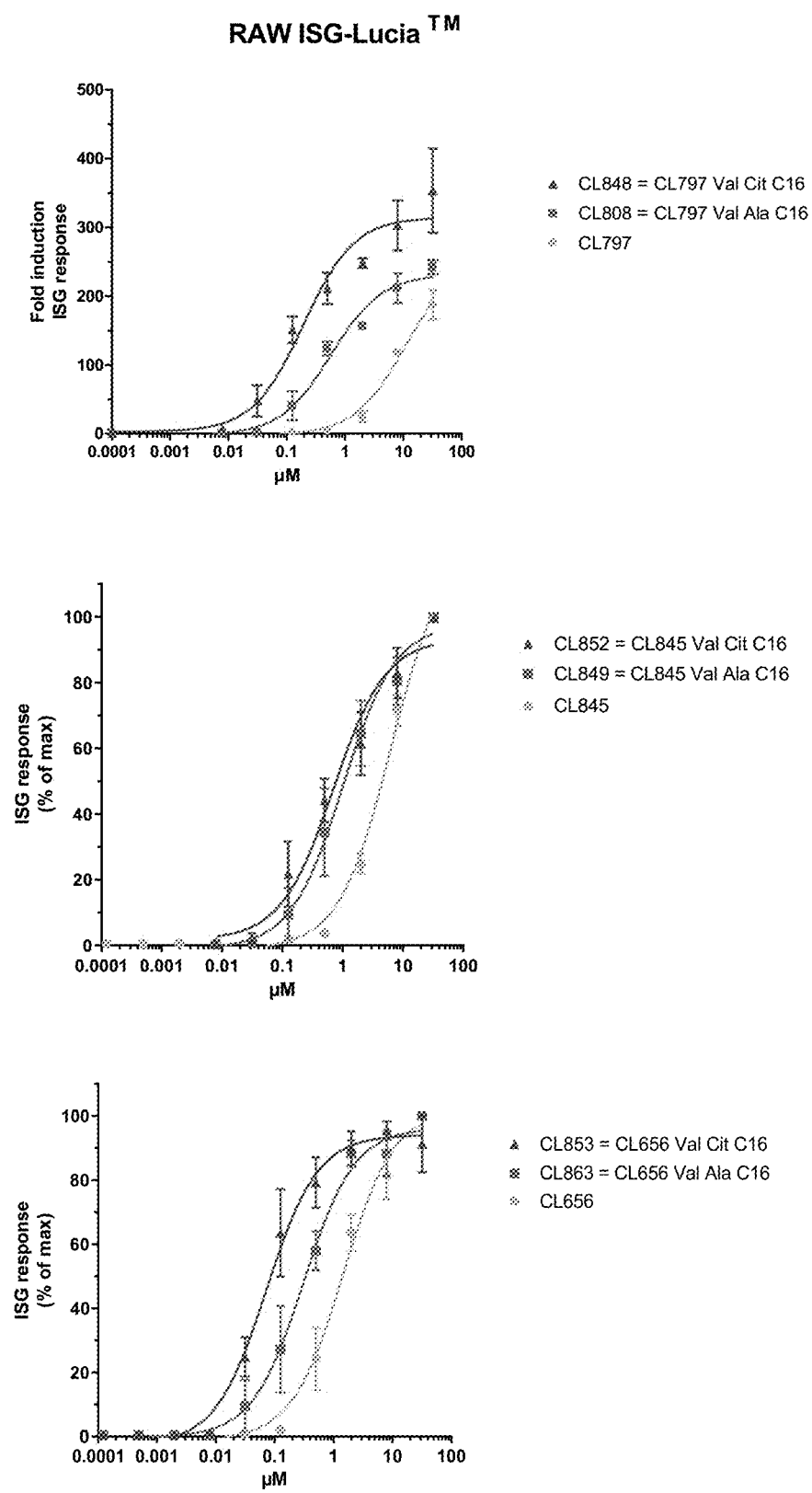
FIG. 7: BAM-CDN dependent ISG Activity. BAM-CDN dependent ISG activity from the present invention was assessed in RAW ISG in comparison with the unmodified CDN (CL797 upper panels, CL845 in the middle section and CL656 lower part).

The results presented in FIG. 7 show that a dipeptide specifier used to link STING agonists to a biologically active molecule (here a lipid moiety) is highly efficient to induce an ISG response. In THP1 Dual and RAW ISG cells, CL848 and CL808, CL852 and CL849, CL853 and CL863, exert higher ISG activity than the unmodified parental CDN, CL797, CL845 and CL656 respectively. The cathespins-cleavable linkers allow the release of the active form of CDN and the use of Valine-Citrulline appears better than Valine-Alanine to improve the ISG response.

Example 4.3 BAM=Detection System

Defining, visualizing and sorting the cells that are able to uptake a functional CDN is a challenge for researchers and

| Pro-CDN/Compound | CDN | Connector | Specifier | Spacer | BAM = lipid | PdI | Z Ave (nm) | $EC_{50}$ (μM) THP1-Dual | $EC_{50}$ (μM) IFN in WBA |
|---|---|---|---|---|---|---|---|---|---|
| CL821 | CL797 | PAB | Val-Ala | / | $C_8$ | 0.27 | 54.9 | 0.23 | 7.1 |
| CL838 | CL797 | PAB | Val-Ala | / | $C_{14}/C_{14}$ | 0.214 | 91 | 0.09 | 0.009 |
| CL859 | CL797 | PAB | Val-Cit | / | $C_{14}/C_{14}$ | 0.372 | 39.2 | 1.35 | 0.59 |
| CL808 | CL797 | PAB | Val-Ala | / | $C_{16}$ | 0.382 | 173.9 | 0.006 | 0.24 |
| CL848 | CL797 | PAB | Val-Cit | / | $C_{16}$ | 0.18 | 84.3 | 0.01 | 0.11 |
| CL840 | CL656 | PAB | Val-Ala | / | $C_8$ | 0.08 | 168.9 | 0.005 | 0.13 |
| CL842 | CL656 | PAB × 2 | bis(Val-Ala) | / | $C_8 \times 2$ | 0.086 | 184 | 0.006 | 1.4 |
| CL861 | CL656 | PAB | Val-Cit | / | $C_{14}/C_{14}$ | 0.183 | 36.8 | 0.27 | 0.01 |
| CL863 | CL656 | PAB | Val-Ala | / | $C_{16}$ | 0.416 | 106.6 | 0.04 | 0.15 |
| CL853 | CL656 | PAB | Val-Cit | / | $C_{16}$ | 0.188 | 155.9 | 0.02 | 0.14 |
| CL841 | CL845 | PAB | Val-Ala | / | $C_8$ | 0.475 | 264.3 | 0.19 | 3.03 |
| CL849 | CL845 | PAB | Val-Ala | / | $C_{16}$ | 0.56 | 152.4 | 0.12 | 0.12 |
| CL852 | CL845 | PAB | Val-Cit | / | $C_{16}$ | 0.468 | 100.7 | 1.01 | 0.41 |
| CL860 | CL845 | PAB | Val-Cit | / | $C_{14}/C_{14}$ | 0.248 | 33 | 0.44 | 0.009 | pharmaceutical companies. Several fluorescent cGAMP analogs are commercially available but none of them have been reported to have a STING dependent ISG activity. In the present invention, we evaluated the immunostimulatory properties of a novel chimeric compound designed that have both a STING agonist activity and a detection system (Fluorescent tag or biotin).

Cytokine reporter cell line used: THP1-Dual™ cells (InvivoGen cat code: thpd-nfis)
Compounds tested: CL832 (Compound 34), CL833 (Compound 35)
Reference compounds: CL797 (Intermediate 1.5) and fluorescent-CDN (Fluorescent cGAMP available from www.biolog.de, cat no C 178-001)
Cytokines evaluated: IFN-α/β

Figure 8:
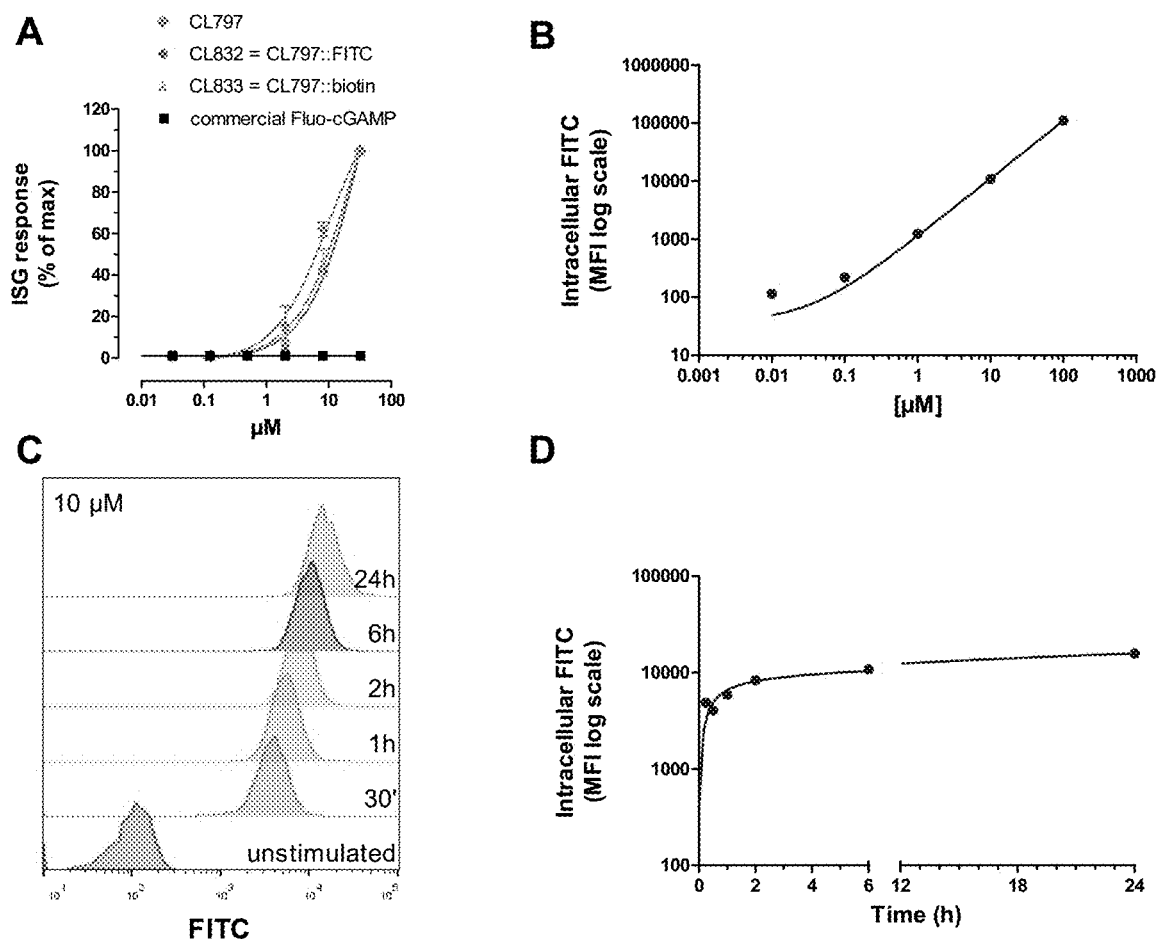
FIG. 8: BAM-CDN dependent ISG activity and Internalization quantitation. A—BAM-CDN dependent ISG activity from the present invention was assessed in THP1 Dual in comparison with a commercially available fluorescent-CDN B-D: Fluorescence Intensity in the intracellular compartment of THP1-Dual cells stimulated with CL832 was measured by flow cytometry in a dose dependent manner (B) or time dependently (C and D) at 10 μM.

The results presented in FIG. 8 show that STING agonists linked to a detection system have the same ISG activity than the unmodified corresponding CDN CL797, while a commercially available fluorescent CDN (www.biolog.de, cat n° C. 178-001) is not able to induce an IRF response. The chemistry coupling of a detectable biologically active molecule allows to visualize and quantify STING agonists internalization in a dose and time-dependent manner.

Example 4.4 BAM=PRR Ligand (TLR)

For vaccination purpose, potent new adjuvants are required to facilitate the development of more effective vaccines. PRR (including TLRs) ligands have distinct functions in the innate immune system and are commonly used as vaccine adjuvants. Synergistic crosstalk between TLRs has been in the spotlight recently (Goff et al 2015. J. Virol. 89: 3221-3235). Among them, TLR7, a nucleic acid sensor, plays an important role in the immune response to viral infection by recognizing ssRNAs. In the present invention, we evaluated the Immunostimulatory properties of a novel chimeric compound designed to stimulate both Intracellular STING and TLR7 pathways.

Reporter cell lines used: THP1-Dual™ cells, RAW-ISG-Lucia™ or HEK-Blue TLR7™ (InvivoGen cat code: thpd-nfis, rawl-isg and hkb-htlr7)
Compounds tested: CL834 (Compound 36)
Reference compounds: CL804 (Compound 3) and CL264 (InvivoGen cat code tlrl-c264e)
Cytokines evaluated: IFN-α/β

Figure 9:
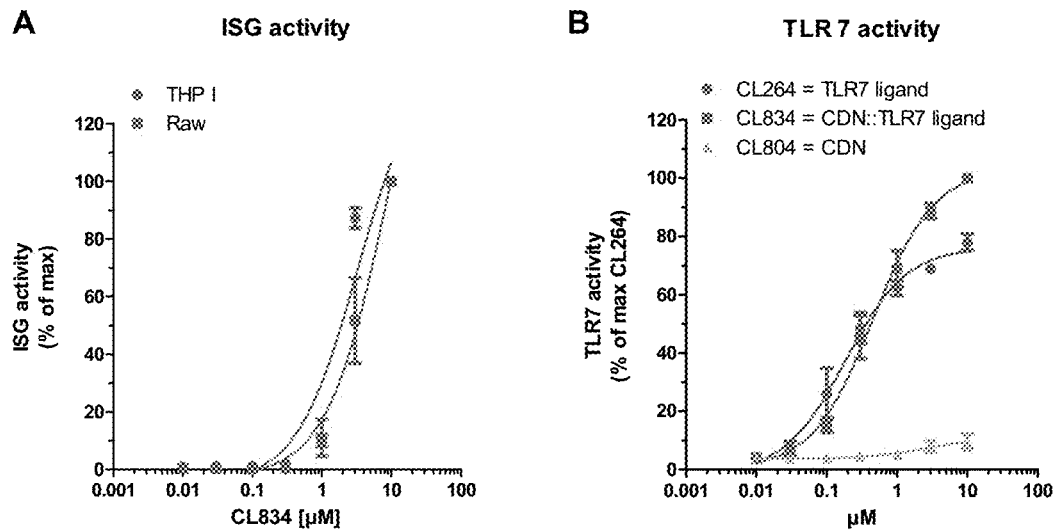
FIG. 9: BAM-CDN dependent ISG and TLR7 activity. A—BAM-CDN dependent ISG activity from the present invention was assessed in THP1 Dual (circle) or Raw ISG (square) after 24h of stimulation. B— In comparison with a free TLR7 agonist (CL264), CL264-CDN dependent TLR7 activity from the present invention was assessed in HEK Blue TLR7 cell line after 24h of stimulation.

The results presented in FIG. 9 show that STING agonists linked to a TLR7 agonist have similar ISG activity than the unmodified corresponding CDN CL797 (in comparison with data presented in Example 4.2) or and similar TLR7 activity than the corresponding TLR7 ligand (CL264). The chemistry coupling of a PRR ligand to a CDN allows to simultaneously stimulate in the same cell different innate immune signaling pathways.

Example 4.5 BAM=Heterocyclic Molecule (Folic Acid)

The selective delivery of cytotoxic agent has been widely investigated including linking folic acid to a suitable heterobifunctional PEG coupled to a cytotoxic agent like Gemcitabine (G. Pasut et al., Journal of Controlled Release 127 (2008) 239-248). Folic acid (FA) was chosen because its cell surface receptor GP38 is generally over-expressed in several types of human epithelial cancers, especially ovarian, but also kidney, uterus, brain, colon and lung and has been established as a tumor cellular-surface marker for targeted drug delivery. In normal human tissues GP38 has limited distribution, mainly in kidneys, lungs, choroids plexus and placenta (Weitman et al., Cancer Res. 52 (12) (1992) 3396-3401).

In addition, previous works have also demonstrated that a subset of macrophages expresses folate receptors that can mediate Internalization of folate-linked molecules and that can be used to target drugs to activated macrophages (W. Xia et al., Blood (2009) 113:438-446).

In the present invention, we evaluated the ability to use folic acid as a way to target CDN compound to cancer cells or tumor-infiltrated macrophages using the methodology described in Example 2.1.

Cytokine reporter cell lines used: THP1-Dual™ cells and RAW-ISG-Lucia™ (InvivoGen cat code: thpd-nfis, rawl-isg)
Compounds tested: CL826 (Compound 33)
Cytokines evaluated: IFN-α/β

Figure 10:
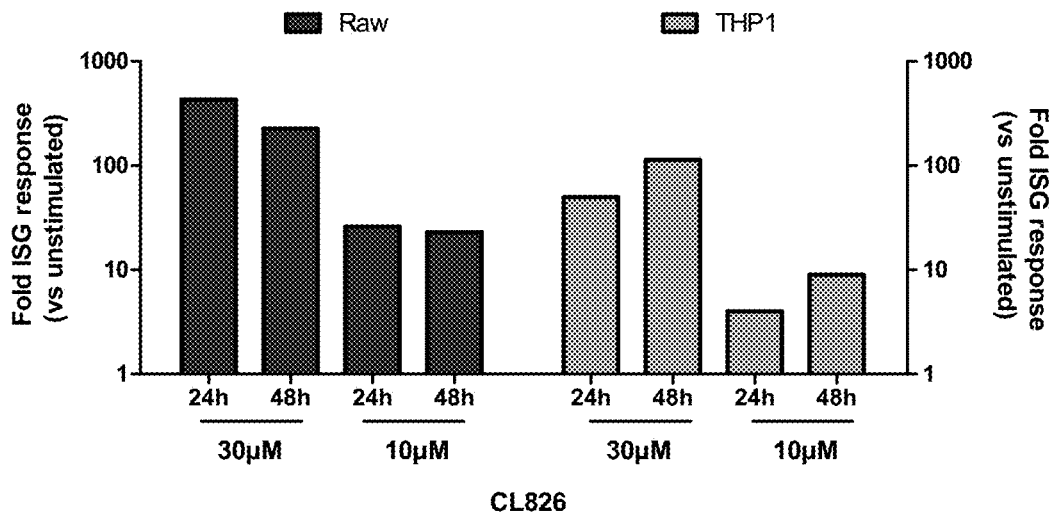
FIG. 10: Folk acid-CDN dependent ISG activity. FA-CDN dependent ISG activity from the present invention was assessed in RAW ISG (black) or THP1 Dual (grey) after 24h or 48h of stimulation using 10 or 30 μM dose.

The results presented in FIG. 10 show that STING agonists linked to folic acid have the ability to induce an ISG response in immortalized monocyte/macrophage-like cell lines. The chemistry coupling of folic acid to a CDN (FA-small molecule immunoconjugate) with a releasable linker might be a way to vector STING agonists into cells (including tumoral or antigen-presenting cells) expressing folate receptor.

5. Example BAM=Protein 5.1 BAM=Immune Checkpoint Inhibitor (ICI) Antibody

Therapeutic blockade of T-cell coinhibitory receptors such as CTL-associated antigen 4 (CTLA-4, programmed death 1 (PD-1) and programmed death ligand 1 (PDL-1) is sufficient to promote durable immune-mediated tumor regression across multiple cancers in mouse and man. However in multiple applications the efficacy is limited to a percentage of patients. Thus strategies involving simultaneous manipulation of multiple, non-redundant immune regulatory pathways to activate potent antitumor immune responses in mouse and man are currently evaluated. Several reports showed that an optimized cocktail of immunomodulators engaging both innate (using PRR ligand) and adaptive immunity (using immune checkpoint Inhibitors aka ICI) mediates efficient rejection of poorly immunogenic cancers (Fu, et al 2015. Sci. Transl. Med. 7, 283ra52; Charlebois, et al (2017). Cancer Res. 77, 312-319. Corrales et al. (2015). Cell Rep. 11, 1018-1030. Kranz, L et al. (2016). Nature 534, 396-401. Shekarian, et al (2017). Ann. Oncol. 28, 1756-1766). While combination therapies are extensively investigated, linking immunomodulators to a functional immune checkpoint antibody is poorly described. In this application we describe the functionality of a single molecule consisting of an ICI:CDN conjugate which exhibits several advantages over mixtures of both individual molecules. An ICI-conjugated-CDN is expected to gain the pharmacodynamic properties of the antibody and in addition may be administered systemically due to a new PK profile. Further, ICI:CDN conjugates are simultaneously delivered to the same cell in a fixed molecular ratio, thereby preventing potentially detrimental bystander effect when the antibody used also targets STING expressing cells.

In the present invention, we evaluate the IFN activity and antibody recognition property of a CDN compound linked to an immune checkpoint inhibitor antibody (here PDL-1 antibody). We aimed to use this compound to boost both the innate and adaptive immune system and to target CDN delivery into the vicinity of PDL-1 expressing cells like tumoral cells or antigen presenting cells (APCs) which are known to express STING.

We performed Whole Blood Assay on healthy human donors to evaluate the ability of the anti-PDL1mAb:CDN conjugate (Compound 47) to induce type I interferons as described previously in Example 2.2. The binding properties of the anti-PDL1mAb:CDN conjugate have been evaluated using ELISA.

Figure 41:
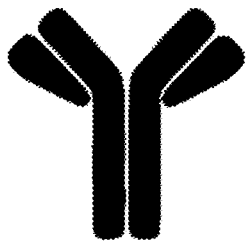
FIG. 41: Atezolizumab: hIgG1 N298A-anti h/m PDL1

| Compound | Structure | DAR (UV) | DAR (Mass Spec.) | IFN activity @ 50 µg/mL in WBA (% of CL656 @ 1 µM) | Antigen binding (% of anti PDL1 @ 10 µg/mL) |
|---|---|---|---|---|---|
| Compound 47 | CL855-hIgG1 N298A-anti h/m PDL1 (atezolizumab) As represented in FIG. 27 | 7.2 | 7.8 | 161 | 93 |
| Atezolizumab | hIgG1 N298A-anti h/m PDL1 As represented in FIG. 41 | n.a. | n.a. | 0 | 100 |
| CL656 (Intermediate 1.22) | [chemical structure] | n.a. | n.a. | 100 | n.a. |

The results presented in the table above show that the Pro-CDN CL855 (Compound 11) has been conjugated with the anti-PDL1 mAb with a CDN load of ~8 (DAR 7.8) and the mAb:CDN conjugate is as efficient as the unmodified CDN CL656 (Intermediate 1.22) to induce type I IFNs. The mAb:CDN conjugate retains its antigen binding capacity compared to the anti-PDL1 mAb alone.

5.2 BAM=Protein (Including Antibody)

In this application, we describe the generation of novel conjugates consisting of a CDN and a protein (that can include any antibody). Protein:CDN conjugates have several advantages over simple non-conjugated mixtures of both components. Similarly to the ICI:CDN conjugate, Protein:CDN conjugates have a new pharmacokinetic profile. If the protein is an antibody, the new compound will be part of the ADC (antibody drug conjugate) family. Such immunoconjugates combine the immunomodulatory potency of CDNs with the high selectivity, stability and favorable pharmacokinetic profile of mAbs.

In the present invention, we evaluated using reporter cell lines the ISG activity of protein:CDN conjugates using in vitro conditions favorable to the release of both components.

| Compound | Structure | Specifier | DAR (UV) | ISG activity @ 50 µg/mL (% of parental CND @ 1 µM) |
|---|---|---|---|---|
| Compound 48 | Anti-GP75-mAb2-CL843 As represented in FIG. 28 | Val-Ala. | 1.8 | 16 |
| Compound 49 | Anti-GP75-mAb2-CL851 As represented in FIG. 29 | GLU | 8.7 | 24.5 |
| Compound 50 | Anti-CTLA4-mAb2-CL855 As represented in FIG. 30 | GLU | 9.8 | 121 |
| Compound 51 | Anti-PDL1-mAb3-CL855 As represented in FIG. 31 | GLU | t.b.d. | t.b.d. |
| Compound 53 | Anti-PDL1-mAb1-CL862 As represented in FIG. 33 | Val-Cit. | 4.5 | 109 |
| Compound 54 | Anti-PDL1-mAb3-CL862 As represented in FIG. 34 | Val-Cit. | 3 | 84 |
| Compound 55 | Anti-GP75-mAb2-CL862 As represented in FIG. 35 | Val-Cit. | 2.7 | 122 |
| Compound 56 | Anti-CTLA4-mAb2-CL862 As represented in FIG. 36 | Val-Cit. | 3.4 | 193 |
| Compound 57 | Anti-HER2-mAb4-CL862 As represented in FIG. 37 | Val-Cit. | 3.2 | 94 |

-continued

| Compound | Structure | Specifier | DAR (UV) | ISG activity @ 50 µg/mL (% of parental CND @ 1 µM) |
|---|---|---|---|---|
| Compound 58 | Anti-βGAL-mAb4-CL862 As represented in FIG. 38 | Val-Cit. | 4.6 | 153 |
| Compound 60 | PE-CL862 As represented in FIG. 40 | Val-Cit. | n.t. | 86 |
| CL656 (Intermediate 1.22) | [structure shown] | n.a. | n.a. | 100 | t.b.d. is for to be determined

The results presented in the table above show that, using in vitro conditions favorable to the release of both components of the conjugate, released CDNs are able to induce an ISG activity and retain their capacity to bind to the target receptor STING. Indeed, none of the tested Protein:CDN conjugates displayed ISG activity on STING KO reporter cells. Moreover, CDN linkage using Glucuronic acid (Valine-Alanine) or Valine-Citrulline as specifiers Is feasible. Notably, the complex consisting of Anti-CTLA4-mAb2-CL862 (Compound 56) has a surprisingly greater ISG activity than the parental CDN. This observation might be due to a nanocomplex formation with compound 56 that allows an optimal uptake by the target cells.

5.3 BAM=Antigen

In this application, we describe the generation and immunological characterization of a novel vaccine candidate consisting of the CDN as an adjuvant and an Antigen such as the model allergen Ovalbumin. Antigen:adjuvant conjugates have several advantages over simple non-conjugated mixtures of both components: (1) they target the conjugate to the respective Immune cells by binding to specific immune receptors (in this case STING); (2) adjuvant and allergen are simultaneously delivered to the same cell in a fixed molecular ratio, thereby preventing potentially detrimental bystander activation or adjuvant leakage to other cells. Kastenmüller and colleagues reported a conjugate vaccine combining a TLR7/8-ligand and Ova and showed that this conjugate elicits potent Th1-biased T cell responses by activation and recruitment of dendritic cells to draining lymph nodes and the subsequent induction of type I interferon production (Kastenmüller et al., The Journal of Clinical Investigation, vol. 121, no. 5, pp. 1782-1796, 2011).

The adjuvant potency of STING agonist linked to the antigen disclosed in the present invention has been measured by monitoring the OVA specific immunoglobulin title according the protocol described below.

Immunization Protocol:

Swiss mice were immunized with a total dose of 10 µg of OVA protein with or without uncoupled STING agonist or a conjugate vaccine (CL855-OVA—Compound 52, CL862-OVA—Compound 59). The regimens were administered sub-cutaneously in a volume of 200 µL at day 0 and challenged on day 15. For analysis of OVA specific immunoglobulin title, blood withdrawal was performed 15 days after primary or secondary immunization.

First, we evaluated the ISG activity of antigen:CDN conjugates using in vitro condition favorable to release of both components in order to ensure that we had a linkage.

| Compound | Structure | Specifier | DAR (UV) | ISG activity @ 50 µg/mL (% of CL656 @ 1 µM) |
|---|---|---|---|---|
| Compound 52 | Ova-CL855 As represented in FIG. 32 | GLU | 7.1 | 109 |
| Compound 59 | Ova-CL862 As represented in FIG. 39 | Val-Cit | 2.3 | 100 |

| Compound | Structure | Specifier | DAR (UV) | ISG activity @ 50 µg/mL (% of CL656 @ 1 µM) |
|---|---|---|---|---|
| CL656 (Intermediate 1.22) | 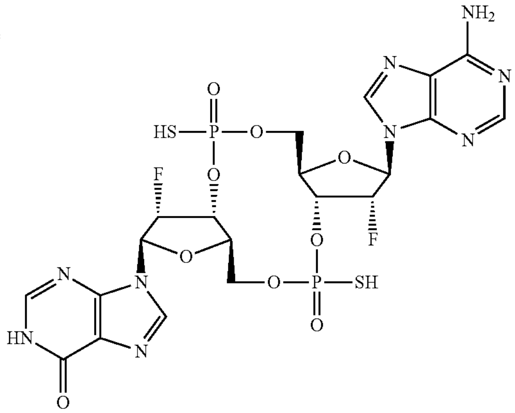 [SMILES: Nc1ncnc2c1ncn2[C@@H]1O[C@@H]2COP(=O)(S)O[C@H]3[C@@H](F)[C@H](n4cnc5c(=O)[nH]cnc54)O[C@@H]3COP(=O)(S)O[C@H]2[C@H]1F] | n.a. | n.a. | 100 |

The results presented in the table above show that, using in vitro condition favorable to release of both components of the conjugate, released CDN are able to induce an ISG activity and to retain their capacity to bind to target receptor STING. The Compound 52 (Ova-CL855) and Compound 59 (Ova-CL862) exhibit a similar ISG activity in comparison with the unmodified CDN CL656.

Then we measured the ability of Compound 52 and Compound 59 to induce an immune response against ovalbumin by assessing the antibody title reacting against the antigen. We compared Compound 52 and Compound 59 to the combination of both molecules (OVA and CL656) by adapting the amount of CL656 injected based on the DAR (Drug Antigen Ratio) described in table above. A positive control consisting of Alum as adjuvant for ovalbumin was used.

Figure 11:
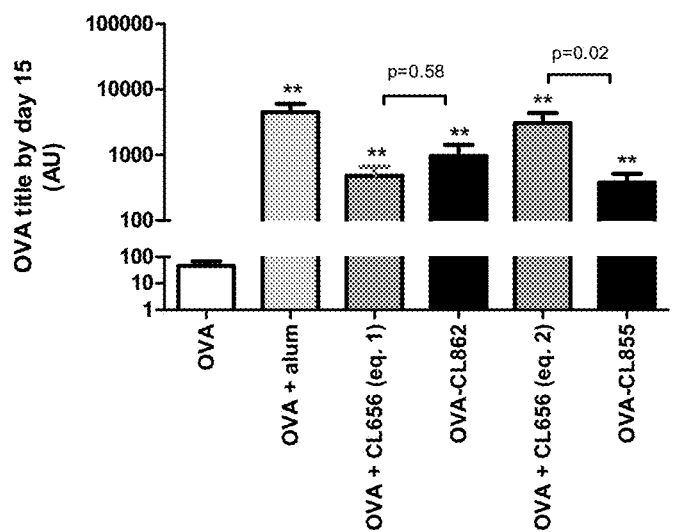
FIG. 11: Adjuvantation potential of compound from the present invention. Mice were subcutaneously immunized with 10 μg of Ovalbumin alone or linked with CDN of the present Invention. Antibody title reacting against Ova was quantified 2 weeks after the first immunization in comparison with the positive control (Ova+Alum) or with OVA in combination with an equivalent amount of free CDN (CL656 eq. 1 for OVA-CL862 and CL656 eq. 2 for OVA-CL855) based on the DAR estimated by UV. ** means significantly different from Ova.
Figure 12:
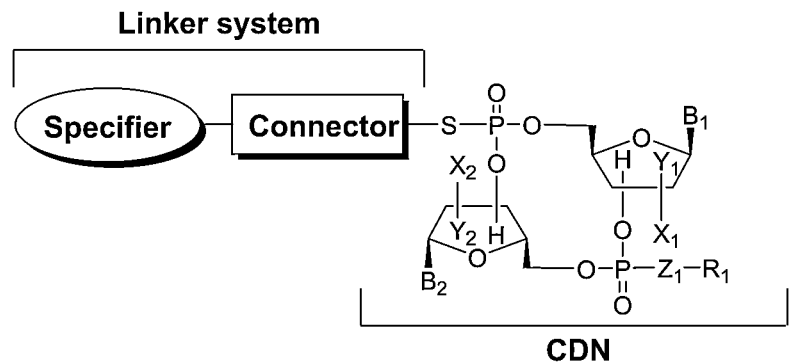
FIG. 12: Formula (I).
Figure 13:
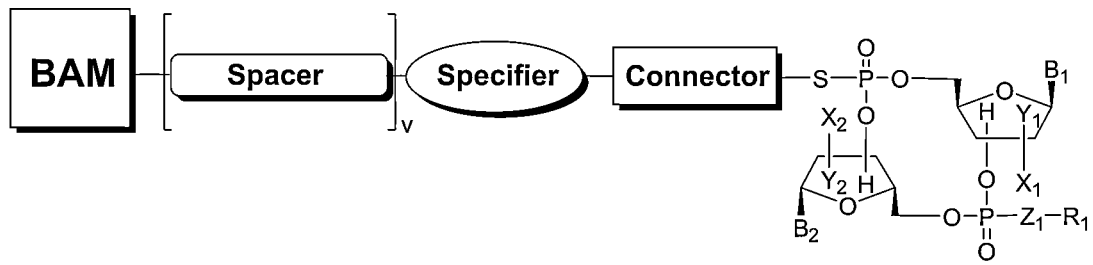
FIG. 13: Formula ($V_a$)
Figure 14:
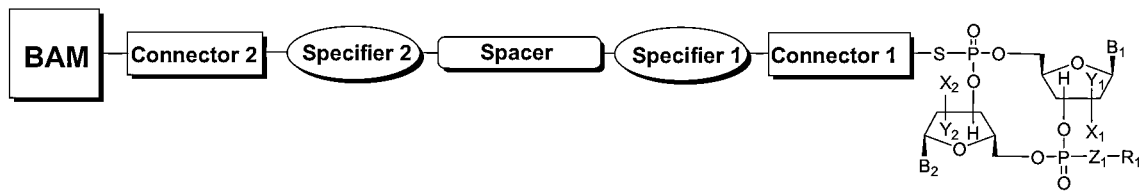
FIG. 14: Formula ($V_b$)
Figure 15:
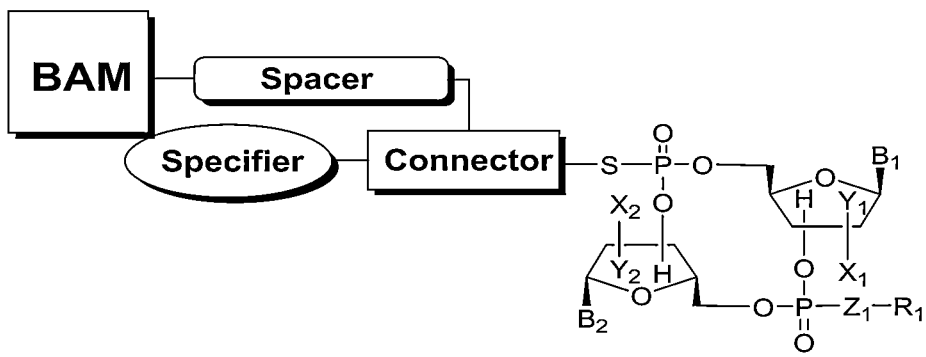
FIG. 15: Formula ($V_c$)
Figure 16:
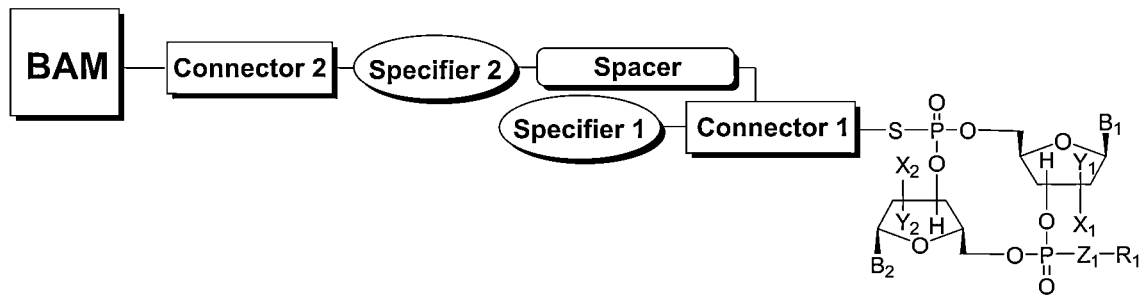
FIG. 16: Formula ($V_d$)
Figure 17:
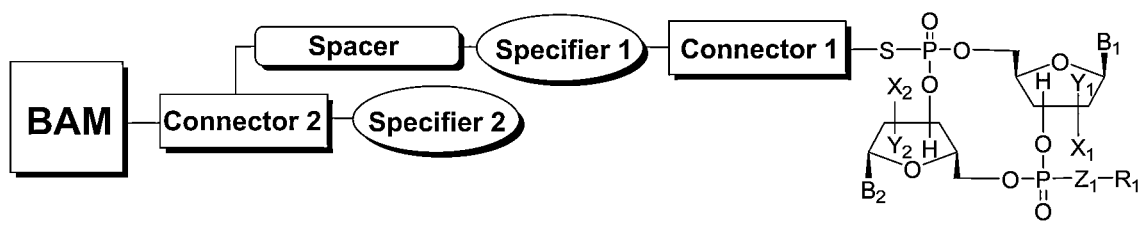
FIG. 17: Formula ($V_e$)
Figure 18:
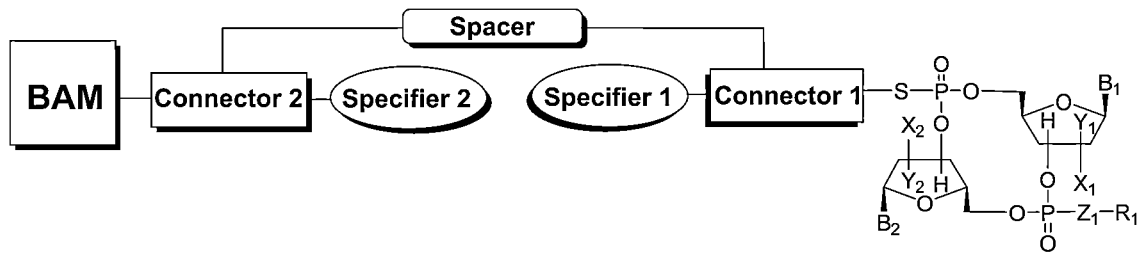
FIG. 18: Formula ($V_f$)
Figure 19:
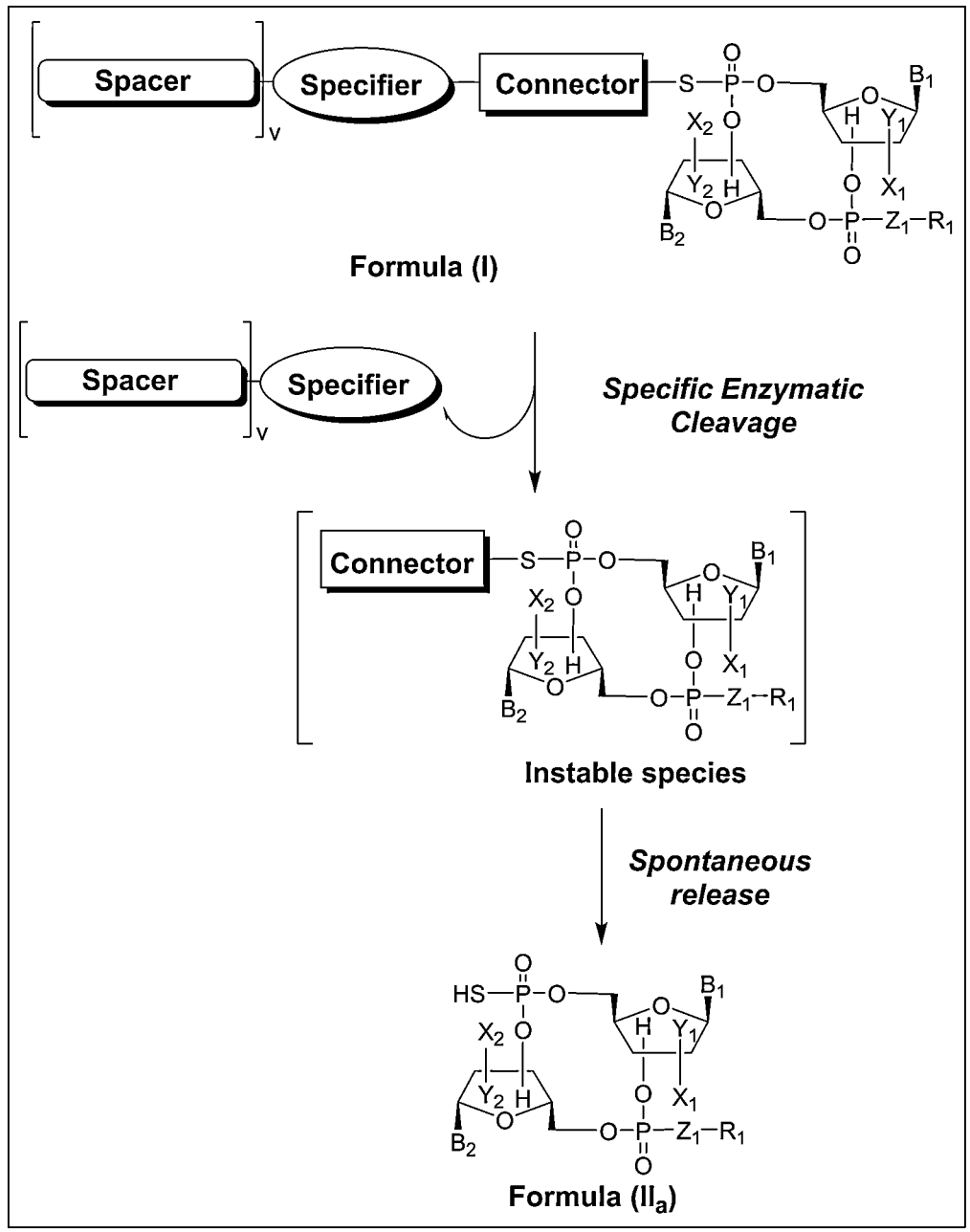
FIG. 19: Scheme 1.1
Figure 20:
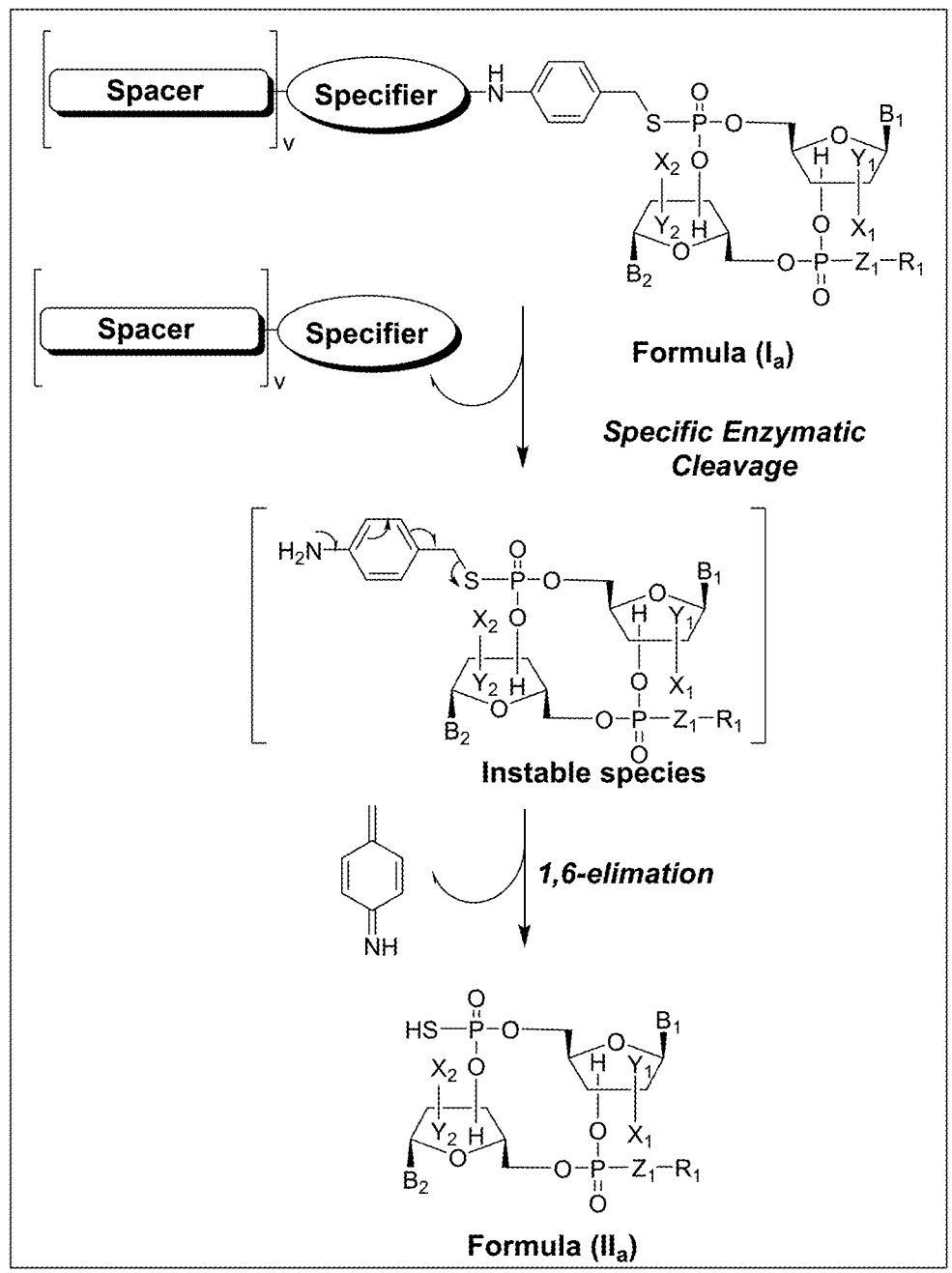
FIG. 20: Scheme 1.2
Figure 21:
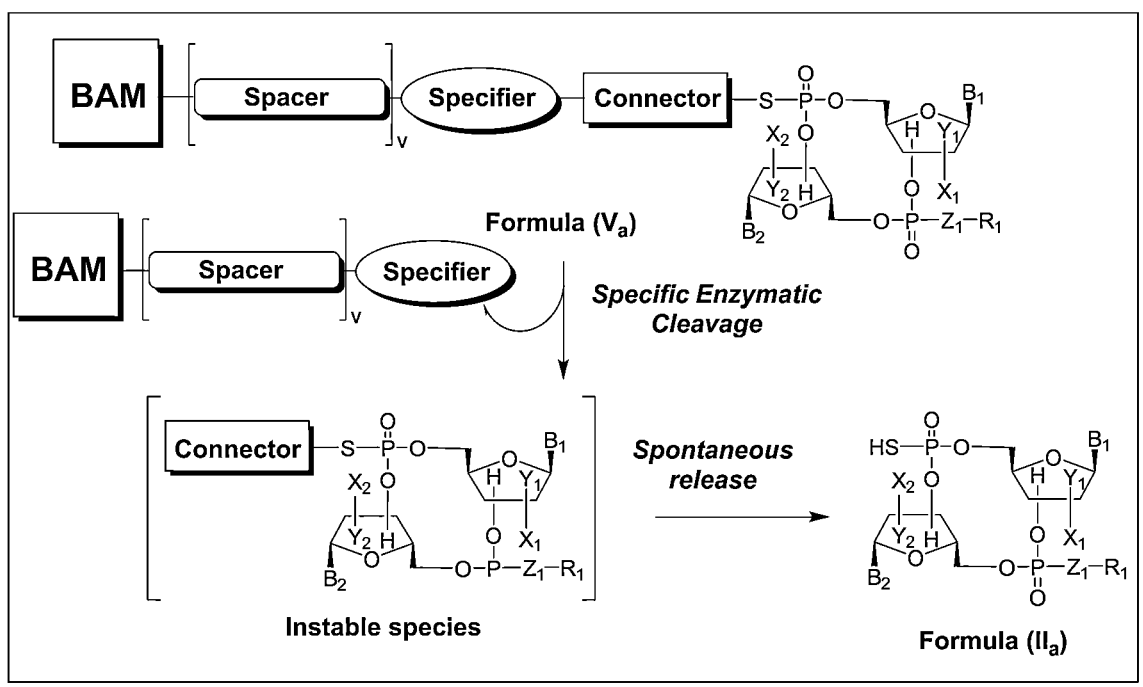
FIG. 21: Scheme 1.3
Figure 22:
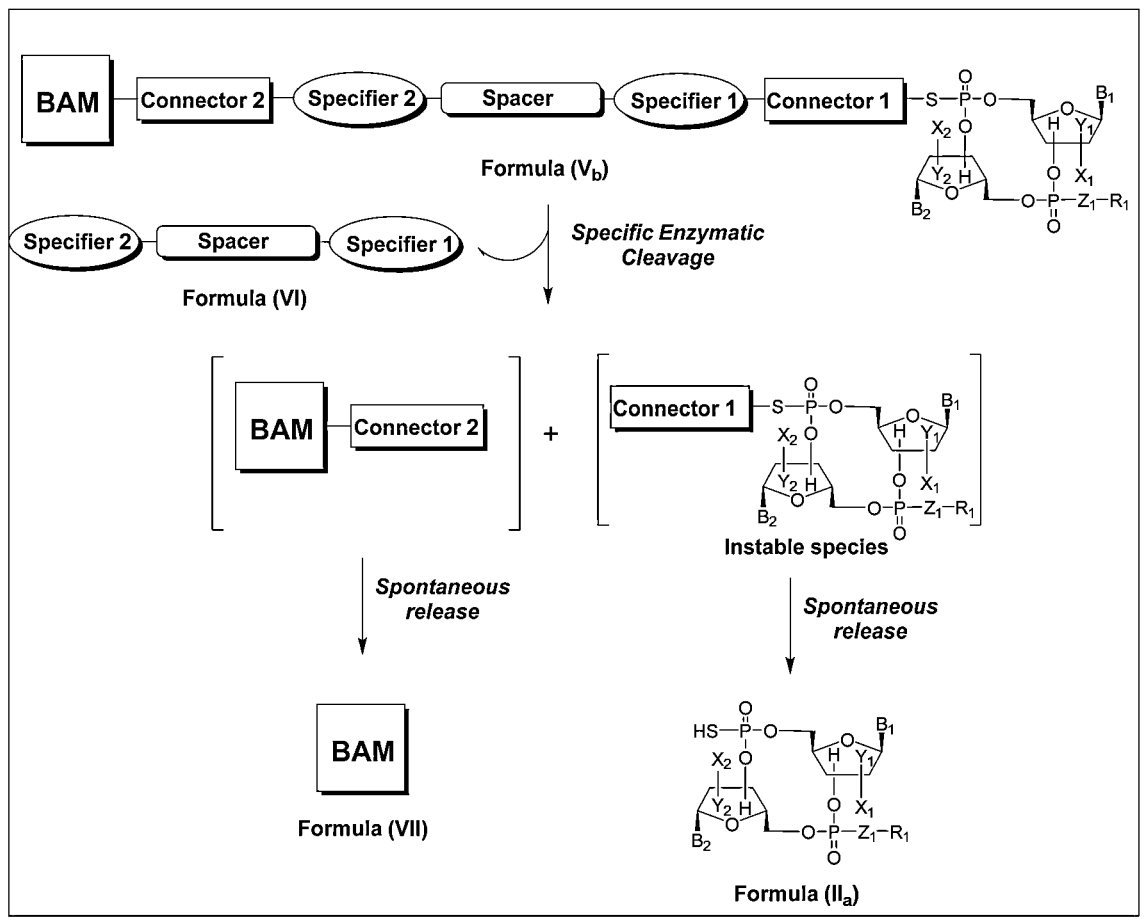
FIG. 22: Scheme 1.4
Figure 23:
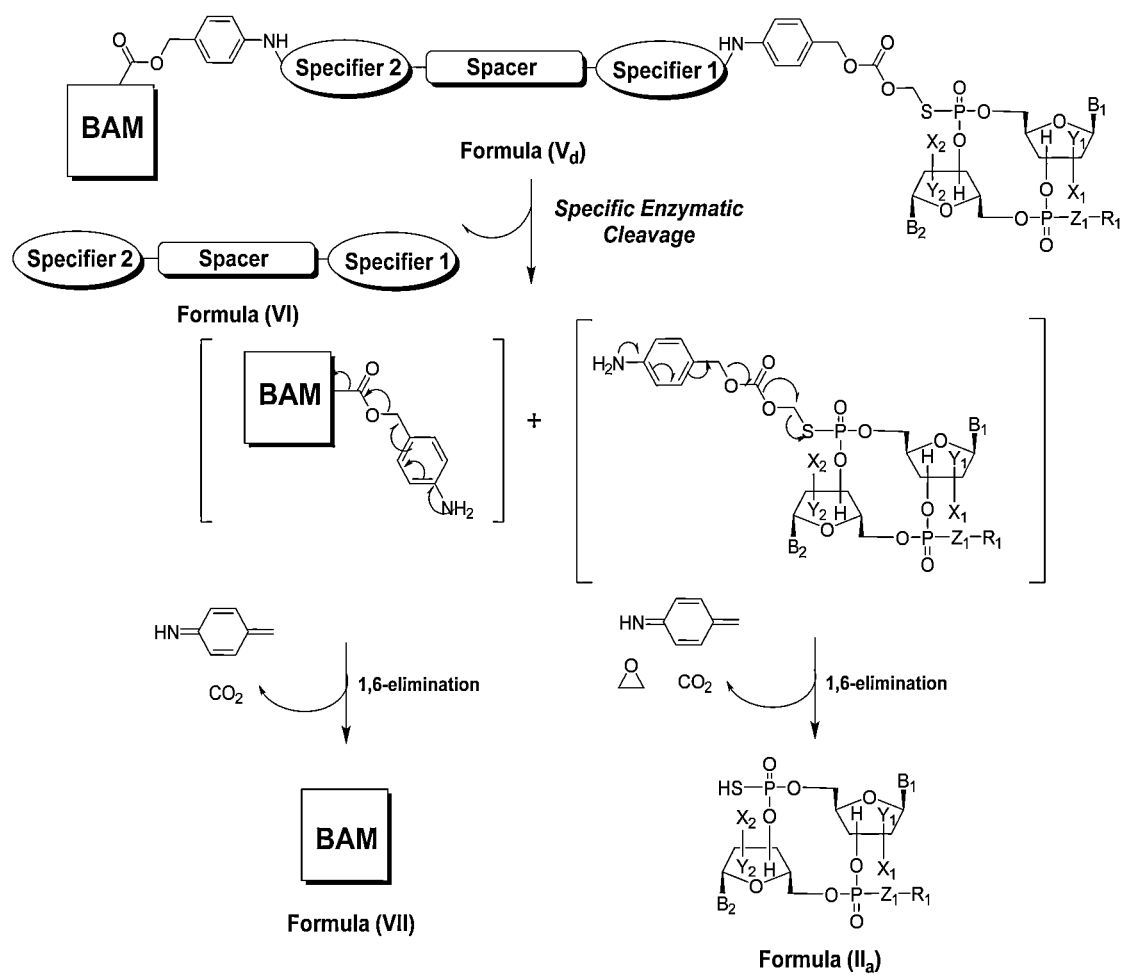
FIG. 23: Scheme 1.5
Figure 24:
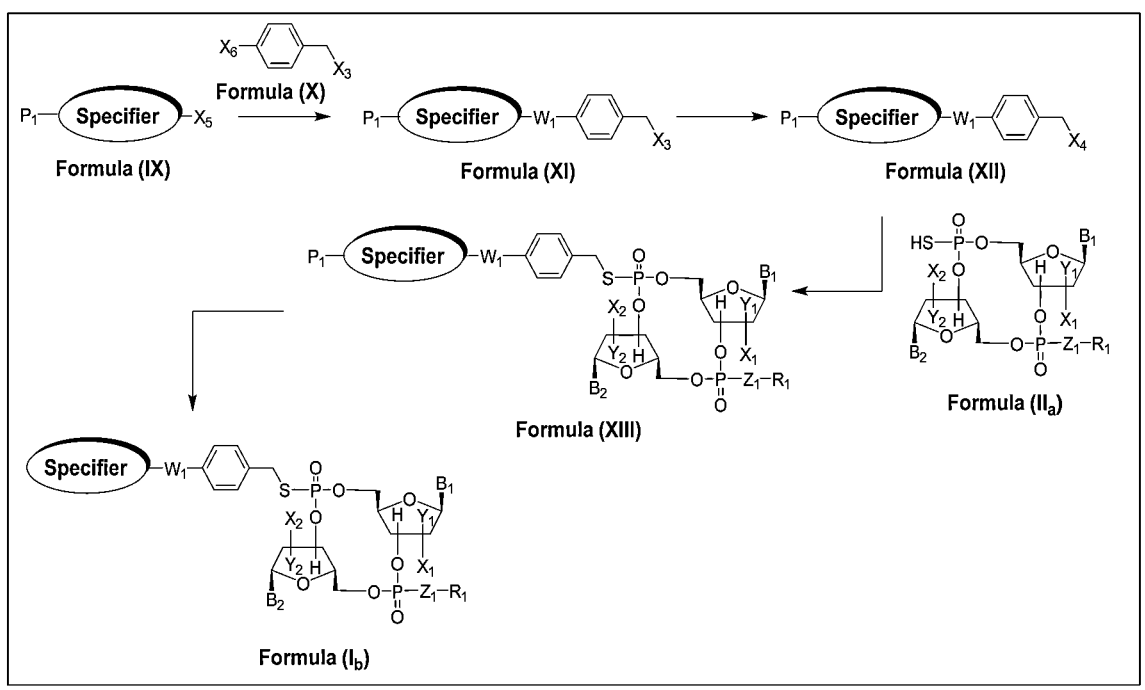
FIG. 24: Scheme 2.1
Figure 25:
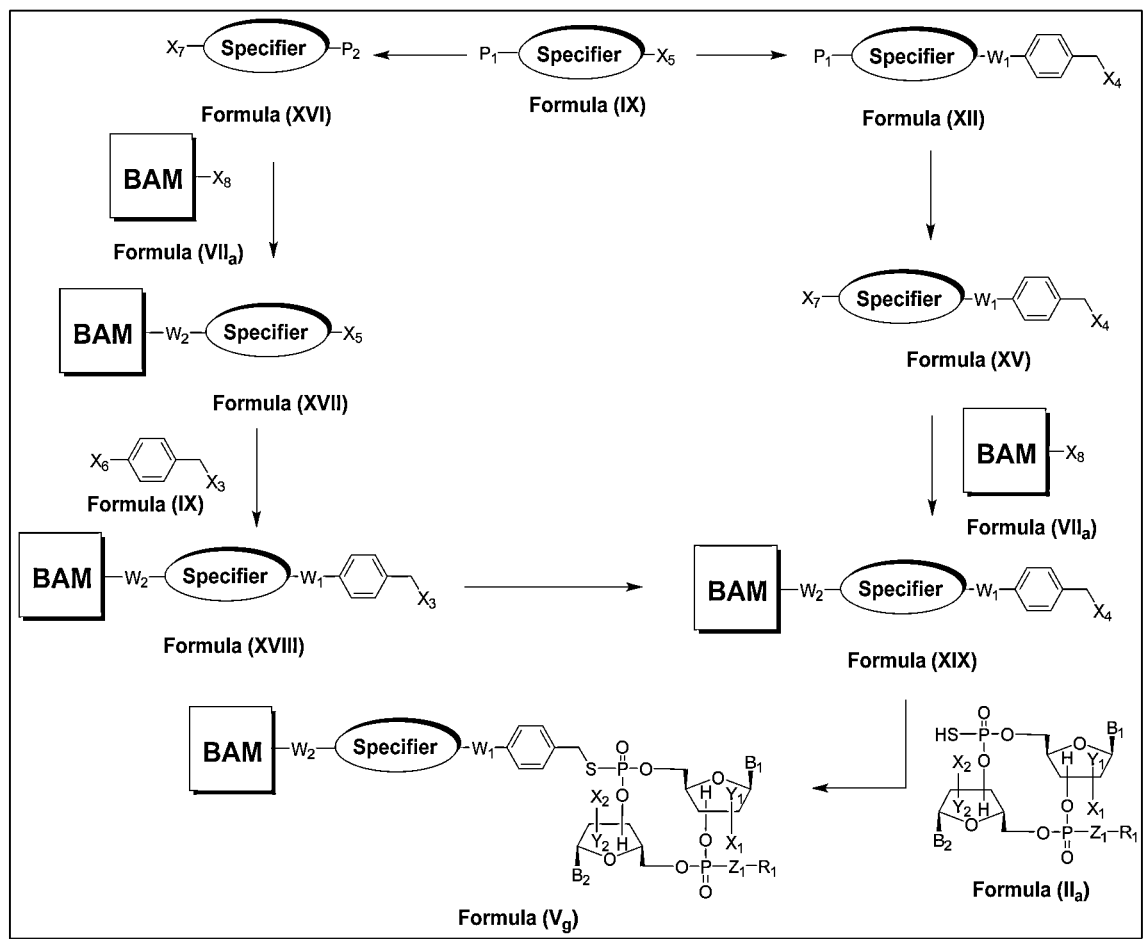
FIG. 25: Scheme 2.2
Figure 26:
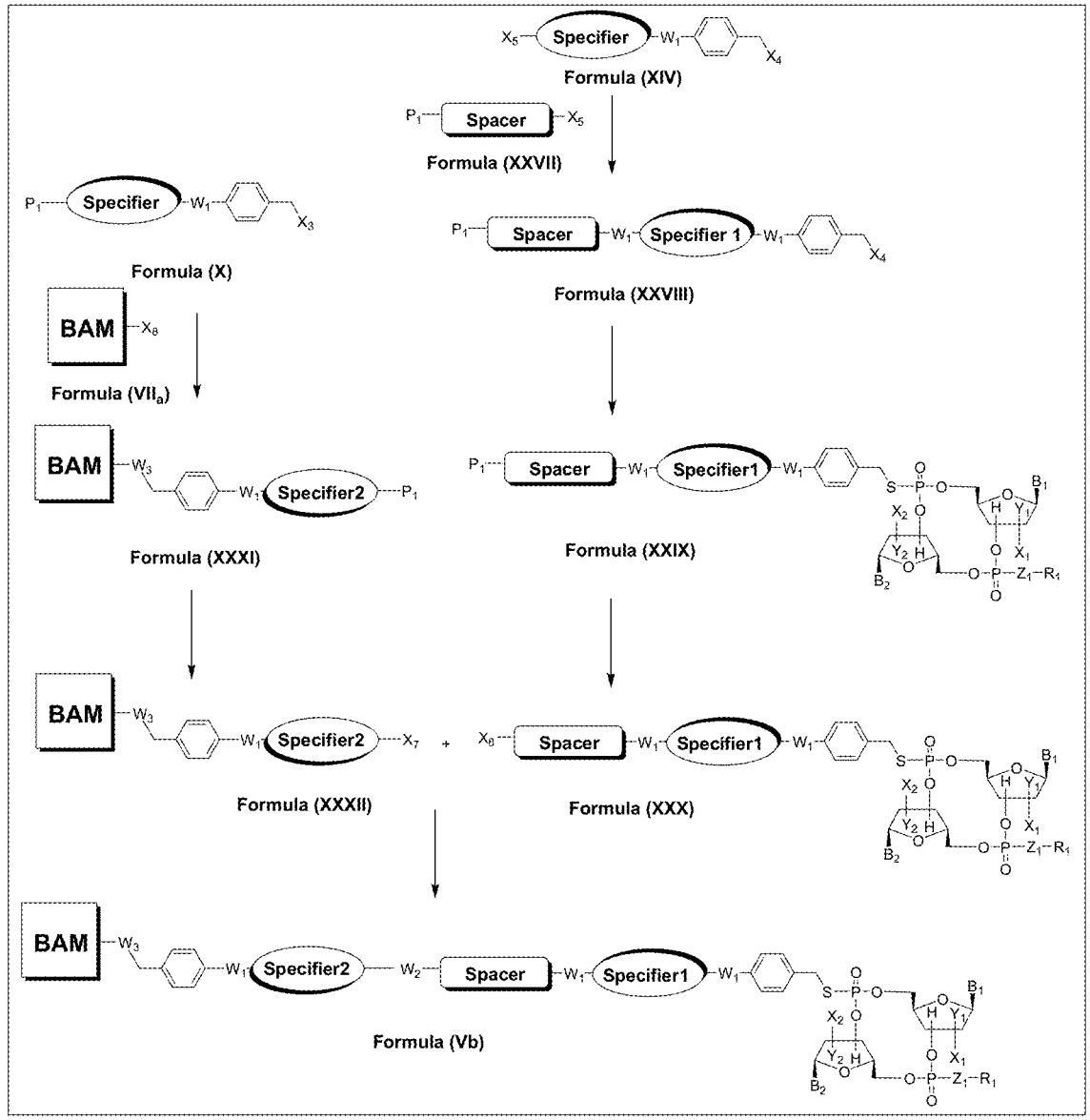
FIG. 26: Scheme 2.3

As shown in FIG. 11, the coupling of a CDN to an antigen is efficient to induce a significant immunization by day 15 which is in the same range than the one induced by Alum-complexed ovalbumin. The example described above is not limited to OVA antigen. Trying to overcome issues related to tumor escape and immunosuppression is the current challenge for the development of more efficient immunotherapeutic vaccines. Pro-CDN linkage to tumoral antigen can be a way to boost immunity against cancer cell. Several studies have produced database referencing all human tumor antigens recognized by T lymphocytes and usable in cancer immunotherapy approaches according to the invention (Van der Bruggen et al. Cancer Immun. 2013; 13: 15. Novellino L et al, Cancer Immunol Immunother, 2005 March; 54(3): 187-207). The most well-known (but not exhaustive) tumor antigens that can be easily coupled to pro-CDN can be selected from the group consisting of alpha-actinin-4; ARTC1; BCR-ABL fusion protein (b3a2); B-RAF; CASP-5; CASP-8; beta-catenin; Cdc27; CDK4; CDKN2A; COA-1; dek-can fusion protein; EFTUD2; Elongation factor 2; ETV6-AML1 fusion protein; FN1; GPNMB; LDLR-fucosyltransferaseAS fusion protein; HLA-A2d; HLA-A11d; hsp70-2; KIAAO205; MART2; ME1; MUM-1f; MUM-2; MUM-3; neo-PAP; Myosin class I; NFYC; OGT; OS-9; pml-RARalpha fusion protein; PRDXS; PTPRK; K-ras; N-ras; RBAF600; SIRT2; SNRPD1; SYT-SSX1 or -SSX2 fusion protein; Thosephosphate Isomerase; BAGE-1; GAGE-1,2,8; GAGE-3,4,5,6,7; GnTVf; HERV-K-MEL; KK-LC-1; KM-HN-1; LAGE-1; MAGE-Ai; MAGE-A2; MAGE-A3; MAGE-A4; MAGE-A6; MAGE-A9; MAGE-A10; MAGE-A12; MAGE-C2; mucin k; NA-88; NY-ESO-1/LAGE-2; SAGE; Sp17; SSX-2; SSX-4; TRAG-3; TRP2-INT2g; CEA; gp100/Pme117; Kallikrein 4; mammaglobin-A; Melan-A/MART-1; NY-BR-1; OA1; PSA; RAB38/NY-MEL-1; TRP-1/gp75; TRP-2; tyrosinase; adipophilin; AIM-2; BING-4; CPSF; cyclin D1; Ep-CAM; EphA3; FGF5; G250/MN/CAIX; HER-2/neu; IL13Ralpha2; Intestinal carboxyl esterase; alpha-foetoprotein; M-CSF; mdm-2; MMP-2; MUC1; p53; PBF; PRAME; PSMA; RAGE-1; RNF43; RU2AS; secernin 1; SOX10; STEAP1; survivin; Telomerase; WT1; FLT3-ITD; BCLX(L); DKK1; ENAH(hMena); MCSP; RGS5; Gastrin-17; Human Chorionic Gonadotropin, EGFRvIII, HER2, HER2/neu, P501, Guanylyl Cyclase C, and PAP. The chemistry coupling of a CDN to an antigen (viral, bacterial, tumor antigens) with a releasable linker is a suitable way to improve the quality of the innate immune response because of the co-delivery of both adjuvant and antigen to the same antigen-presenting cell.

The invention claimed is:
1. A Pro-CDN compound of Formula (Ib):

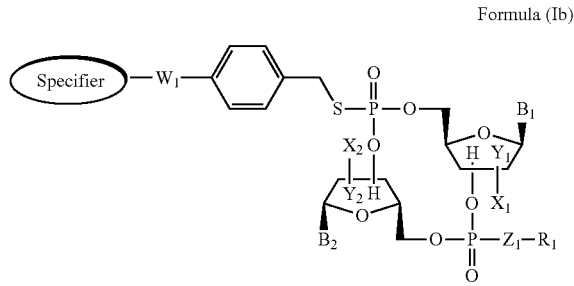

Formula (Ib)

or pharmaceutically acceptable salts, stereoisomers, tautomers or solvates thereof;

wherein:
   the CDN unit is a cyclic dinucleotide monophosphorothioate or diphosphorothioate of Formula (II$_a$):

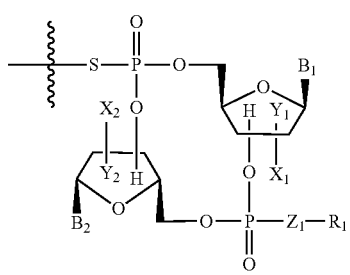

Formula (II$_a$)

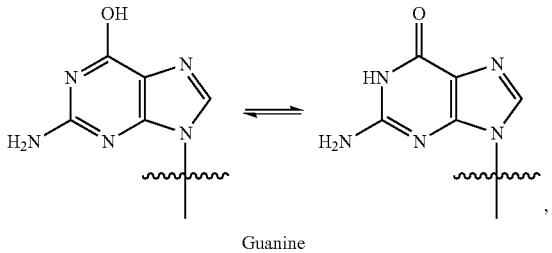

Guanine the specifier is a peptide sequence which can be cleaved by a specific protease; and W$_1$ is an amide, an ester, a urea, a disulfide bridge, a carbamate, a hydrazone, an imine, an oxime, or a triazole group.

2. A Pro-CDN compound, having the Formula (XXX):

(XXX)

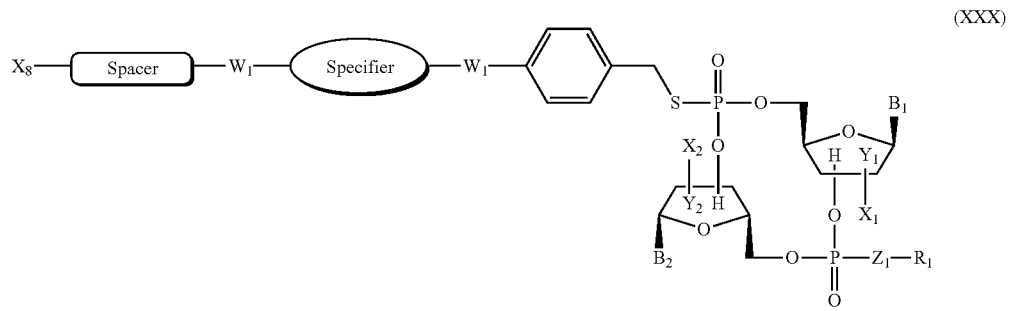

or pharmaceutically acceptable salts, stereoisomers, tautomers or solvates thereof;

wherein:
   the CDN unit is a cyclic dinucleotide monophosphorothioate or diphosphorothioate of Formula (II$_a$):

Formula (II$_a$)

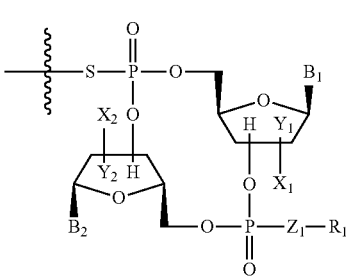

wherein:
   X$_1$ and Y$_1$ are independently H or F;
   X$_2$ and Y$_2$ are independently H or F;
   Z$_1$ is O or S;
   R$_1$ is H when Z$_1$ is O;
   R$_1$ is H or a linker system when Z$_1$ is S;
   B$_1$ and B$_2$ are purine bases chosen from:

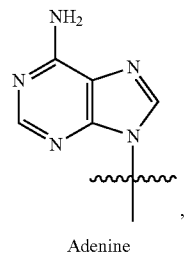

Adenine

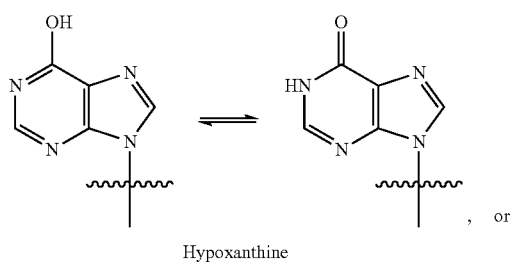, or

Hypoxanthine wherein
   X$_1$ and Y$_1$ are independently H or F;
   X$_2$ and Y$_2$ are independently H or F;
   Z$_1$ is O or S;
   R$_1$ is H when Z$_1$ is O;
   R$_1$ is H or a linker system when Z$_1$ is S;

$B_1$ and $B_2$ are purine bases chosen from:

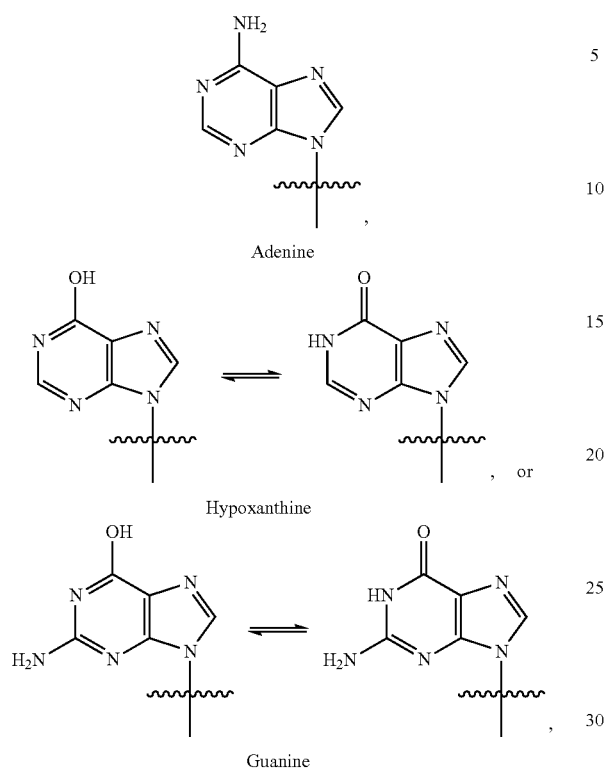

or pharmaceutically acceptable salts, stereoisomers, tautomers or solvates thereof,
the specifier is a peptide sequence which can be cleaved by a specific protease;
the spacer absent or is a hydrophilic group selected from:
  a polyethylene glycol (PEG);
  a polyamine;
  a compound of Formula ($IV_a$):

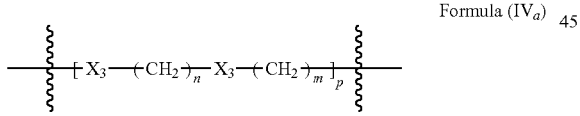

Formula ($IV_a$)

wherein $X_3$ is —O— or —NH—, m, n and p are an integer ranging from 0 to 12;
a compound of Formula ($IV_b$):

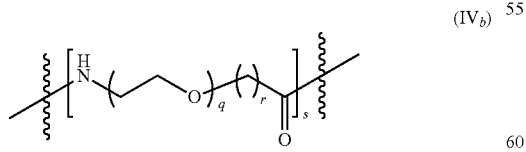

($IV_b$)

wherein q is an integer ranging from 1 to 6;
r is an integer ranging from 1 to 6;
s is an integer ranging from 1 to 6;
$W_1$ is an amide, an ester, a urea, a disulfide bridge, a carbamate, a hydrazone, an imine, an oxime, or a triazole group;

$X_8$ is a function group selected from:
  —COOR$_3$ wherein $R_3$ is H or N-hydroxysuccinimide;
  —NH$_2$;
  —OH or —SH;
  —N$_3$;
  a maleimide group of Formula (XX):

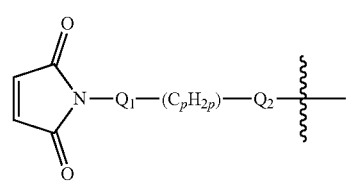

Formula (XX)

wherein:
  p is an integer ranging from 0 to 12,
  $Q_1$ is —CH$_2$— or —CO—,
  $Q_2$ is —CH$_2$—, —NH— or —CO—;
a 3-arylpropionitrile (APN) group of Formula (XXI):

Formula (XXI)

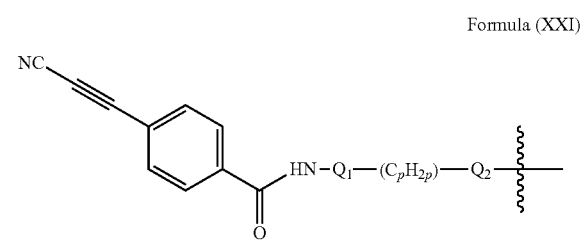

wherein:
  p is an integer ranging from 0 to 12,
  $Q_1$ is —CH$_2$— or —CO—;
  $Q_2$ is —CH$_2$—, —NH—, —O—, —S—, or —CO—;
a halogen (F, I, Br, Cl);
a group of Formula (XXII):

Formula (XXII)

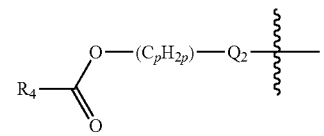

wherein $R_4$ is a halogen (Cl, Br, I, F) or a 4-nitrophenoxy group;
an aldehyde group of Formula (XXIII):

Formula (XXIII)

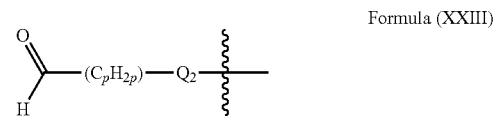

wherein p and $Q_2$ are as defined above;

an alkyne of Formula (XXIV):

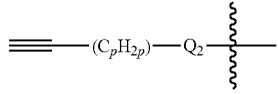

Formula (XXIV)

wherein p and $Q_2$ are as defined above;

a cyclo-octyl group of Formula (XXV):

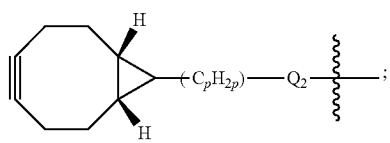

Formula (XXV)

a dibenzocyclooctyne (DBCO) group of Formula (XXVI):

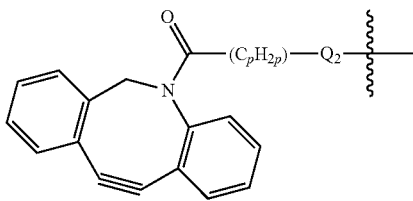

Formula (XXVI)

wherein p and $Q_2$ are as defined above.

3. The Pro-CDN compound according to claim 1, wherein the CDN is a (3',3') CDN of Formula ($II_b$):

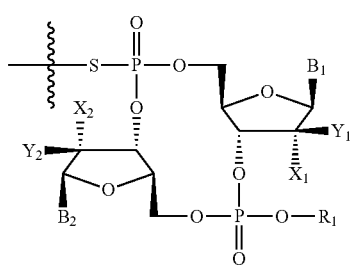

Formula ($II_b$)

wherein $X_1$, $Y_1$, $X_2$, $Y_2$, $B_1$, $B_2$, and $R_1$ are as defined in claim 1.

4. The Pro-CDN compound according to claim 1, wherein the CDN is a (3',3') CDN of Formulae ($II_g$):

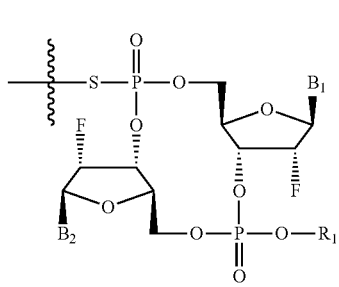

Formula ($II_g$)

wherein $B_1$, $B_2$, and $R_1$ are as defined in claim 1.

5. The Pro-CDN compound according to claim 3, wherein the CDN unit of compounds of Formula ($II_b$) is selected from one of the following formulas:

CL797

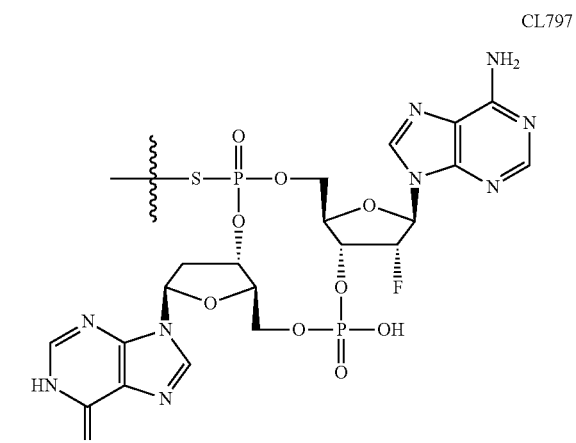

CL702

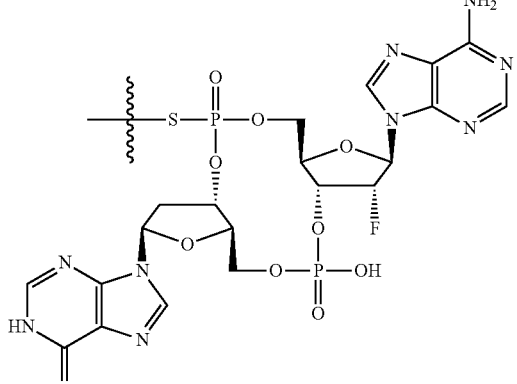

6. The Pro-CDN compound according to claim 4, wherein the CDN unit of compounds of Formula (II$_g$) is selected from one of the following formulas:

CL656

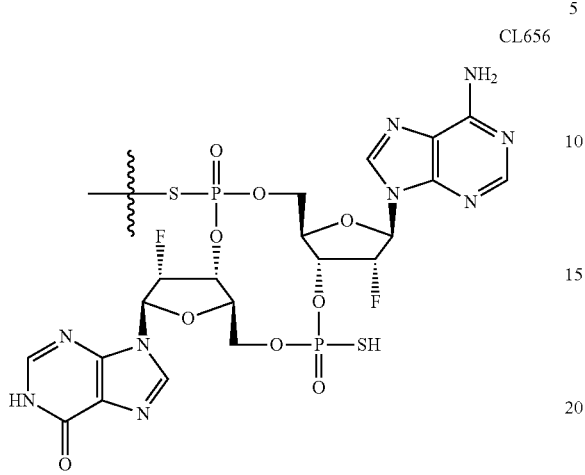

CL845

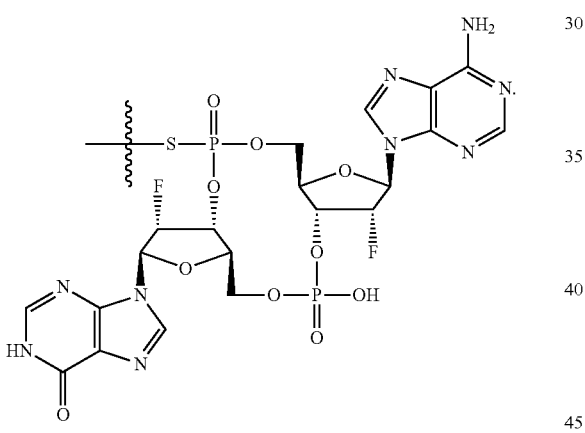

7. The Pro-CDN compound according to claim 1, wherein the specifier is a dipeptide selected from the group consisting of valine-citrulline and valine-alanine.

8. The Pro-CDN compound according to claim 2, wherein X$_8$ is
—OH or —SH;
—NH$_2$;
—N$_3$;
a maleimide group of Formula (XX):

Formula (XX)

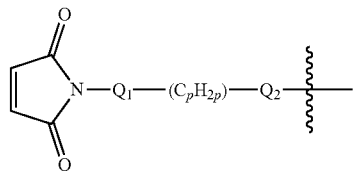

wherein
p is an integer ranging from 0 to 12,
Q$_1$ is —CH$_2$— or —CO—,
Q$_2$ is —CH$_2$—, —NH— or —CO—;
an halogen (F, I, Br, Cl);
an alkyne of Formula (XXIV):

Formula (XXIV)

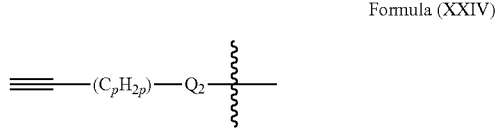

wherein p and Q$_2$ are as defined above;
a cyclo-octyl group of Formula (XXV):

Formula (XXV)

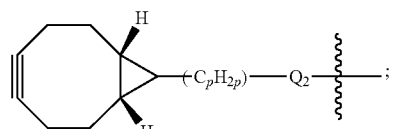

a dibenzocyclooctyne (DBCO) group of Formula (XXVI):

Formula (XXVI)

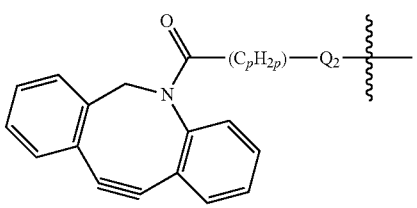

wherein p and Q$_2$ are as defined above.

9. The Pro-CDN compound of Formula (I) according to claim 1, wherein said Pro-CDN compound is chosen from:
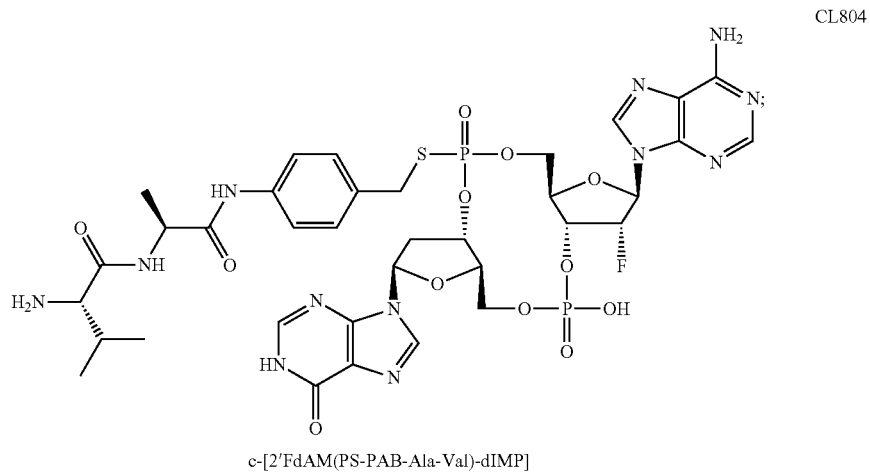
c-[2'FdAM(PS-PAB-Ala-Val)-dIMP]
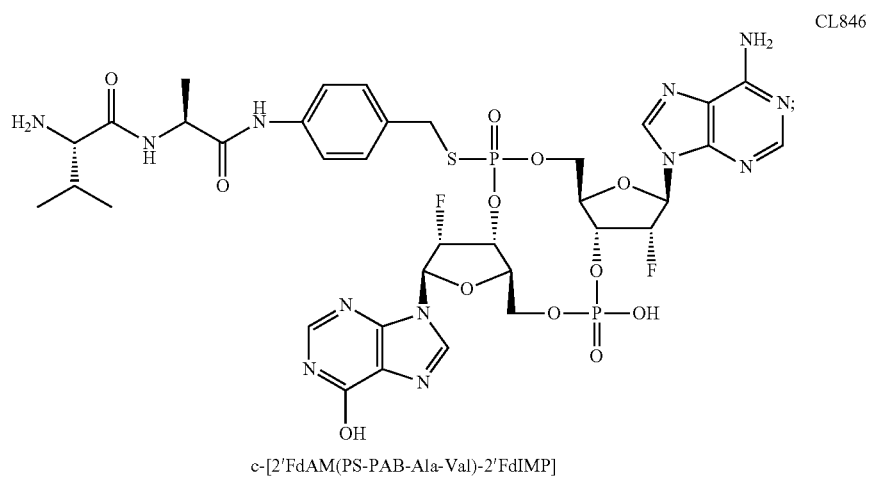
c-[2'FdAM(PS-PAB-Ala-Val)-2'FdIMP]
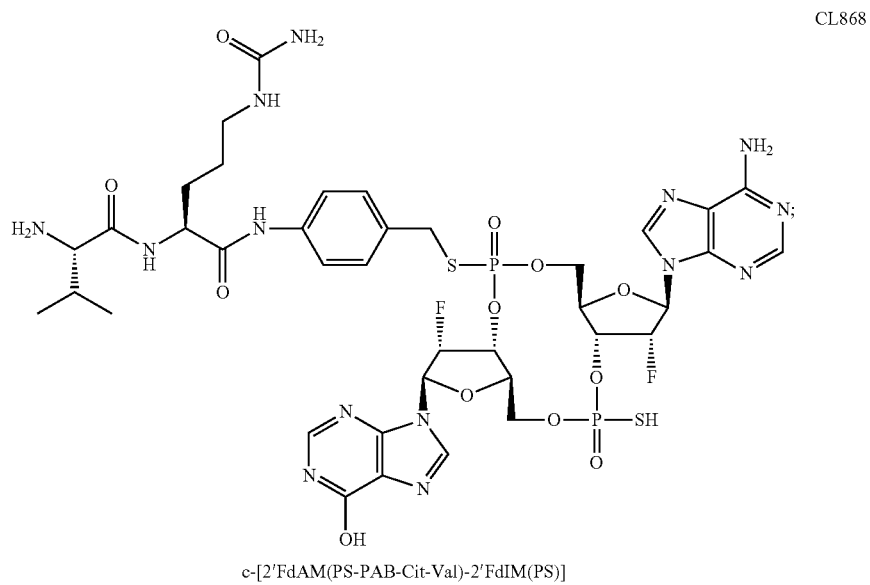
c-[2'FdAM(PS-PAB-Cit-Val)-2'FdIM(PS)]

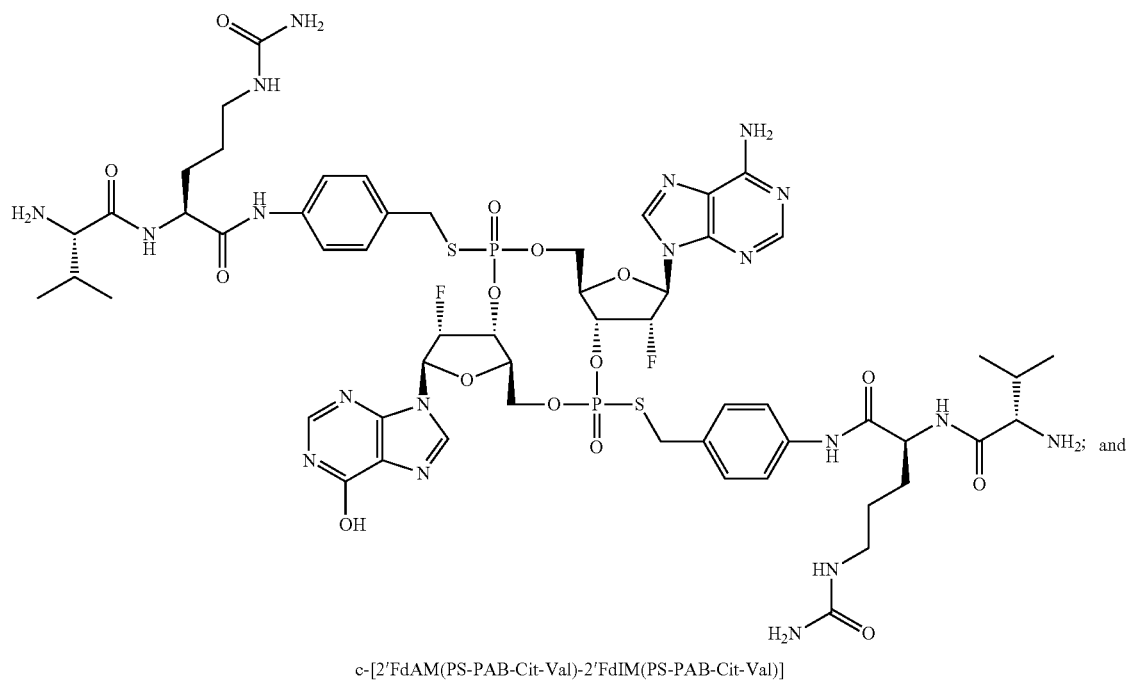

c-[2'FdAM(PS-PAB-Cit-Val)-2'FdIM(PS-PAB-Cit-Val)]

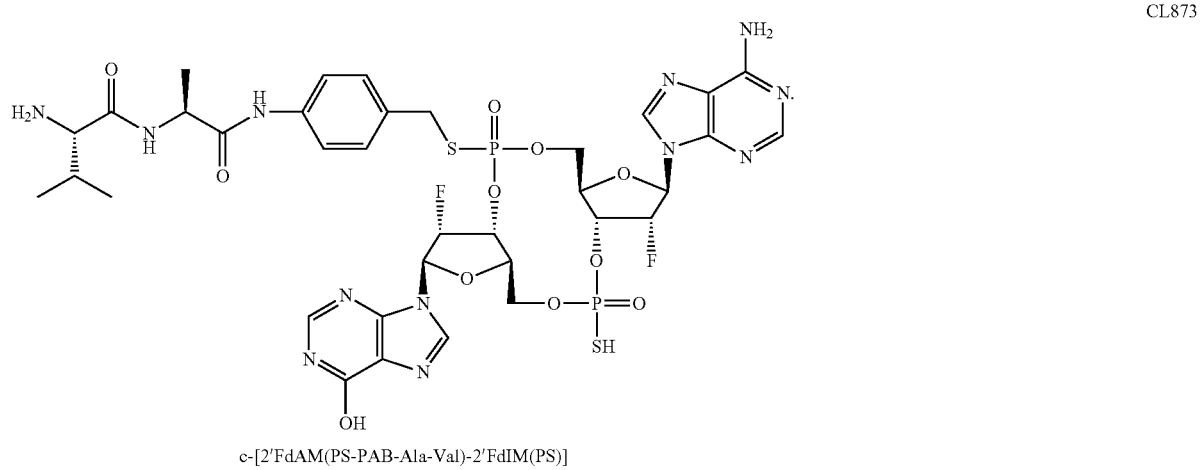

c-[2'FdAM(PS-PAB-Ala-Val)-2'FdIM(PS)]

10. A pharmaceutical composition comprising a Pro-CDN according to claim 1 and a pharmaceutically acceptable excipient.

11. A method of treatment of a disease that may be alleviated by the induction of an immune response via the STING pathway comprising the administration to a patient of an effective amount of a Pro-CDN according to claim 1.

12. An immunomodulatory agent comprising Pro-CDN according to claim 1.

13. A method of treatment of cancer or pre-cancerous syndromes or infectious diseases, comprising the administration to a patient of an effective amount of a Pro-CDN according to claim 1.

14. An immunoadjuvant comprising a Pro-CDN according to claim 1.

15. A therapeutic combination comprising a Pro-CDN according to claim 1 and a therapeutic agent.

16. A method for treating cancer, said method comprising administering to a patient in need thereof:
a Pro-CDN according to claim 1 and
a chemotherapeutic agent.

17. A pharmaceutical composition comprising a Pro-CDN according to claim 2 and a pharmaceutically acceptable excipient.

18. A method of treatment of a disease that may be alleviated by the induction of an immune response via the STING pathway comprising the administration to a patient of an effective amount of a Pro-CDN according to claim 2.

19. An immunomodulatory agent comprising Pro-CDN according to claim 2.

20. A method of treatment of cancer or pre-cancerous syndromes or infectious diseases, comprising the administration to a patient of an effective amount of a Pro-CDN according to claim 2.

21. An immunoadjuvant comprising a Pro-CDN according to claim 2.

22. A therapeutic combination comprising a Pro-CDN according to claim 2 and a therapeutic agent.

23. A method for treating cancer, said method comprising administering to a patient in need thereof:

a Pro-CDN according to claim 2 and
a chemotherapeutic agent.

24. The Pro-CDN compound of Formula (XXX) according to claim 2, wherein said Pro-CDN compound is chosen from:

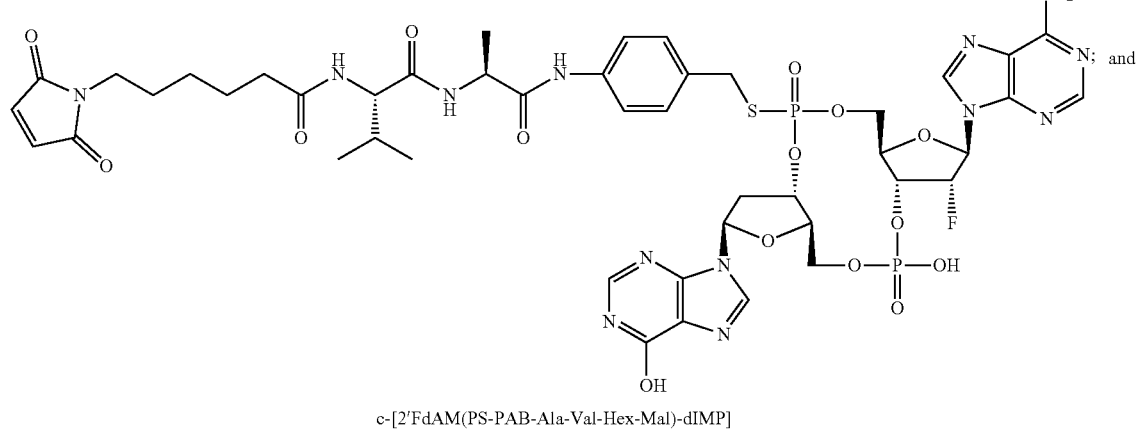

c-[2'FdAM(PS-PAB-Ala-Val-Hex-Mal)-dIMP]

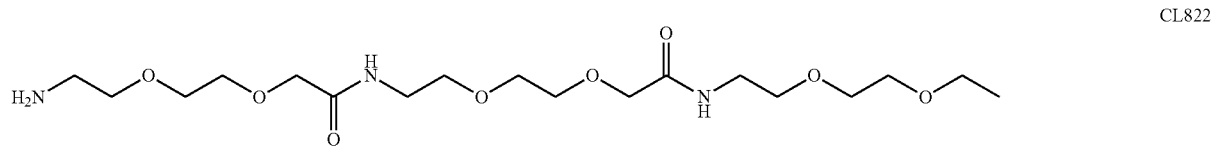

CL822

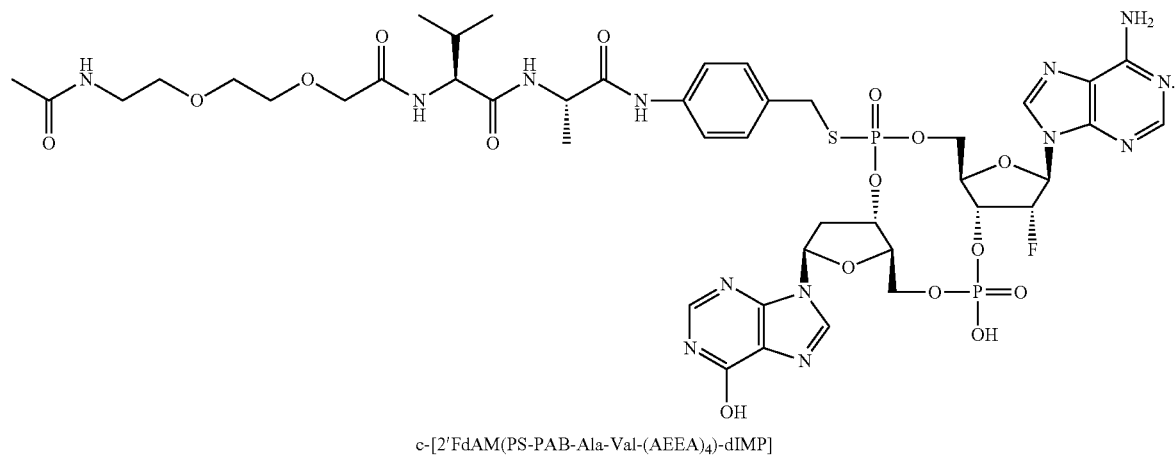

c-[2'FdAM(PS-PAB-Ala-Val-(AEEA)₄)-dIMP]

25. A Pro-CDN compound chosen from:
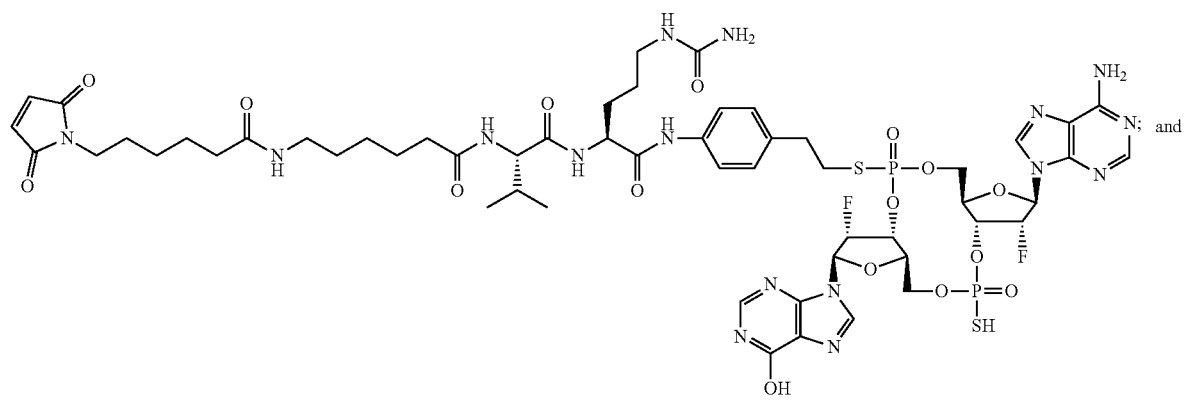
c-[2′FdAM(PS-PAB-Cit-Val-Aca-Aca-Mal)-2′FdIM(PS)]
CL862; and
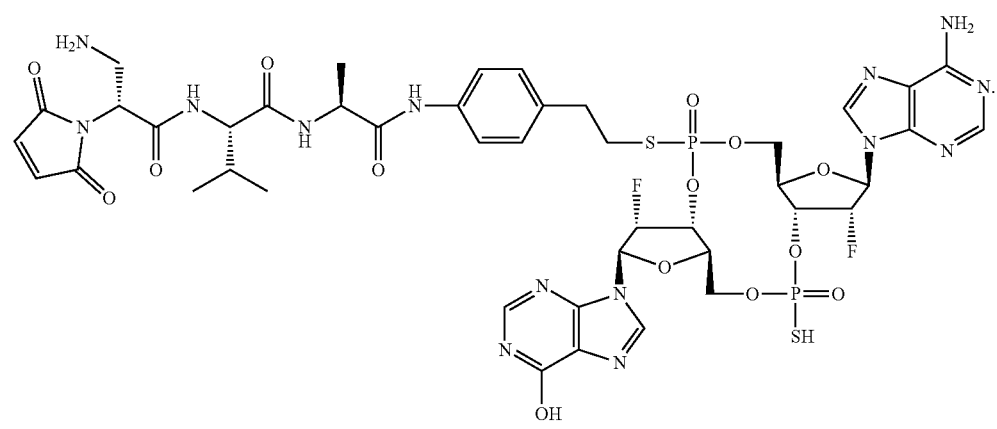
c-[2′FdAM(PS-PAB-Ala-Val-Dap-Mal)-2′FdIM(PS)]
CL874
* * * * *